US012733399B2

(12) United States Patent
Kushida et al.

(10) Patent No.: US 12,733,399 B2
(45) Date of Patent: Sep. 8, 2026

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Tomokatsu Kushida, Chiba (JP); Kei Yoshida, Chiba (JP); Masatoshi Saito, Ichihara (JP); Yoshinao Shirasaki, Chiba (JP); Masato Nakamura, Sumida-ku (JP); Michelle Groarke, Binningen (CH); Heinz Wolleb, Fehren (CH); Natalia Chebotareva, Hagenthal le Bas (FR)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1154 days.

(21) Appl. No.: 17/635,957

(22) PCT Filed: Aug. 19, 2020

(86) PCT No.: PCT/JP2020/031327
§ 371 (c)(1),
(2) Date: Feb. 16, 2022

(87) PCT Pub. No.: WO2021/033730
PCT Pub. Date: Feb. 25, 2021

(65) Prior Publication Data

US 2022/0359831 A1 Nov. 10, 2022

(30) Foreign Application Priority Data

Aug. 19, 2019 (JP) ................................ 2019-149959

(51) Int. Cl.
*H10K 85/60* (2023.01)
*C07D 409/10* (2006.01)
(Continued)

(52) U.S. Cl.
CPC ......... *H10K 85/654* (2023.02); *C07D 409/10* (2013.01); *H10K 85/6576* (2023.02); *H10K 50/11* (2023.02); *H10K 50/16* (2023.02)

(58) Field of Classification Search
CPC .. C07D 409/04; C07D 409/10; C07D 409/14; C07D 471/10; H10K 50/11; H10K 50/16;
(Continued)

(56) References Cited

U.S. PATENT DOCUMENTS

2002/0076576 A1* 6/2002 Li ........................ H10K 85/342 428/917
2016/0028021 A1 1/2016 Zeng et al.
(Continued)

FOREIGN PATENT DOCUMENTS

JP 2016-19002 A 2/2016
JP 2017-524699 A 8/2017
(Continued)

OTHER PUBLICATIONS

International Search Report mailed on Oct. 20, 2020 in PCT/JP2020/031327 filed on Aug. 19, 2020 (3 pages).

*Primary Examiner* — Elizabeth M. Dahlburg
(74) *Attorney, Agent, or Firm* — Oblon, McClelland, Maier & Neustadt, L.L.P.

(57) ABSTRACT

To provide a compound that further improves the capability of an organic EL device, an organic EL device having a further improved device capability, and an electronic device including the organic EL device. A compound represented by the following formula (1) (wherein *p, *q, *r, *s, *b, *a,
(Continued)

$R^1$, $R^2$, $R^{11}$ to $R^{18}$, L, and $R^{31}$ to $R^{35}$ are defined in the description), an organic electroluminescent device containing the compound, and an electronic device including the organic electroluminescent device.

(1)

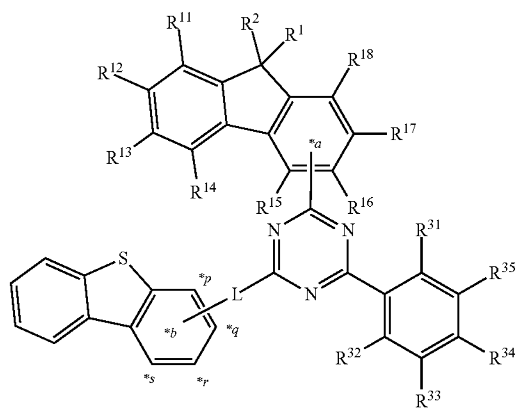

24 Claims, 1 Drawing Sheet

(51) Int. Cl.
*H10K 50/11* (2023.01)
*H10K 50/16* (2023.01)

(58) Field of Classification Search
CPC ...... H10K 50/17; H10K 50/171; H10K 50/18; H10K 85/615; H10K 85/654; H10K 85/6576
See application file for complete search history.

(56) References Cited

U.S. PATENT DOCUMENTS

| | | | |
|---|---|---|---|
| 2016/0099422 | A1 | 4/2016 | Zeng et al. |
| 2017/0213983 | A1 | 7/2017 | Hayama et al. |
| 2017/0222157 | A1 | 8/2017 | Jatsch et al. |
| 2018/0222872 | A1 | 8/2018 | Jatsch et al. |
| 2019/0259957 | A1 | 8/2019 | Zeng et al. |
| 2019/0280212 | A1 | 9/2019 | Zeng et al. |

FOREIGN PATENT DOCUMENTS

| | | | |
|---|---|---|---|
| JP | 2018-531883 | A | 11/2018 |
| KR | 10-2017-0116944 | A | 10/2017 |
| WO | WO 2007/069569 | A1 | 6/2007 |
| WO | WO 2013/077352 | A1 | 5/2013 |
| WO | WO 2015/152633 | A1 | 10/2015 |
| WO | WO 2016/084962 | A1 | 6/2016 |
| WO | WO 2018/095393 | A1 | 5/2018 |
| WO | WO 2019/004612 | A1 | 1/2019 |

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

CROSS-REFERENCE TO RELATED APPLICATIONS

The present application is the national stage of international application PCT/JP2020/031327, filed on Aug. 19, 2020, and claims the benefit of the filing date of Japanese Appl. No. 2019-149959, filed on Aug. 19, 2019, the content of each of which is incorporated by reference.

TECHNICAL FIELD

The present invention relates to a compound, a material for organic electroluminescent devices, an organic electroluminescent device, and an electronic device including the organic luminescent device.

BACKGROUND ART

In general, an organic electroluminescent device (which may be hereinafter referred to as an "organic EL device") is constituted by an anode, a cathode, and an organic layer intervening between the anode and the cathode. In application of a voltage between both the electrodes, electrons from the cathode side and holes from the anode side are injected into a light emitting region, and the injected electrons and holes are recombined in the light emitting region to generate an excited state, which then returns to the ground state to emit light. Accordingly, development of a material that efficiently transports electrons or holes into the light emitting region, and promotes recombination of the electrons and holes is important for providing a high-performance organic EL device.

PTLs 1 to 3 describe compounds used for a material for organic electroluminescent devices.

CITATION LIST

Patent Literatures

PTL 1: WO 2007/069569A1

PTL 2: WO 2013/077352A1

PTL 3: WO 2015/152633A1

Technical Problem

Various compounds for organic EL devices have been reported, but a compound that further enhances the capability of an organic EL device has been still demanded.

The present invention has been made for solving the problem, and an object thereof is to provide a compound that further improves the capability of an organic EL device, an organic EL device having a further improved device capability, and an electronic device including the organic EL device.

Solution to Problem

As a result of the continued investigations by the present inventors on the capabilities of organic EL devices containing the compounds described in PTLs 1 to 3, it has been found that a triazine compound having a fluorene skeleton, a phenyl group having a particular substituent or an unsubstituted phenyl group, and an unsubstituted benzothiophene through a particular linking group, which each are bonded to the center triazine skeleton, can provide an organic EL device having a further improved capability.

In one embodiment, the present invention provides a compound represented by the following formula (1):

(1)

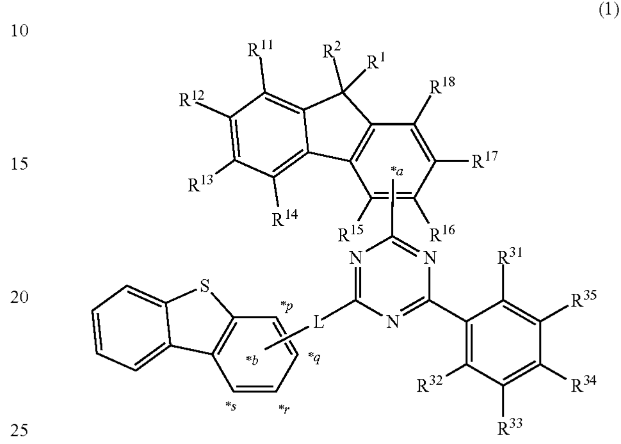

wherein $R^1$ and $R^2$ each are independently selected from a hydrogen atom, a substituted or unsubstituted aryl group having 6 to 30 ring carbon atoms, and a substituted or unsubstituted heterocyclic group having 5 to 30 ring atoms, in which $R^1$ and $R^2$ may be bonded to each other to form a ring structure;

p, *q, *r, and *s each represent a carbon atom, provided that *b is bonded to one selected from the carbon atoms represented by *p, *q, *r, and *s;

$R^{11}$ to $R^{18}$ each are independently selected from a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 50 carbon atoms, a substituted or unsubstituted cycloalkyl group having 3 to 50 ring carbon atoms, and a cyano group;

provided that one selected from $R^{11}$ to $R^{18}$ represents a single bond bonded to *a;

L is selected from a substituted or unsubstituted arylene group having 6 to 30 ring carbon atoms and a substituted or unsubstituted divalent heterocyclic group having 5 to 30 ring atoms; and $R^{31}$ to $R^{35}$ each are independently selected from a hydrogen atom, a substituted or unsubstituted aryl group having 6 to 30 ring carbon atoms, and a substituted or unsubstituted heterocyclic group having 5 to 30 ring atoms, in which one or more combinations of combinations each including adjacent two or more selected from $R^{31}$ to $R^{35}$ each are not bonded to each other to form a ring.

In another embodiment, the present invention provides a material for an organic EL device containing the compound represented by the formula (1).

In still another embodiment, the present invention provides an organic electroluminescent device including an anode, a cathode, and organic layers intervening between the anode and the cathode, the organic layers including a light emitting layer, at least one layer of the organic layers containing the compound represented by the formula (1).

In a further embodiment, the present invention provides an electronic device including the organic electroluminescent device.

Advantageous Effects of Invention

An organic EL device containing the compound represented by the formula (1) shows an improved device capability.

DESCRIPTION OF EMBODIMENT

Definitions

Figure 1:
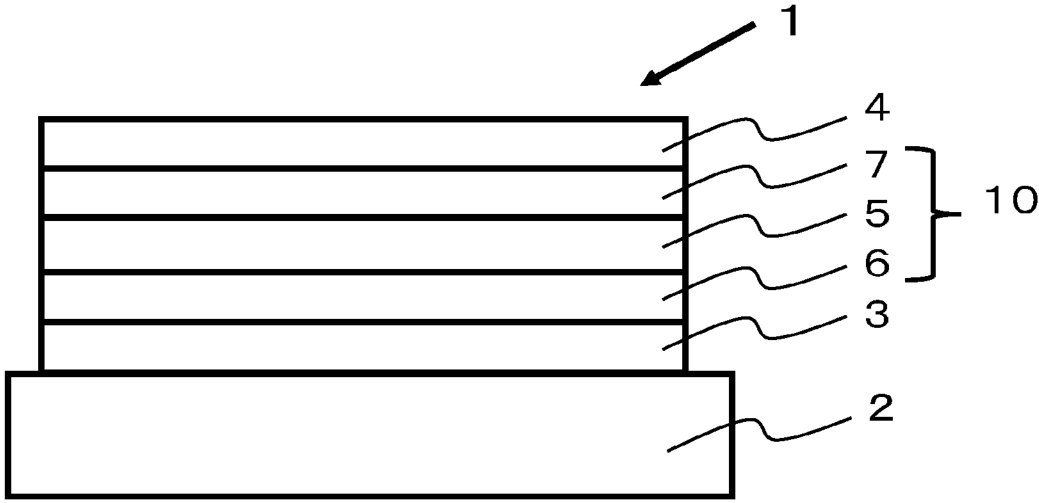
FIG. 1 is a schematic illustration showing an example of the layer configuration of the organic EL device according to one embodiment of the present invention.

In the description herein, the hydrogen atom encompasses isotopes thereof having different numbers of neutrons, i.e., a light hydrogen atom (protium), a heavy hydrogen atom (deuterium), and tritium.

In the description herein, the bonding site where the symbol, such as "R", or "D" representing a deuterium atom is not shown is assumed to have a hydrogen atom, i.e., a protium atom, a deuterium atom, or a tritium atom, bonded thereto.

In the description herein, the number of ring carbon atoms shows the number of carbon atoms among the atoms constituting the ring itself of a compound having a structure including atoms bonded to form a ring (such as a monocyclic compound, a condensed ring compound, a bridged compound, a carbocyclic compound, and a heterocyclic compound). In the case where the ring is substituted by a substituent, the carbon atom contained in the substituent is not included in the number of ring carbon atoms. The same definition is applied to the "number of ring carbon atoms" described hereinafter unless otherwise indicated. For example, a benzene ring has 6 ring carbon atoms, a naphthalene ring has 10 ring carbon atoms, a pyridine ring has 5 ring carbon atoms, and a furan ring has 4 ring carbon atoms. For example, 9,9-diphenylfluorenyl group has 13 ring carbon atoms, and 9,9'-spirobifluorenyl group has 25 ring carbon atoms.

In the case where a benzene ring has, for example, an alkyl group substituted thereon as a substituent, the number of carbon atoms of the alkyl group is not included in the number of ring carbon atoms of the benzene ring. Accordingly, a benzene ring having an alkyl group substituted thereon has 6 ring carbon atoms. In the case where a naphthalene ring has, for example, an alkyl group substituted thereon as a substituent, the number of carbon atoms of the alkyl group is not included in the number of ring carbon atoms of the naphthalene ring. Accordingly, a naphthalene ring having an alkyl group substituted thereon has 10 ring carbon atoms.

In the description herein, the number of ring atoms shows the number of atoms constituting the ring itself of a compound having a structure including atoms bonded to form a ring (such as a monocyclic ring, a condensed ring, and a set of rings) (such as a monocyclic compound, a condensed ring compound, a bridged compound, a carbocyclic compound, and a heterocyclic compound). The atom that does not constitute the ring (such as a hydrogen atom terminating the bond of the atom constituting the ring) and, in the case where the ring is substituted by a substituent, the atom contained in the substituent are not included in the number of ring atoms. The same definition is applied to the "number of ring atoms" described hereinafter unless otherwise indicated. For example, a pyridine ring has 6 ring atoms, a quinazoline ring has 10 ring atoms, and a furan ring has 5 ring atoms. For example, the number of hydrogen atoms bonded to a pyridine ring or atoms constituting a substituent is not included in the number of ring atoms of the pyridine ring. Accordingly, a pyridine ring having a hydrogen atom or a substituent bonded thereto has 6 ring atoms. For example, the number of hydrogen atoms bonded to carbon atoms of a quinazoline ring or atoms constituting a substituent is not included in the number of ring atoms of the quinazoline ring. Accordingly, a quinazoline ring having a hydrogen atom or a substituent bonded thereto has 10 ring atoms.

In the description herein, the expression "having XX to YY carbon atoms" in the expression "substituted or unsubstituted ZZ group having XX to YY carbon atoms" means the number of carbon atoms of the unsubstituted ZZ group, and, in the case where the ZZ group is substituted, the number of carbon atoms of the substituent is not included. Herein, "YY" is larger than "XX", "XX" represents an integer of 1 or more, and "YY" represents an integer of 2 or more.

In the description herein, the expression "having XX to YY atoms" in the expression "substituted or unsubstituted ZZ group having XX to YY atoms" means the number of atoms of the unsubstituted ZZ group, and, in the case where the ZZ group is substituted, the number of atoms of the substituent is not included. Herein, "YY" is larger than "XX", "XX" represents an integer of 1 or more, and "YY" represents an integer of 2 or more.

In the description herein, an unsubstituted ZZ group means the case where the "substituted or unsubstituted ZZ group" is an "unsubstituted ZZ group", and a substituted ZZ group means the case where the "substituted or unsubstituted ZZ group" is a "substituted ZZ group".

In the description herein, the expression "unsubstituted" in the expression "substituted or unsubstituted ZZ group" means that hydrogen atoms in the ZZ group are not substituted by a substituent. The hydrogen atoms in the "unsubstituted ZZ group" each are a protium atom, a deuterium atom, or a tritium atom.

In the description herein, the expression "substituted" in the expression "substituted or unsubstituted ZZ group" means that one or more hydrogen atom in the ZZ group is substituted by a substituent. The expression "substituted" in the expression "BB group substituted by an AA group" similarly means that one or more hydrogen atom in the BB group is substituted by the AA group.

Substituents in Description

The substituents described in the description herein will be explained.

In the description herein, the number of ring carbon atoms of the "unsubstituted aryl group" is 6 to 50, preferably 6 to 30, and more preferably 6 to 18, unless otherwise indicated in the description.

In the description herein, the number of ring atoms of the "unsubstituted heterocyclic group" is 5 to 50, preferably 5 to 30, and more preferably 5 to 18, unless otherwise indicated in the description.

In the description herein, the number of carbon atoms of the "unsubstituted alkyl group" is 1 to 50, preferably 1 to 20, and more preferably 1 to 6, unless otherwise indicated in the description.

In the description herein, the number of carbon atoms of the "unsubstituted alkenyl group" is 2 to 50, preferably 2 to 20, and more preferably 2 to 6, unless otherwise indicated in the description.

In the description herein, the number of carbon atoms of the "unsubstituted alkynyl group" is 2 to 50, preferably 2 to 20, and more preferably 2 to 6, unless otherwise indicated in the description.

In the description herein, the number of ring carbon atoms of the "unsubstituted cycloalkyl group" is 3 to 50, preferably 3 to 20, and more preferably 3 to 6, unless otherwise indicated in the description.

In the description herein, the number of ring carbon atoms of the "unsubstituted arylene group" is 6 to 50, preferably 6 to 30, and more preferably 6 to 18, unless otherwise indicated in the description.

In the description herein, the number of ring atoms of the "unsubstituted divalent heterocyclic group" is 5 to 50, preferably 5 to 30, and more preferably 5 to 18, unless otherwise indicated in the description.

In the description herein, the number of carbon atoms of the "unsubstituted alkylene group" is 1 to 50, preferably 1 to 20, and more preferably 1 to 6, unless otherwise indicated in the description.

Substituted or Unsubstituted Aryl Group

In the description herein, specific examples (set of specific examples G1) of the "substituted or unsubstituted aryl group" include the unsubstituted aryl groups (set of specific examples G1A) and the substituted aryl groups (set of specific examples G1B) shown below. (Herein, the unsubstituted aryl group means the case where the "substituted or unsubstituted aryl group" is an "unsubstituted aryl group", and the substituted aryl group means the case where the "substituted or unsubstituted aryl group" is a "substituted aryl group".) In the description herein, the simple expression "aryl group" encompasses both the "unsubstituted aryl group" and the "substituted aryl group".

The "substituted aryl group" means a group formed by substituting one or more hydrogen atom of the "unsubstituted aryl group" by a substituent. Examples of the "substituted aryl group" include groups formed by one or more hydrogen atom of each of the "unsubstituted aryl groups" in the set of specific examples G1A by a substituent, and the examples of the substituted aryl groups in the set of specific examples G1B. The examples of the "unsubstituted aryl group" and the examples of the "substituted aryl group" enumerated herein are mere examples, and the "substituted aryl group" in the description herein encompasses groups formed by substituting a hydrogen atom bonded to the carbon atom of the aryl group itself of each of the "substituted aryl groups" in the set of specific examples G1B by a substituent, and groups formed by substituting a hydrogen atom of the substituent of each of the "substituted aryl groups" in the set of specific examples G1B by a substituent.

Unsubstituted Aryl Group (Set of Specific Examples G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenarenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and monovalent aryl groups derived by removing one hydrogen atom from each of the ring structures represented by the following general formulae (TEMP-1) to (TEMP-15):

(TEMP-1)

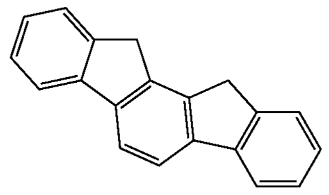

(TEMP-2)

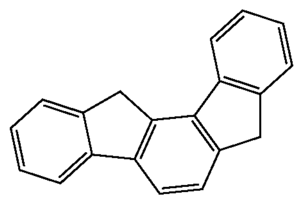

(TEMP-3)

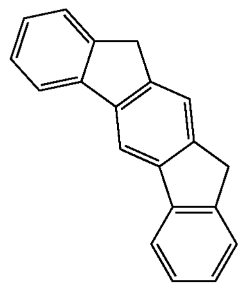

(TEMP-4)

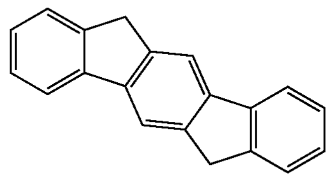

-continued (TEMP-5)

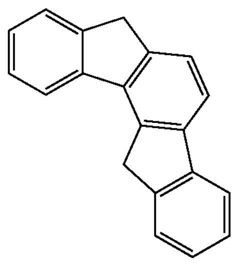

(TEMP-6)

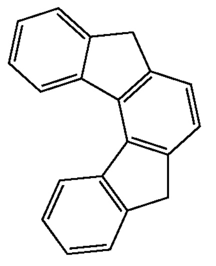

(TEMP-7)

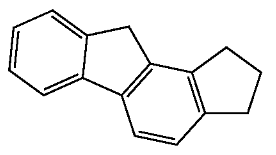

(TEMP-8)

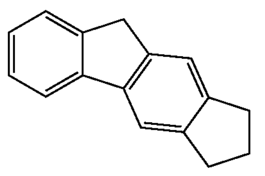

(TEMP-9)

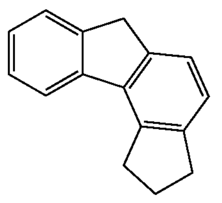

(TEMP-10)

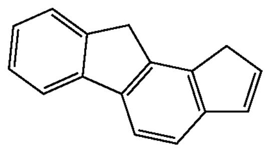

(TEMP-11)

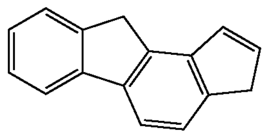

(TEMP-12)

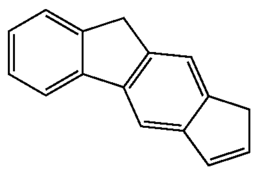

-continued (TEMP-13)

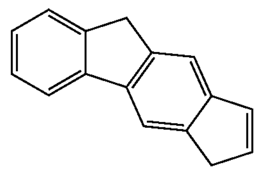

(TEMP-14)

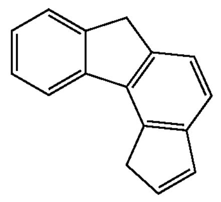

(TEMP-15)

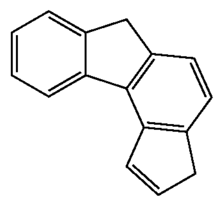

Substituted Aryl Group (Set of Specific Examples G1B):

an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
a o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
groups formed by substituting one or more hydrogen atom of each of monovalent aryl groups derived from the ring structures represented by the general formulae (TEMP-1) to (TEMP-15) by a substituent.

Substituted or Unsubstituted Heterocyclic Group

In the description herein, the "heterocyclic group" means a cyclic group containing at least one hetero atom in the ring atoms. Specific examples of the hetero atom include a nitrogen atom, an oxygen atom, a sulfur atom, a silicon atom, a phosphorus atom, and a boron atom.

In the description herein, the "heterocyclic group" is a monocyclic group or a condensed ring group.

In the description herein, the "heterocyclic group" is an aromatic heterocyclic group or a non-aromatic heterocyclic group.

In the description herein, specific examples (set of specific examples G2) of the "substituted or unsubstituted heterocyclic group" include the unsubstituted heterocyclic groups (set of specific examples G2A) and the substituted heterocyclic groups (set of specific examples G2B) shown below. (Herein, the unsubstituted heterocyclic group means the case where the "substituted or unsubstituted heterocyclic group" is an "unsubstituted heterocyclic group", and the substituted heterocyclic group means the case where the "substituted or unsubstituted heterocyclic group" is a "substituted heterocyclic group".) In the description herein, the simple expression "heterocyclic group" encompasses both the "unsubstituted heterocyclic group" and the "substituted heterocyclic group".

The "substituted heterocyclic group" means a group formed by substituting one or more hydrogen atom of the "unsubstituted heterocyclic group" by a substituent. Specific examples of the "substituted heterocyclic group" include groups formed by substituting a hydrogen atom of each of the "unsubstituted heterocyclic groups" in the set of specific examples G2A by a substituent, and the examples of the substituted heterocyclic groups in the set of specific examples G2B. The examples of the "unsubstituted heterocyclic group" and the examples of the "substituted heterocyclic group" enumerated herein are mere examples, and the "substituted heterocyclic group" in the description herein encompasses groups formed by substituting a hydrogen atom bonded to the ring atom of the heterocyclic group itself of each of the "substituted heterocyclic groups" in the set of specific examples G2B by a substituent, and groups formed by substituting a hydrogen atom of the substituent of each of the "substituted heterocyclic groups" in the set of specific examples G2B by a substituent.

The set of specific examples G2A includes, for example, the unsubstituted heterocyclic group containing a nitrogen atom (set of specific examples G2A1), the unsubstituted heterocyclic group containing an oxygen atom (set of specific examples G2A2), the unsubstituted heterocyclic group containing a sulfur atom (set of specific examples G2A3), and monovalent heterocyclic groups derived by removing one hydrogen atom from each of the ring structures represented by the following general formulae (TEMP-16) to (TEMP-33) (set of specific examples G2A4).

The set of specific examples G2B includes, for example, the substituted heterocyclic groups containing a nitrogen atom (set of specific examples G2B1), the substituted heterocyclic groups containing an oxygen atom (set of specific examples G2B2), the substituted heterocyclic groups containing a sulfur atom (set of specific examples G2B3), and groups formed by substituting one or more hydrogen atom of each of monovalent heterocyclic groups derived from the ring structures represented by the following general formulae (TEMP-16) to (TEMP-33) by a substituent (set of specific examples G2B4).

Unsubstituted Heterocyclic Group Containing Nitrogen Atom (Set of Specific Examples G2A1):

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolinyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing Oxygen Atom (Set of Specific Examples G2A2):

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group Containing Sulfur Atom (Set of Specific Examples G2A3):

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and a diazanaphthobenzothiophenyl group (diazanaphthobenzothienyl group).
Monovalent Heterocyclic Group Derived by Removing One Hydrogen Atom from Ring Structures Represented by General Formulae (TEMP-16) to (TEMP-33) (Set of Specific Examples G2A4)
(TEMP-16)
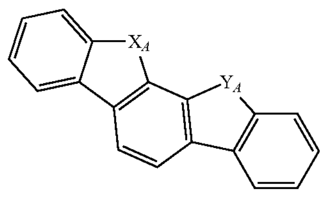
(TEMP-17)
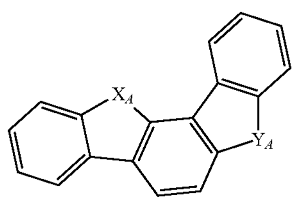
(TEMP-18)
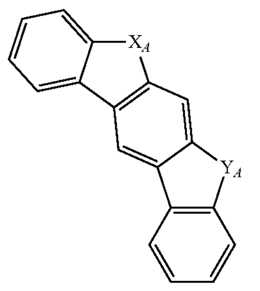
(TEMP-19)
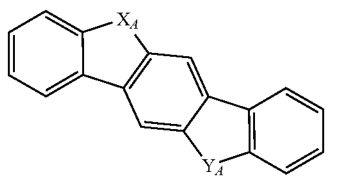
(TEMP-20)
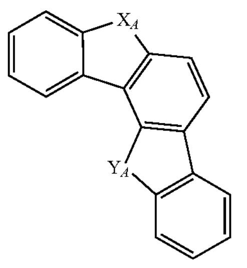
(TEMP-21)
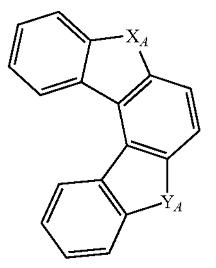
-continued
(TEMP-22)
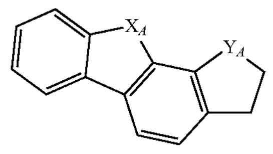
(TEMP-23)
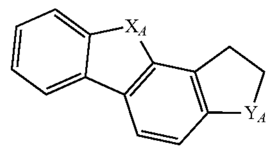
(TEMP-24)
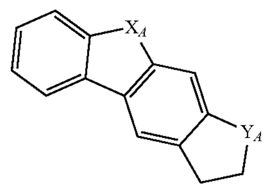
(TEMP-25)
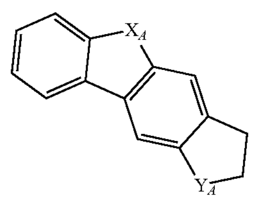
(TEMP-26)
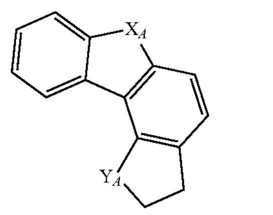
(TEMP-27)
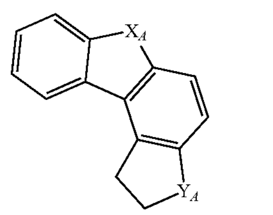
(TEMP-28)
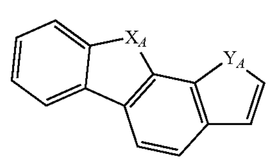
(TEMP-29)
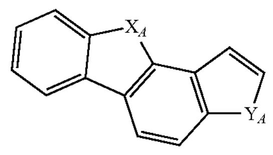

-continued (TEMP-30)

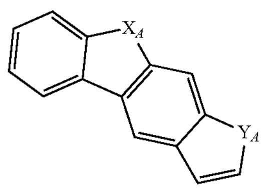

(TEMP-31)

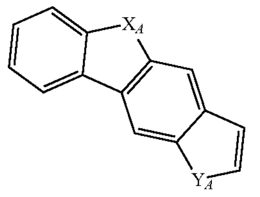

(TEMP-32)

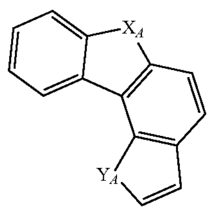

(TEMP-33)

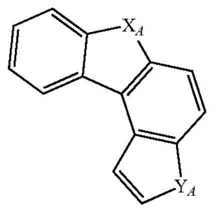

In the general formulae (TEMP-16) to (TEMP-33), $X_A$ and $Y_A$ each independently represent an oxygen atom, a sulfur atom, NH, or $CH_2$, provided that at least one of $X_A$ and $Y_A$ represents an oxygen atom, a sulfur atom, or NH.

In the general formulae (TEMP-16) to (TEMP-33), in the case where at least one of $X_A$ and $Y_A$ represents NH or $CH_2$, the monovalent heterocyclic groups derived from the ring structures represented by the general formulae (TEMP-16) to (TEMP-33) include monovalent groups formed by removing one hydrogen atom from the NH or $CH_2$.

Substituted Heterocyclic Group Containing Nitrogen Atom (Set of Specific Examples G2B1):

- a (9-phenyl)carbazolyl group,
- a (9-biphenylyl)carbazolyl group,
- a (9-phenyl)phenylcarbazolyl group,
- a (9-naphthyl)carbazolyl group,
- a diphenylcarbazol-9-yl group,
- a phenylcarbazol-9-yl group,
- a methylbenzimidazolyl group,
- an ethylbenzimidazolyl group,
- a phenyltriazinyl group,
- a biphenyltriazinyl group,
- a diphenyltriazinyl group,
- a phenylquinazolinyl group, and
- a biphenylquinazolinyl group.

Substituted Heterocyclic Group Containing Oxygen Atom (Set of Specific Examples G2B2):

- a phenyldibenzofuranyl group,
- a methyldibenzofuranyl group,
- a t-butyldibenzofuranyl group, and
- a monovalent residual group of spiro[9H-xanthene-9,9'[9H]fluorene].

Substituted Heterocyclic Group Containing Sulfur Atom (Set of Specific Examples G2B3):

- a phenyldibenzothiophenyl group,
- a methyldibenzothiophenyl group,
- a t-butyldibenzothiophenyl group, and
- a monovalent residual group of spiro[9H-thioxanthene-9,9'[9H]fluorene].

Group Formed by Substituting One or More Hydrogen Atom of Monovalent Heterocyclic Group Derived from Ring Structures Represented by General Formulae (TEMP-16) to (TEMP-33) by Substituent (Set of Specific Examples G2B4)

The "one or more hydrogen atom of the monovalent heterocyclic group" means one or more hydrogen atom selected from the hydrogen atom bonded to the ring carbon atom of the monovalent heterocyclic group, the hydrogen atom bonded to the nitrogen atom in the case where at least one of $X_A$ and $Y_A$ represents NH, and the hydrogen atom of the methylene group in the case where one of $X_A$ and $Y_A$ represents $CH_2$.

Substituted or Unsubstituted Alkyl Group

In the description herein, specific examples (set of specific examples G3) of the "substituted or unsubstituted alkyl group" include the unsubstituted alkyl groups (set of specific examples G3A) and the substituted alkyl groups (set of specific examples G3B) shown below. (Herein, the unsubstituted alkyl group means the case where the "substituted or unsubstituted alkyl group" is an "unsubstituted alkyl group", and the substituted alkyl group means the case where the "substituted or unsubstituted alkyl group" is a "substituted alkyl group".) In the description herein, the simple expression "alkyl group" encompasses both the "unsubstituted alkyl group" and the "substituted alkyl group".

The "substituted alkyl group" means a group formed by substituting one or more hydrogen atom of the "unsubstituted alkyl group" by a substituent. Specific examples of the "substituted alkyl group" include groups formed by substituting one or more hydrogen atom of each of the "unsubstituted alkyl groups" (set of specific examples G3A) by a substituent, and the examples of the substituted alkyl groups (set of specific examples G3B). In the description herein, the alkyl group in the "unsubstituted alkyl group" means a chain-like alkyl group. Accordingly, the "unsubstituted alkyl group" encompasses an "unsubstituted linear alkyl group" and an "unsubstituted branched alkyl group". The examples of the "unsubstituted alkyl group" and the examples of the "substituted alkyl group" enumerated herein are mere examples, and the "substituted alkyl group" in the description herein encompasses groups formed by substituting a hydrogen atom of the alkyl group itself of each of the "substituted alkyl groups" in the set of specific examples G3B by a substituent, and groups formed by substituting a hydrogen atom of the substituent of each of the "substituted alkyl groups" in the set of specific examples G3B by a substituent.

Unsubstituted Alkyl Group (Set of Specific Examples G3A):

- a methyl group,
- an ethyl group,
- a n-propyl group,
- an isopropyl group,
- a n-butyl group,
- an isobutyl group,
- a s-butyl group, and
- a t-butyl group.

Substituted Alkyl Group (Set of Specific Examples G3B):

a heptafluoropropyl group (including isomers),
a pentafluoroethyl group,
a 2,2,2-trifluoroethyl group, and
a trifluoromethyl group.

Substituted or Unsubstituted Alkenyl Group

In the description herein, specific examples (set of specific examples G4) of the "substituted or unsubstituted alkenyl group" include the unsubstituted alkenyl groups (set of specific examples G4A) and the substituted alkenyl groups (set of specific examples G4B) shown below. (Herein, the unsubstituted alkenyl group means the case where the "substituted or unsubstituted alkenyl group" is an "unsubstituted alkenyl group", and the substituted alkenyl group means the case where the "substituted or unsubstituted alkenyl group" is a "substituted alkenyl group".) In the description herein, the simple expression "alkenyl group" encompasses both the "unsubstituted alkenyl group" and the "substituted alkenyl group".

The "substituted alkenyl group" means a group formed by substituting one or more hydrogen atom of the "unsubstituted alkenyl group" by a substituent. Specific examples of the "substituted alkenyl group" include the "unsubstituted alkenyl groups" (set of specific examples G4A) that each have a substituent, and the examples of the substituted alkenyl groups (set of specific examples G4B). The examples of the "unsubstituted alkenyl group" and the examples of the "substituted alkenyl group" enumerated herein are mere examples, and the "substituted alkenyl group" in the description herein encompasses groups formed by substituting a hydrogen atom of the alkenyl group itself of each of the "substituted alkenyl groups" in the set of specific examples G4B by a substituent, and groups formed by substituting a hydrogen atom of the substituent of each of the "substituted alkenyl groups" in the set of specific examples G4B by a substituent.

Unsubstituted Alkenyl Group (Set of Specific Examples G4A):

a vinyl group,
an allyl group,
a 1-butenyl group,
a 2-butenyl group, and
a 3-butenyl group.

Substituted Alkenyl Group (Set of Specific Examples G4B):

a 1,3-butanedienyl group,
a 1-methylvinyl group,
a 1-methylallyl group,
a 1,1-dimethylallyl group,
a 2-methylallyl group, and
a 1,2-dimethylallyl group.

Substituted or Unsubstituted Alkynyl Group

In the description herein, specific examples (set of specific examples G5) of the "substituted or unsubstituted alkynyl group" include the unsubstituted alkynyl group (set of specific examples G5A) shown below. (Herein, the unsubstituted alkynyl group means the case where the "substituted or unsubstituted alkynyl group" is an "unsubstituted alkynyl group".) In the description herein, the simple expression "alkynyl group" encompasses both the "unsubstituted alkynyl group" and the "substituted alkynyl group".

The "substituted alkynyl group" means a group formed by substituting one or more hydrogen atom of the "unsubstituted alkynyl group" by a substituent. Specific examples of the "substituted alkenyl group" include groups formed by substituting one or more hydrogen atom of the "unsubstituted alkynyl group" (set of specific examples G5A) by a substituent.

Unsubstituted Alkynyl Group (Set of Specific Examples G5A):

an ethynyl group.

Substituted or Unsubstituted Cycloalkyl Group

In the description herein, specific examples (set of specific examples G6) of the "substituted or unsubstituted cycloalkyl group" include the unsubstituted cycloalkyl groups (set of specific examples G6A) and the substituted cycloalkyl group (set of specific examples G6B) shown below. (Herein, the unsubstituted cycloalkyl group means the case where the "substituted or unsubstituted cycloalkyl group" is an "unsubstituted cycloalkyl group", and the substituted cycloalkyl group means the case where the "substituted or unsubstituted cycloalkyl group" is a "substituted cycloalkyl group".) In the description herein, the simple expression "cycloalkyl group" encompasses both the "unsubstituted cycloalkyl group" and the "substituted cycloalkyl group".

The "substituted cycloalkyl group" means a group formed by substituting one or more hydrogen atom of the "unsubstituted cycloalkyl group" by a substituent. Specific examples of the "substituted cycloalkyl group" include groups formed by substituting one or more hydrogen atom of each of the "unsubstituted cycloalkyl groups" (set of specific examples G6A) by a substituent, and the example of the substituted cycloalkyl group (set of specific examples G6B). The examples of the "unsubstituted cycloalkyl group" and the examples of the "substituted cycloalkyl group" enumerated herein are mere examples, and the "substituted cycloalkyl group" in the description herein encompasses groups formed by substituting one or more hydrogen atom bonded to the carbon atoms of the cycloalkyl group itself of the "substituted cycloalkyl group" in the set of specific examples G6B by a substituent, and groups formed by substituting a hydrogen atom of the substituent of the "substituted cycloalkyl group" in the set of specific examples G6B by a substituent.

Unsubstituted Cycloalkyl Group (Set of Specific Examples G6A):

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted Cycloalkyl Group (Set of Specific Examples G6B):

a 4-methylcyclohexyl group.

Group Represented by $-Si(R_{901})(R_{902})(R_{903})$

In the description herein, specific examples (set of specific examples G7) of the group represented by $-Si(R_{901})(R_{902})(R_{903})$ include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —Si(G1)(G1)(G1) are the same as or different from each other.

Plural groups represented by G2 in —Si(G1)(G2)(G2) are the same as or different from each other.

Plural groups represented by G1 in —Si(G1)(G1)(G2) are the same as or different from each other.

Plural groups represented by G2 in —Si(G2)(G2)(G2) are the same as or different from each other.

Plural groups represented by G3 in —Si(G3)(G3)(G3) are the same as or different from each other.

Plural groups represented by G6 in —Si(G6)(G6)(G6) are the same as or different from each other.

Group represented by —O—($R_{904}$)

In the description herein, specific examples (set of specific examples G8) of the group represented by —O—($R_{904}$) include:

—O(G1),

—O(G2),

—O(G3), and

—O(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group Represented by —S—($R_{905}$)

In the description herein, specific examples (set of specific examples G9) of the group represented by —S—($R_{905}$) include:

—S(G1),

—S(G2),

—S(G3), and

—S(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group Represented by —N($R_{906}$)($R_{907}$)

In the description herein, specific examples (set of specific examples G10) of the group represented by —N($R_{906}$)($R_{907}$) include:

—N(G1)(G1),

—N(G2)(G2),

—N(G1)(G2),

—N(G3)(G3), and

—N(G6)(G6).

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —N(G1)(G1) are the same as or different from each other.

Plural groups represented by G2 in —N(G2)(G2) are the same as or different from each other.

Plural groups represented by G3 in —N(G3)(G3) are the same as or different from each other.

Plural groups represented by G6 in —N(G6)(G6) are the same as or different from each other.

Halogen Atom

In the description herein, specific examples (set of specific examples G11) of the "halogen atom" include a fluorine atom, a chlorine atom, a bromine atom, and an iodine atom.

Substituted or Unsubstituted Fluoroalkyl Group

In the description herein, the "substituted or unsubstituted fluoroalkyl group" means a group formed by substituting at least one hydrogen atom bonded to the carbon atom constituting the alkyl group in the "substituted or unsubstituted alkyl group" by a fluorine atom, and encompasses a group formed by substituting all the hydrogen atoms bonded to the carbon atoms constituting the alkyl group in the "substituted or unsubstituted alkyl group" by fluorine atoms (i.e., a perfluoroalkyl group). The number of carbon atoms of the "unsubstituted fluoroalkyl group" is 1 to 50, preferably 1 to 30, and more preferably 1 to 18, unless otherwise indicated in the description. The "substituted fluoroalkyl group" means a group formed by substituting one or more hydrogen atom of the "fluoroalkyl group" by a substituent. In the description herein, the "substituted fluoroalkyl group" encompasses a group formed by substituting one or more hydrogen atom bonded to the carbon atom of the alkyl chain in the "substituted fluoroalkyl group" by a substituent, and a group formed by substituting one or more hydrogen atom of the substituent in the "substituted fluoroalkyl group" by a substituent. Specific examples of the "unsubstituted fluoroalkyl group" include examples of groups formed by substituting one or more hydrogen atom in each of the "alkyl group" (set of specific examples G3) by a fluorine atom.

Substituted or Unsubstituted Haloalkyl Group

In the description herein, the "substituted or unsubstituted haloalkyl group" means a group formed by substituting at least one hydrogen atom bonded to the carbon atom constituting the alkyl group in the "substituted or unsubstituted alkyl group" by a halogen atom, and encompasses a group formed by substituting all the hydrogen atoms bonded to the carbon atoms constituting the alkyl group in the "substituted or unsubstituted alkyl group" by halogen atoms. The number of carbon atoms of the "unsubstituted haloalkyl group" is 1 to 50, preferably 1 to 30, and more preferably 1 to 18, unless otherwise indicated in the description. The "substituted haloalkyl group" means a group formed by substituting one or more hydrogen atom of the "haloalkyl group" by a substituent. In the description herein, the "substituted haloalkyl group" encompasses a group formed by substituting one or more hydrogen atom bonded to the carbon atom of the alkyl chain in the "substituted haloalkyl group" by a substituent, and a group formed by substituting one or more hydrogen atom of the substituent in the "substituted haloalkyl group" by a substituent. Specific examples of the "unsubstituted haloalkyl group" include examples of groups formed by substituting one or more hydrogen atom in each of the "alkyl group" (set of specific examples G3) by a halogen atom. A haloalkyl group may be referred to as a halogenated alkyl group in some cases.

Substituted or Unsubstituted Alkoxy Group

In the description herein, specific examples of the "substituted or unsubstituted alkoxy group" include a group represented by —O(G3), wherein G3 represents the "substituted or unsubstituted alkyl group" described in the set of specific examples G3. The number of carbon atoms of the "unsubstituted alkoxy group" is 1 to 50, preferably 1 to 30, and more preferably 1 to 18, unless otherwise indicated in the description.

Substituted or Unsubstituted Alkylthio Group

In the description herein, specific examples of the "substituted or unsubstituted alkylthio group" include a group represented by —S(G3), wherein G3 represents the "substituted or unsubstituted alkyl group" described in the set of specific examples G3. The number of carbon atoms of the "unsubstituted alkylthio group" is 1 to 50, preferably 1 to 30, and more preferably 1 to 18, unless otherwise indicated in the description.

Substituted or Unsubstituted Aryloxy Group

In the description herein, specific examples of the "substituted or unsubstituted aryloxy group" include a group represented by —O(G1), wherein G1 represents the "substituted or unsubstituted aryl group" described in the set of specific examples G1. The number of ring carbon atoms of the "unsubstituted aryloxy group" is 6 to 50, preferably 6 to 30, and more preferably 6 to 18, unless otherwise indicated in the description.

Substituted or Unsubstituted Arylthio Group

In the description herein, specific examples of the "substituted or unsubstituted arylthio group" include a group represented by —S(G1), wherein G1 represents the "substituted or unsubstituted aryl group" described in the set of specific examples G1. The number of ring carbon atoms of the "unsubstituted arylthio group" is 6 to 50, preferably 6 to 30, and more preferably 6 to 18, unless otherwise indicated in the description.

Substituted or Unsubstituted Trialkylsilyl Group

In the description herein, specific examples of the "trialkylsilyl group" include a group represented by —Si(G3)(G3)(G3), wherein G3 represents the "substituted or unsubstituted alkyl group" described in the set of specific examples G3. Plural groups represented by G3 in —Si(G3)(G3)(G3) are the same as or different from each other. The number of carbon atoms of each of alkyl groups of the "substituted or unsubstituted trialkylsilyl group" is 1 to 50, preferably 1 to 20, and more preferably 1 to 6, unless otherwise indicated in the description.

Substituted or Unsubstituted Aralkyl Group

In the description herein, specific examples of the "substituted or unsubstituted aralkyl group" include a group represented by -(G3)-(G1), wherein G3 represents the "substituted or unsubstituted alkyl group" described in the set of specific examples G3, and G1 represents the "substituted or unsubstituted aryl group" described in the set of specific examples G1. Accordingly, the "aralkyl group" is a group formed by substituting a hydrogen atom of an "alkyl group" by an "aryl group" as a substituent, and is one embodiment of the "substituted alkyl group". The "unsubstituted aralkyl group" is an "unsubstituted alkyl group" that is substituted by an "unsubstituted aryl group", and the number of carbon atoms of the "unsubstituted aralkyl group" is 7 to 50, preferably 7 to 30, and more preferably 7 to 18, unless otherwise indicated in the description.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

In the description herein, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, a 9,9-diphenylfluorenyl group, and the like, unless otherwise indicated in the description.

In the description herein, the substituted or unsubstituted heterocyclic group is preferably a pyridyl group, a pyrimiclinyl group, a triazinyl group, a quinolyl group, an isoquinolyl group, a quinazolinyl group, a benzimidazolyl group, a phenanthrolinyl group, a carbazolyl group (e.g., a 1-carbazolyl, group, a 2-carbazolyl, group, a 3-carbazolyl, group, a 4-carbazolyl, group, or a 9-carbazolyl, group), a benzocarbazolyl group, an azacarbazolyl group, a diazacarbazolyl group, a dibenzofuranyl group, a naphthobenzofuranly group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (e.g., a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like, unless otherwise indicated in the description.

In the description herein, the carbazolyl group is specifically any one of the following groups unless otherwise indicated in the description.

(TEMP-Cz1)

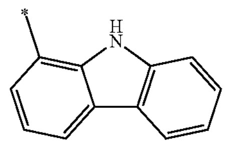

(TEMP-Cz2)

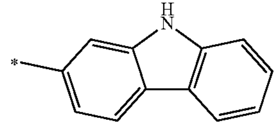

-continued (TEMP-Cz3)

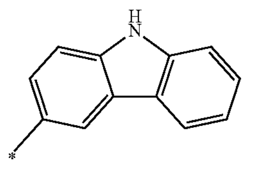

(TEMP-Cz4)

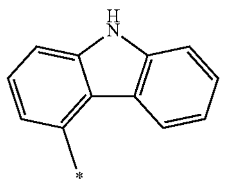

(TEMP-Cz5)

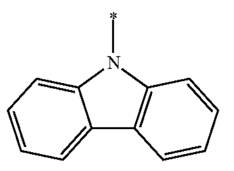

In the description herein, the (9-phenyl)carbazolyl group is specifically any one of the following groups unless otherwise indicated in the description.

(TEMP-Cz6)

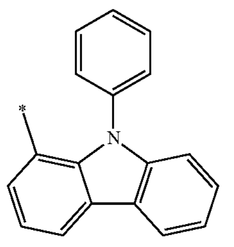

(TEMP-Cz7)

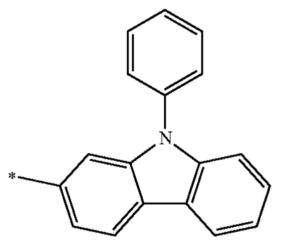

(TEMP-Cz8)

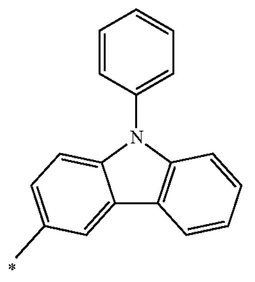

-continued (TEMP-Cz9)

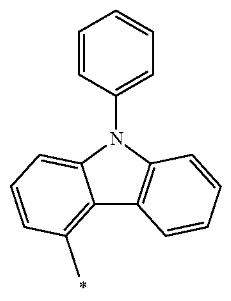

In the general formulae (TEMP-Cz1) to (TEMP-Cz9), * represents a bonding site.

In the description herein, the dibenzofuranyl group and the dibenzothiophenyl group are specifically any one of the following groups unless otherwise indicated in the description.

(TEMP-34)

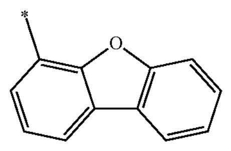

(TEMP-35)

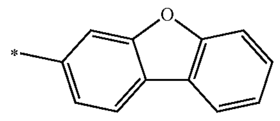

(TEMP-36)

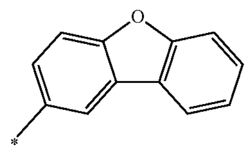

(TEMP-37)

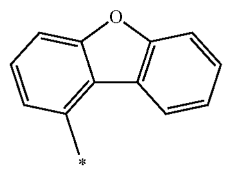

(TEMP-38)

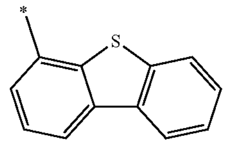

(TEMP-39)

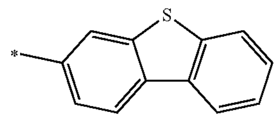

(TEMP-40)

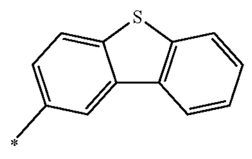

-continued (TEMP-41)

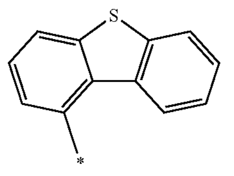

In the general formulae (TEMP-34) to (TEMP-41), * represents a bonding site.

In the description herein, the substituted or unsubstituted alkyl group is preferably a methyl group, an ethyl group, a propyl group, an isopropyl group, a n-butyl group, an isobutyl group, a t-butyl group, or the like unless otherwise indicated in the description.

Substituted or Unsubstituted Arylene Group

In the description herein, the "substituted or unsubstituted arylene group" is a divalent group derived by removing one hydrogen atom on the aryl ring from the "substituted or unsubstituted aryl group" described above unless otherwise indicated in the description. Specific examples (set of specific examples G12) of the "substituted or unsubstituted arylene group" include divalent groups derived by removing one hydrogen atom on the aryl ring from the "substituted or unsubstituted aryl groups" described in the set of specific examples G1.

Substituted or Unsubstituted Divalent Heterocyclic Group

In the description herein, the "substituted or unsubstituted divalent heterocyclic group" is a divalent group derived by removing one hydrogen atom on the heterocyclic ring from the "substituted or unsubstituted heterocyclic group" described above unless otherwise indicated in the description. Specific examples (set of specific examples G13) of the "substituted or unsubstituted divalent heterocyclic group" include divalent groups derived by removing one hydrogen atom on the heterocyclic ring from the "substituted or unsubstituted heterocyclic groups" described in the set of specific examples G2.

Substituted or Unsubstituted Alkylene Group

In the description herein, the "substituted or unsubstituted alkylene group" is a divalent group derived by removing one hydrogen atom on the alkyl chain from the "substituted or unsubstituted alkyl group" described above unless otherwise indicated in the description. Specific examples (set of specific examples G14) of the "substituted or unsubstituted alkylene group" include divalent groups derived by removing one hydrogen atom on the alkyl chain from the "substituted or unsubstituted alkyl groups" described in the set of specific examples G3.

In the description herein, the substituted or unsubstituted arylene group is preferably any one of the groups represented by the following general formulae (TEMP-42) to (TEMP-68) unless otherwise indicated in the description.

(TEMP-42)

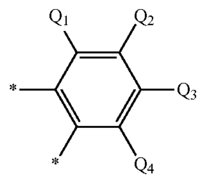

-continued (TEMP-43)

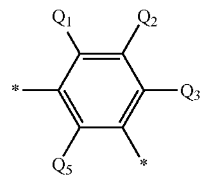

(TEMP-44)

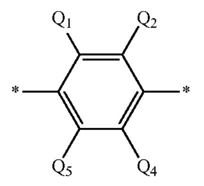

(TEMP-45)

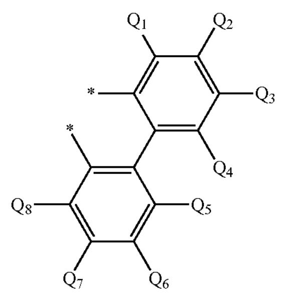

(TEMP-46)

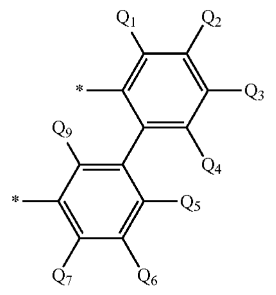

(TEMP-47)

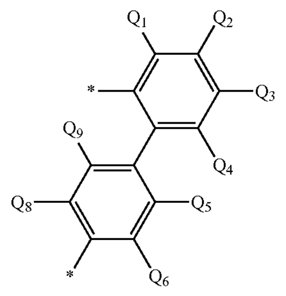

(TEMP-48)

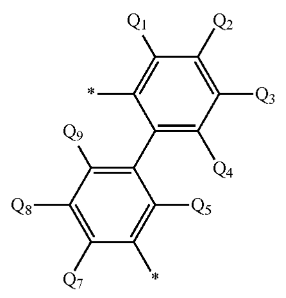

-continued
(TEMP-49)
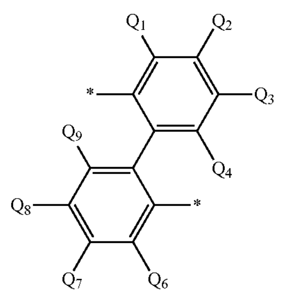
(TEMP-50)
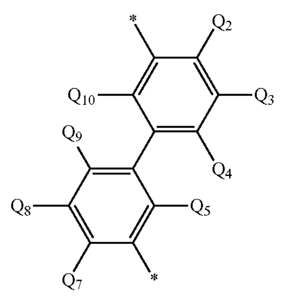
(TEMP-51)
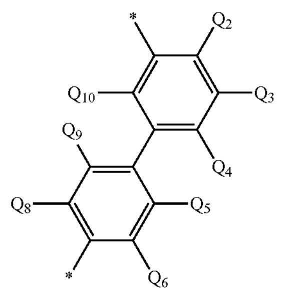
(TEMP-52)
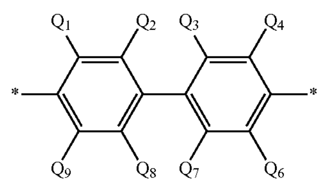
In the general formulae (TEMP-42) to (TEMP-52), $Q_1$ to $Q_{10}$ each independently represent a hydrogen atom or a substituent.
In the general formulae (TEMP-42) to (TEMP-52), * represents a bonding site.
(TEMP-53)
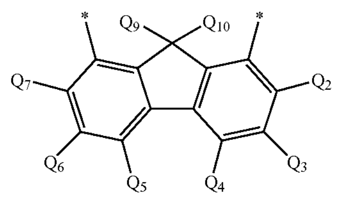
-continued
(TEMP-54)
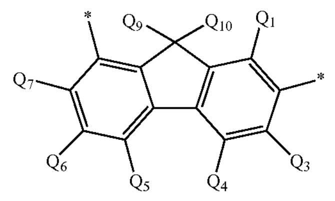
(TEMP-55)
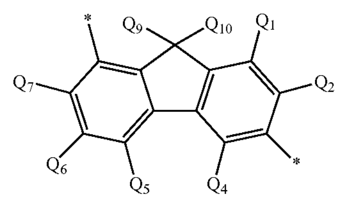
(TEMP-56)
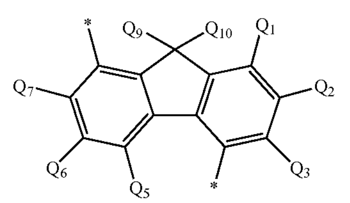
(TEMP-57)
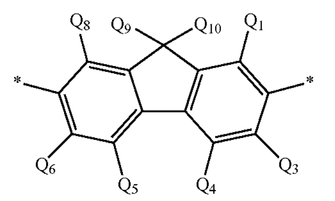
(TEMP-58)
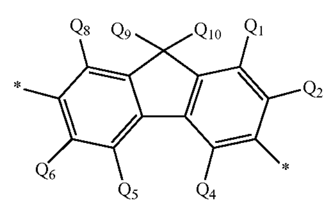
(TEMP-59)
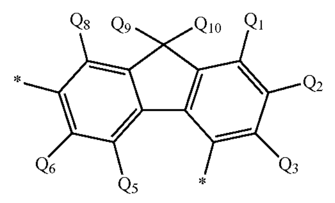
(TEMP-60)
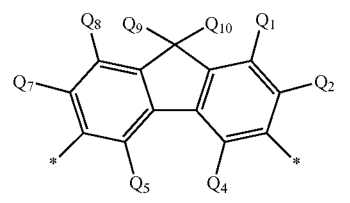
(TEMP-61)
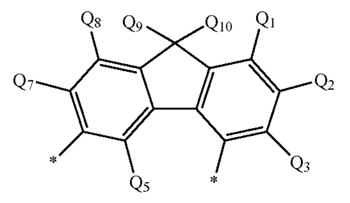

-continued (TEMP-62)

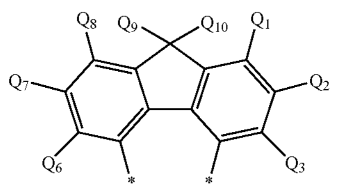

In the general formulae (TEMP-53) to (TEMP-62), $Q_1$ to $Q_{10}$ each independently represent a hydrogen atom or a substituent.

The formulae $Q_9$ and $Q_{10}$ may be bonded to each other to form a ring via a single bond.

In the general formulae (TEMP-53) to (TEMP-62), * represents a bonding site.

(TEMP-63)

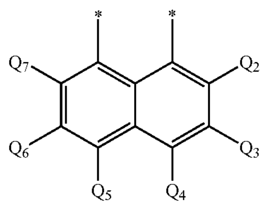

(TEMP-64)

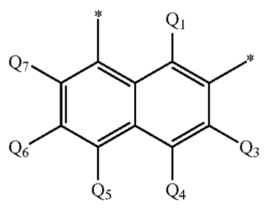

(TEMP-65)

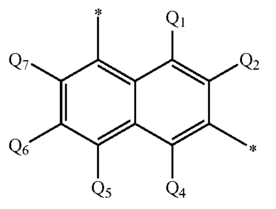

(TEMP-66)

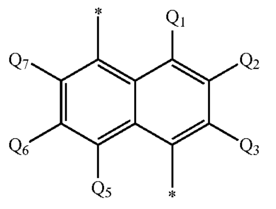

(TEMP-67)

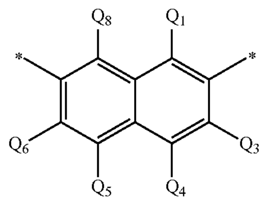

-continued (TEMP-68)

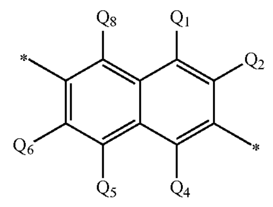

In the general formulae (TEMP-63) to (TEMP-68), $Q_1$ to $Q_8$ each independently represent a hydrogen atom or a substituent.

In the general formulae (TEMP-63) to (TEMP-68), * represents a bonding site.

In the description herein, the substituted or unsubstituted divalent heterocyclic group is preferably the groups represented by the following general formulae (TEMP-69) to (TEMP-102) unless otherwise indicated in the description.

(TEMP-69)

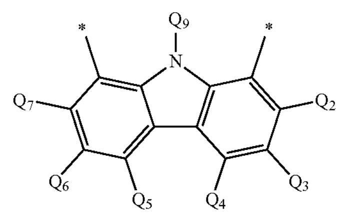

(TEMP-70)

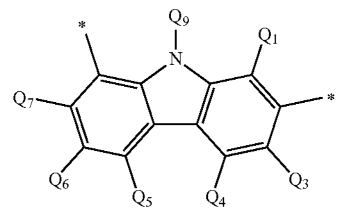

(TEMP-71)

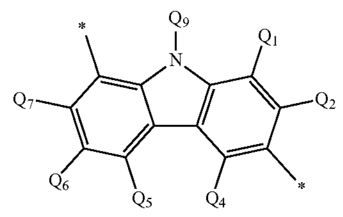

(TEMP-72)

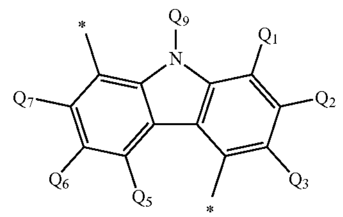

(TEMP-73)

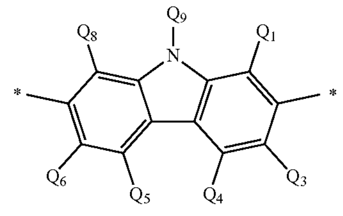

-continued
(TEMP-74)
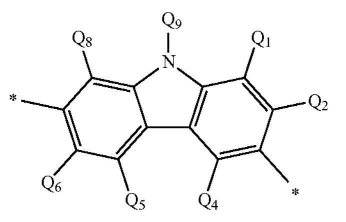
(TEMP-75)
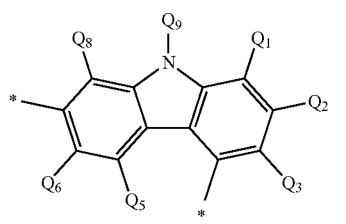
(TEMP-76)
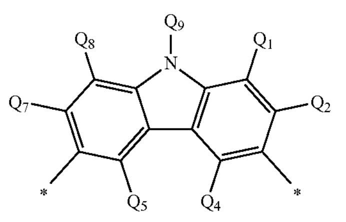
(TEMP-77)
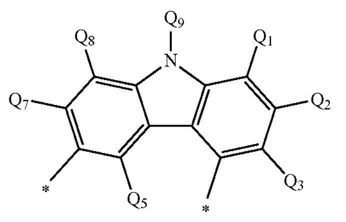
(TEMP-78)
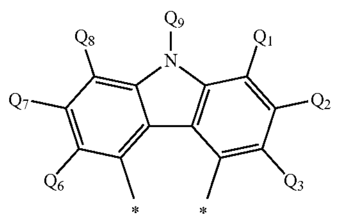
(TEMP-79)
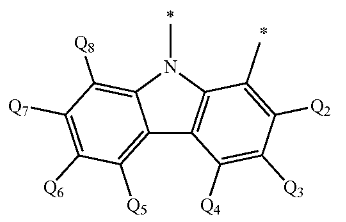
(TEMP-80)
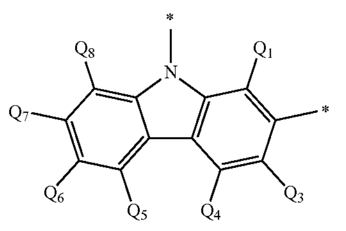
-continued
(TEMP-81)
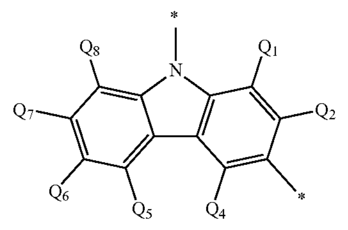
(TEMP-82)
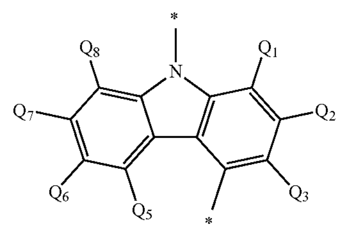
In the general formulae (TEMP-69) to (TEMP-82), $Q_1$ to $Q_9$ each independently represent a hydrogen atom or a substituent.
(TEMP-83)
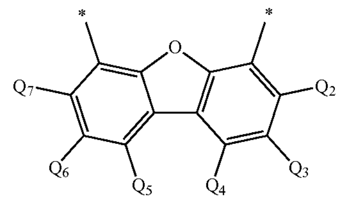
(TEMP-84)
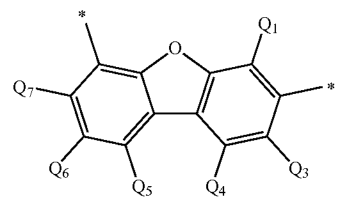
(TEMP-85)
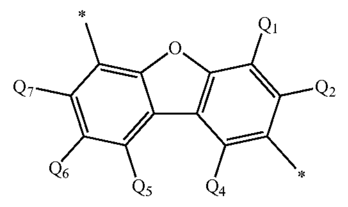
(TEMP-86)
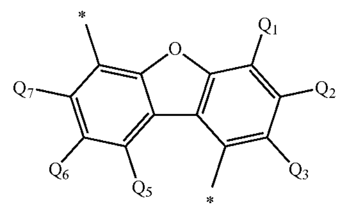

-continued
(TEMP-87)
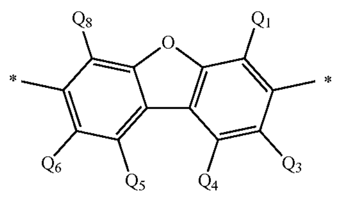
(TEMP-88)
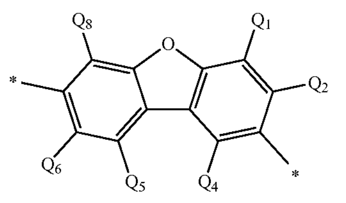
(TEMP-89)
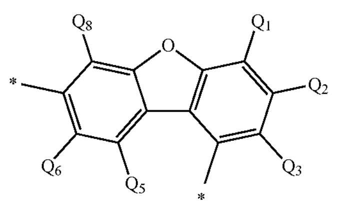
(TEMP-90)
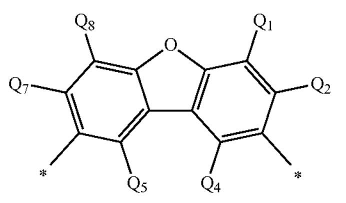
(TEMP-91)
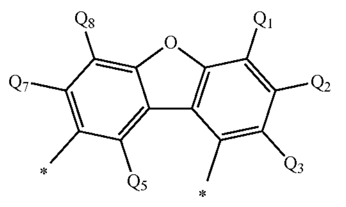
(TEMP-92)
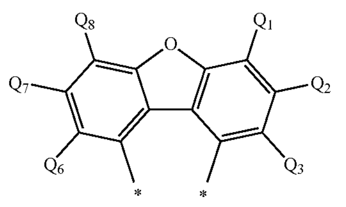
(TEMP-93)
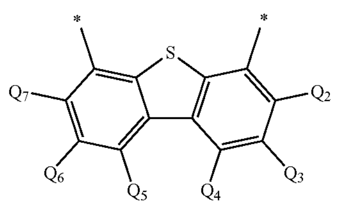
-continued
(TEMP-94)
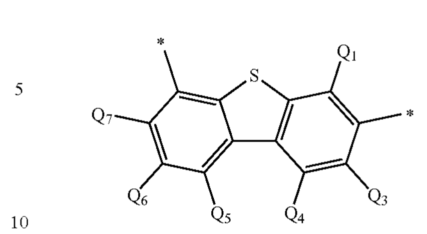
(TEMP-95)
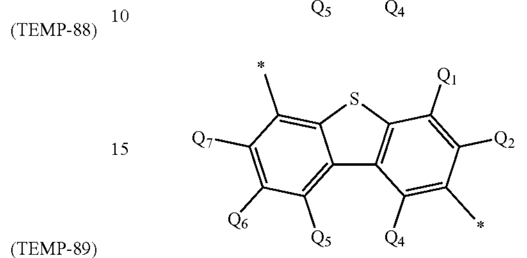
(TEMP-96)
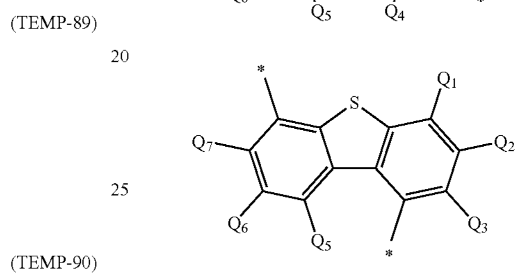
(TEMP-97)
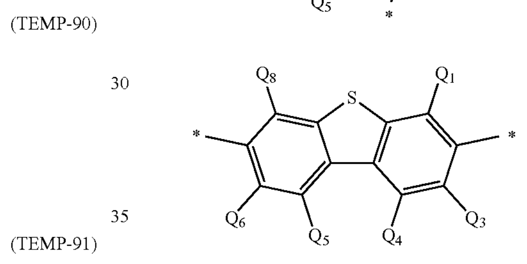
(TEMP-98)
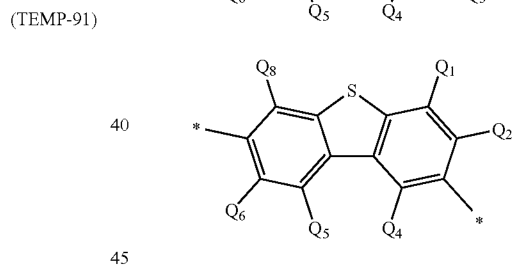
(TEMP-99)
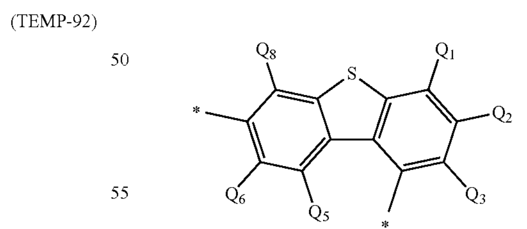
(TEMP-100)
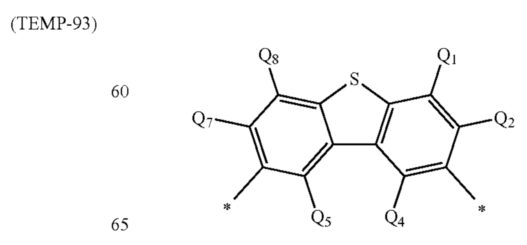

-continued (TEMP-101)

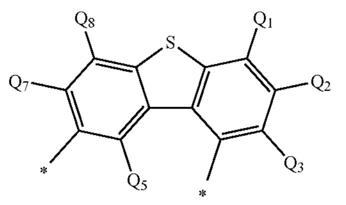

(TEMP-102)

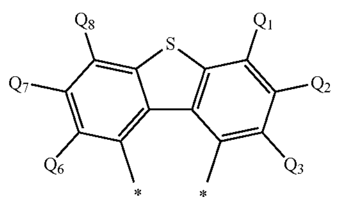

In the general formulae (TEMP-83) to (TEMP-102), $Q_1$ to $Q_8$ each independently represent a hydrogen atom or a substituent.

The above are the explanation of the "substituents in the description herein".

Case Forming Ring by Bonding

In the description herein, the case where "one or more combinations of combinations each including adjacent two or more each are bonded to each other to form a substituted or unsubstituted monocyclic ring, or each are bonded to each other to form a substituted or unsubstituted condensed ring, or each are not bonded to each other" means a case where "one or more combinations of combinations each including adjacent two or more each are bonded to each other to form a substituted or unsubstituted monocyclic ring", a case where "one or more combinations of combinations each including adjacent two or more each are bonded to each other to form a substituted or unsubstituted condensed ring", and a case where "one or more combinations of combinations each including adjacent two or more each are not bonded to each other".

In the description herein, the case where "one or more combinations of combinations each including adjacent two or more each are bonded to each other to form a substituted or unsubstituted monocyclic ring" and the case where "one or more combinations of combinations each including adjacent two or more each are bonded to each other to form a substituted or unsubstituted condensed ring" (which may be hereinafter collectively referred to as a "case forming a ring by bonding") will be explained below. The cases will be explained for the anthracene compound represented by the following general formula (TEMP-103) having an anthracene core skeleton as an example.

(TEMP-103)

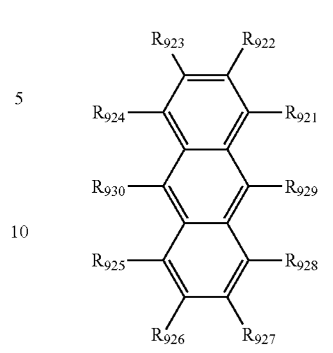

For example, in the case where "one or more combinations of combinations each including adjacent two or more each are bonded to each other to form a ring" among $R_{921}$ to $R_{930}$, the combinations each including adjacent two as one combination include a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, and a combination of $R_{929}$ and $R_{921}$.

The "one or more combinations" mean that two or more combinations each including adjacent two or more may form rings simultaneously. For example, in the case where $R_{921}$ and $R_{922}$ are bonded to each other to form a ring $Q_A$, and simultaneously $R_{925}$ and $R_{926}$ are bonded to each other to form a ring $Q_B$, the anthracene compound represented by the general formula (TEMP-103) is represented by the following general formula (TEMP-104).

(TEMP-104)

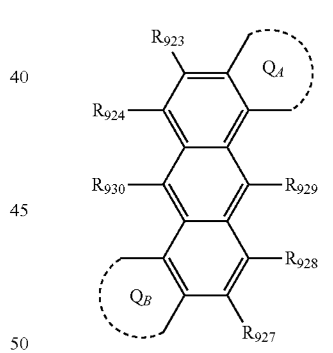

The case where the "combination including adjacent two or more forms rings" encompasses not only the case where adjacent two included in the combination are bonded as in the aforementioned example, but also the case where adjacent three or more included in the combination are bonded. For example, this case means that $R_{921}$ and $R_{922}$ are bonded to each other to form a ring $Q_A$, $R_{922}$ and $R_{923}$ are bonded to each other to form a ring $Q_C$, and adjacent three ($R_{921}$, $R_{922}$, and $R_{923}$) included in the combination are bonded to each other to form rings, which are condensed to the anthracene core skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

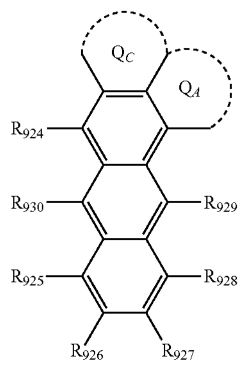

The formed "monocyclic ring" or "condensed ring" may be a saturated ring or an unsaturated ring in terms of structure of the formed ring itself. In the case where the "one combination including adjacent two" forms a "monocyclic ring" or a "condensed ring", the "monocyclic ring" or the "condensed ring" may form a saturated ring or an unsaturated ring. For example, the ring $Q_A$ and the ring $Q_B$ formed in the general formula (TEMP-104) each are a "monocyclic ring" or a "condensed ring". The ring $Q_A$ and the ring $Q_C$ formed in the general formula (TEMP-105) each are a "condensed ring". The ring $Q_A$ and the ring $Q_C$ in the general formula (TEMP-105) form a condensed ring through condensation of the ring $Q_A$ and the ring $Q_C$. In the case where the ring $Q_A$ in the general formula (TMEP-104) is a benzene ring, the ring $Q_A$ is a monocyclic ring. In the case where the ring $Q_A$ in the general formula (TMEP-104) is a naphthalene ring, the ring $Q_A$ is a condensed ring.

The "unsaturated ring" means an aromatic hydrocarbon ring or an aromatic heterocyclic ring. The "saturated ring" means an aliphatic hydrocarbon ring or a non-aromatic heterocyclic ring.

Specific examples of the aromatic hydrocarbon ring include the structures formed by terminating the groups exemplified as the specific examples in the set of specific examples G1 with a hydrogen atom.

Specific examples of the aromatic heterocyclic ring include the structures formed by terminating the aromatic heterocyclic groups exemplified as the specific examples in the set of specific examples G2 with a hydrogen atom.

Specific examples of the aliphatic hydrocarbon ring include the structures formed by terminating the groups exemplified as the specific examples in the set of specific examples G6 with a hydrogen atom.

The expression "to form a ring" means that the ring is formed only with the plural atoms of the core structure or with the plural atoms of the core structure and one or more arbitrary element. For example, the ring $Q_A$ formed by bonding $R_{921}$ and $R_{922}$ each other shown in the general formula (TEMP-104) means a ring formed with the carbon atom of the anthracene skeleton bonded to $R_{921}$, the carbon atom of the anthracene skeleton bonded to $R_{922}$, and one or more arbitrary element. As a specific example, in the case where the ring $Q_A$ is formed with $R_{921}$ and $R_{922}$, and in the case where a monocyclic unsaturated ring is formed with the carbon atom of the anthracene skeleton bonded to $R_{921}$, the carbon atom of the anthracene skeleton bonded to $R_{922}$, and four carbon atoms, the ring formed with $R_{921}$ and $R_{922}$ is a benzene ring.

Herein, the "arbitrary element" is preferably at least one kind of an element selected from the group consisting of a carbon element, a nitrogen element, an oxygen element, and a sulfur element, unless otherwise indicated in the description. For the arbitrary element (for example, for a carbon element or a nitrogen element), a bond that does not form a ring may be terminated with a hydrogen atom or the like, and may be substituted by an "arbitrary substituent" described later. In the case where an arbitrary element other than a carbon element is contained, the formed ring is a heterocyclic ring.

The number of the "one or more arbitrary element" constituting the monocyclic ring or the condensed ring is preferably 2 or more and 15 or less, more preferably 3 or more and 12 or less, and further preferably 3 or more and 5 or less, unless otherwise indicated in the description.

What is preferred between the "monocyclic ring" and the "condensed ring" is the "monocyclic ring" unless otherwise indicated in the description.

What is preferred between the "saturated ring" and the "unsaturated ring" is the "unsaturated ring" unless otherwise indicated in the description.

The "monocyclic ring" is preferably a benzene ring unless otherwise indicated in the description.

The "unsaturated ring" is preferably a benzene ring unless otherwise indicated in the description.

In the case where the "one or more combinations of combinations each including adjacent two or more" each are "bonded to each other to form a substituted or unsubstituted monocyclic ring", or each are "bonded to each other to form a substituted or unsubstituted condensed ring", it is preferred that the one or more combinations of combinations each including adjacent two or more each are bonded to each other to form a substituted or unsubstituted "unsaturated ring" containing the plural atoms of the core skeleton and 1 or more and 15 or less at least one kind of an element selected from the group consisting of a carbon element, a nitrogen element, an oxygen element, and a sulfur element, unless otherwise indicated in the description.

In the case where the "monocyclic ring" or the "condensed ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

In the case where the "saturated ring" or the "unsaturated ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

The above are the explanation of the case where "one or more combinations of combinations each including adjacent two or more" each are "bonded to each other to form a substituted or unsubstituted monocyclic ring", and the case where "one or more combinations of combinations each including adjacent two or more" each are "bonded to each other to form a substituted or unsubstituted condensed ring" (i.e., the "case forming a ring by bonding").

Substituent for "Substituted or Unsubstituted"

In one embodiment in the description herein, the substituent for the case of "substituted or unsubstituted" (which may be hereinafter referred to as an "arbitrary substituent") is, for example, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, an unsubstituted aryl group having 6 to 50 ring carbon atoms, and an unsubstituted heterocyclic group having 5 to 50 ring atoms, wherein $R_{901}$ to $R_{907}$ each independently represent a hydrogen atom, a substituted or unsubstituted alkyl group having 1 to 50 carbon atoms a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the case where two or more groups each represented by $R_{901}$ exist, the two or more groups each represented by $R_{901}$ are the same as or different from each other, in the case where two or more groups each represented by $R_{902}$ exist, the two or more groups each represented by $R_{902}$ are the same as or different from each other, in the case where two or more groups each represented by $R_{903}$ exist, the two or more groups each represented by $R_{903}$ are the same as or different from each other, in the case where two or more groups each represented by $R_{904}$ exist, the two or more groups each represented by $R_{904}$ are the same as or different from each other, in the case where two or more groups each represented by $R_{905}$ exist, the two or more groups each represented by $R_{905}$ are the same as or different from each other, in the case where two or more groups each represented by $R_{906}$ exist, the two or more groups each represented by $R_{906}$ are the same as or different from each other, and in the case where two or more groups each represented by $R_{907}$ exist, the two or more groups each represented by $R_{907}$ are the same as or different from each other.

In one embodiment, the substituent for the case of "substituted or unsubstituted" may be a group selected from the group consisting of an alkyl group having 1 to 50 carbon atoms, an aryl group having 6 to 50 ring carbon atoms, and a heterocyclic group having 5 to 50 ring atoms.

In one embodiment, the substituent for the case of "substituted or unsubstituted" may be a group selected from the group consisting of an alkyl group having 1 to 18 carbon atoms, an aryl group having 6 to 18 ring carbon atoms, and a heterocyclic group having 5 to 18 ring atoms.

The specific examples of the groups for the arbitrary substituent described above are the specific examples of the substituent described in the section "Substituents in Description" described above.

In the description herein, the arbitrary adjacent substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring, unless otherwise indicated.

In the description herein, the arbitrary substituent may further have a substituent unless otherwise indicated in the description. The definition of the substituent that the arbitrary substituent further has may be the same as the arbitrary substituent.

In the description herein, a numerical range shown by "AA to BB" means a range including the numerical value AA as the former of "AA to BB" as the lower limit value and the numerical value BB as the latter of "AA to BB" as the upper limit value.

The compound of the present invention will be described below.

The compound of the present invention is represented by the following formula (1). In the following description, the compounds of the present invention represented by the formula (1) and the subordinate formulae of the formula (1) described later each may be referred simply to as an "inventive compound".

(1)

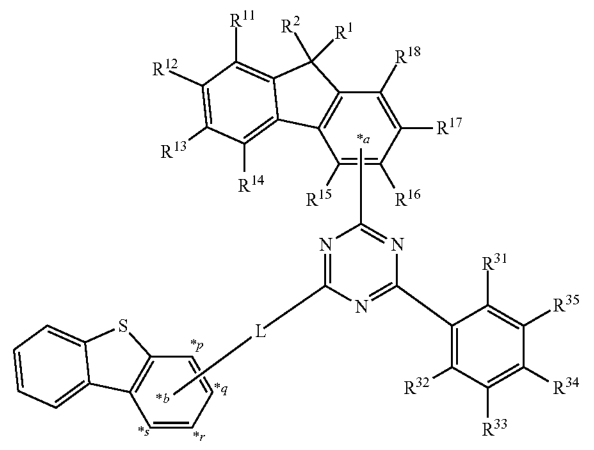

The formula (1) may be represented by the following formula (2) or (3).

(2)

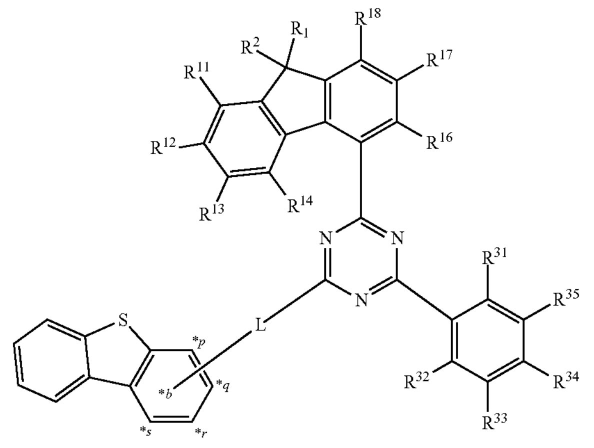

-continued (3)

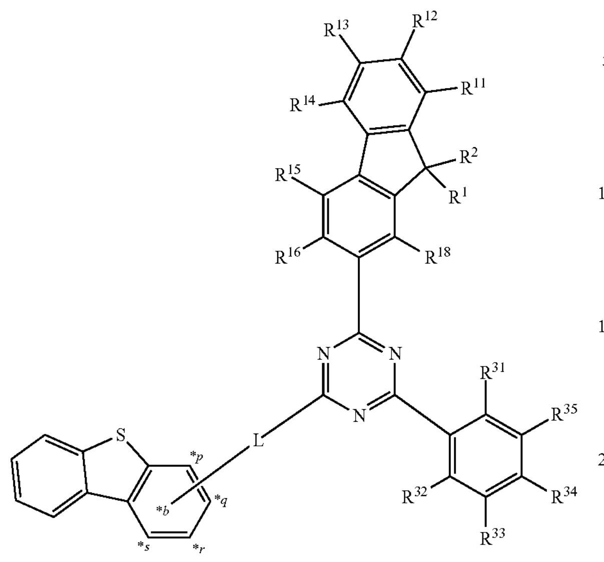

The symbols in the aforementioned formulae and the formulae described later will be explained below.

$R^1$ and $R^2$ each are independently selected from a hydrogen atom, a substituted or unsubstituted aryl group having 6 to 30 ring carbon atoms, and a substituted or unsubstituted heterocyclic group having 5 to 30 ring atoms, and each preferably represent a substituted or unsubstituted aryl group having 6 to 30 ring carbon atoms or a substituted or unsubstituted heterocyclic group having 5 to 30 ring atoms.

In the substituted or unsubstituted aryl group having 6 to 30 ring carbon atoms represented by $R^1$ and $R^2$, examples of the aryl group include a phenyl group, a biphenylyl group, a terphenylyl group, a biphenylenyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrisenyl group, a fluorenyl group, a fluoranthenyl group, a perylenyl group, and a triphenylenyl group. Among these, a phenyl group, a biphenylyl group, a terphenylyl group, and a naphthyl group are preferred, a phenyl group and a naphthyl group are more preferred, and a phenyl group is further preferred.

In the substituted or unsubstituted heterocyclic group having 5 to 30 ring atoms represented by $R^1$ and $R^2$, examples of the heterocyclic group include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a phenanthridinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group (a benzothienyl group, hereinafter the same), an isobenzothiophenyl group (an isobenzothienyl group, hereinafter the same), a naphthobenzothiophenyl group (a naphthobenzothienyl group, hereinafter the same), a dibenzothiophenyl group (a dibenzothienyl group, hereinafter the same), or a carbazolyl group. Among these, a pyridyl group, a quinolyl group, and an isoquinolyl group are preferred, a pyridyl group and a quinolyl group are more preferred, and a pyridyl group is further preferred.

$R^1$ and $R^2$ may be bonded to each other to form a ring structure.

*q, *p, *r, and *s each represents a carbon atom on the dibenzothiophene skeleton, *b is bonded to one selected from the carbon atoms represented by *p, *q, *r, and *s.

$R^{11}$ to $R^{18}$ each are independently selected from a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 50 carbon atoms, a substituted or unsubstituted cycloalkyl group having 3 to 50 ring carbon atoms, and a cyano group, and are preferably independently selected from a hydrogen atom, a substituted or unsubstituted aryl group having 6 to 30 ring carbon atoms, a substituted or unsubstituted heterocyclic group having 5 to 30 ring atoms, and a substituted or unsubstituted alkyl group having 1 to 50 carbon atoms.

One selected from $R^{11}$ to $R^{18}$ represents a single bond bonded to *a.

In a preferred embodiment of the present invention, one or more combinations of combinations each including adjacent two or more selected from $R^{11}$ to $R^{18}$ each are not bonded to each other to form a ring.

The substituted or unsubstituted aryl group having 6 to 30 ring carbon atoms is the same as the substituted or unsubstituted aryl group having 6 to 30 ring carbon atoms described for $R^1$ and $R^2$, and is preferably a phenyl group, a biphenylyl group, a naphthyl group, or a phenanthryl group, and more preferably a phenyl group, a p-biphenyl group, a m-biphenyl group, an o-biphenyl group, a 1-naphthyl group, or a 2-naphthyl group.

The substituted or unsubstituted heterocyclic group having 5 to 30 ring atoms is the same as the substituted or unsubstituted heterocyclic group having 5 to 30 ring atoms described for $R^1$ and $R^2$, and is preferably a pyrrolyl group, a pyridyl group, an imidazopyridyl group, a pyridazinyl group, a pyrimidinyl group, a pyrazinyl group, an indolyl group, an acridinyl group, a quinolyl group, an isoquinolyl group, a dibenzofuranyl group, a dibenzothiophenyl group (a dibenzothienyl group, hereinafter the same), or a carbazolyl group, and more preferably a pyridyl group, a quinolyl group, or an isoquinolyl group.

The substituted or unsubstituted alkyl group having 1 to 50 carbon atoms has been described in detail in the section "Substituents in Description", and is preferably a methyl group, an ethyl group, a n-propyl group, an isopropyl group, a n-butyl group, an isobutyl group, a s-butyl group, or a t-butyl group, and more preferably a methyl group, an isopropyl group, or a t-butyl group.

The substituted or unsubstituted cycloalkyl group having 3 to 50 ring carbon atoms has been described in detail in the section "Substituents in Description", and is preferably a cyclopropyl group, a cyclobutyl group, a cyclopentyl group, or a cyclohexyl group, and more preferably a cyclopropyl group, a cyclopentyl group, or a cyclohexyl group.

$R^{31}$ to $R^{35}$ each are independently selected from a hydrogen atom, a substituted or unsubstituted aryl group having 6 to 30 ring carbon atoms, and a substituted or unsubstituted heterocyclic group having 5 to 30 ring atoms, and preferably selected from a hydrogen atom and a substituted or unsubstituted aryl group having 6 to 30 ring carbon atoms.

The substituted or unsubstituted aryl group having 6 to 30 ring carbon atoms is the same as the substituted or unsubstituted aryl group having 6 to 30 ring carbon atoms described for $R^1$ and $R^2$, is preferably selected from a substituted or unsubstituted phenyl group, a naphthyl group, and a biphenylyl group, and is more preferably a substituted or unsubstituted phenyl group or a substituted or unsubstituted naphthyl group.

The substituted or unsubstituted heterocyclic group having 5 to 30 ring atoms is the same as the substituted or unsubstituted heterocyclic group having 5 to 30 ring atoms described for $R^1$ and $R^2$.

One or more combinations of combinations each including adjacent two or more selected from $R^{31}$ to $R^{35}$ each are not bonded to each other to form a ring.

L is selected from a substituted or unsubstituted arylene group having 6 to 30 ring carbon atoms and a substituted or unsubstituted divalent heterocyclic group having 5 to 30 ring atoms.

In the substituted or unsubstituted arylene group having 6 to 30 ring carbon atoms represented by L, examples of the arylene group include a phenylene group, a biphenyldiyl group, a terphenyldiyl group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, a triphenylenylene group, a fluorantenylene group, a fluorenylene group, and a 9,9'-spirofluorenylene group. Among these, a phenylene group, a biphenyldiyl group, and a terphenyldiyl group are preferred.

In the substituted or unsubstituted divalent heterocyclic group having 5 to 30 ring atoms represented by L, examples of the divalent heterocyclic group include divalent residual groups derived from aromatic heterocyclic rings selected from pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, benzocarbazole, xanthene, benzofuran, isobenzofuran, dibenzofuran, naphthobenzofuran, benzothiophene, dibenzothiophene, naphthobenzothiophene, benzoxazole, benzisoxazole, phenoxazine, benzothiazole, benzisothiazole, and phenothiazine. Among these, the aromatic heterocyclic ring is preferably pyridine, quinoline, or isoquinoline.

In one embodiment of the present invention, L more preferably represents a substituted or unsubstituted phenylene group.

Accordingly, in a preferred embodiment of the present invention, the inventive compound includes a compound represented by the following formula (4) or (5).

(4)

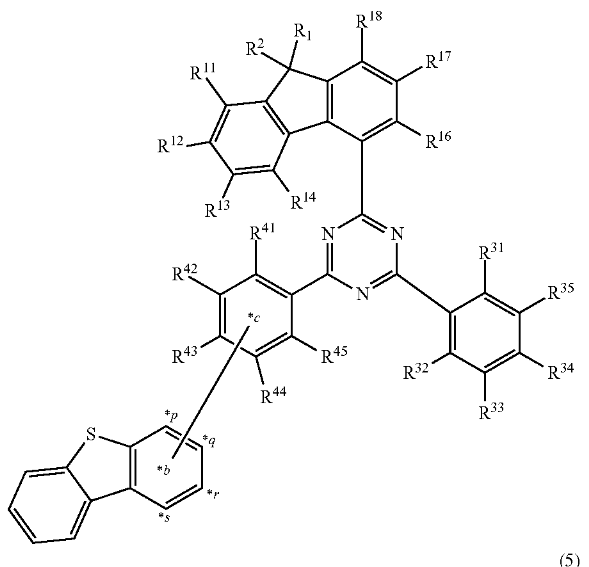

(5)

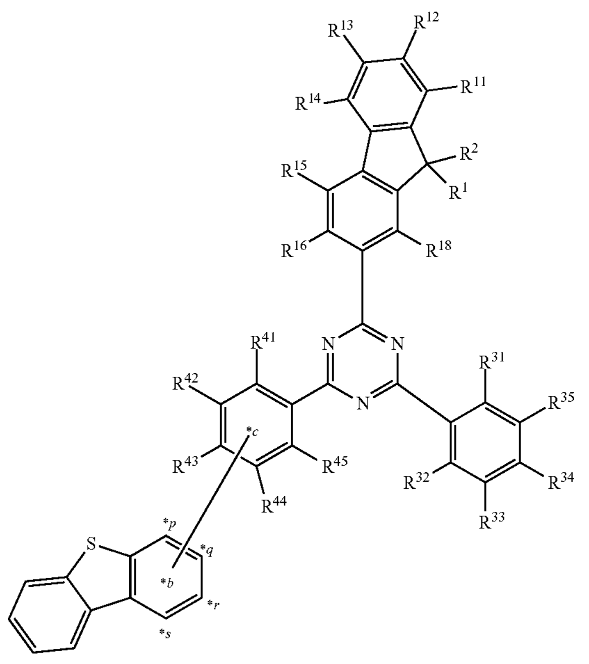

*p, *q, *r, *s, *b, $R^1$, $R^2$, $R^{11}$ to $R^{18}$, and $R^{31}$ to $R^{35}$ have been defined as above.

$R^{41}$ to $R^{45}$ each are independently selected from a hydrogen atom, a substituted or unsubstituted aryl group having 6 to 50 ring carbon atoms, a substituted or unsubstituted heterocyclic group having 5 to 30 ring atoms, a substituted or unsubstituted alkyl group having 1 to 30 carbon atoms, a substituted or unsubstituted cycloalkyl group having 3 to 50 ring carbon atoms, and a cyano group, and are preferably independently selected from a hydrogen atom, a substituted or unsubstituted aryl group having 6 to 30 ring carbon atoms, a substituted or unsubstituted heterocyclic group having 5 to 30 ring atoms, and a substituted or unsubstituted alkyl group having 1 to 50 carbon atoms.

One selected from $R^{41}$ to $R^{45}$ represents a single bond bonded to *c.

The details of the substituted or unsubstituted aryl group having 6 to 30 ring carbon atoms, the substituted or unsubstituted heterocyclic group having 5 to 30 ring atoms, the substituted or unsubstituted alkyl group having 1 to 30 carbon atoms, and the substituted or unsubstituted cycloalkyl group having 3 to 50 ring carbon atoms are the same as the details of the corresponding groups described for $R^{11}$ to $R^{18}$.

In another embodiment of the present invention, L preferably represents a substituted or unsubstituted biphenyldiyl group.

Accordingly, in a preferred embodiment of the present invention the inventive compound includes a compound represented by the following formula (4') or (5').

(4')

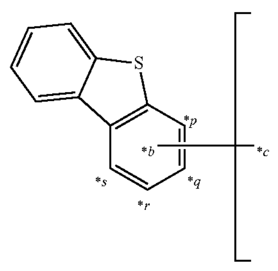
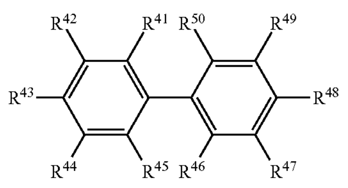
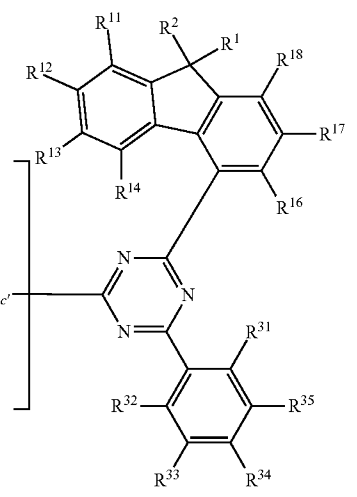

(5')

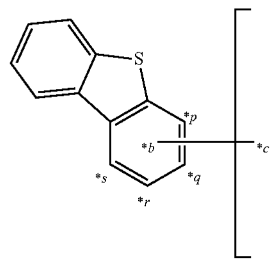
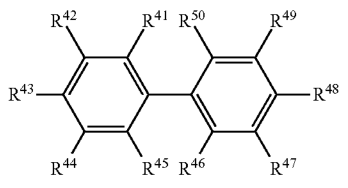
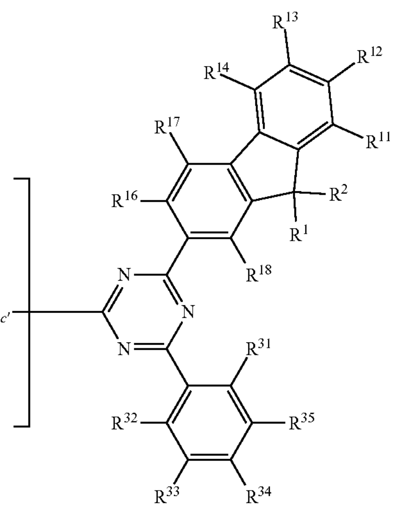

*p, *q, *r, *s, *b, *c, $R^1$, $R^2$, $R^{11}$ to $R^{18}$, $R^{31}$ to $R^{35}$, and $R^{41}$ to $R^{45}$ have been defined as above.

$R^{46}$ to $R^{50}$ each are independently selected from a hydrogen atom, a substituted or unsubstituted aryl group having 6 to 50 ring carbon atoms, a substituted or unsubstituted heterocyclic group having 5 to 30 ring atoms, a substituted or unsubstituted alkyl group having 1 to 30 carbon atoms, a substituted or unsubstituted cycloalkyl group having 3 to 50 ring carbon atoms, and a cyano group, and are preferably independently selected from a hydrogen atom, a substituted or unsubstituted aryl group having 6 to 30 ring carbon atoms, a substituted or unsubstituted heterocyclic group having 5 to 30 ring atoms, and a substituted or unsubstituted alkyl group having 1 to 50 carbon atoms.

One selected from $R^{46}$ to $R^{50}$ represents a single bond bonded to *c'.

The details of the substituted or unsubstituted aryl group having 6 to 30 ring carbon atoms, the substituted or unsubstituted heterocyclic group having 5 to 30 ring atoms, the substituted or unsubstituted alkyl group having 1 to 30 carbon atoms, and the substituted or unsubstituted cycloalkyl group having 3 to 50 ring carbon atoms are the same as the details of the corresponding groups described for $R^{11}$ to $R^{18}$.

The inventive compound also includes a compound represented by the following formula (6) or (7).

(6)

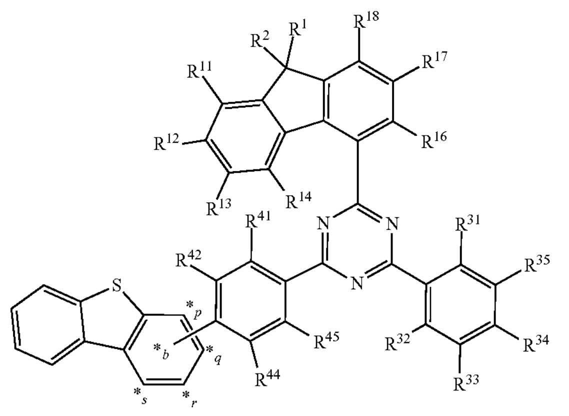

(7)

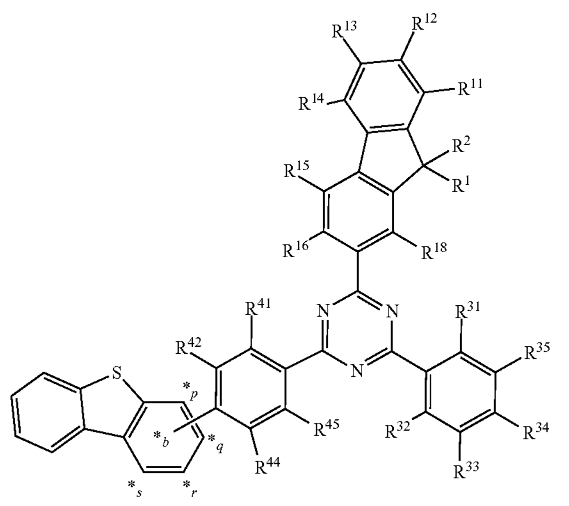

*p, *q, *r, *s, *b, $R^1$, $R^2$, $R^{11}$ to $R^{18}$, $R^{31}$ to $R^{35}$, and $R^{41}$ to $R^{45}$ have been defined as above.

The inventive compound also includes a compound represented by the following formula (8) or (9).

(8)

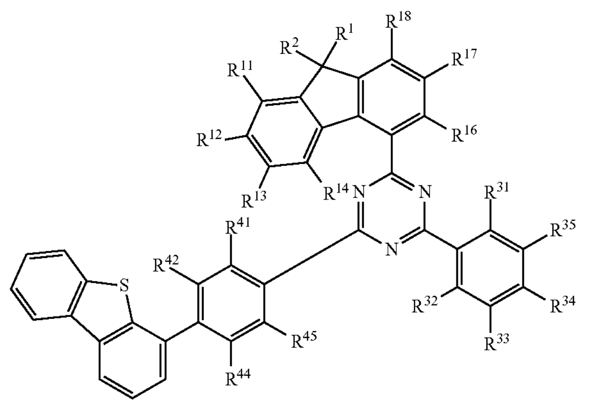

-continued (9)

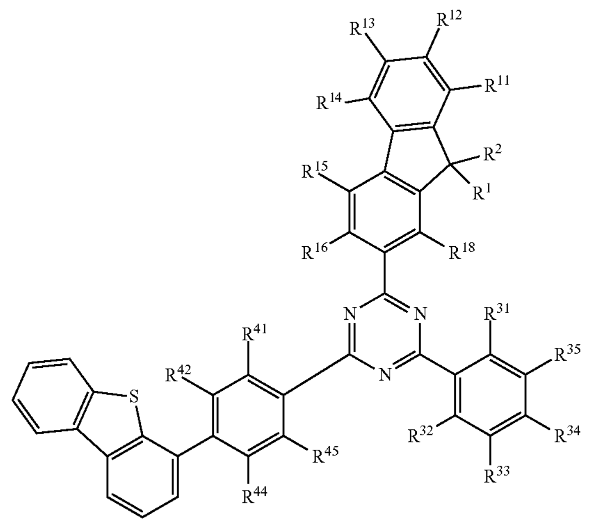

$R^1$, $R^2$, $R^{11}$ to $R^{18}$, $R^{31}$ to $R^{35}$, and $R^{41}$ to $R^{45}$ have been defined as above.

In a preferred embodiment of the present invention, the inventive compound includes a compound represented by any of the following formulae (10) to (13).

(10)

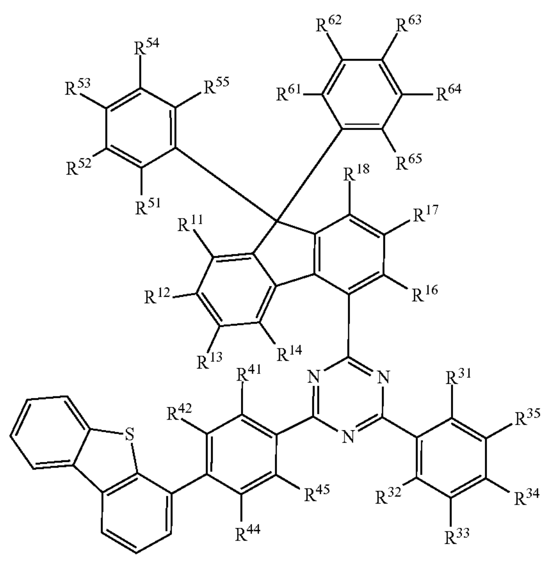

-continued (11)

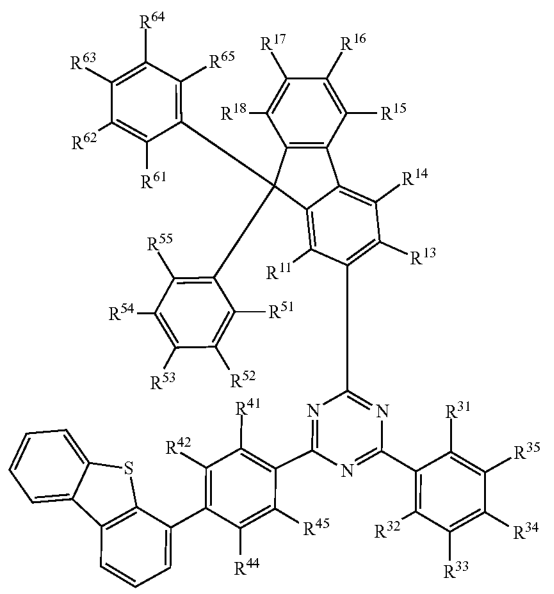

-continued (13)

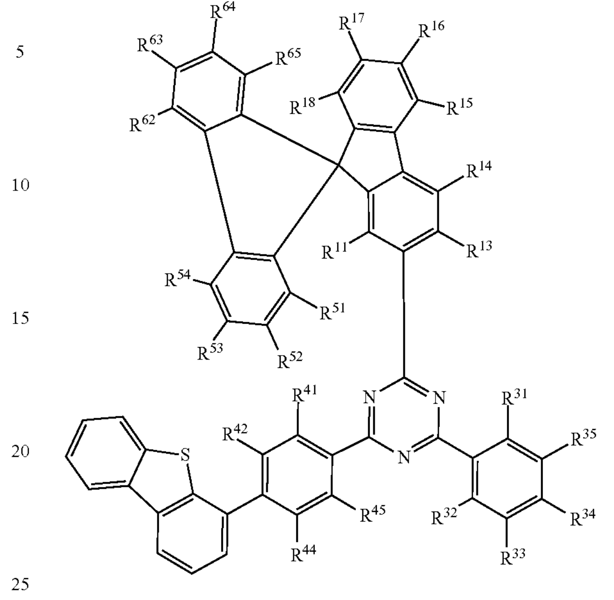

(12)

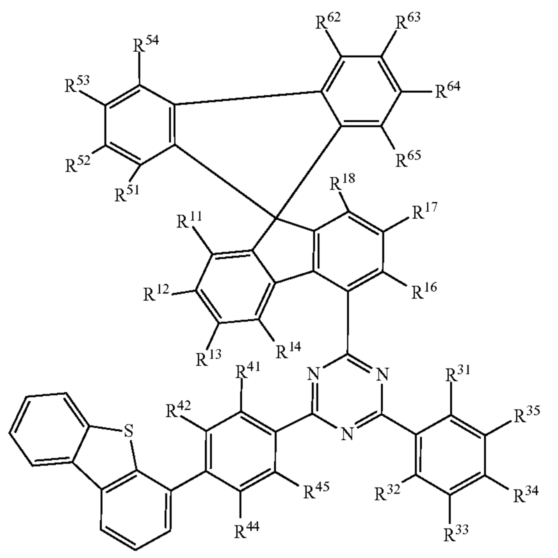

$R^{11}$ to $R^{18}$, $R^{31}$ to $R^{35}$, and $R^{41}$ to $R^{45}$ have been defined as above.

$R^{51}$ to $R^{55}$ and $R^{61}$ to $R^{65}$ each are independently selected from a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 50 carbon atoms, a substituted or unsubstituted cycloalkyl group having 3 to 50 ring carbon atoms, and a cyano group, and are preferably independently selected from a hydrogen atom, a substituted or unsubstituted aryl group having 6 to 30 ring carbon atoms, a substituted or unsubstituted heterocyclic group having 5 to 30 ring atoms, and a substituted or unsubstituted alkyl group having 1 to 50 carbon atoms.

The details of the substituted or unsubstituted aryl group having 6 to 30 ring carbon atoms, the substituted or unsubstituted heterocyclic group having 5 to 30 ring atoms, the substituted or unsubstituted alkyl group having 1 to 30 carbon atoms, and the substituted or unsubstituted cycloalkyl group having 3 to 50 ring carbon atoms are the same as the details of the corresponding groups described for $R^{11}$ to $R^{18}$.

In one embodiment of the present invention, (1) $R^{11}$ to $R^{18}$ that are not a single bond bonded to *a may all be hydrogen atoms, (2) $R^{41}$ to $R^{45}$ that are not a single bond bonded to *c may all be hydrogen atoms, (3) $R^{46}$ to $R^{50}$ that are not a single bond bonded to *c' may all be hydrogen atoms, (4) $R^{31}$ to $R^{35}$ may all be hydrogen atoms, (5) $R^{51}$ to $R^{55}$ ($R^{51}$ to $R^{54}$ in the case where $R^{55}$ and $R^{61}$ are bonded to each other) may all be hydrogen atoms, and (6) $R^{61}$ to $R^{65}$ ($R^{62}$ to $R^{65}$ in the case where $R^{55}$ and $R^{61}$ are bonded to each other) may all be hydrogen atoms.

The inventive compound may satisfy all the conditions (1) to (6) simultaneously, or may satisfy a part of the conditions (1) to (6).

One or more combinations of combinations each including adjacent two or more selected from $R^{11}$ to $R^{18}$, $R^{51}$ to $R^{55}$, and $R^{61}$ to $R^{65}$ each are bonded to each other to form a substituted or unsubstituted monocyclic ring, or each are bonded to each other to form a substituted or unsubstituted condensed ring, or each are not bonded to each other. Specifically, one or more combinations of combinations each including adjacent two or more selected from $R^{11}$ and $R^{12}$, $R^{12}$ and $R^{13}$, $R^{14}$ and $R^{15}$, $R^{15}$ and $R^{16}$, $R^{16}$ and $R^{17}$, and $R^{17}$ and $R^{18}$ each are bonded to each other to form a substituted or unsubstituted monocyclic ring, or each are bonded to each other to form a substituted or unsubstituted condensed ring, or each are not bonded to each other.

For example, in one or more combinations each including adjacent two selected from $R^{11}$ to $R^{18}$, $R^{51}$ to $R^{55}$, and $R^{61}$ to $R^{65}$, the adjacent two included in each of the combinations are bonded to each other to form a substituted or unsubstituted monocyclic ring, or are bonded to each other to form a substituted or unsubstituted condensed ring, or are not bonded to each other.

The one or more combinations each may be selected, for example, in such a manner that one combination (i.e., the first combination) and another combination (i.e., the second combination) share one ring carbon atom (i.e., the ring carbon atom bonded to $R^{12}$) as in a combination including $R^{11}$ and $R^{12}$ and a combination including $R^{12}$ and $R^{13}$, or adjacent two included in each of the combinations (i.e., $R^{11}$ and $R^{12}$, and $R^{12}$ and $R^{13}$) may be bonded to each other to form a substituted or unsubstituted monocyclic ring or a substituted or unsubstituted condensed ring. In this case, the ring formed with adjacent two included in the one combination, the ring formed with adjacent two included in the other combination, and the ring formed with adjacent two included in the one combination and the other combination form an ortho-peri condensed structure.

The substituted or unsubstituted monocyclic ring or the substituted or unsubstituted condensed ring is selected, for example, from a substituted or unsubstituted aromatic hydrocarbon ring, a substituted or unsubstituted aliphatic hydrocarbon ring, a substituted or unsubstituted aromatic heterocyclic ring, and a substituted or unsubstituted aliphatic heterocyclic ring.

The aromatic hydrocarbon ring is, for example, a benzene ring, a biphenylene ring, a naphthalene ring, an anthracene ring, a benzanthracene ring, a phenanthrene ring, a benzophenanthrene ring, a phenalene ring, a pyrene ring, a chrysene ring, a 1,1-dimethylindene ring, or a triphenylene ring, preferably a benzene ring or a naphthalene ring, and more preferably a benzene ring.

The aliphatic hydrocarbon ring is, for example, a cyclopentene ring, a cyclopentadiene ring, a cyclohexene ring, a cyclohexadiene ring, or aliphatic hydrocarbon rings obtained through partial hydrogenation of the aforementioned aromatic hydrocarbon rings.

The aromatic heterocyclic ring is, for example, a pyrrole ring, a furan ring, a thiophene ring, a pyridine ring, an imidazole ring, a pyrazole ring, an indole ring, an isoindole ring, a benzofuran ring, an isobenzofuran ring, a benzothiophene ring, a benzimidazole ring, an indazole ring, a dibenzofuran ring, a naphthobenzofuran ring, a dibenzothiophene ring, a naphthobenzothiophene ring, a carbazole ring, or a benzocarbazole ring.

The aliphatic heterocyclic ring is, for example, aliphatic heterocyclic rings obtained through partial hydrogenation of the aforementioned aromatic heterocyclic rings.

$R^1$ and $R^2$ are bonded to form a single bond bonding the two ring structures bonded thereto, or are bonded to each other to form a substituted or unsubstituted monocyclic ring, or are bonded to each other to form a substituted or unsubstituted condensed ring, or are not bonded to each other.

In one embodiment of the present invention, $R^1$ and $R^2$ are preferably bonded to each other to form the single bond, and in another embodiment thereof, $R^1$ and $R^2$ are not bonded to each other.

As described above, the "hydrogen atom" referred in the description herein encompasses a protium atom, a deuterium atom, and tritium atom. Accordingly, the inventive compound may contain a naturally-derived deuterium atom.

A deuterium atom may be intentionally introduced into the inventive compound by using a deuterated compound as a part or the whole of the raw material. Accordingly, in one embodiment of the present invention, the inventive compound contains at least one deuterium atom. That is, the inventive compound may be a compound represented by the formula (1) or the aforementioned formula included in the formula (1) in which at least one hydrogen atom contained in the compound is a deuterium atom.

At least one hydrogen atom selected from the following hydrogen atoms may be a deuterium atom:

- a hydrogen atom represented by $R^1$ or $R^2$; a hydrogen atom of the substituted or unsubstituted aryl group or heterocyclic group represented by $R^1$ or $R^2$;
- a hydrogen atom represented by any of $R^{11}$ to $R^{18}$ that is not a single bond bonded to *a; a hydrogen atom of the substituted or unsubstituted alkyl group, cycloalkyl group, aryl group, or heterocyclic group represented by any of $R^{11}$ to $R^{18}$ that is not a single bond bonded to *a;
- a hydrogen atom represented by $R^{31}$ to $R^{35}$; a hydrogen atom of the substituted or unsubstituted aryl group or heterocyclic group represented by $R^{31}$ to $R^{35}$;
- a hydrogen atom represented by any of $R^{41}$ to $R^{45}$ that is not a single bond bonded to *c; a hydrogen atom of the substituted or unsubstituted alkyl group, cycloalkyl group, aryl group, or heterocyclic group represented by any of $R^{41}$ to $R^{45}$ that is not a single bond bonded to *c; and
- a hydrogen atom of the substituted or unsubstituted arylene group or divalent heterocyclic group represented by L.

The deuteration rate of the inventive compound (i.e., the proportion of the number of deuterium atoms with respect to the number of all hydrogen atoms in the inventive compound) depends on the deuteration rate of the raw material compound used. The deuteration rate of the inventive compound is less than 100% since it is generally difficult to make the deuteration rates of all the raw material compounds used to 100%.

The deuteration rate of the inventive compound may be 1% or more, and is preferably 3% or more, more preferably 5% or more, and further preferably 10% or more.

The inventive compound may be a mixture of a deuterated compound (i.e., a compound having deuterium atoms intentionally introduced thereto) and a non-deuterated compound, or a mixture of two or more compounds having different deuteration rates from each other. The deuteration rate of the mixture (i.e., the proportion of the number of deuterium atoms with respect to the number of all hydrogen atoms in the inventive compound contained in the mixture) may be 1% or more, is preferably 3% or more, more preferably 5% or more, and still more preferably 10% or more, and is less than 100%.

In the inventive compound, at least one hydrogen atom selected from a hydrogen atom represented by $R^1$ or $R^2$, and a hydrogen atom of the substituted or unsubstituted aryl group or heterocyclic group represented by $R^1$ or $R^2$ may be a deuterium atom. The deuteration rate (i.e., the proportion of the number of deuterium atoms with respect to the number of all hydrogen atoms of $R^1$ or $R^2$) may be 1% or more, is preferably 3% or more, more preferably 5% or more, and still more preferably 10% or more, and is less than 100%.

In the inventive compound, at least one hydrogen atom selected from a hydrogen atom represented by any of $R^{11}$ to $R^{18}$ that is not a single bond bonded to *a, and a hydrogen atom of the substituted or unsubstituted alkyl group, cycloalkyl group, aryl group, or heterocyclic group represented by any of $R^{11}$ to $R^{18}$ that is not a single bond bonded to *a may be a deuterium atom. The deuteration rate (i.e., the proportion of the number of deuterium atoms with respect to the number of all hydrogen atoms of $R^{11}$ to $R^{18}$ that is not a single bond bonded to *a) may be 1% or more, is preferably 3% or more, more preferably 5% or more, and still more preferably 10% or more, and is less than 100%.

In the inventive compound, at least one hydrogen atom selected from a hydrogen atom represented by $R^{31}$ to $R^{35}$, and a hydrogen atom of the substituted or unsubstituted aryl group or heterocyclic group represented by $R^{31}$ to $R^{35}$ may be a deuterium atom. The deuteration rate (i.e., the proportion of the number of deuterium atoms with respect to the number of all hydrogen atoms of $R^{31}$ to $R^{35}$) may be 1% or more, is preferably 3% or more, more preferably 5% or more, and still more preferably 10% or more, and is less than 100%.

In the inventive compound, at least one hydrogen atom selected from a hydrogen atom represented by any of $R^{41}$ to $R^{45}$ that is not a single bond bonded to *c, and a hydrogen atom of the substituted or unsubstituted alkyl group, cycloalkyl group, aryl group, or heterocyclic group represented by any of $R^{41}$ to $R^{45}$ that is not a single bond bonded to *c may be a deuterium atom. The deuteration rate (i.e., the proportion of the number of deuterium atoms with respect to the number of all hydrogen atoms of $R^{41}$ to $R^{45}$ that is not a single bond bonded to *c) may be 1% or more, is preferably 3% or more, more preferably 5% or more, and still more preferably 10% or more, and is less than 100%.

In the inventive compound, at least one hydrogen atom selected from a hydrogen atom of the substituted or unsubstituted arylene group or divalent heterocyclic group represented by L may be a deuterium atom. The deuteration rate (i.e., the proportion of the number of deuterium atoms with respect to the number of all hydrogen atoms of L) may be 1% or more, is preferably 3% or more, more preferably 5% or more, and still more preferably 10% or more, and is less than 100%.

The details of the substituent (arbitrary substituent) in the expression "substituted or unsubstituted" included in the definitions of the aforementioned formulae are the same as in the "substituent in the expression 'substituted or unsubstituted'".

The inventive compound can be readily produced by a person skilled in the art with reference to the following synthesis examples and the known synthesis methods.

Specific examples of the inventive compound will be described below, but the inventive compound is not limited to the following example compounds.

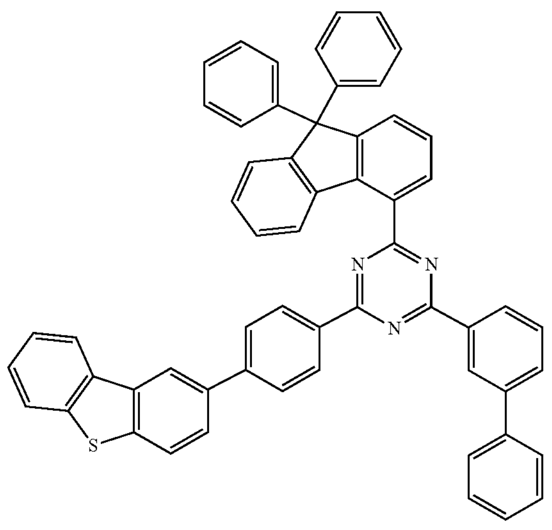

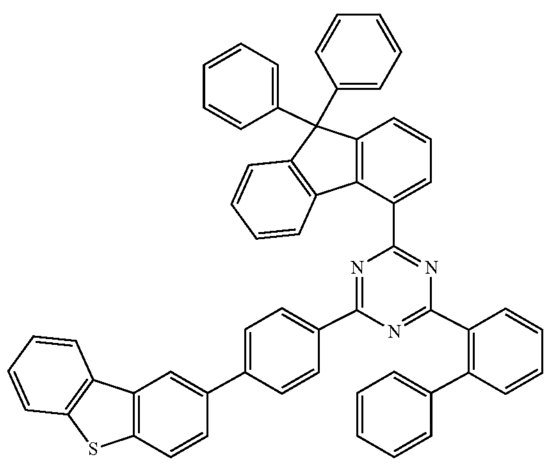

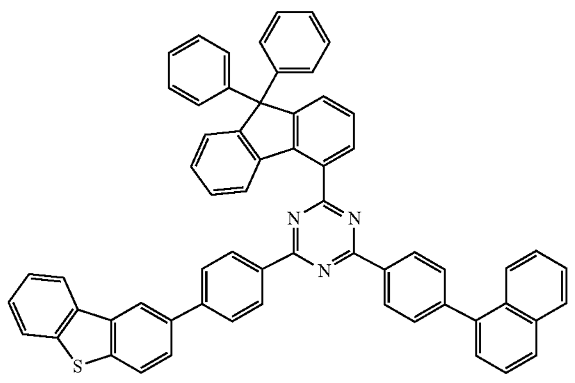

-continued
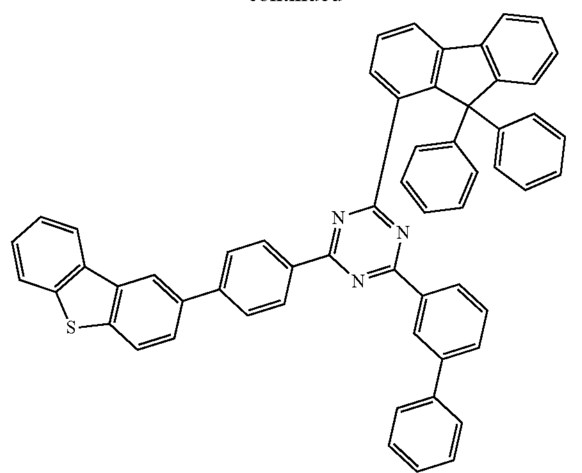
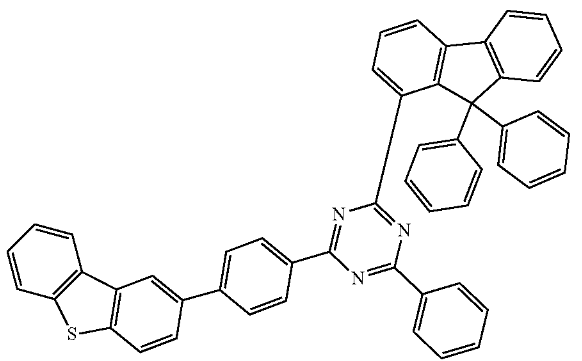
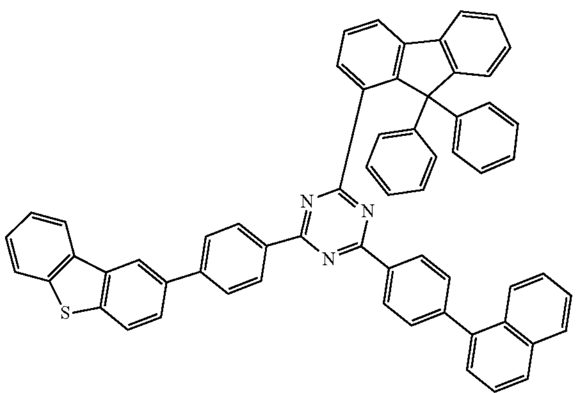
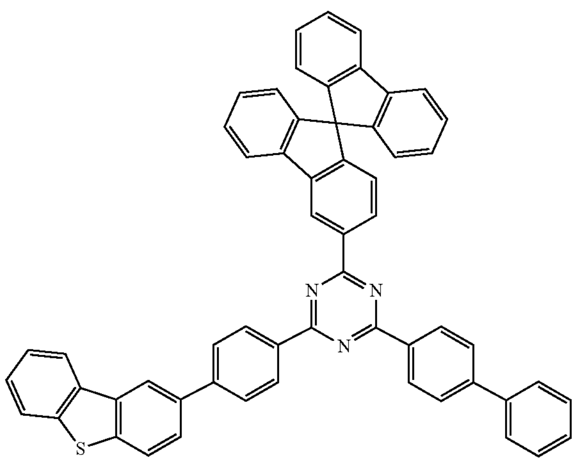
-continued
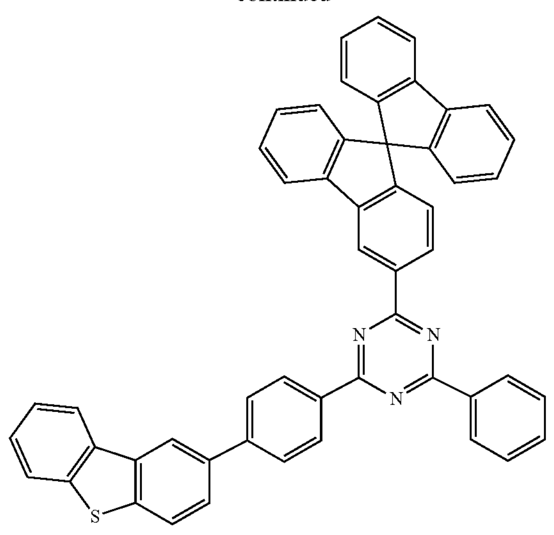
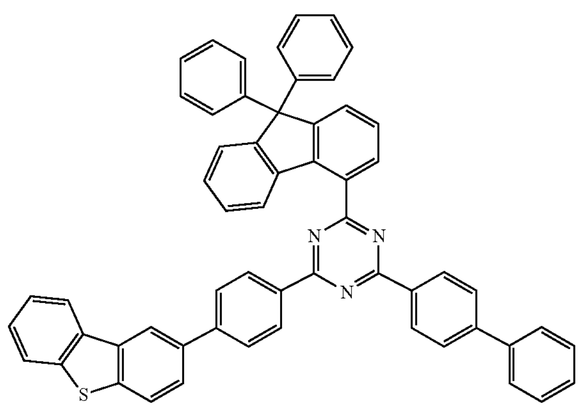
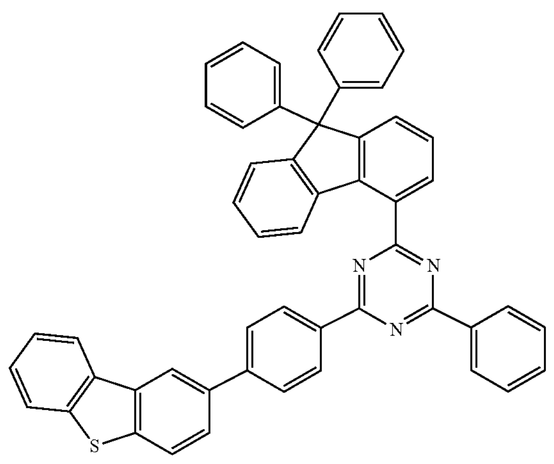

-continued
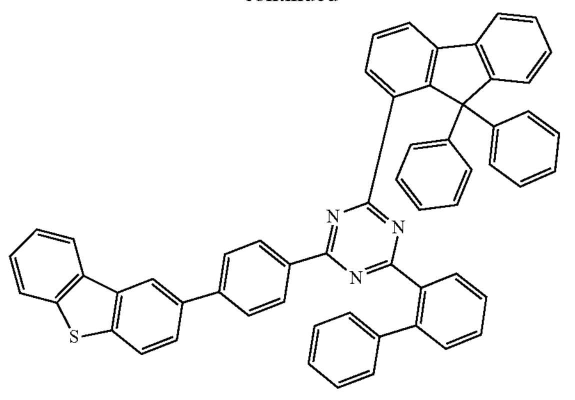
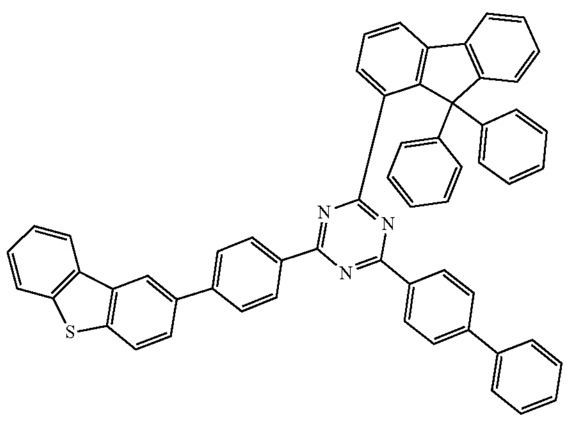
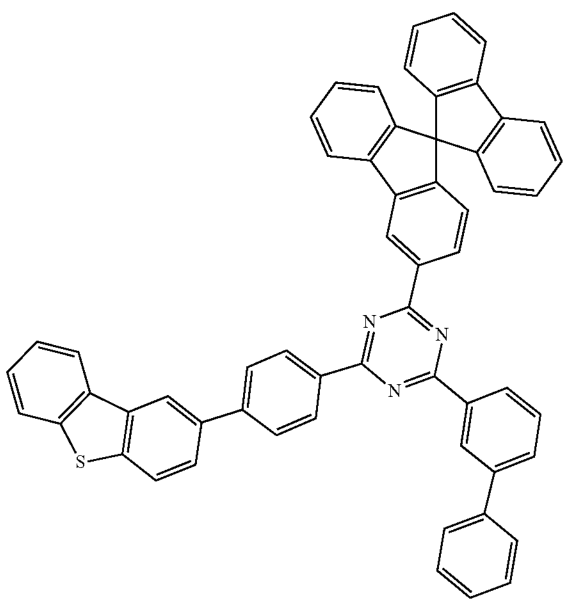
-continued
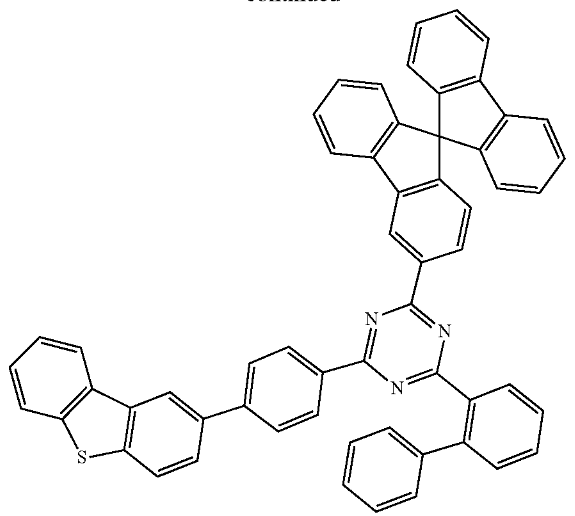
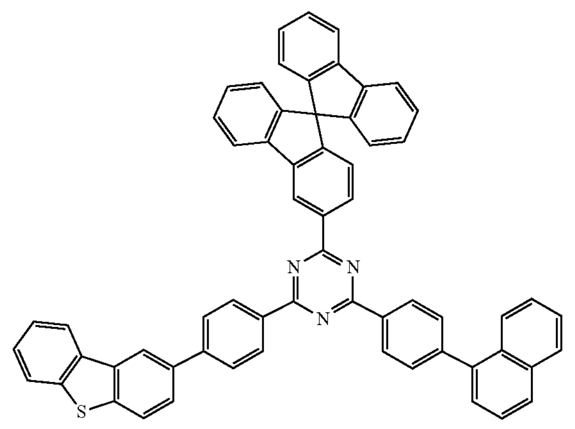
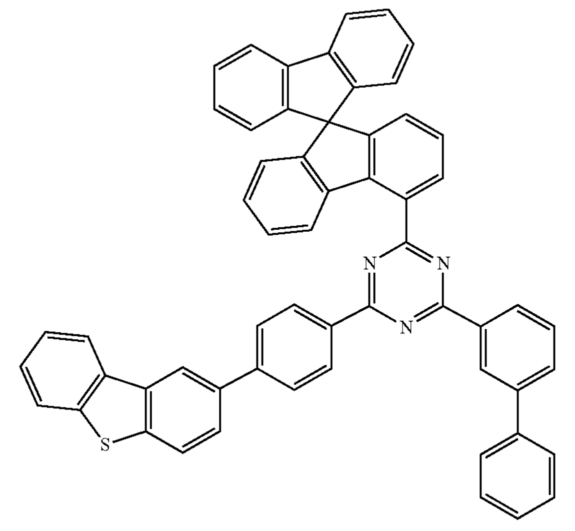

-continued
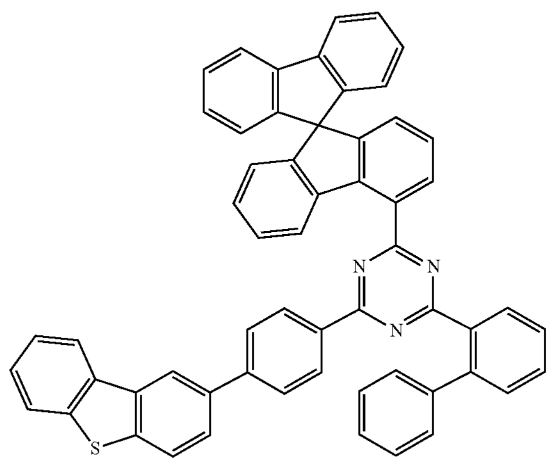
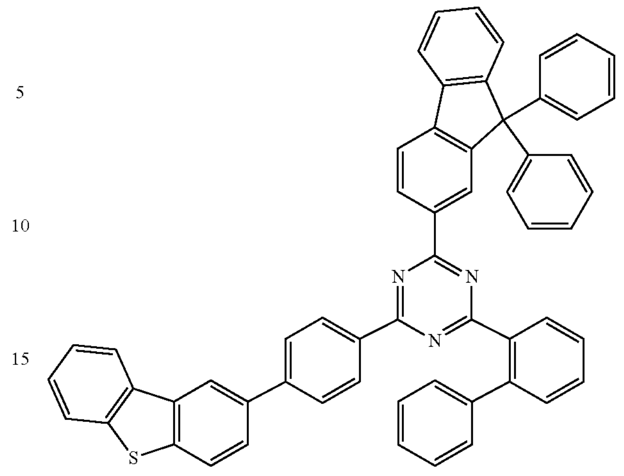
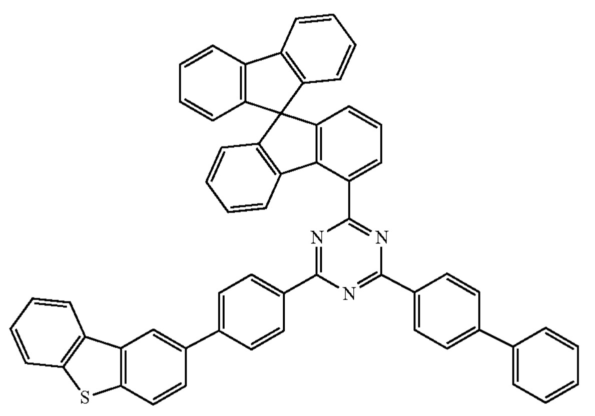
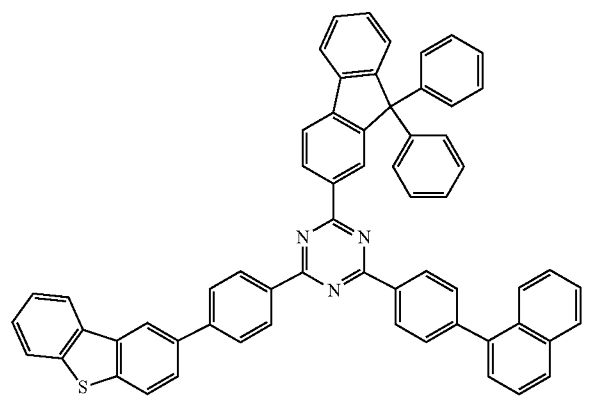
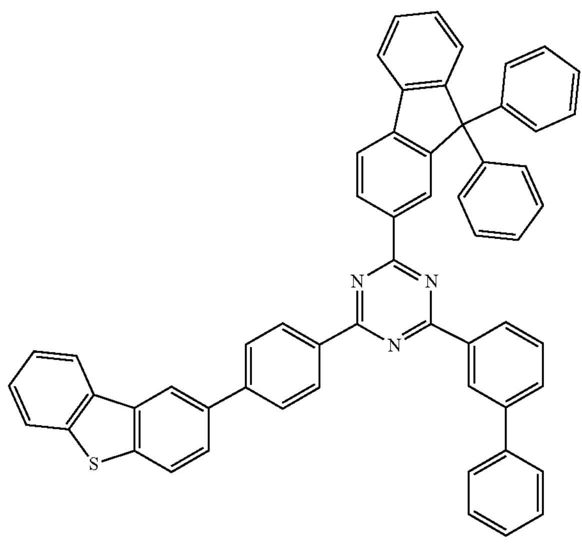
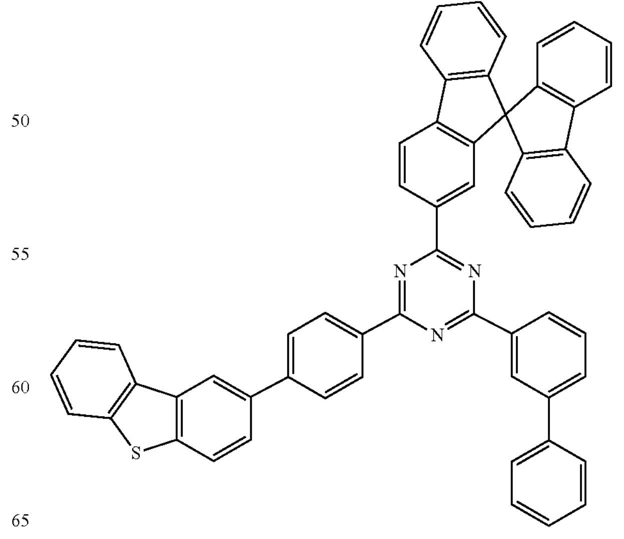
-continued -continued
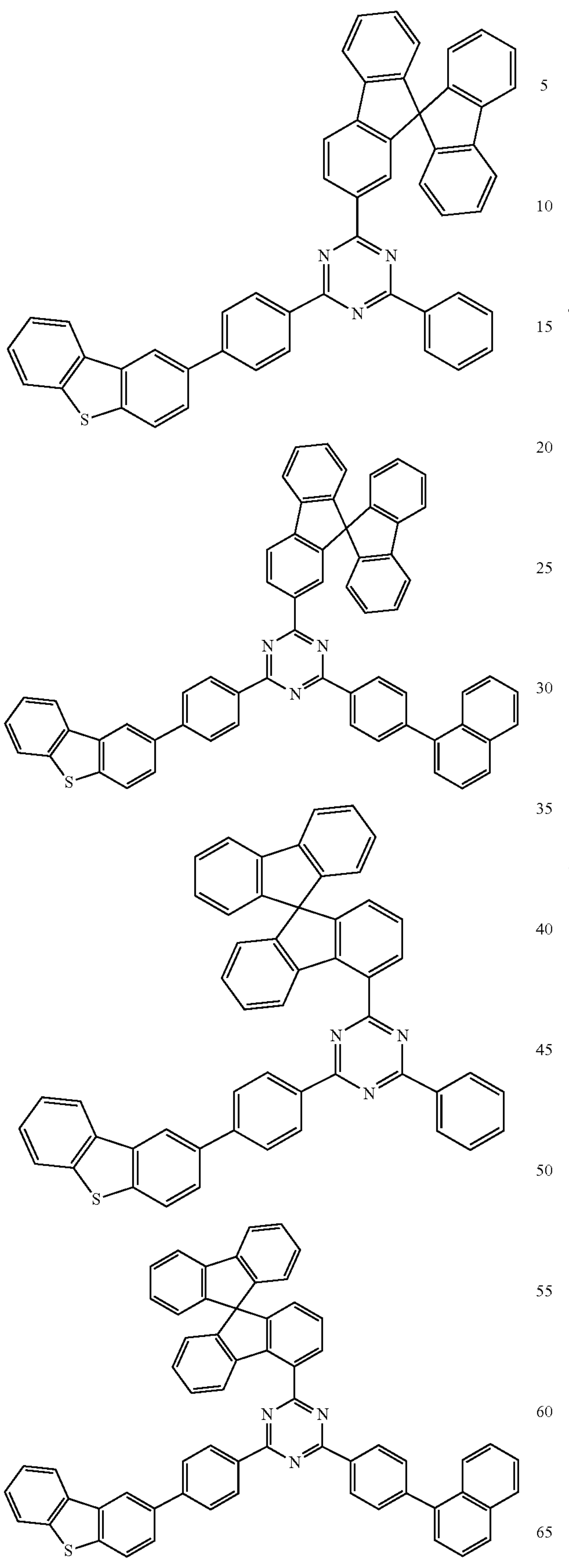
-continued
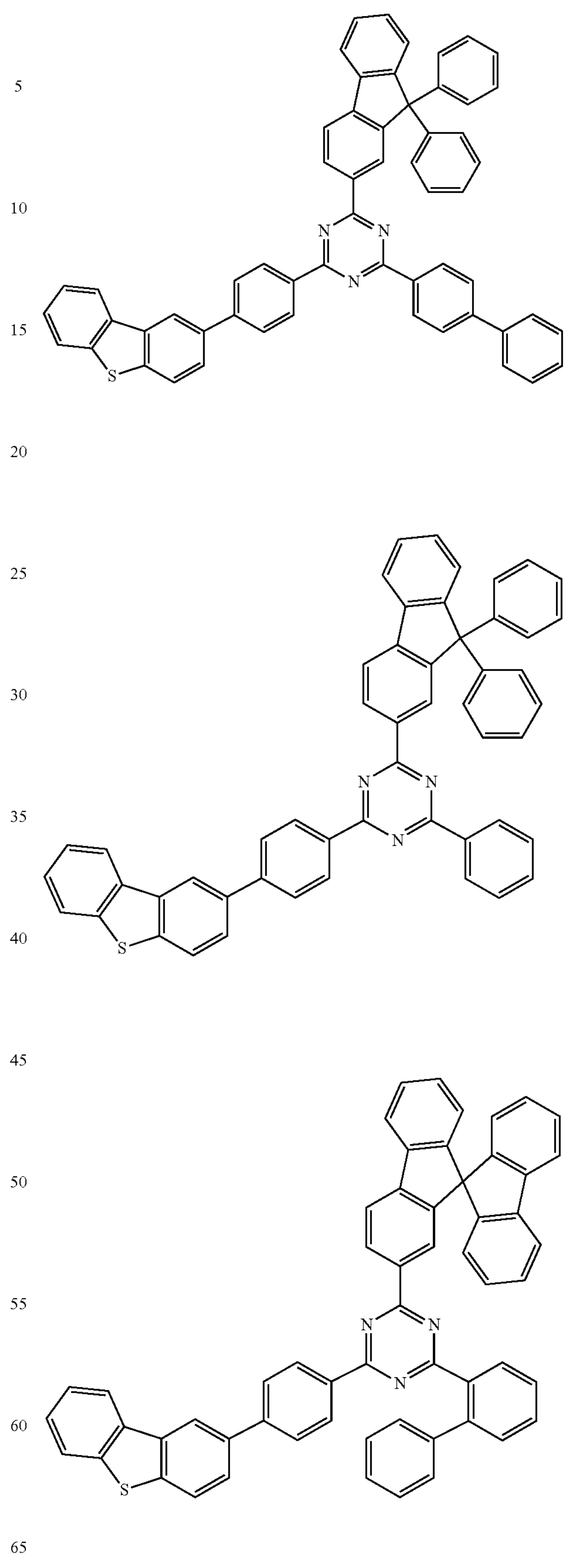

-continued
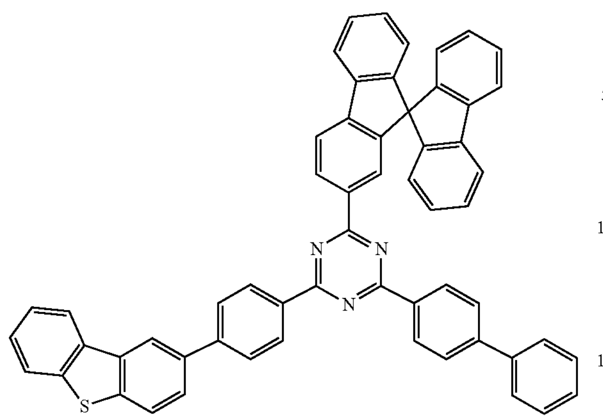
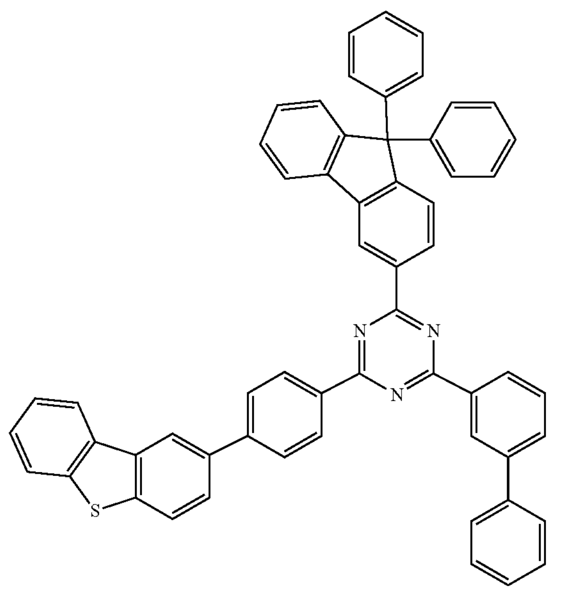
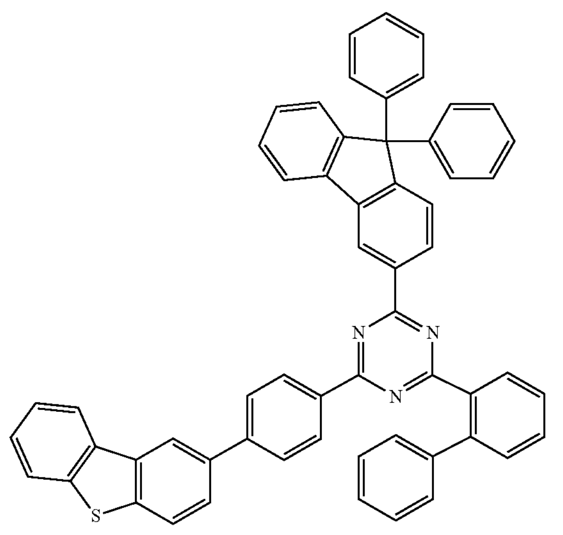
-continued
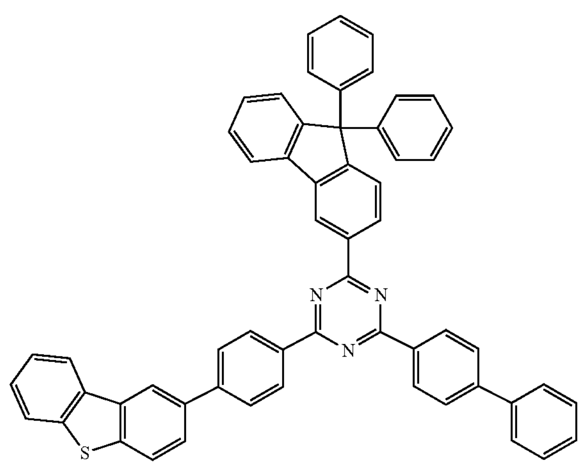
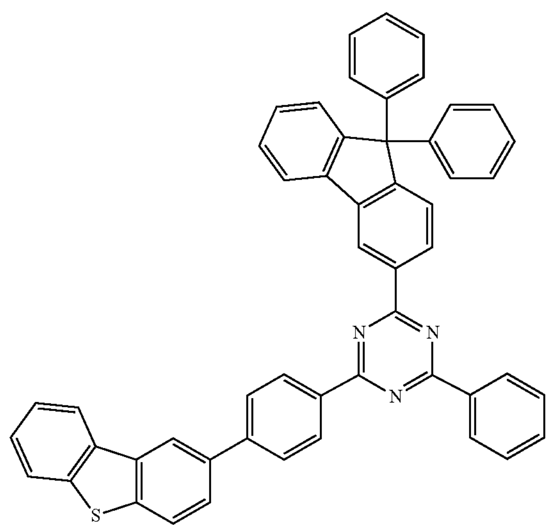
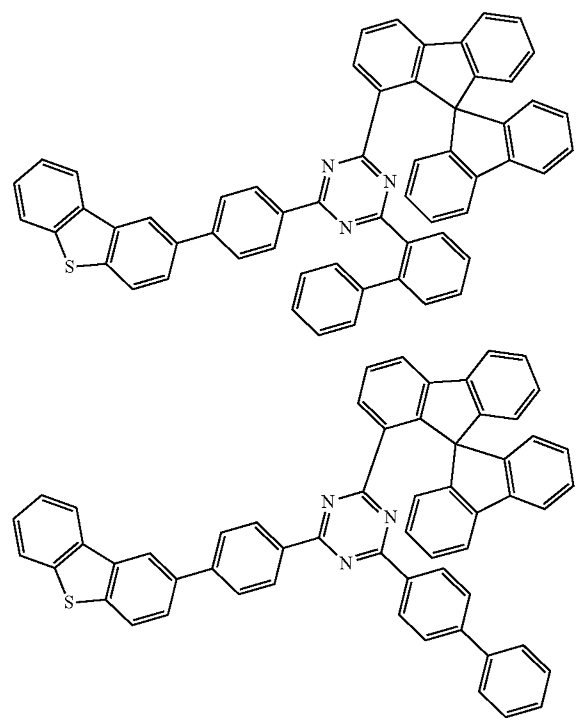

-continued
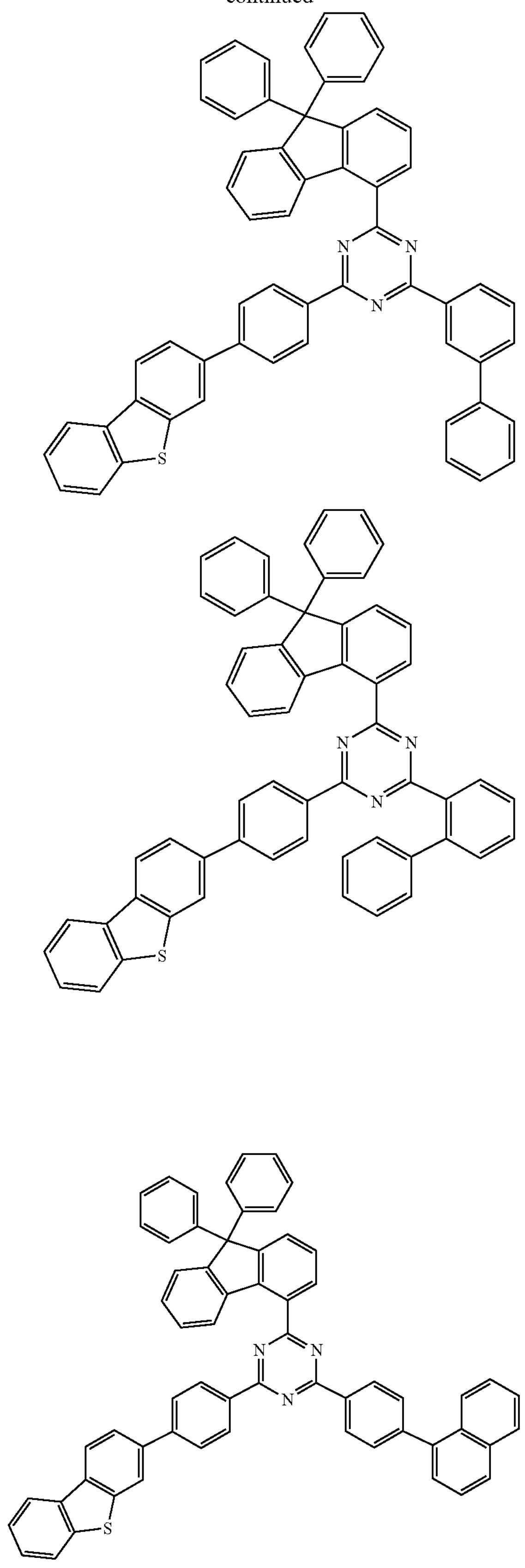
-continued
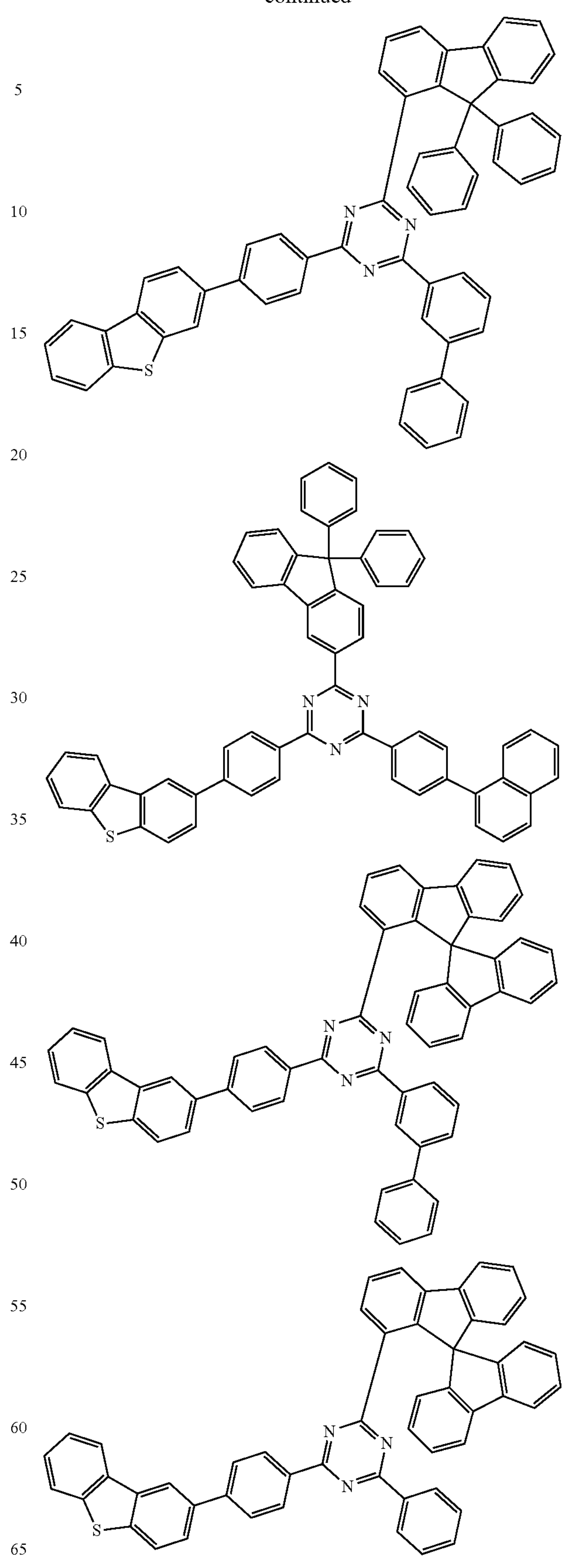

-continued
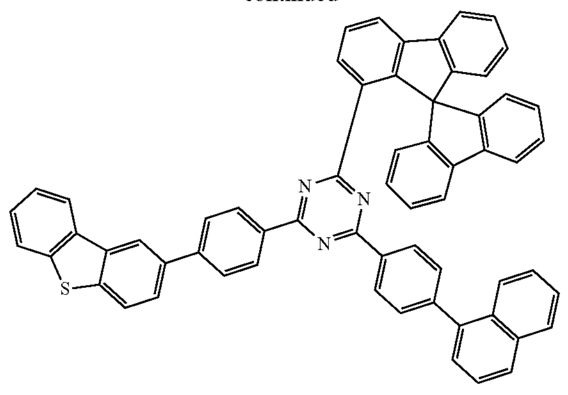
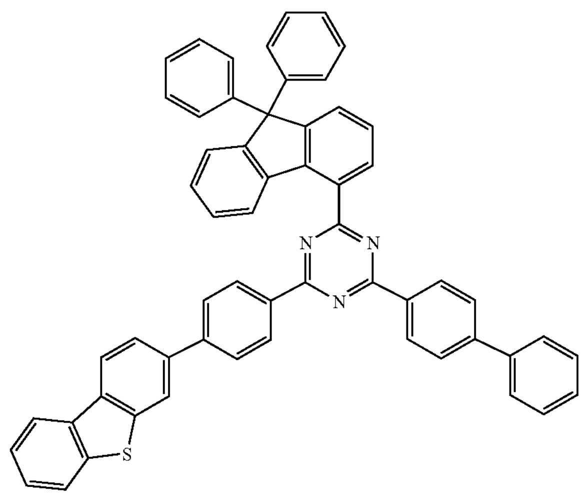
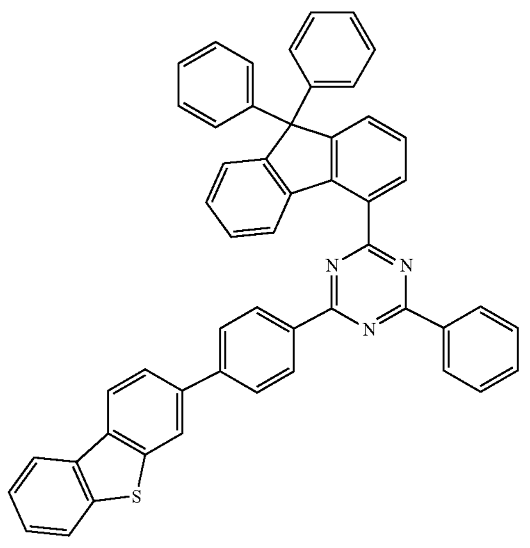
-continued
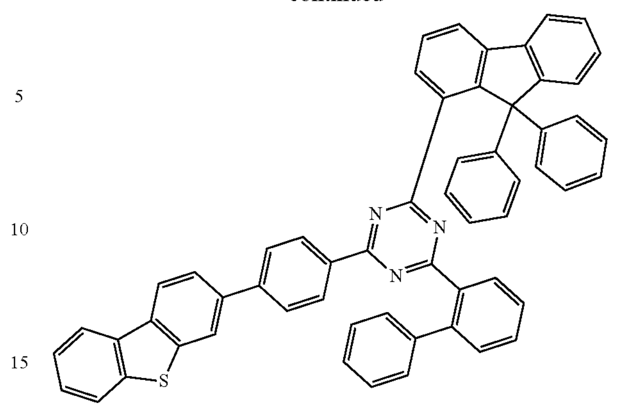
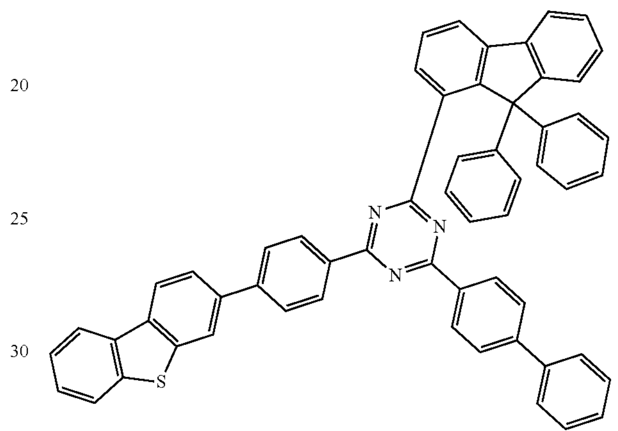
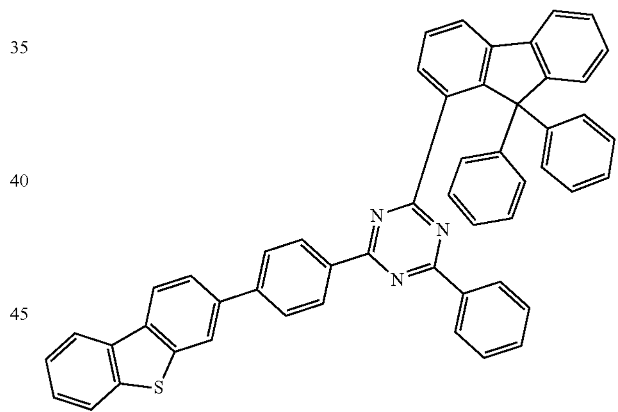
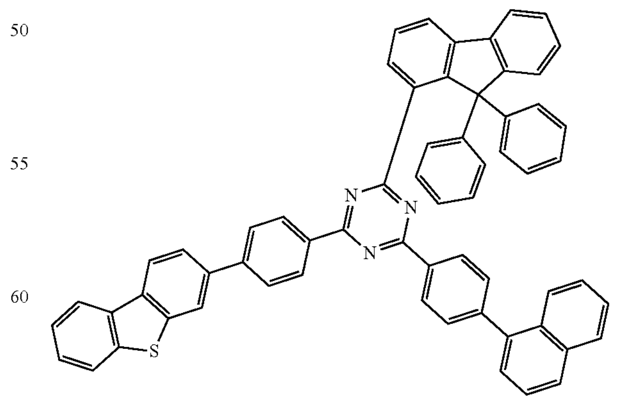

-continued
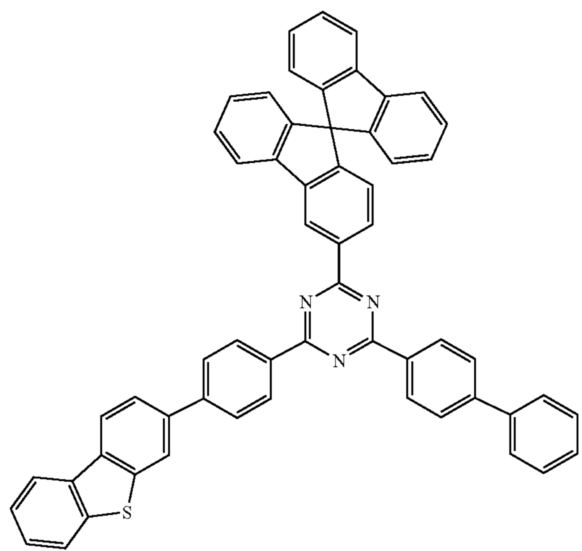
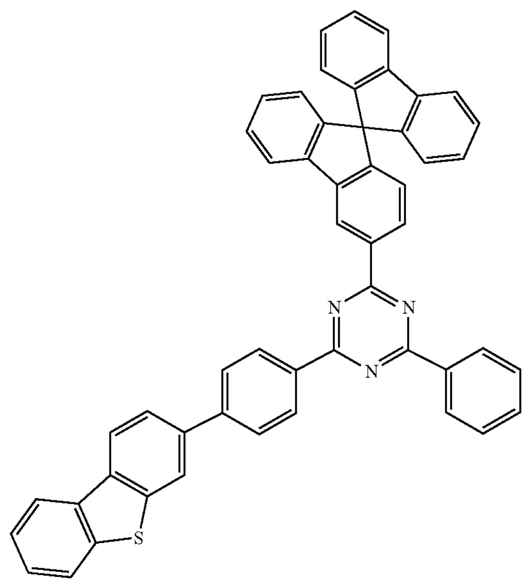
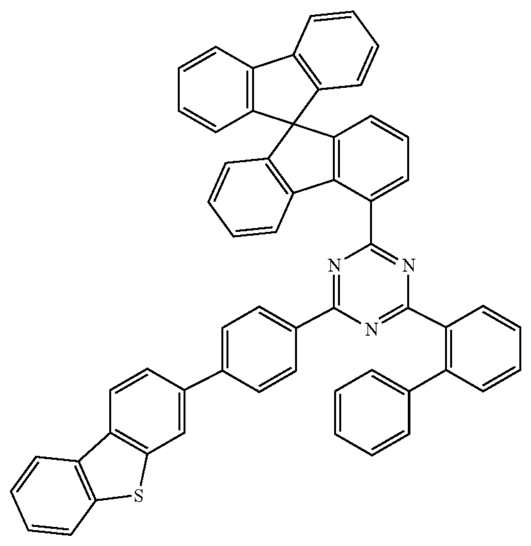
-continued
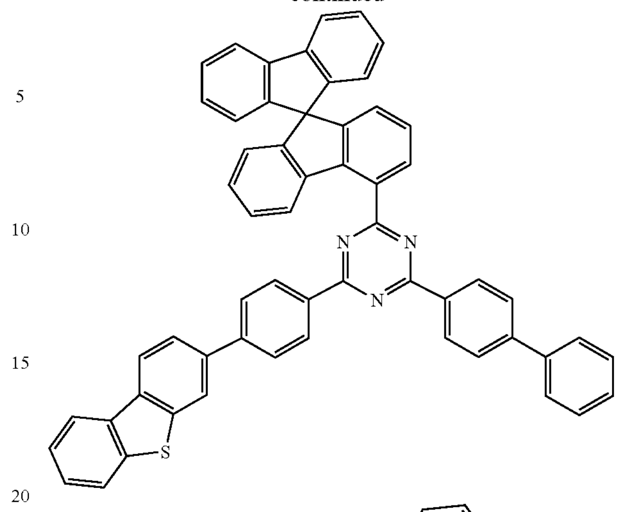
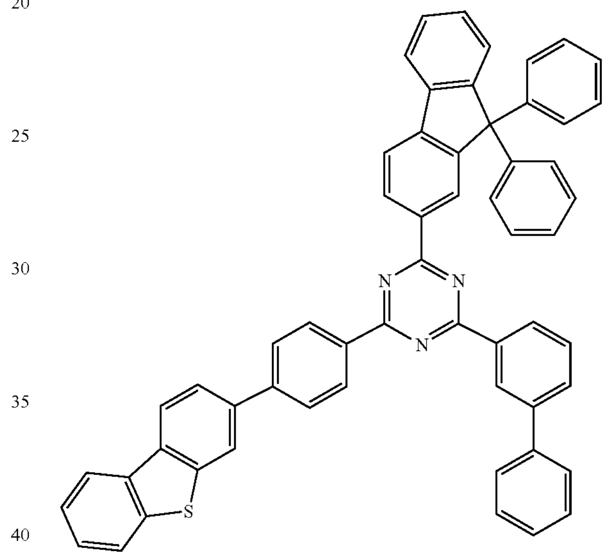
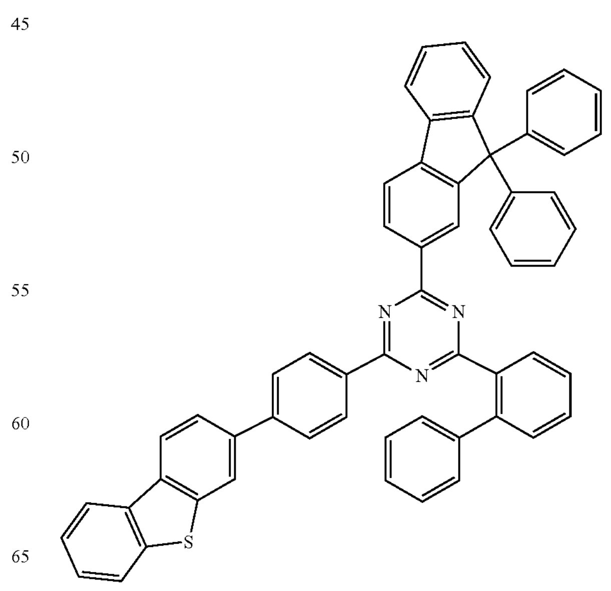

-continued
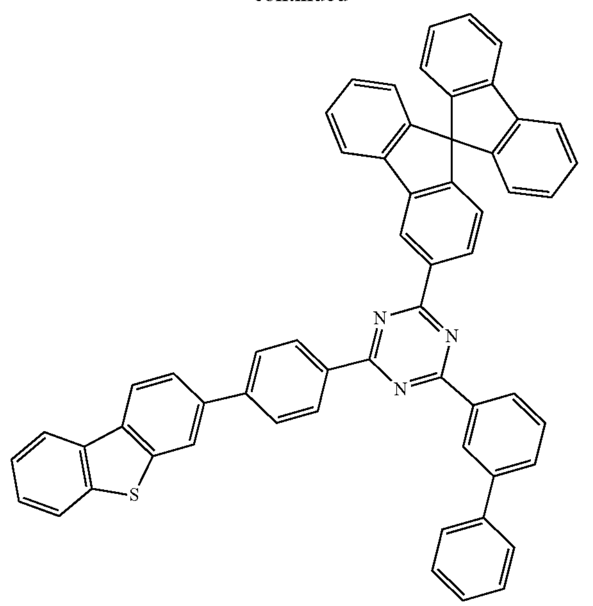
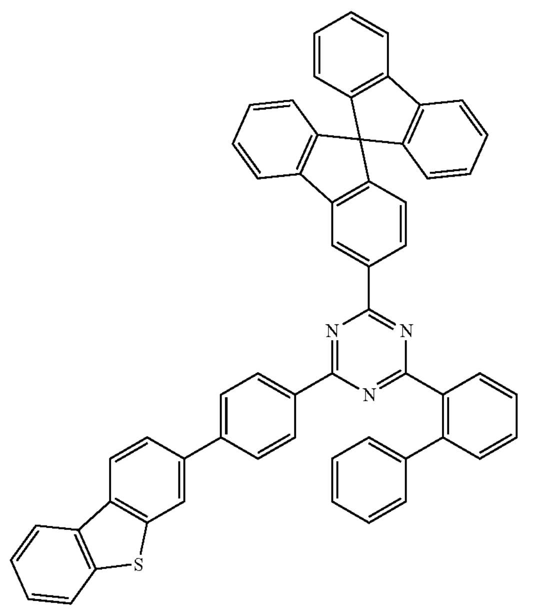
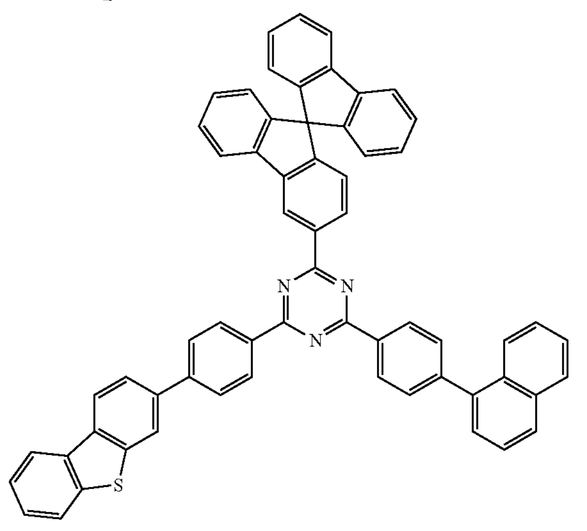
-continued
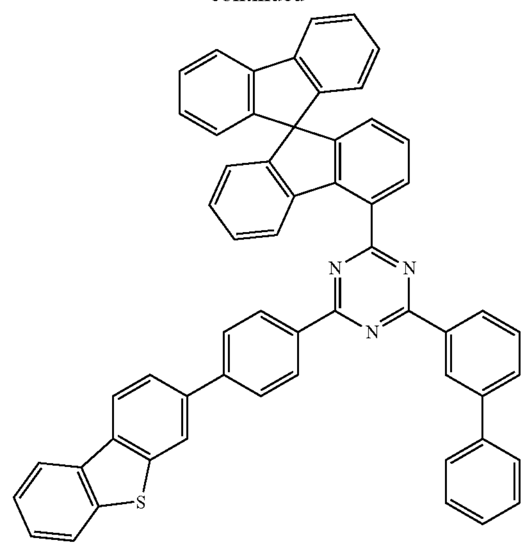
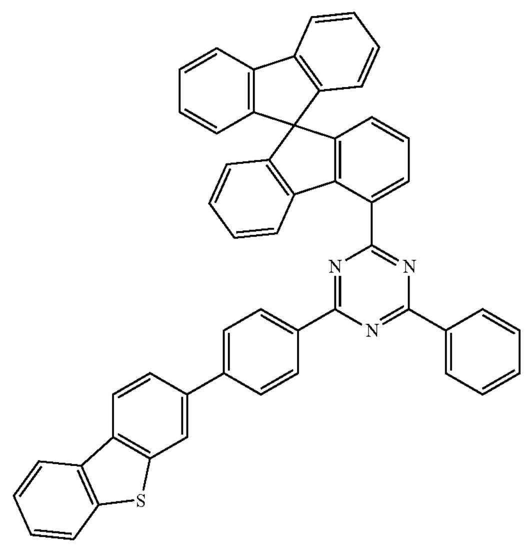
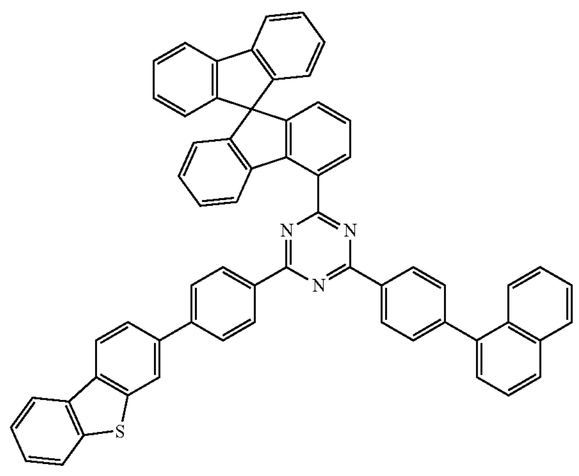

-continued
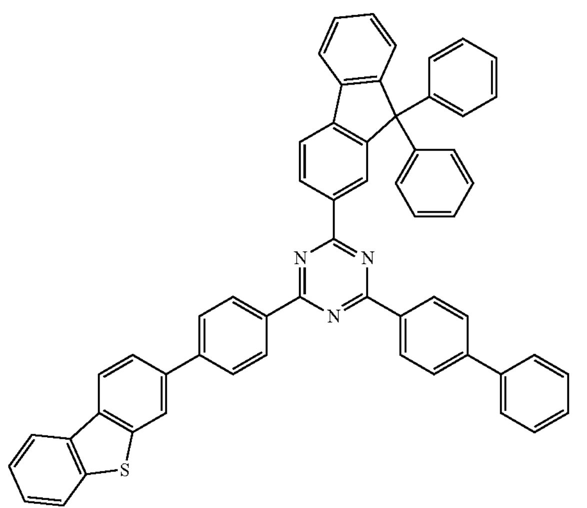
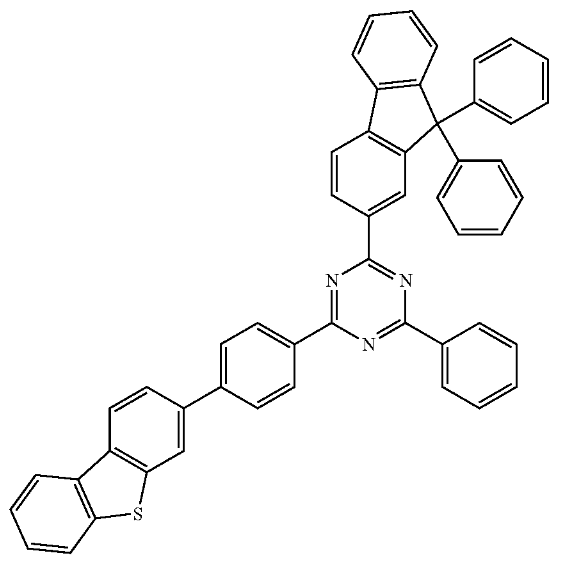
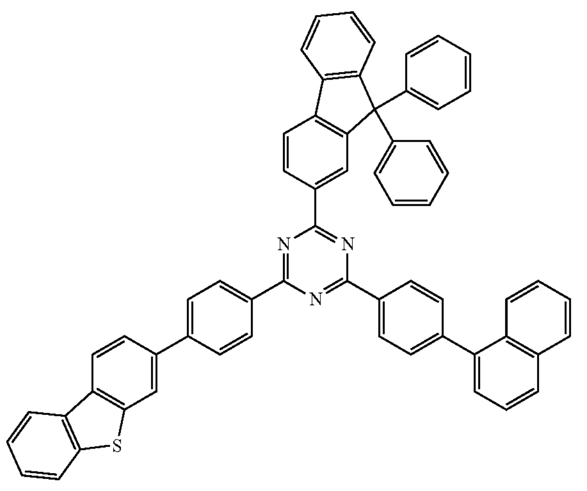
-continued
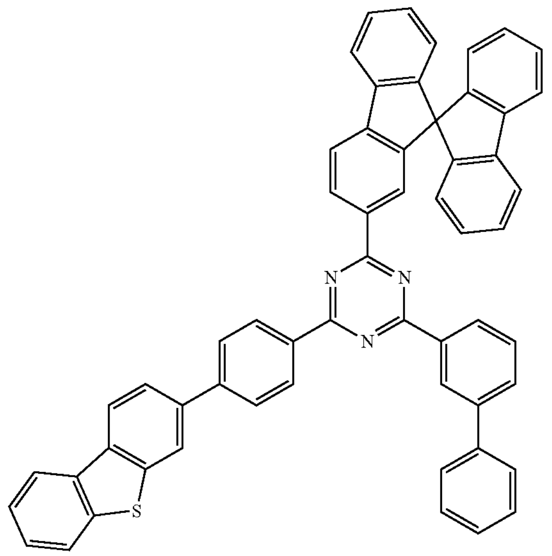
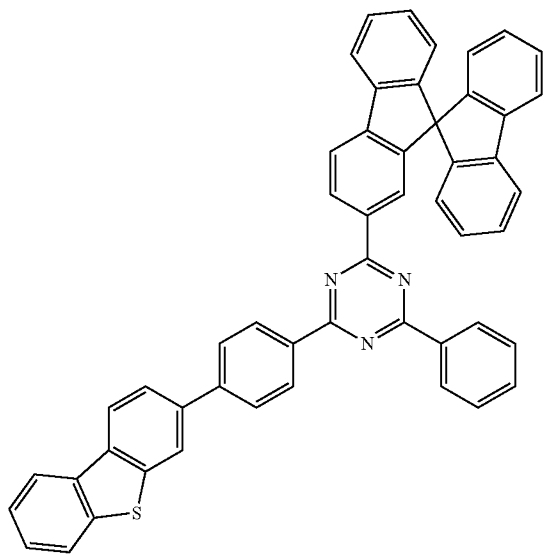
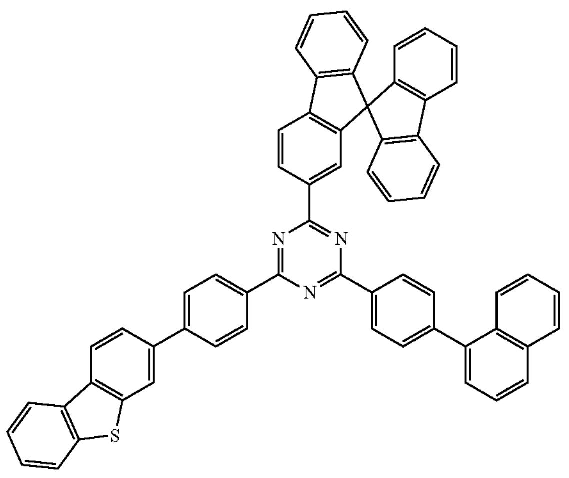

-continued
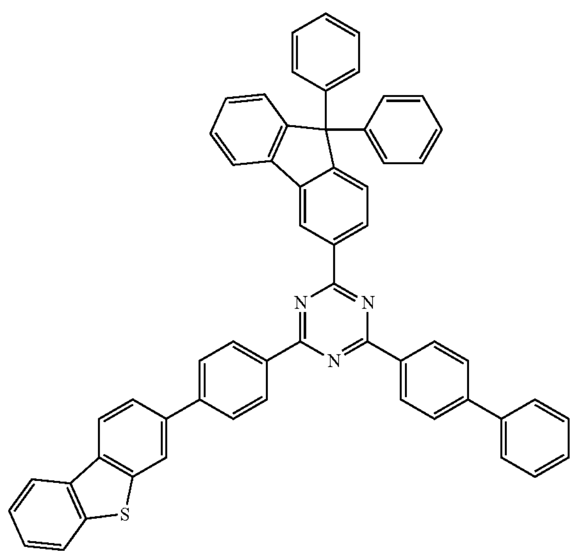
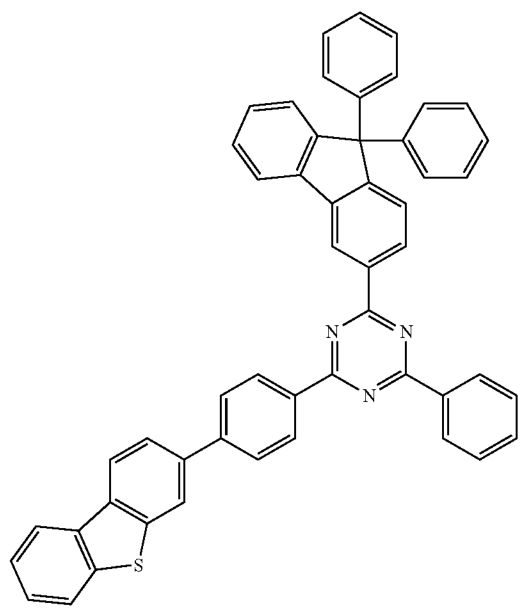
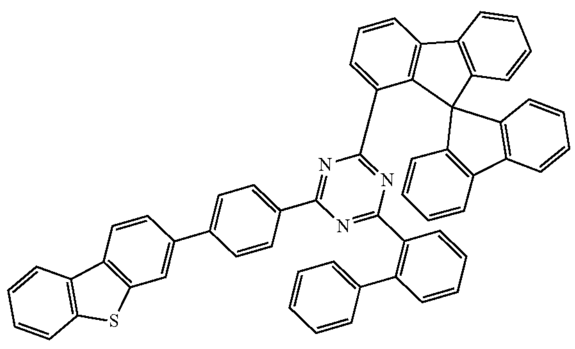
-continued
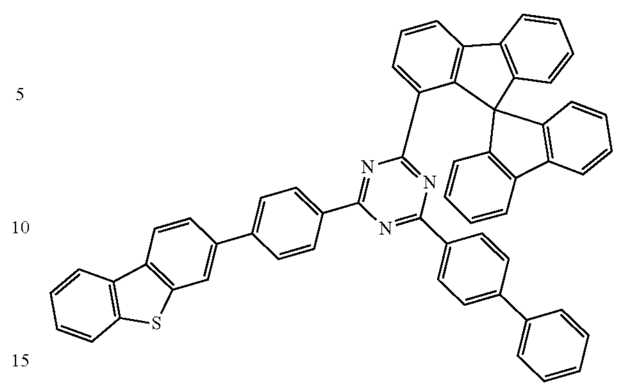
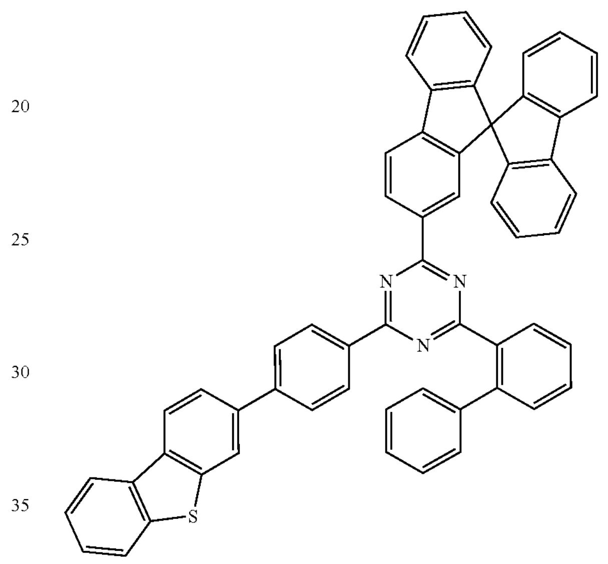
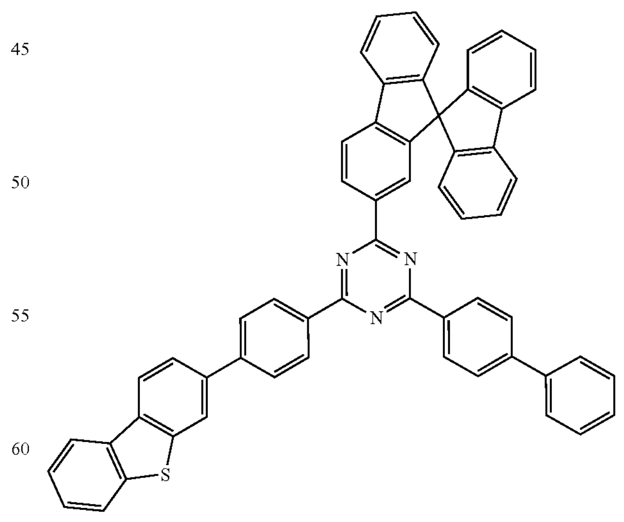

-continued
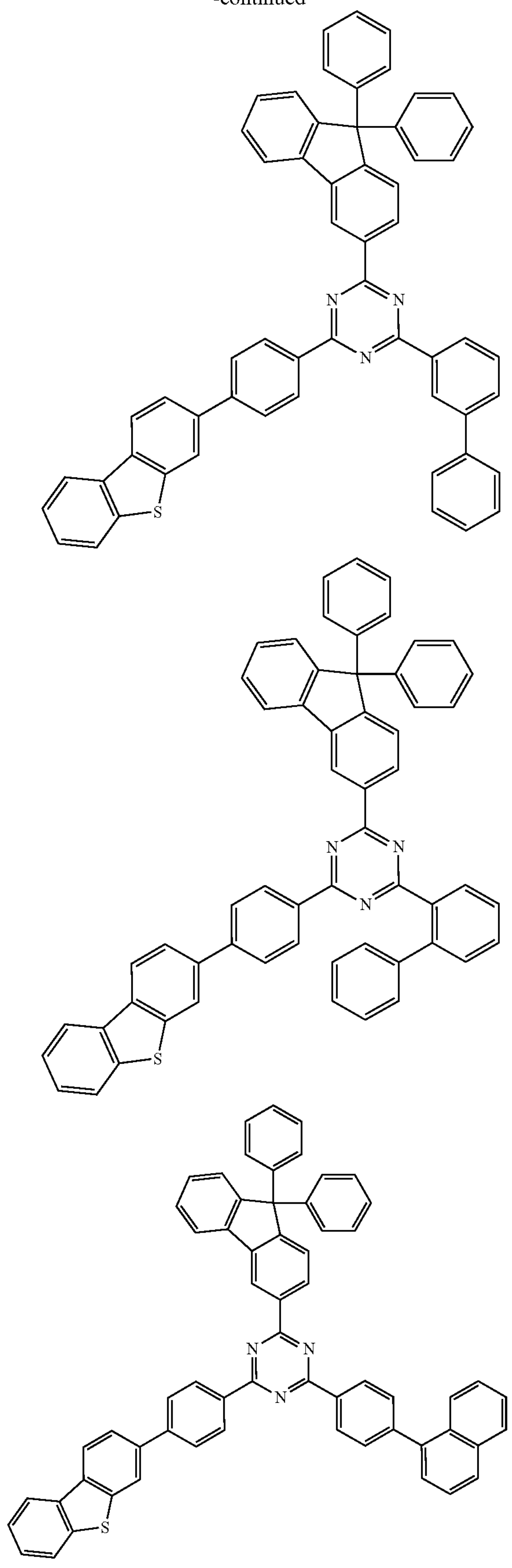
-continued
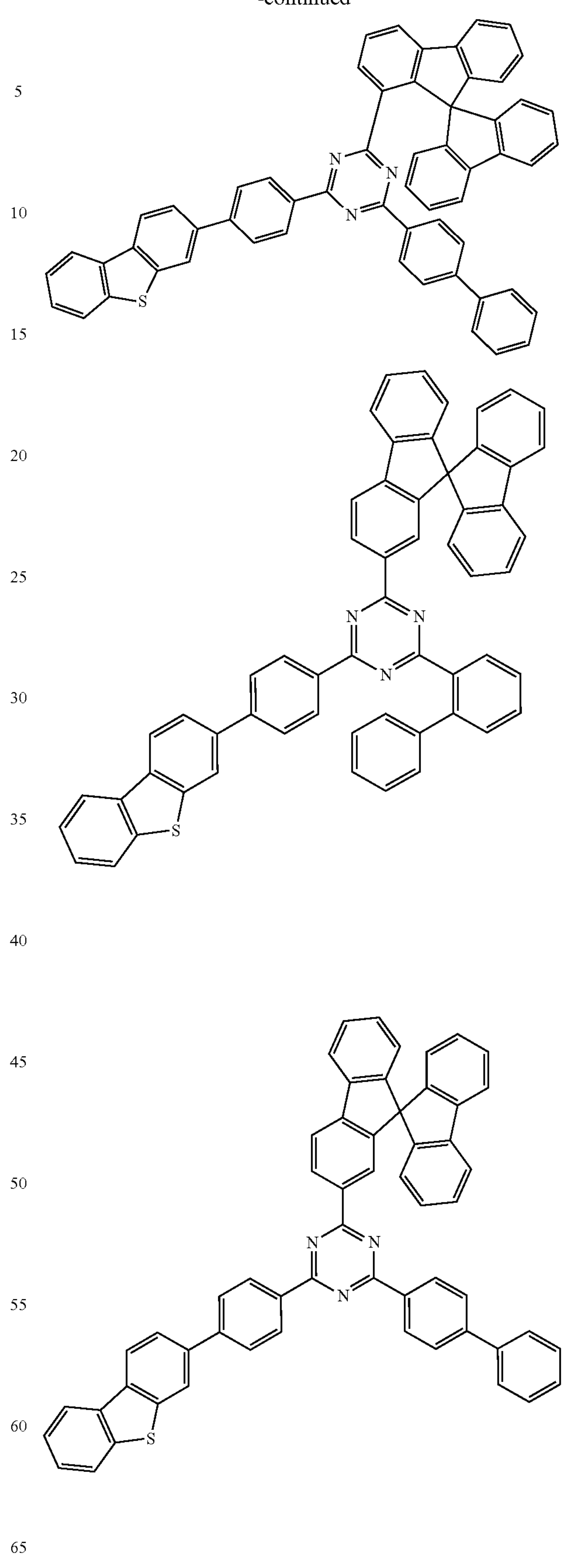

-continued
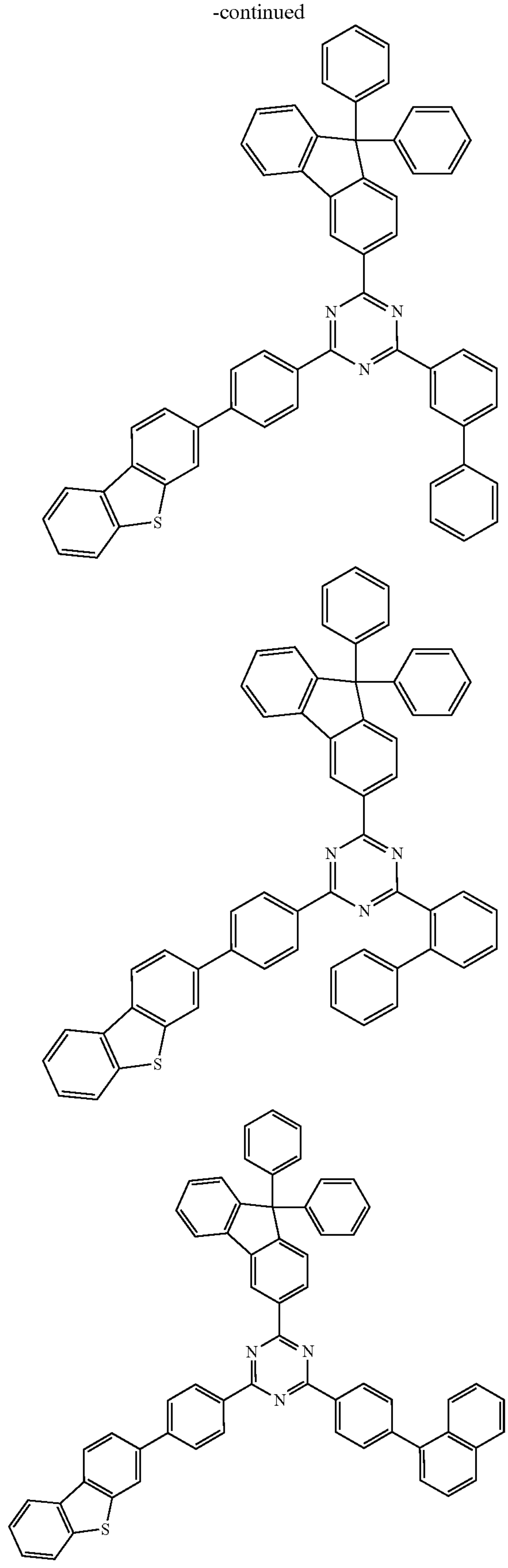
-continued
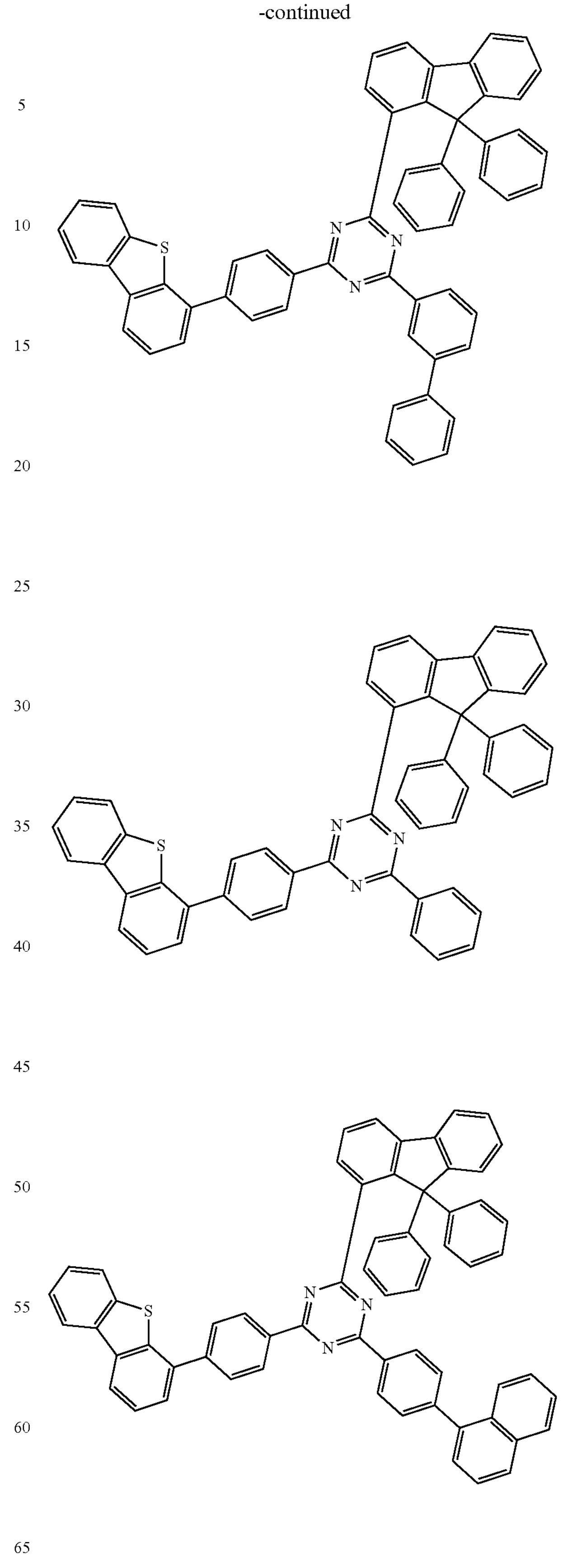

-continued
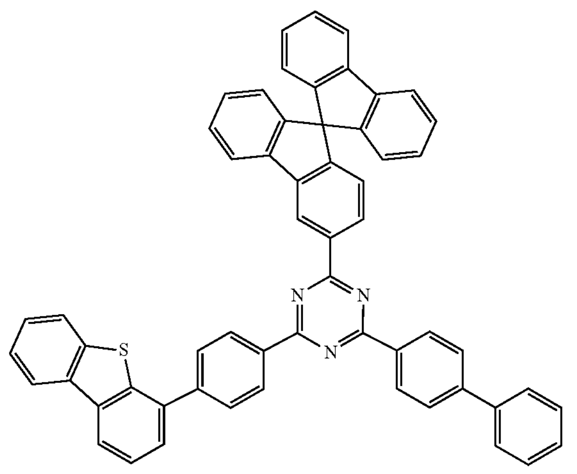
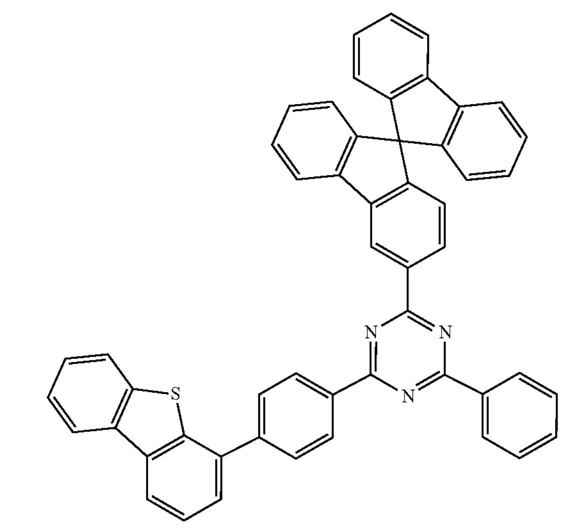
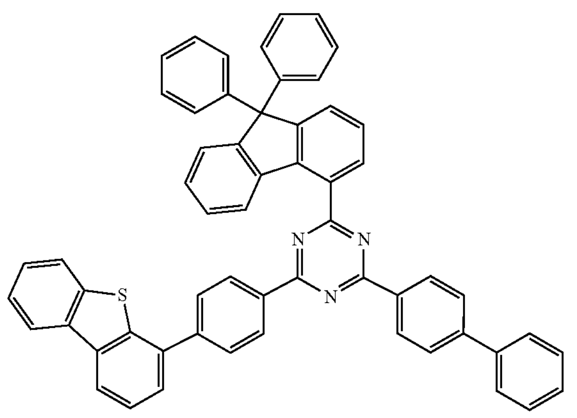
-continued
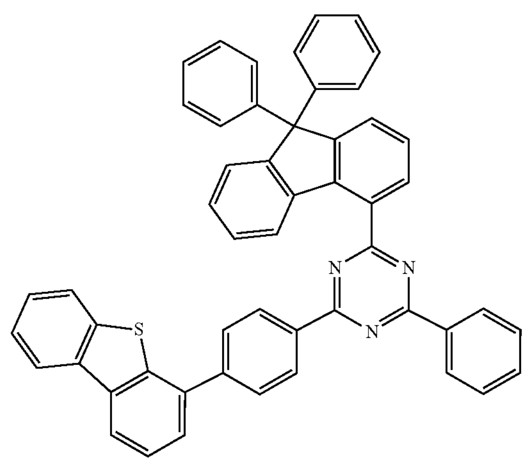
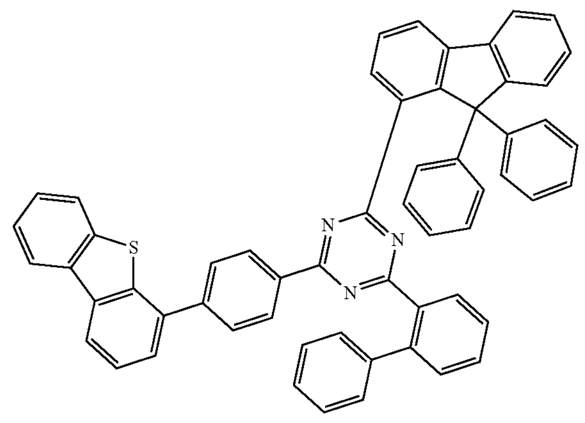
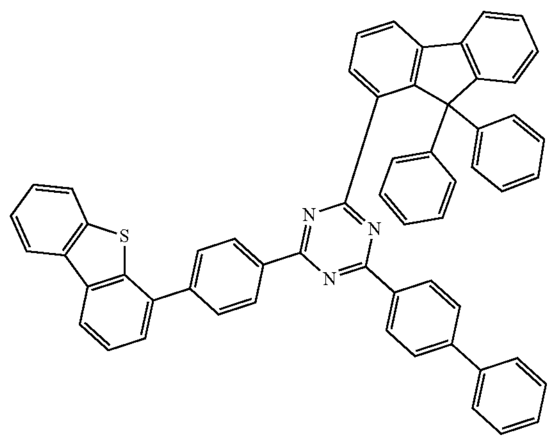

-continued
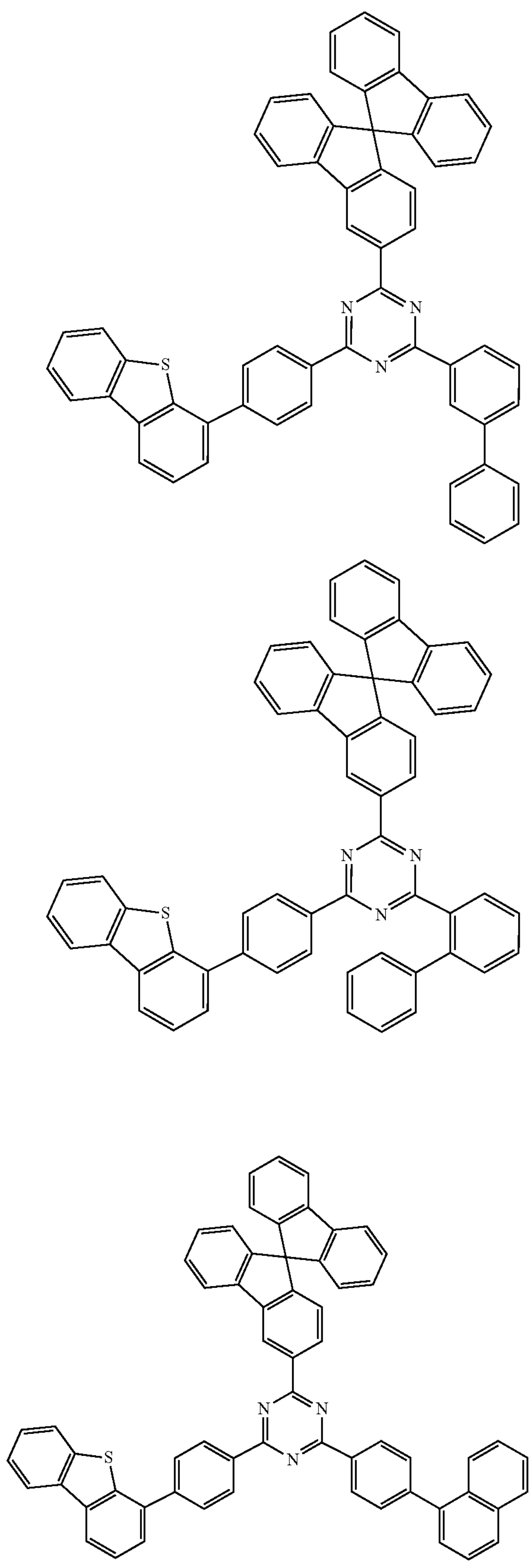
-continued
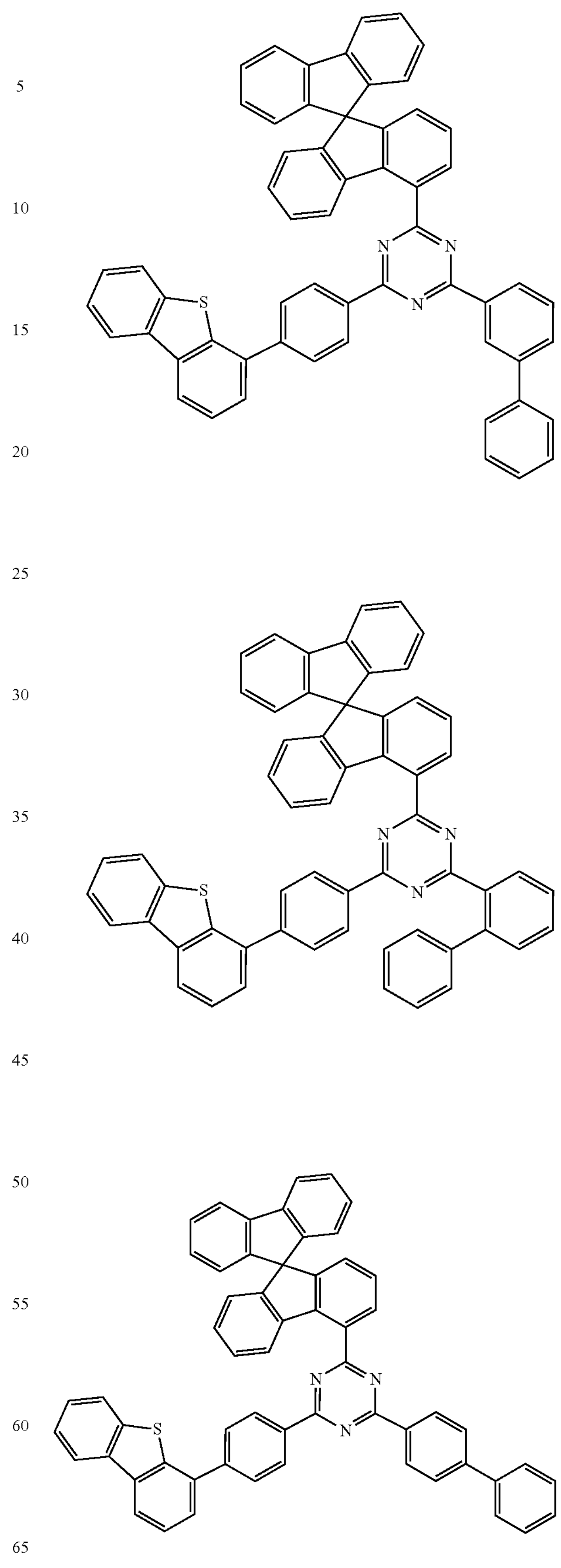

-continued
-continued

-continued
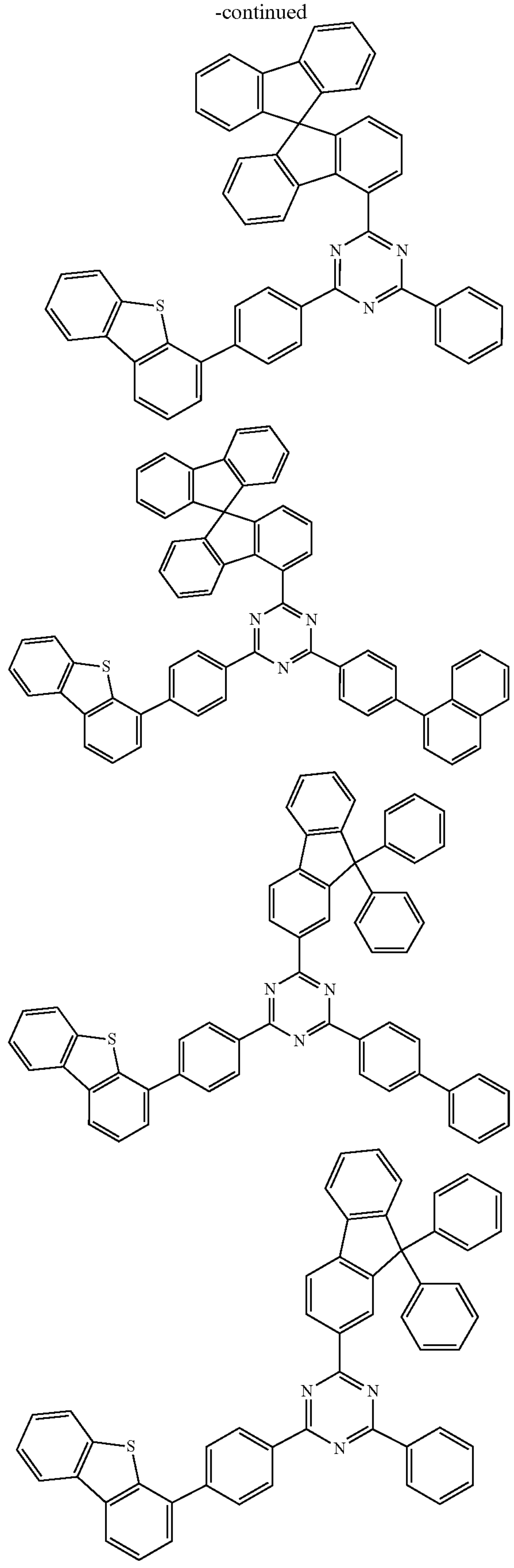
-continued
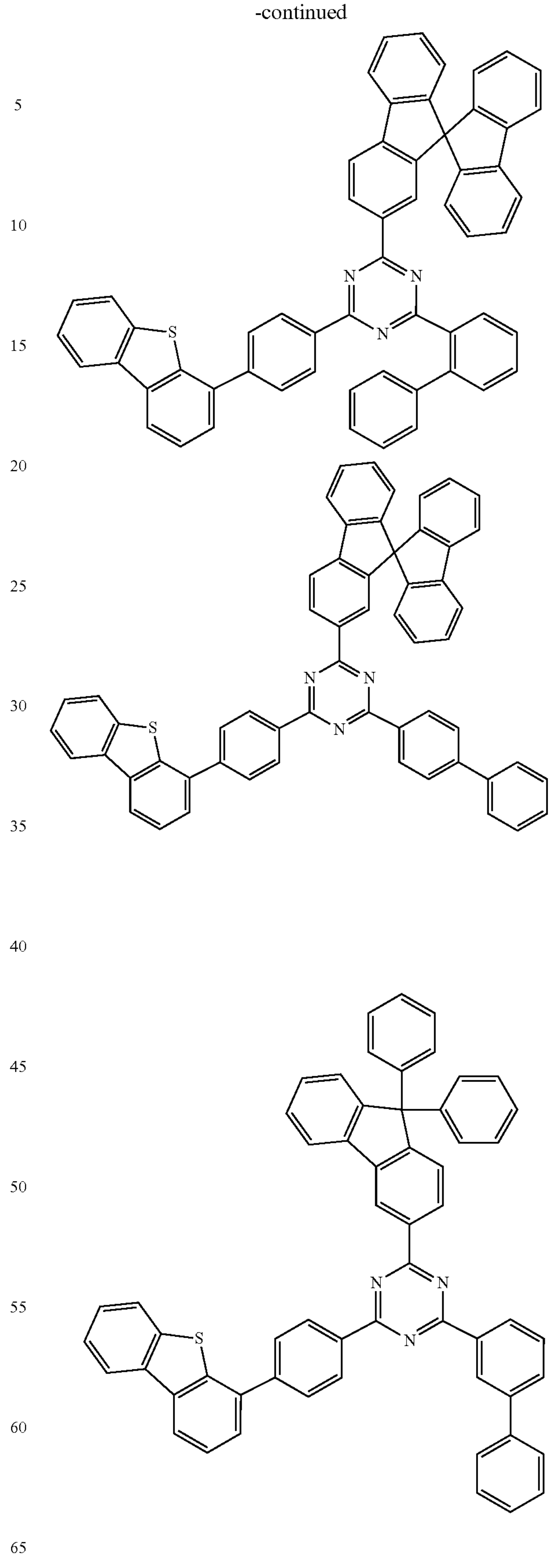

-continued
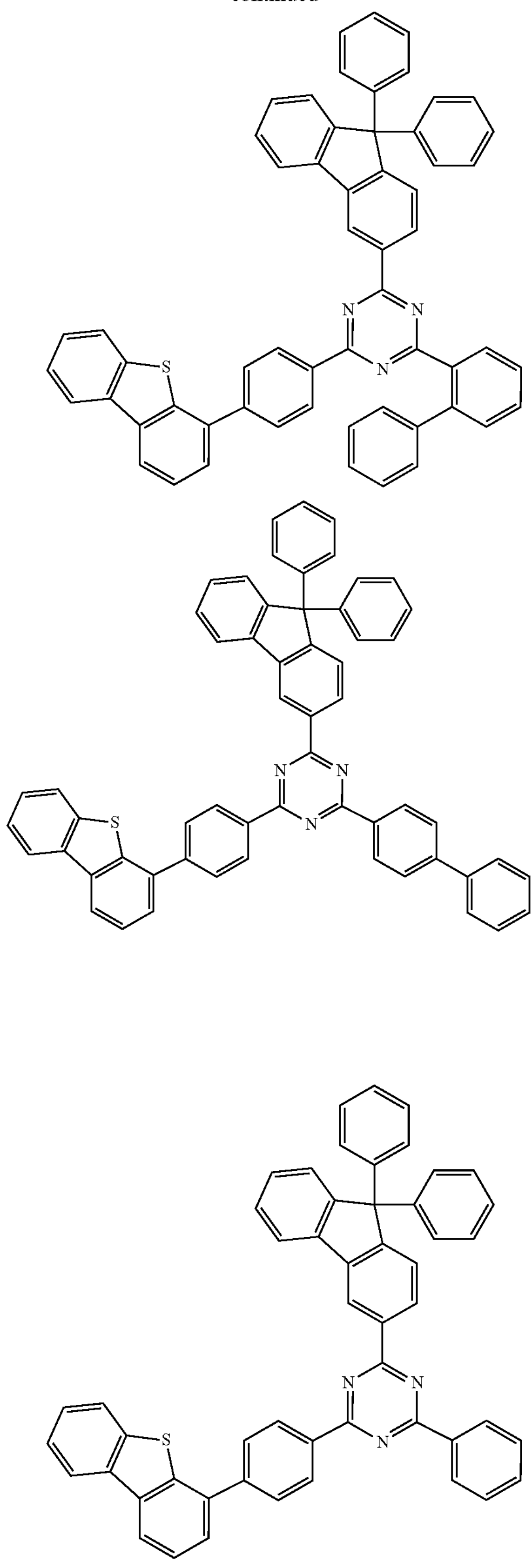
-continued
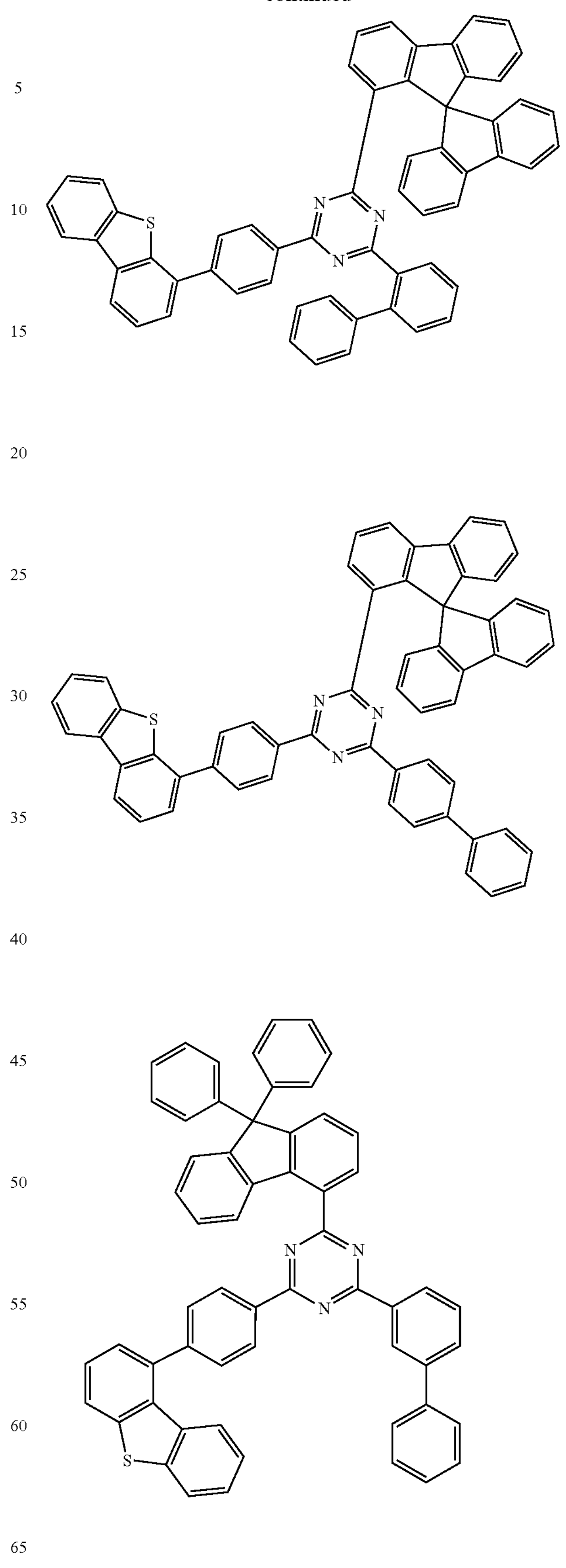

-continued
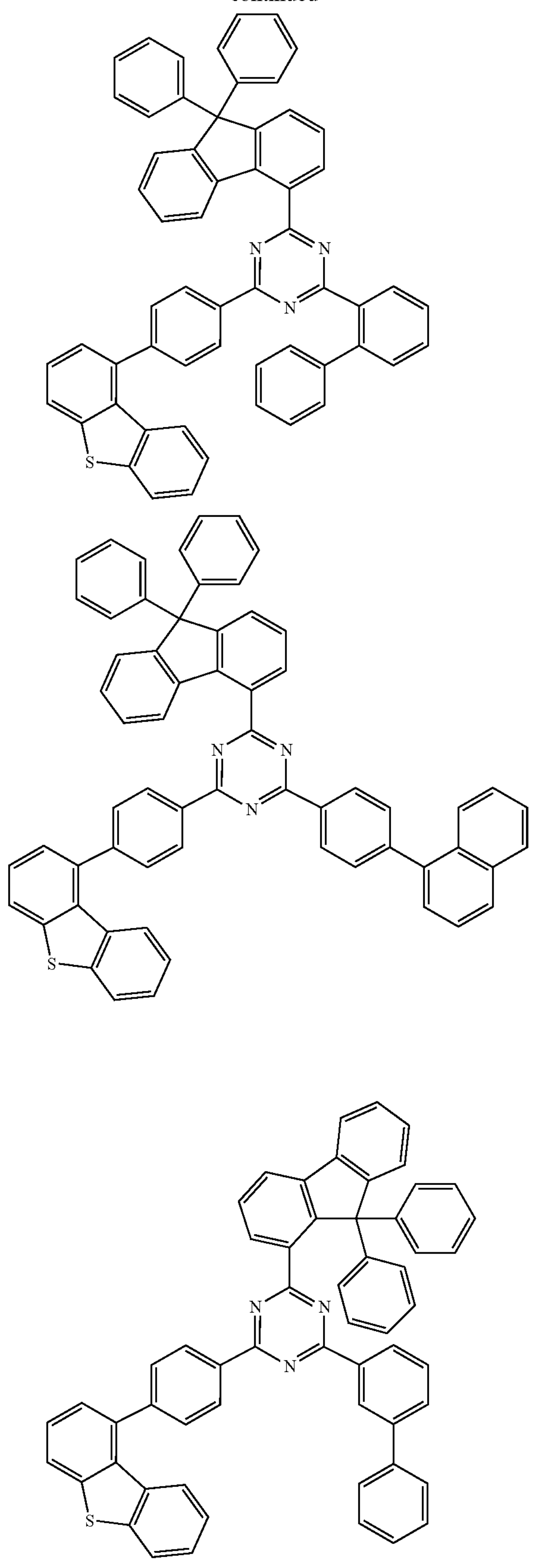
-continued
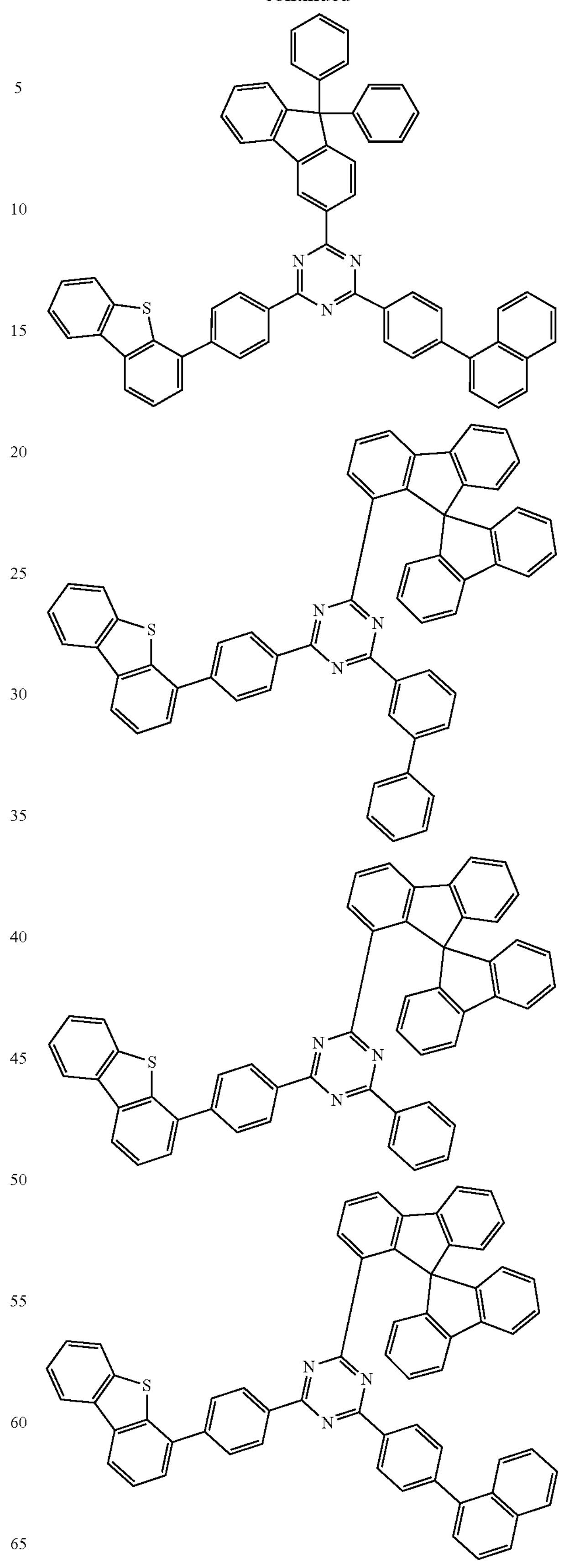

-continued
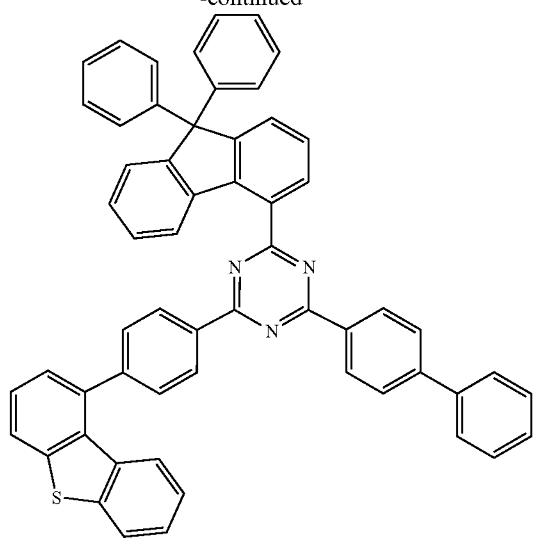
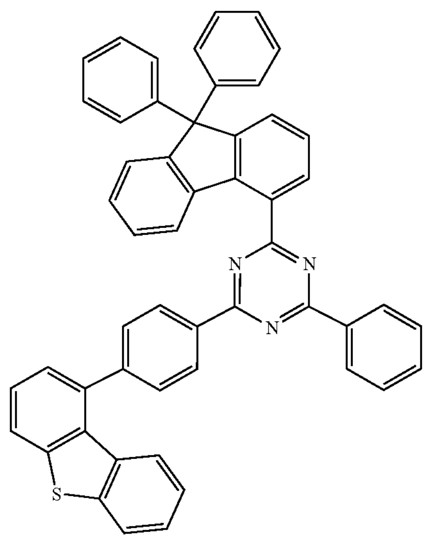
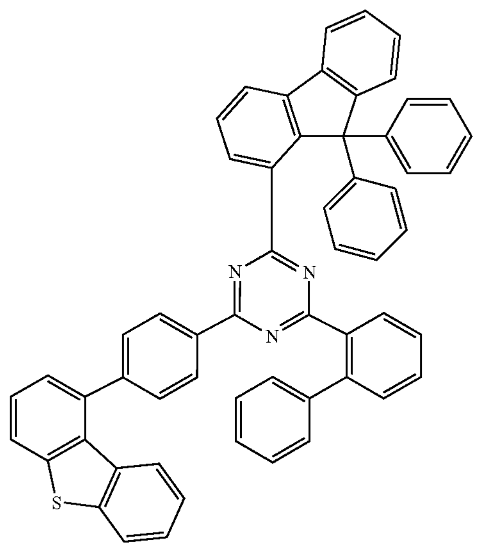
-continued
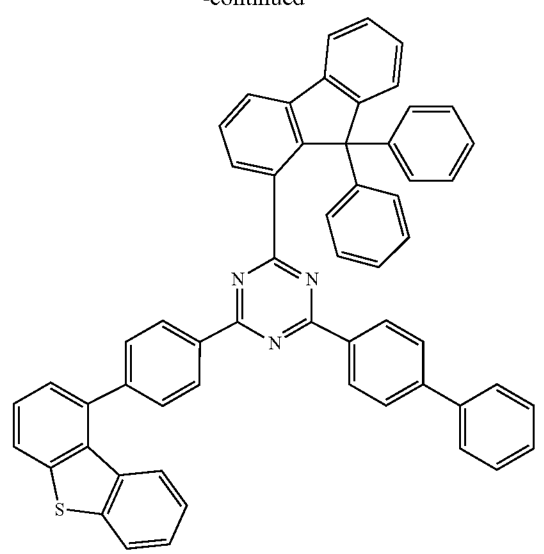
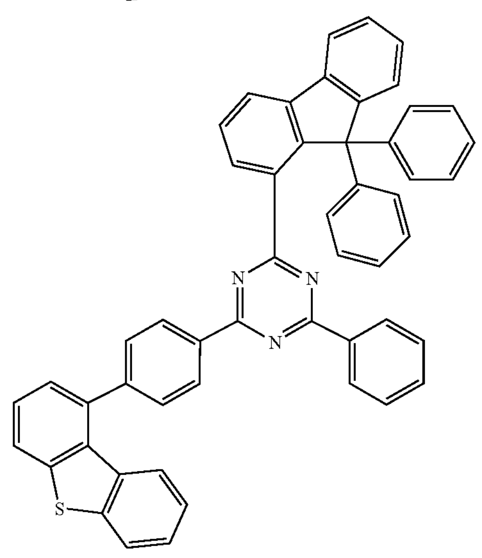
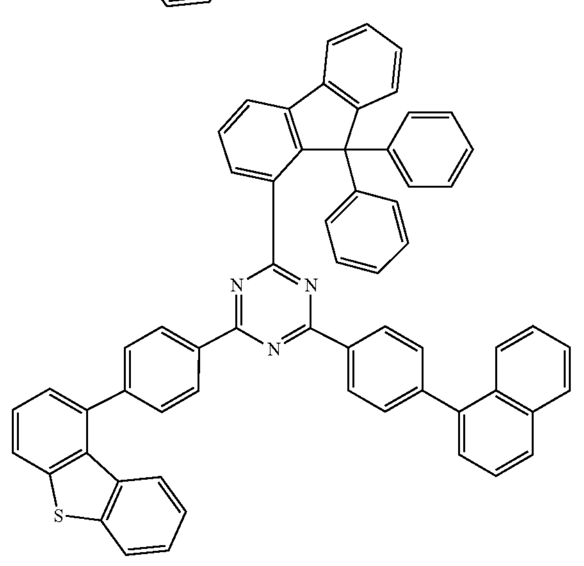

-continued
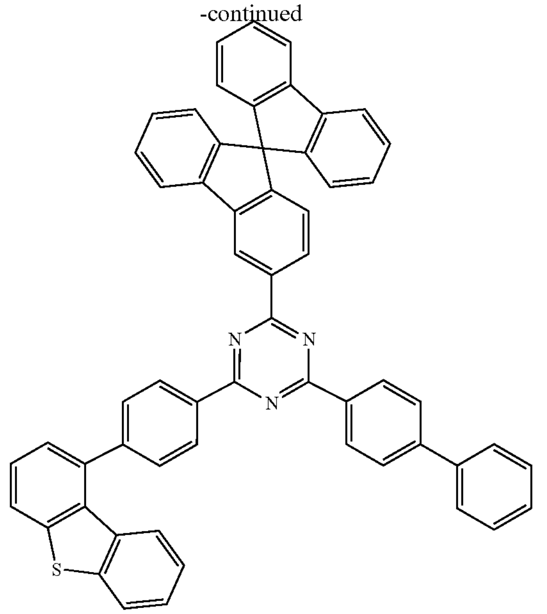
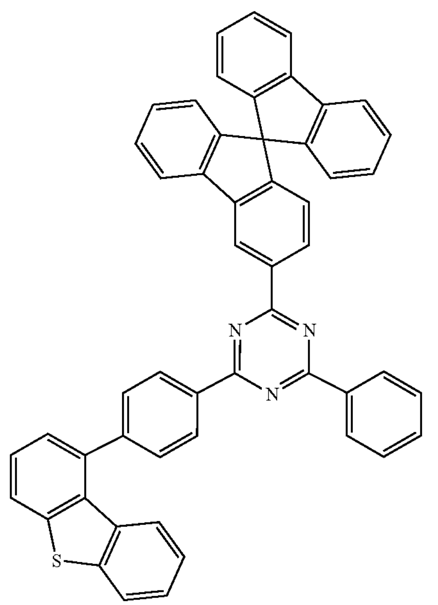
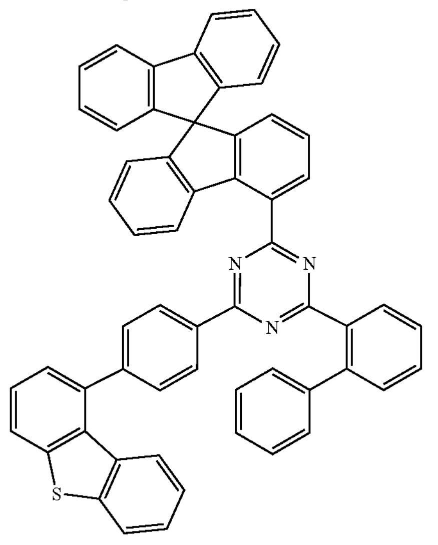
-continued
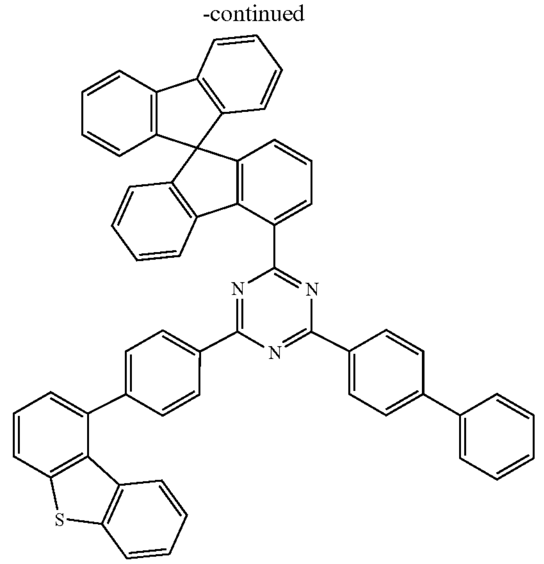
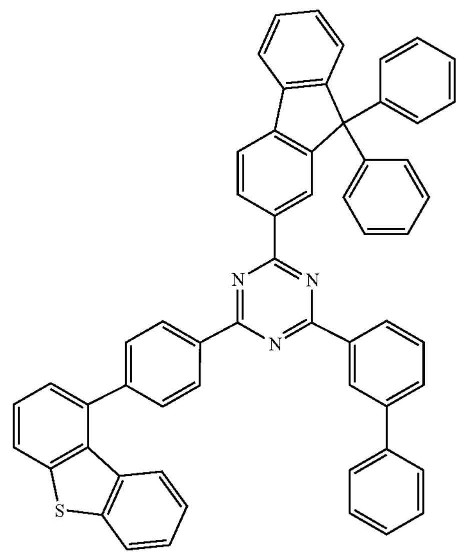
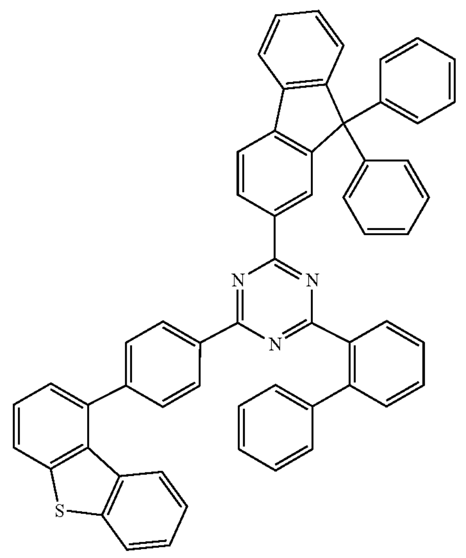

-continued
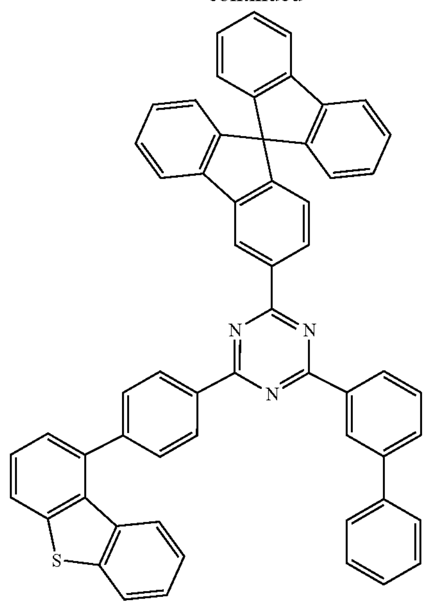
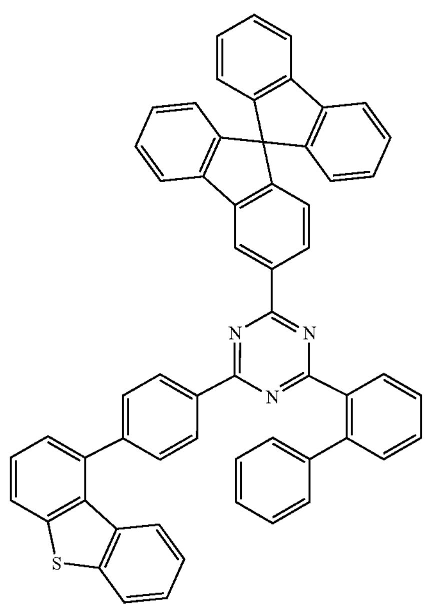
-continued
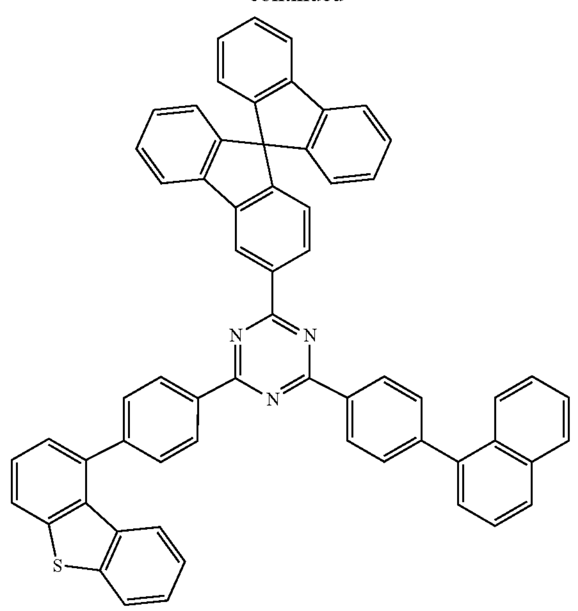
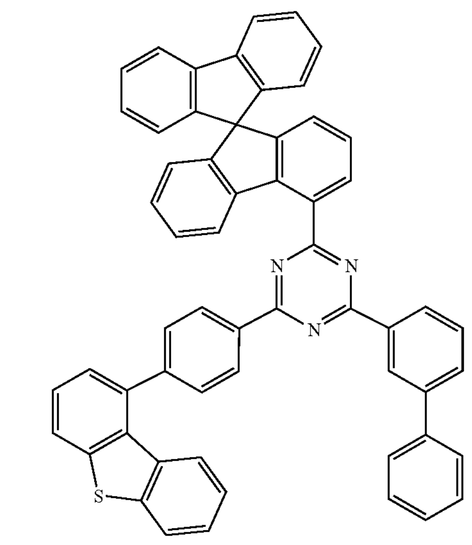

-continued
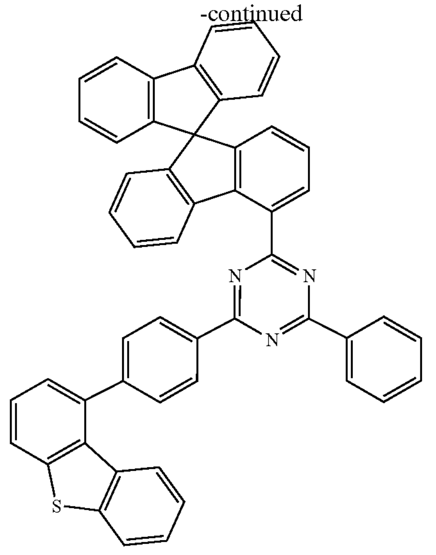
-continued
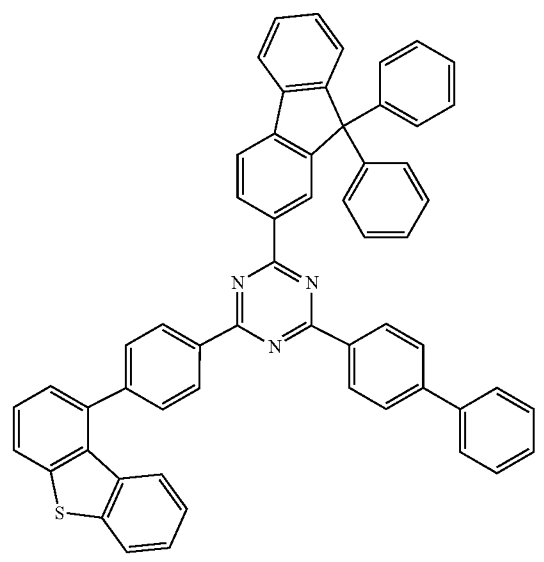
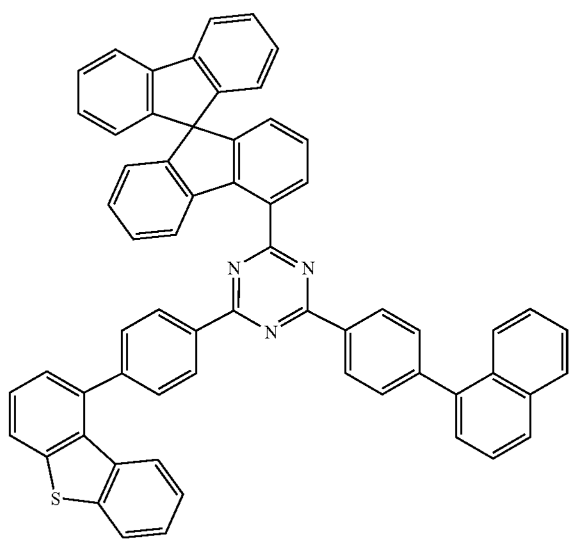
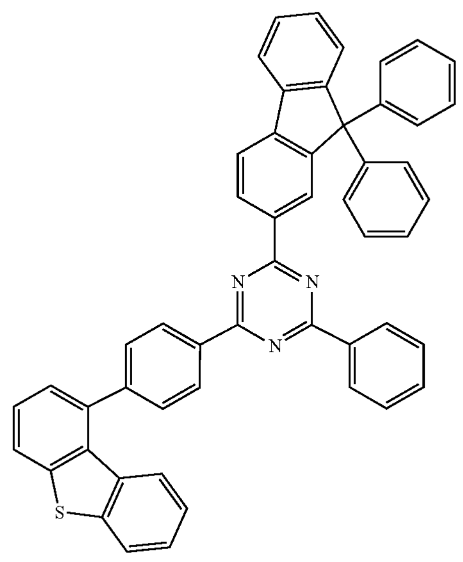

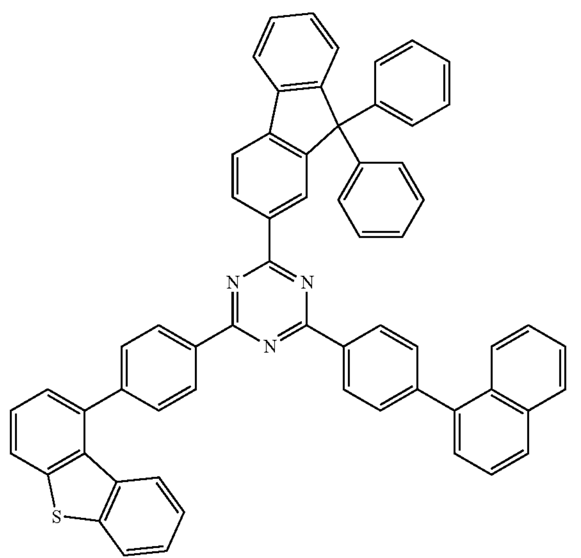
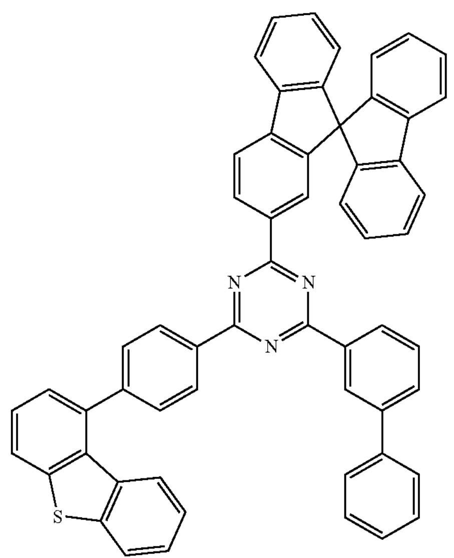
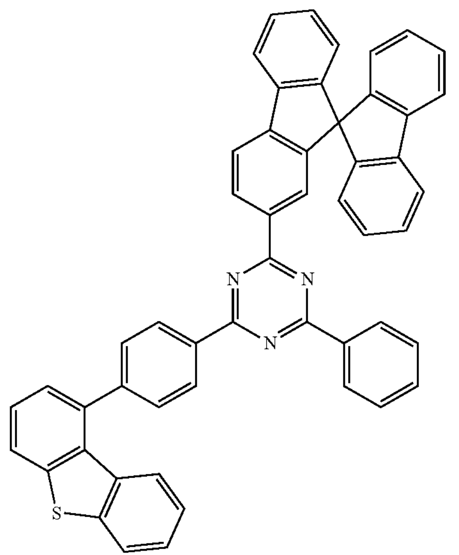
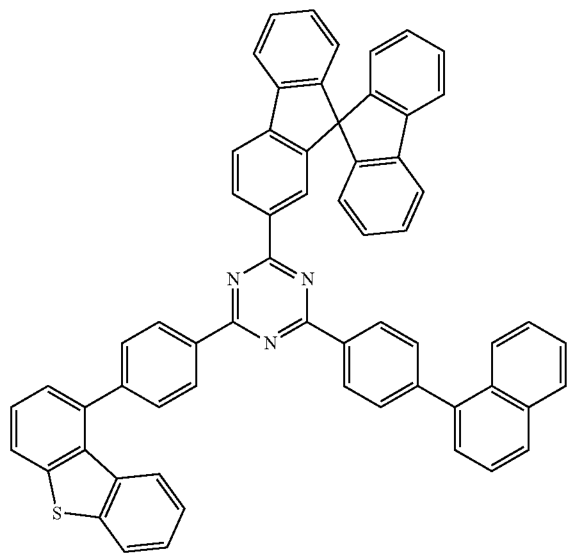
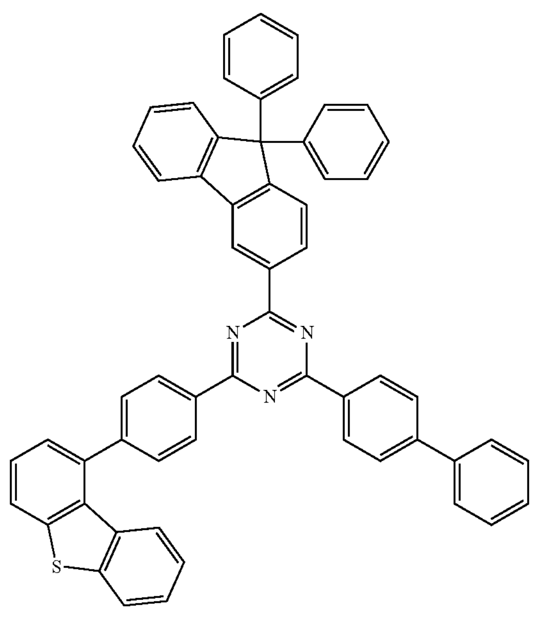
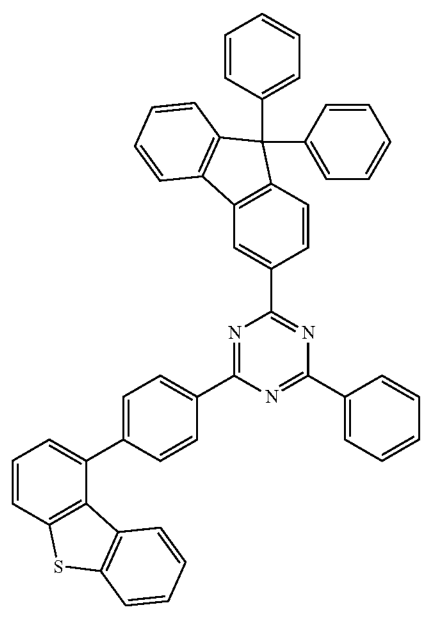

-continued
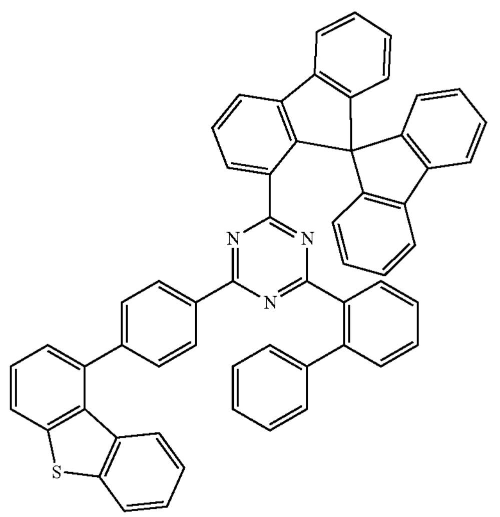
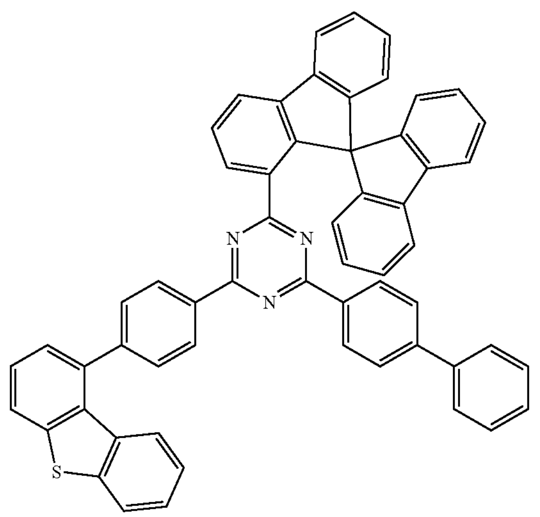
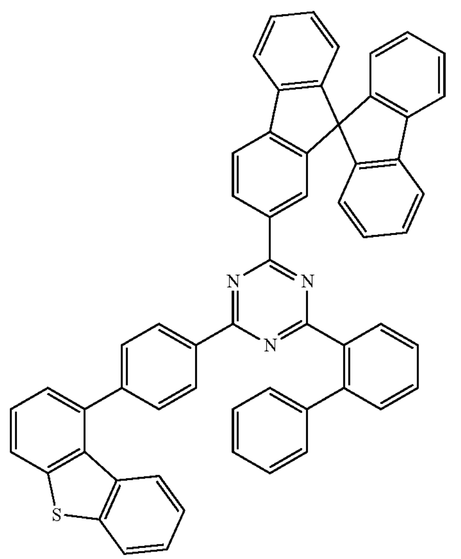
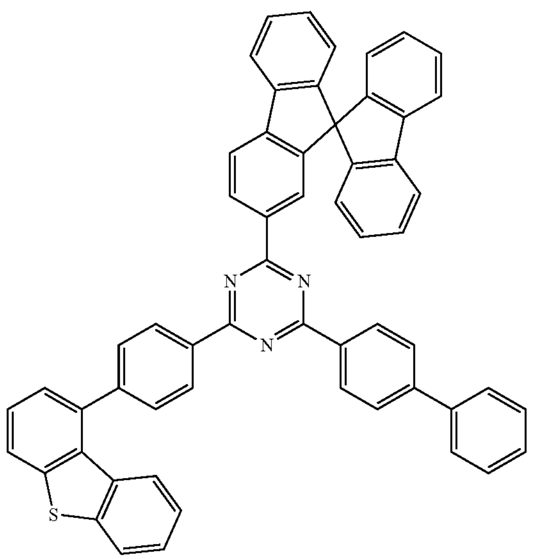
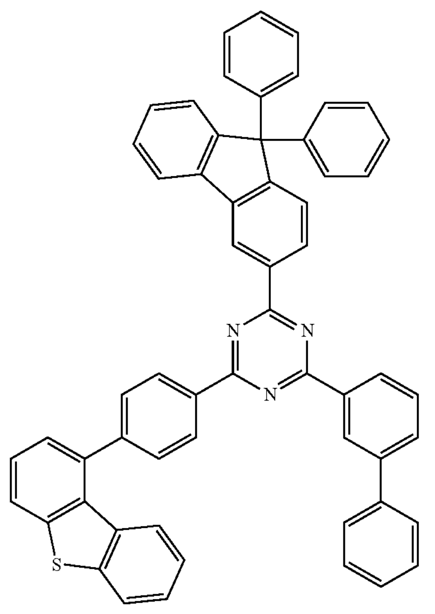
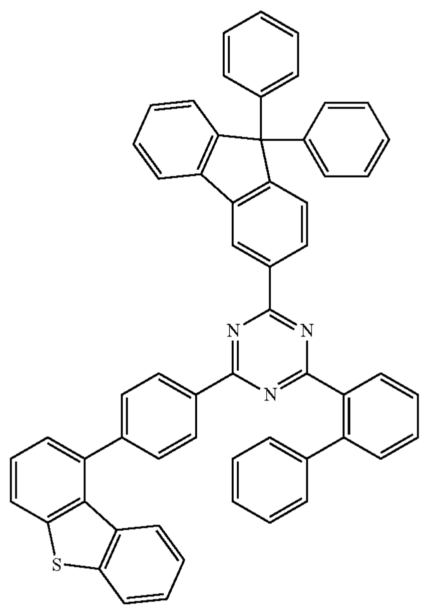

-continued
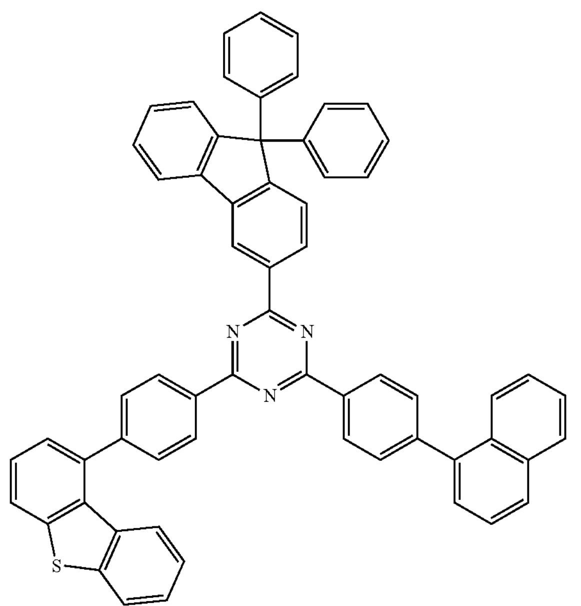
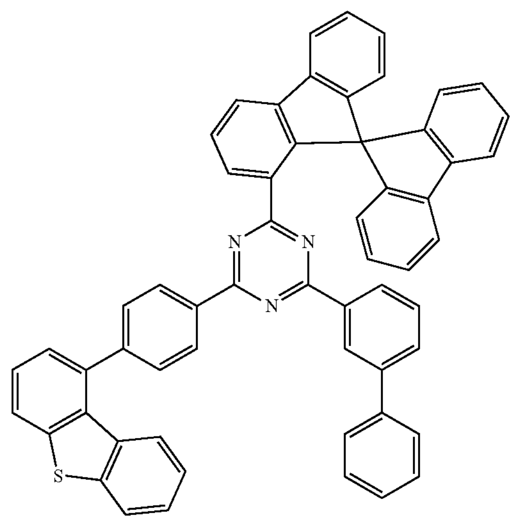
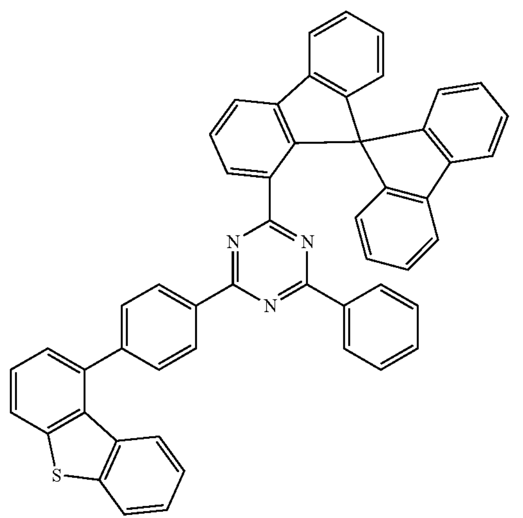
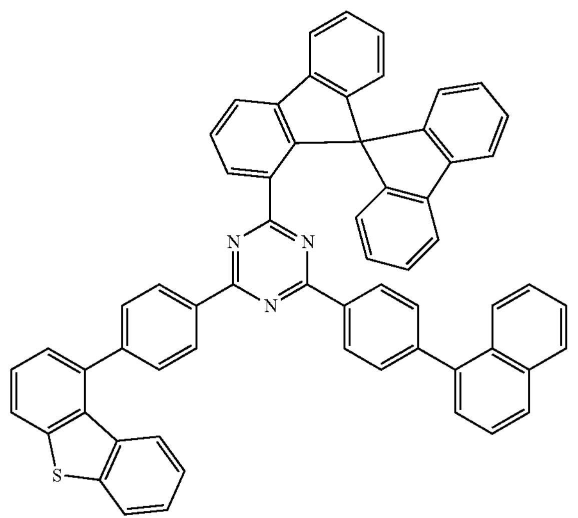
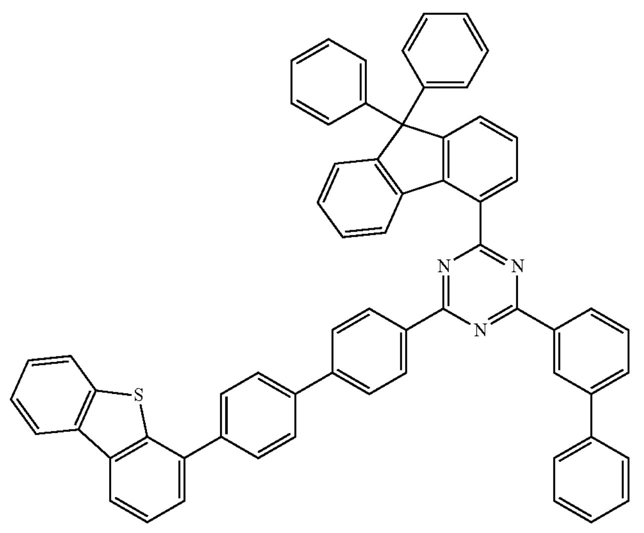

-continued
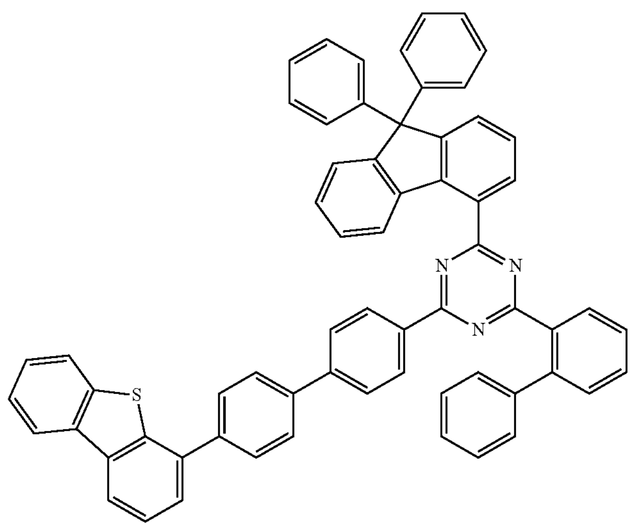
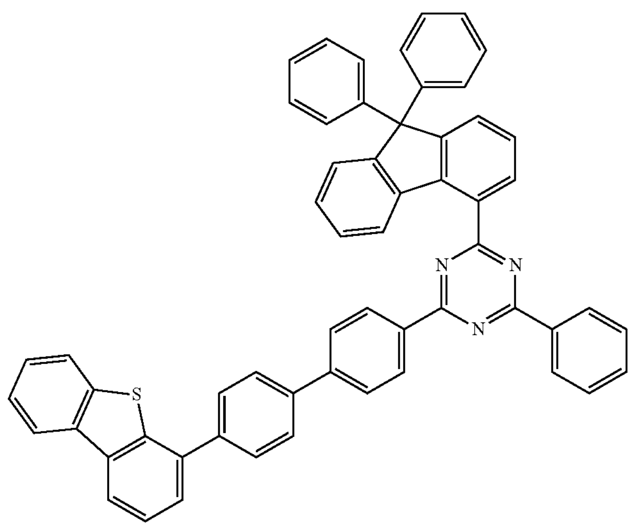
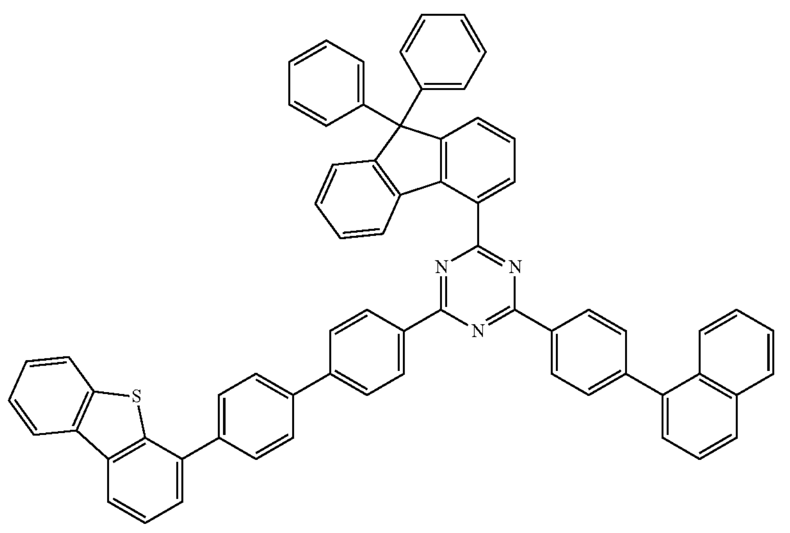

-continued
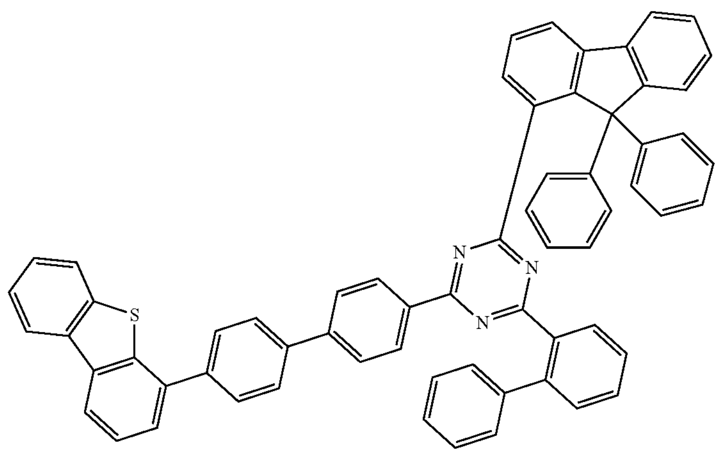
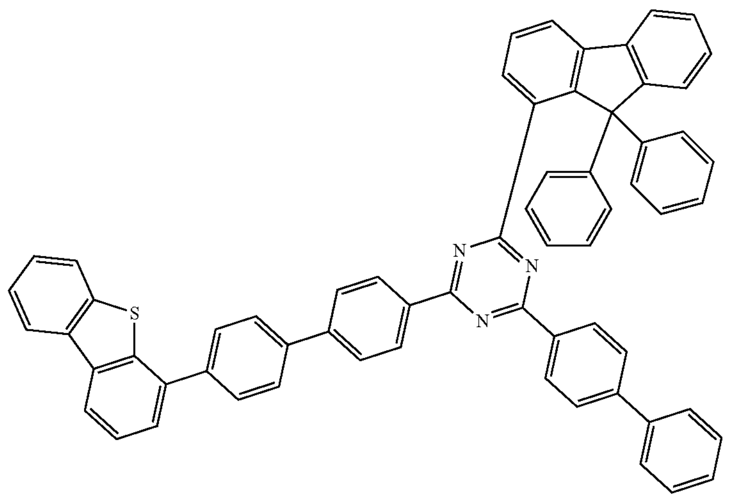
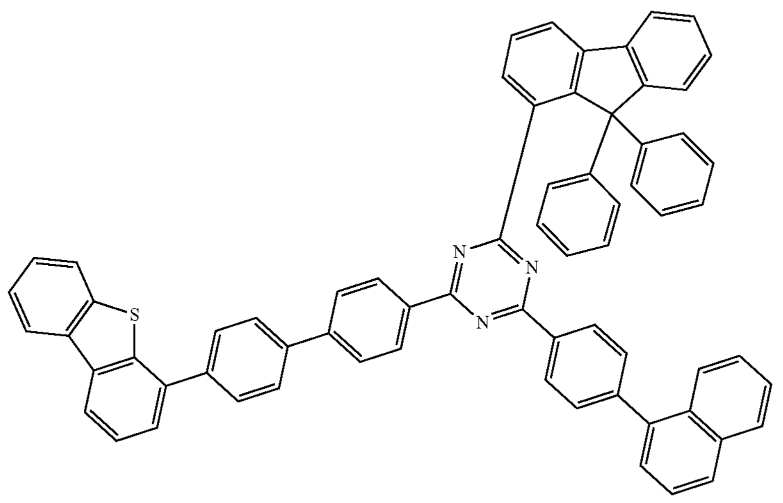

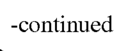
-continued

-continued
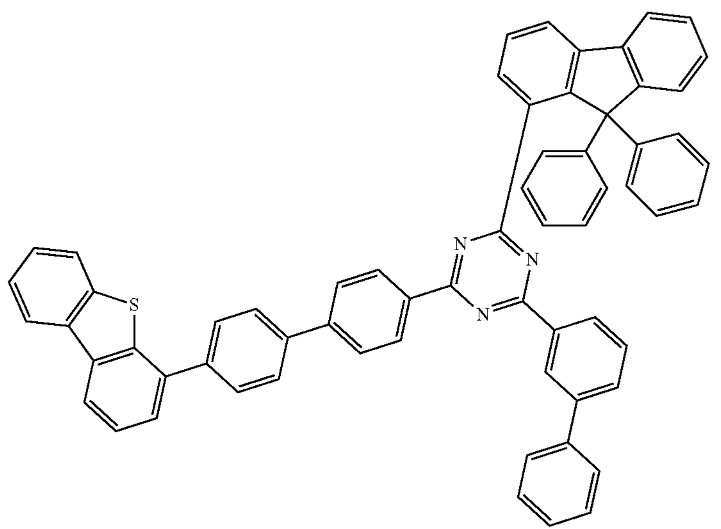
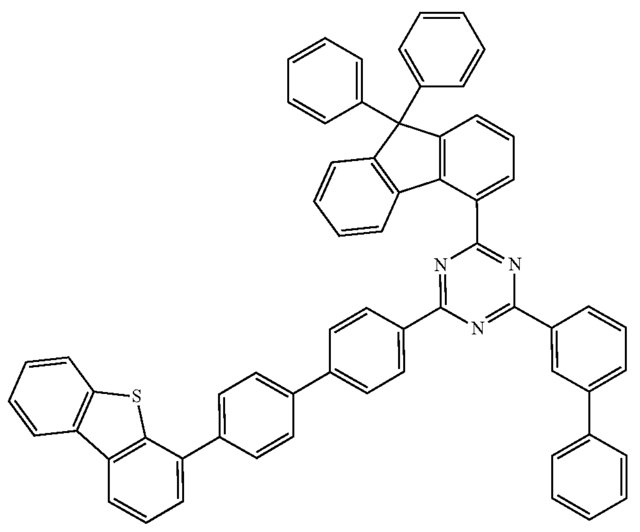
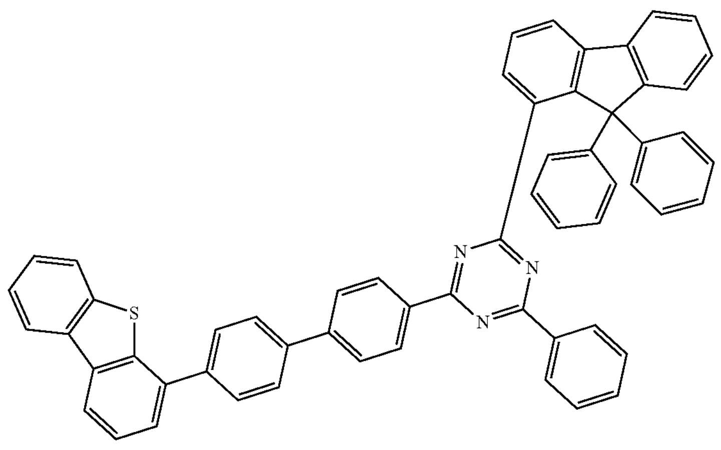

-continued
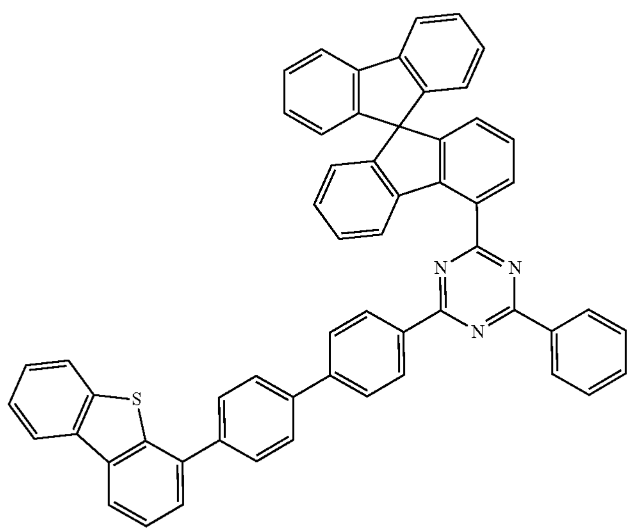
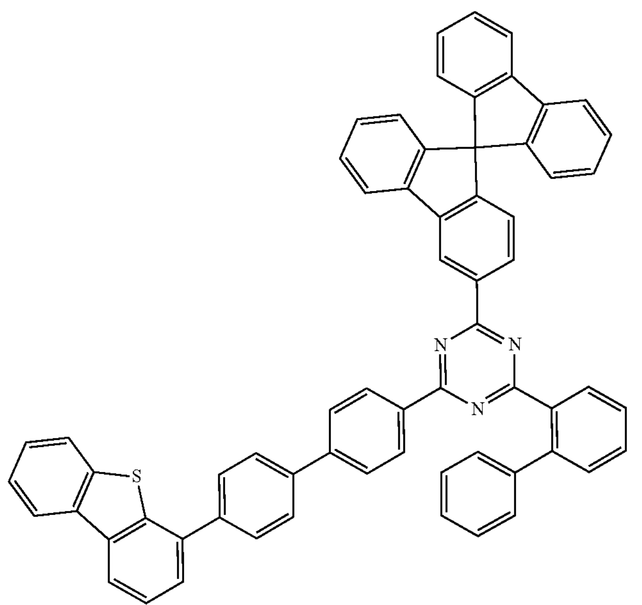
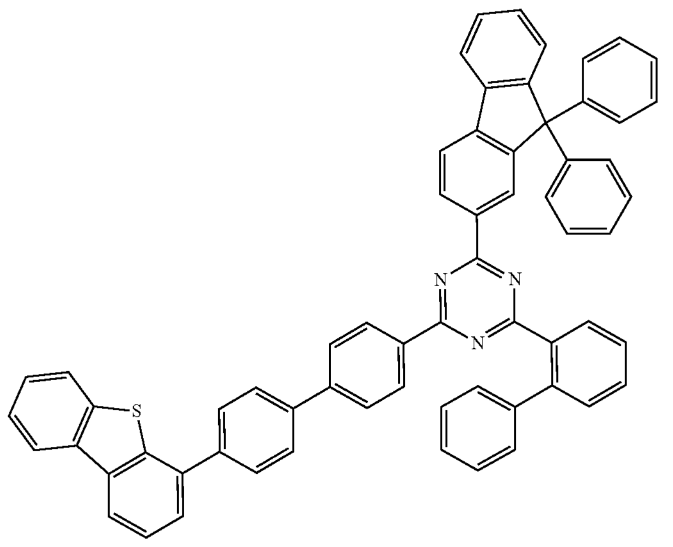

-continued
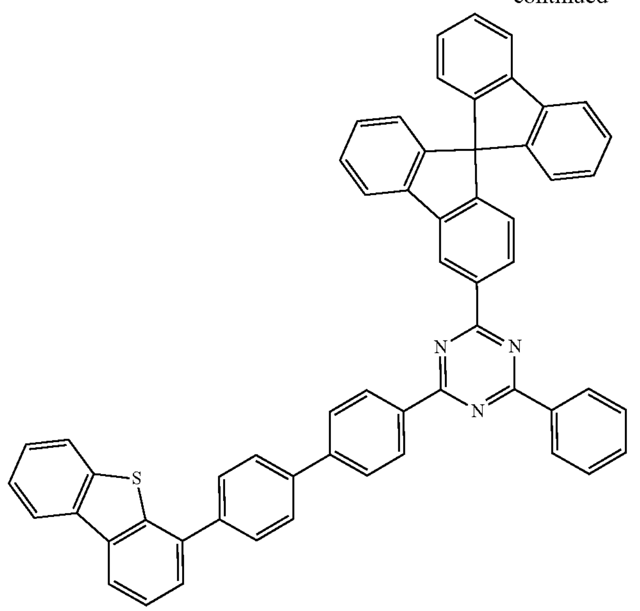
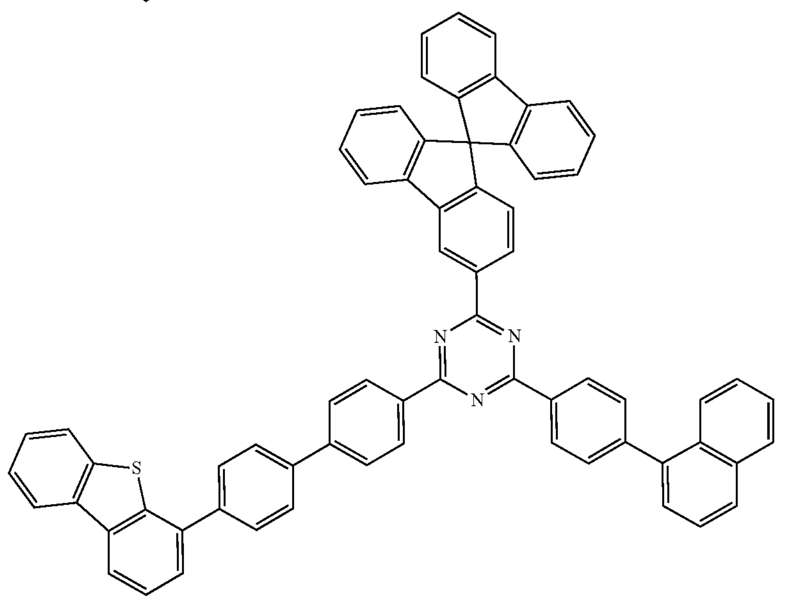
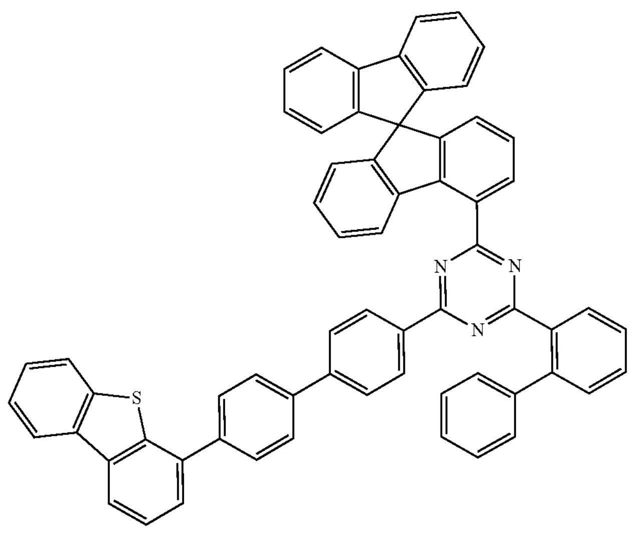

-continued
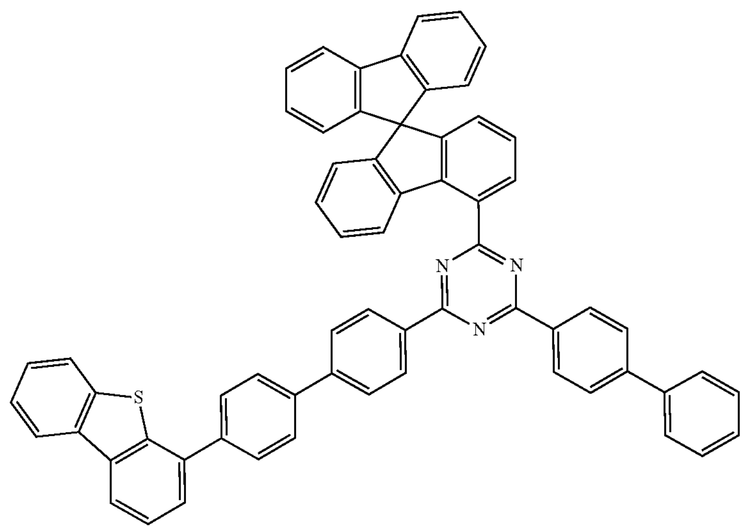
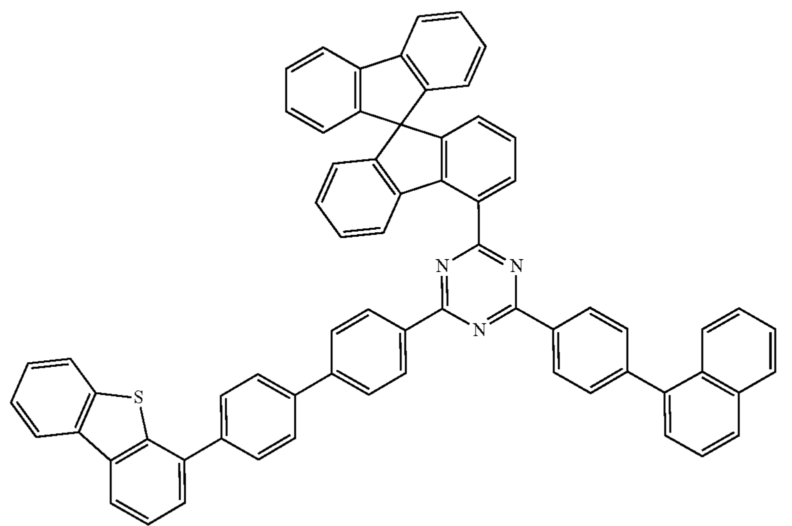
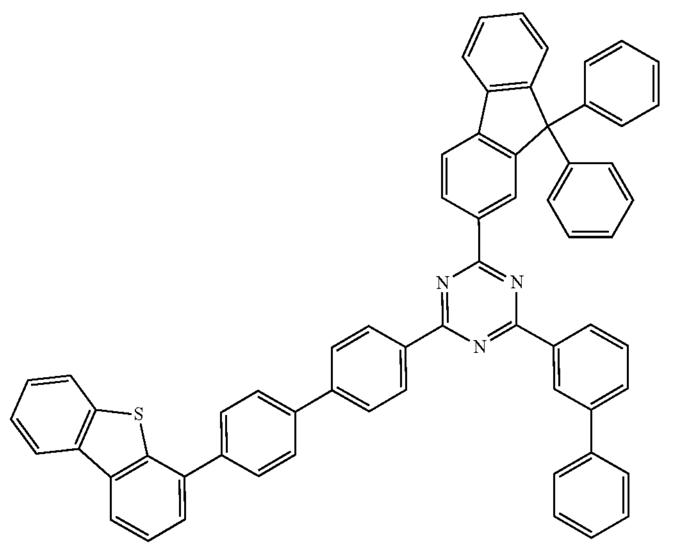

-continued
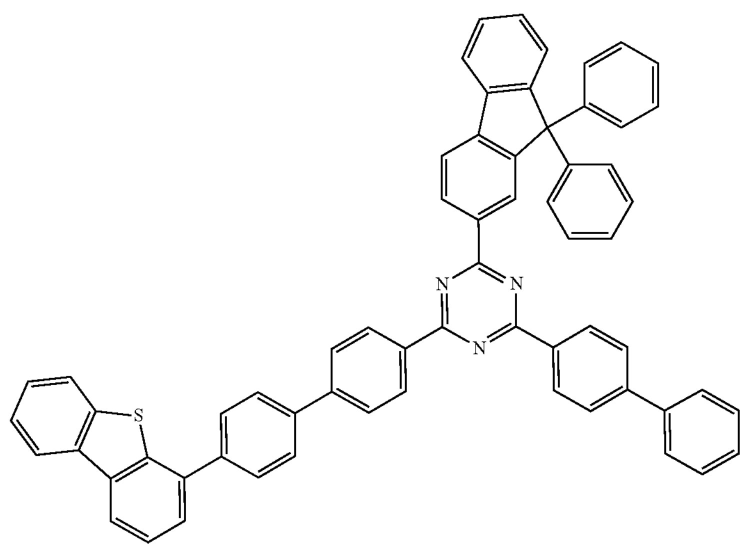
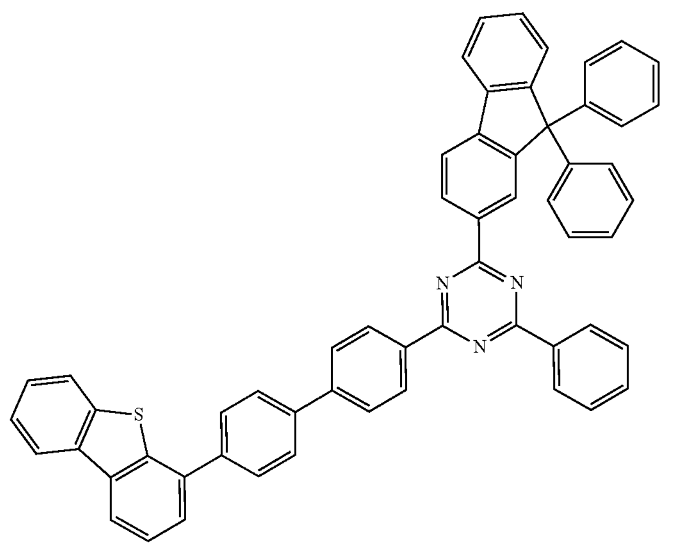
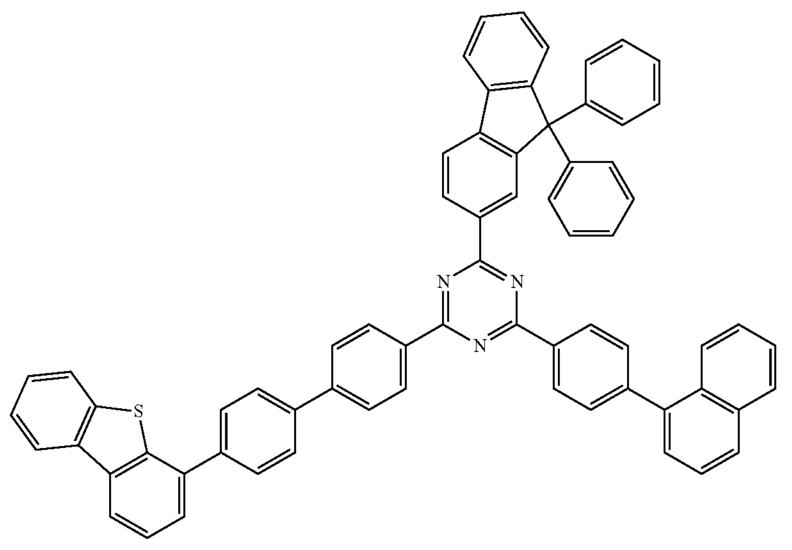

-continued
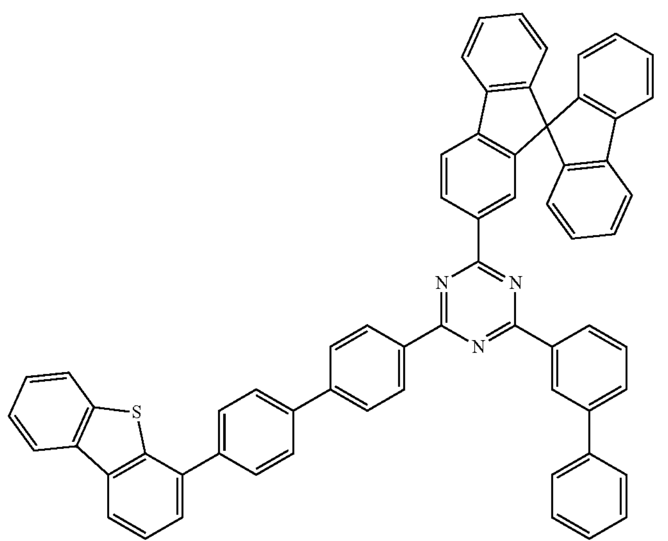
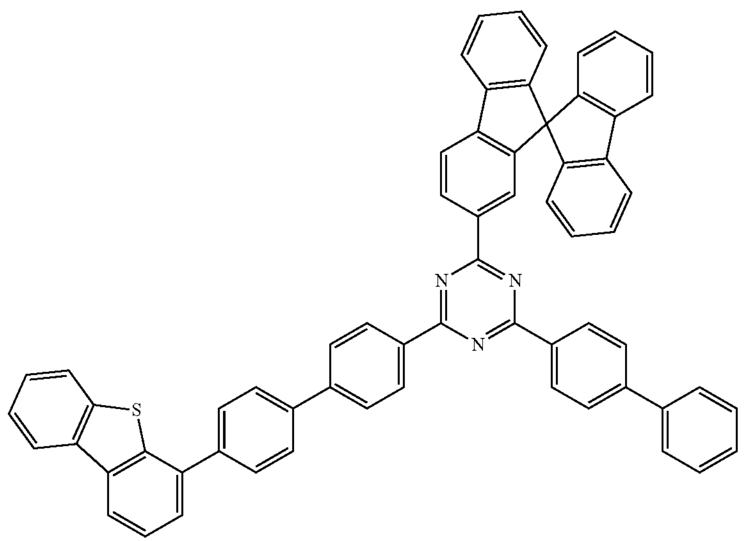
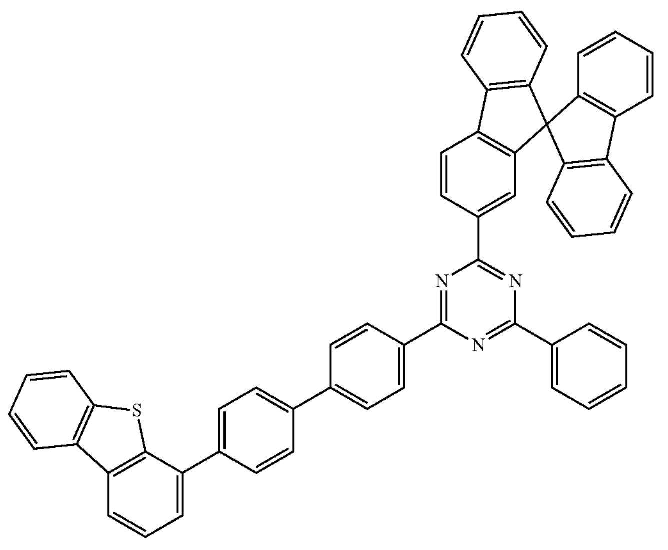

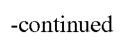
-continued

-continued
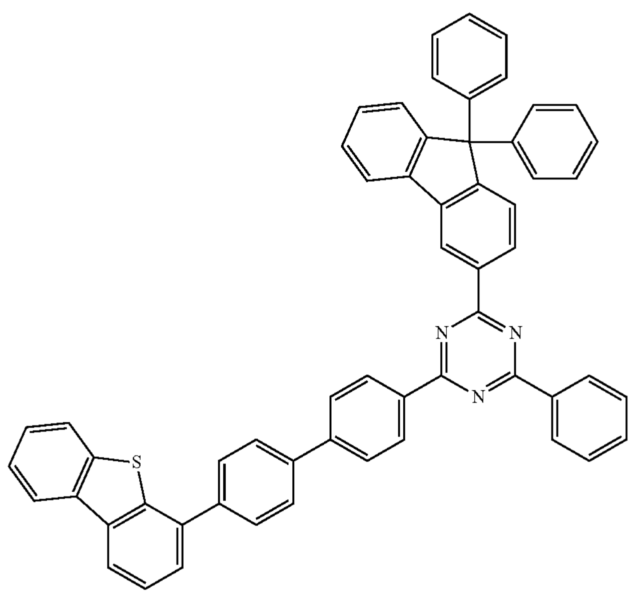
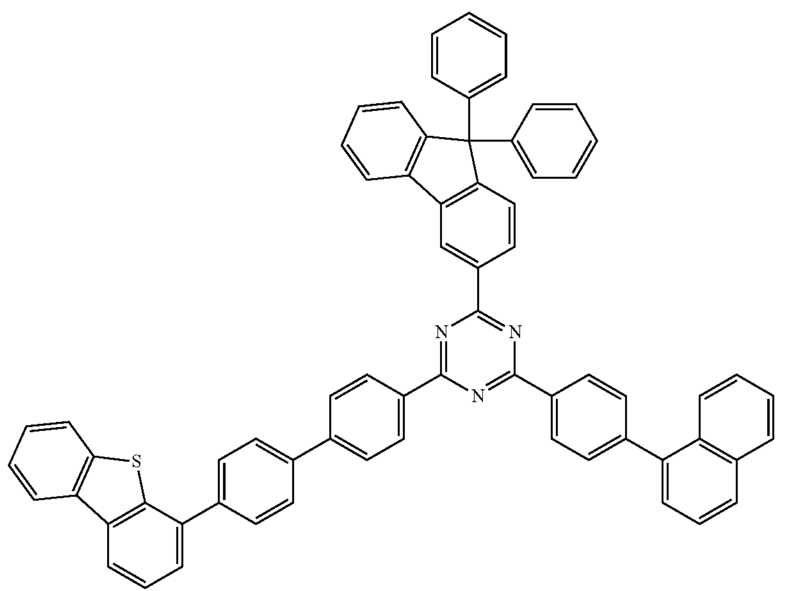
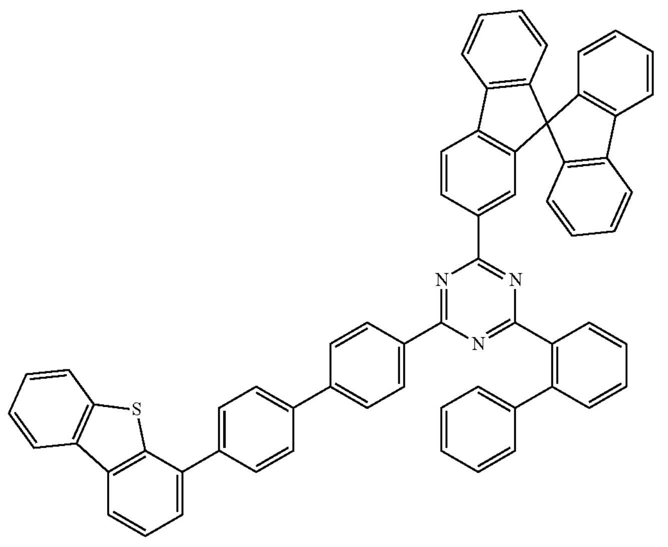

-continued
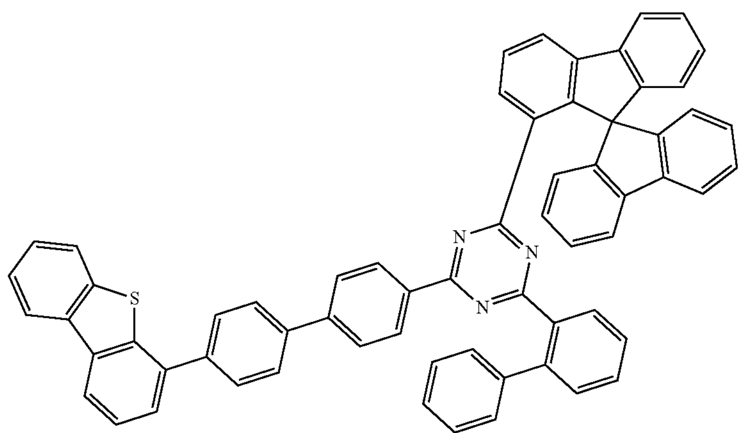
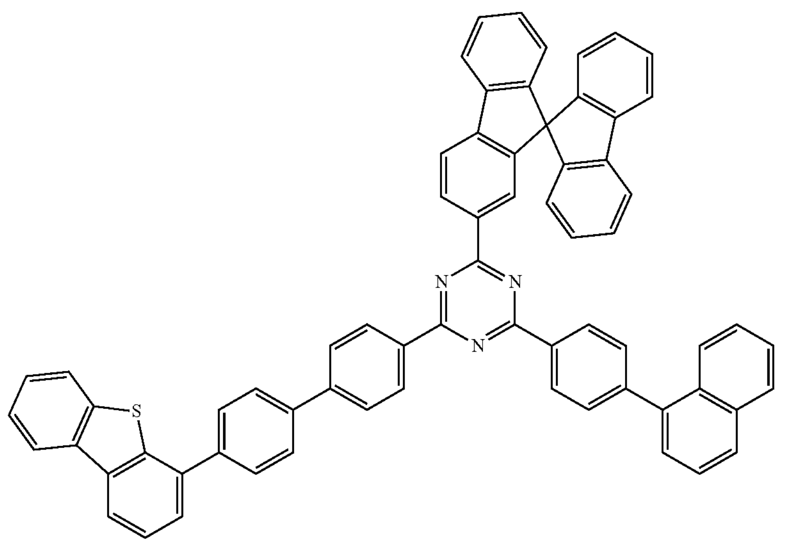
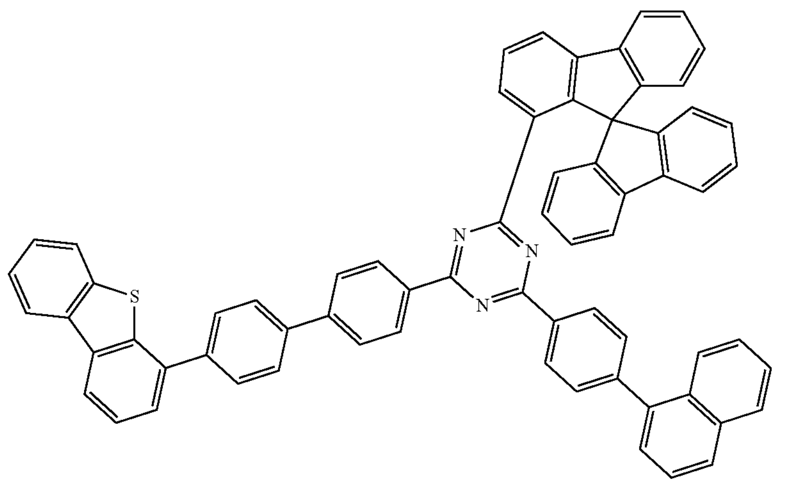

-continued
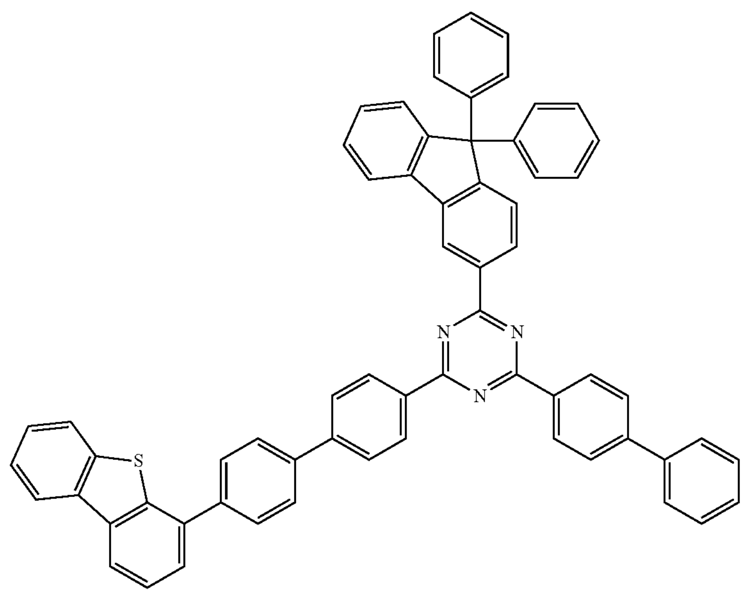
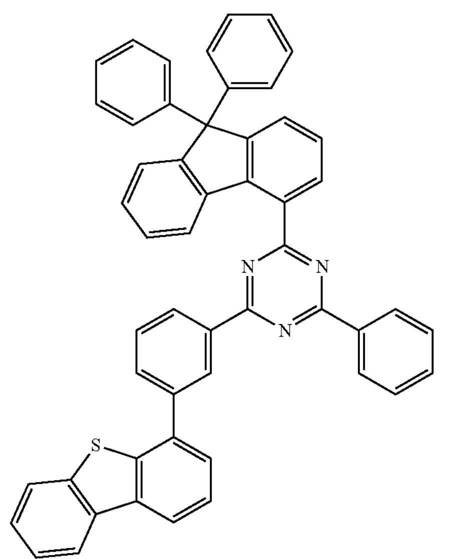
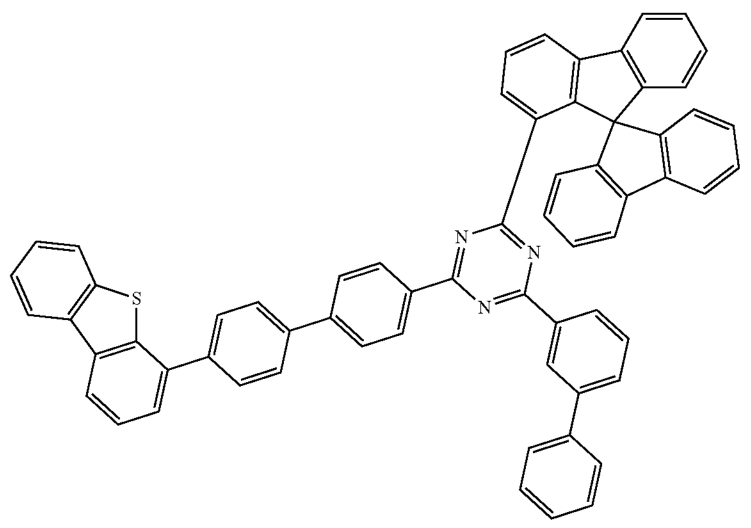

-continued
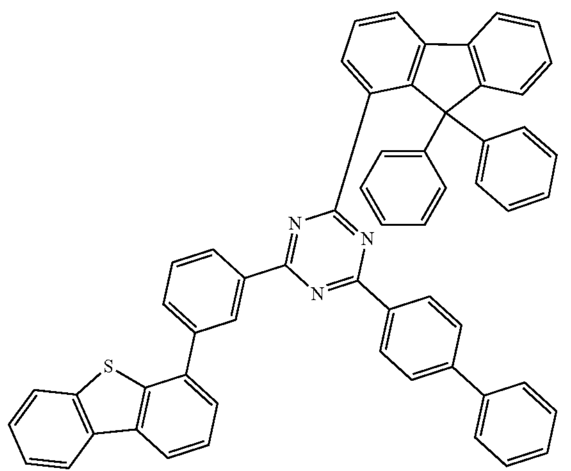
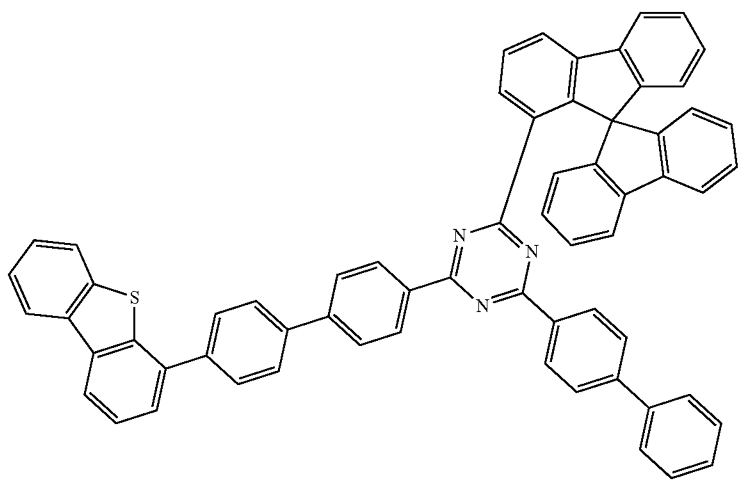
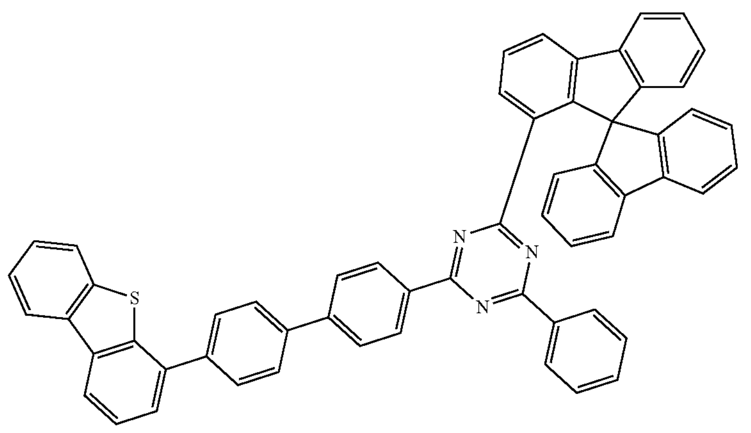

-continued
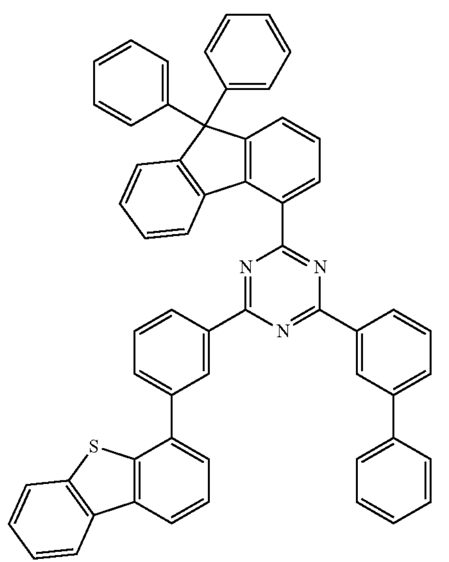
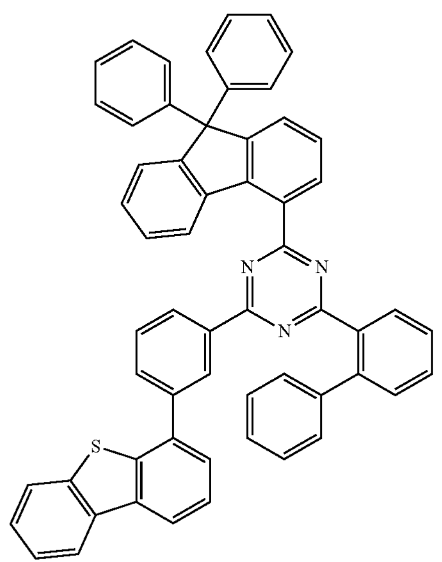
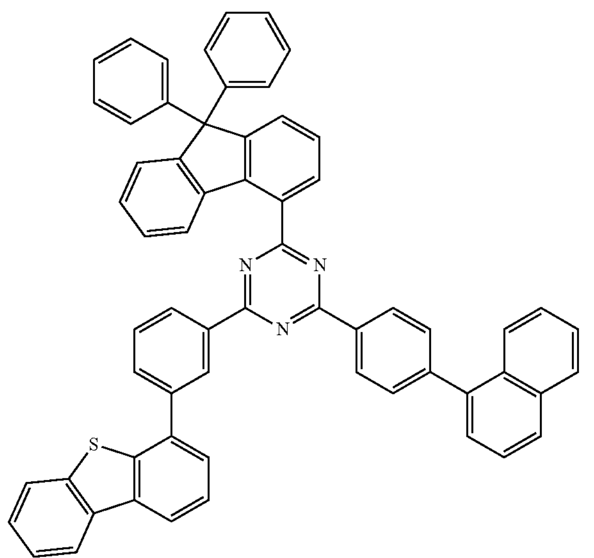
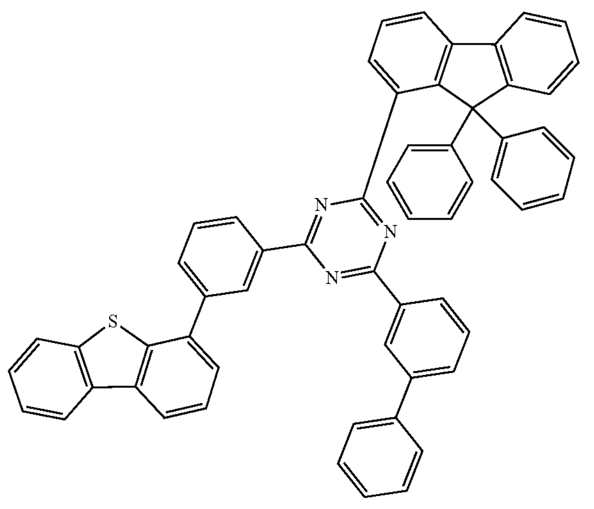

-continued
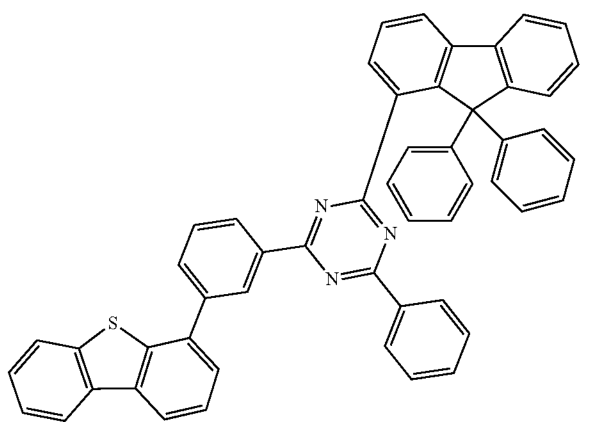
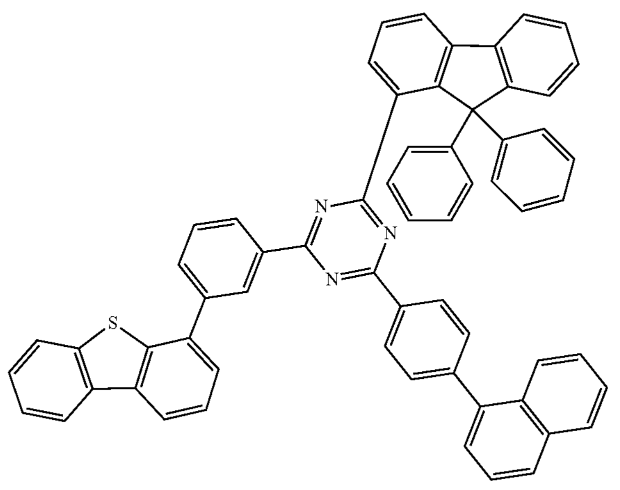 [SMILES: c1ccc(C2(c3ccccc3)c3ccccc3-c3cccc(-c4nc(-c5ccc(-c6cccc7ccccc67)cc5)nc(-c5cccc(-c6cccc7c6sc6ccccc67)c5)n4)c32)cc1]
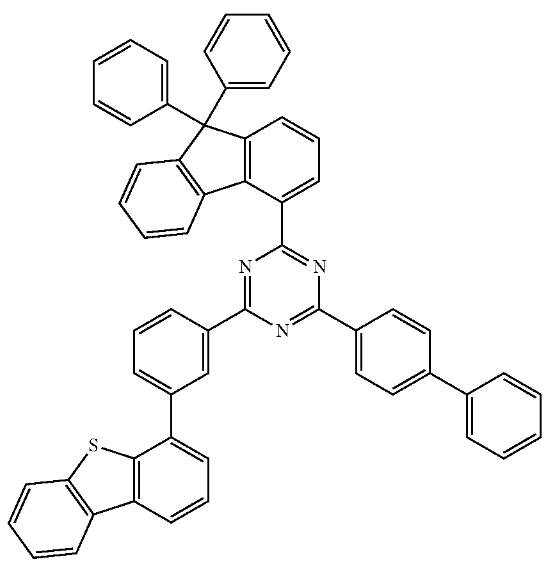
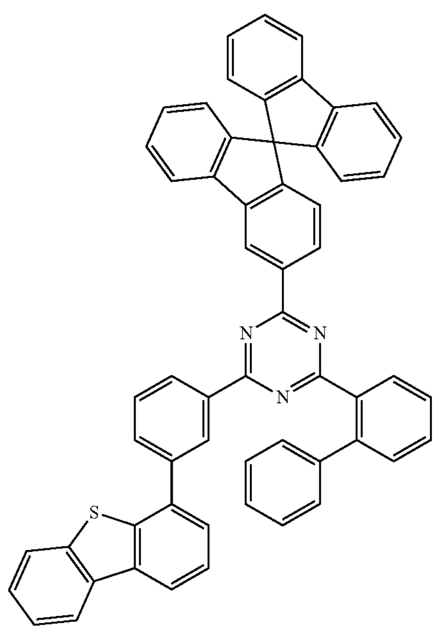

-continued
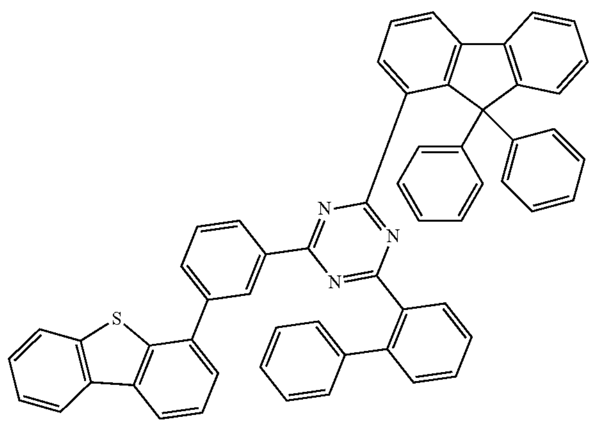
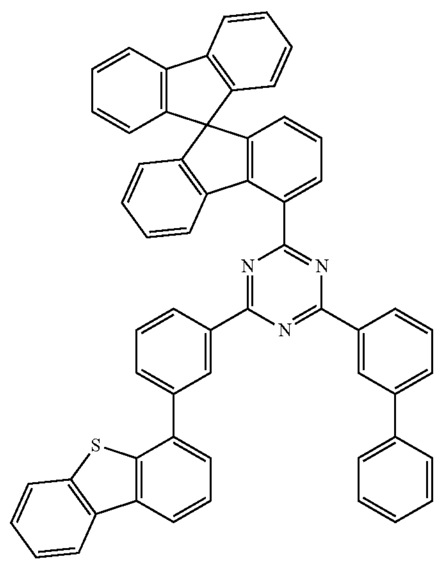
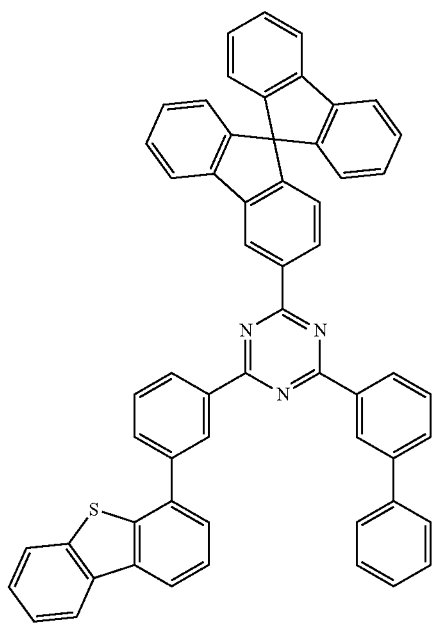
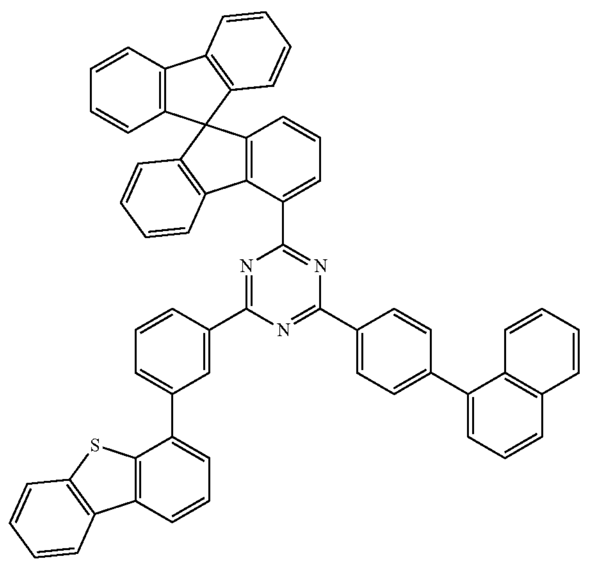

-continued
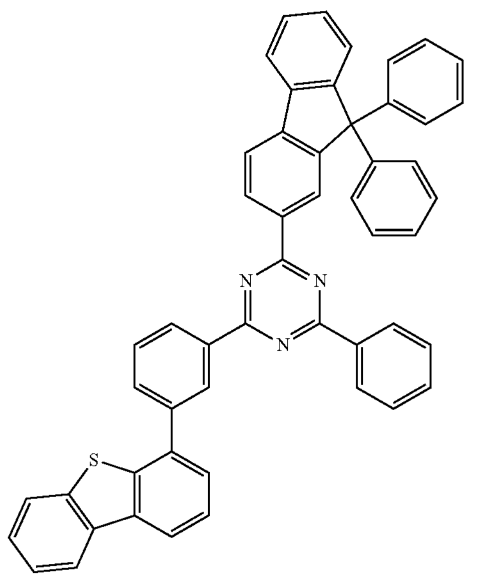
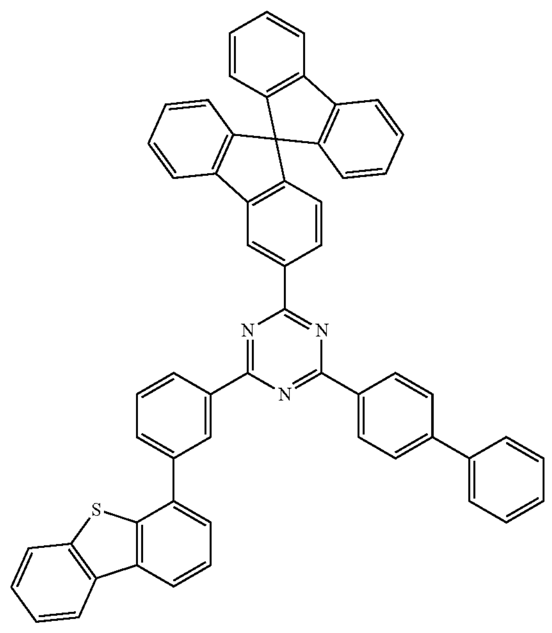
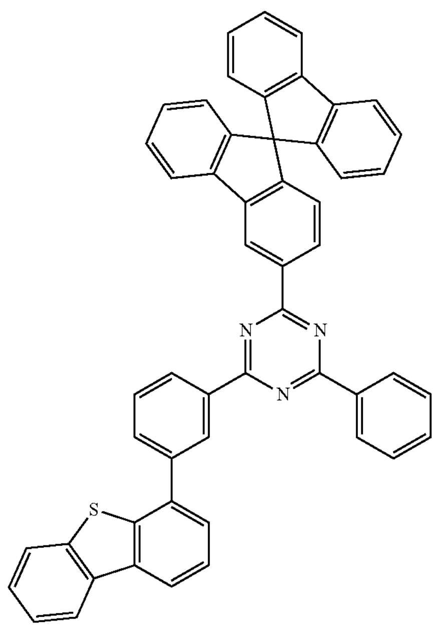
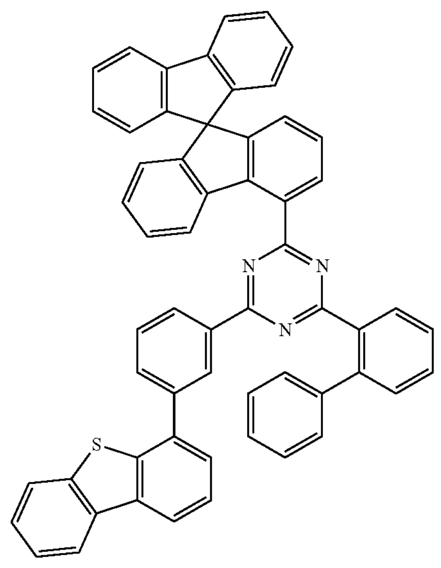

-continued
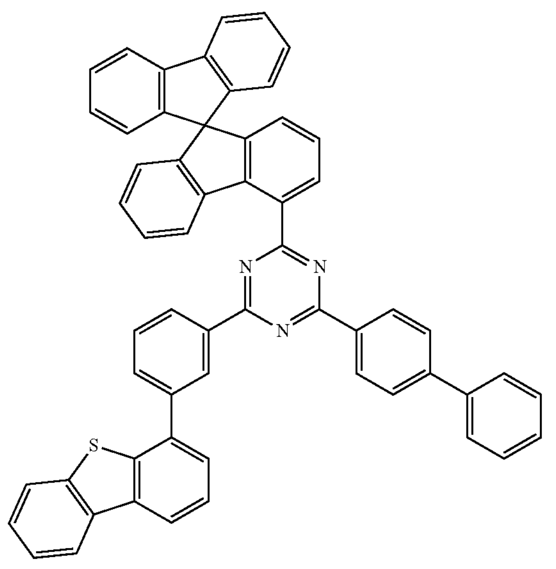
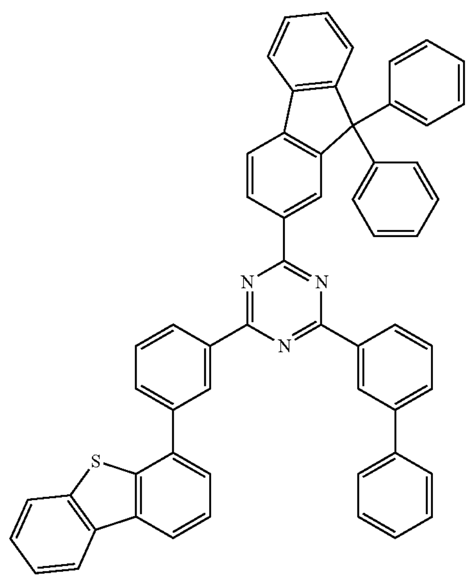
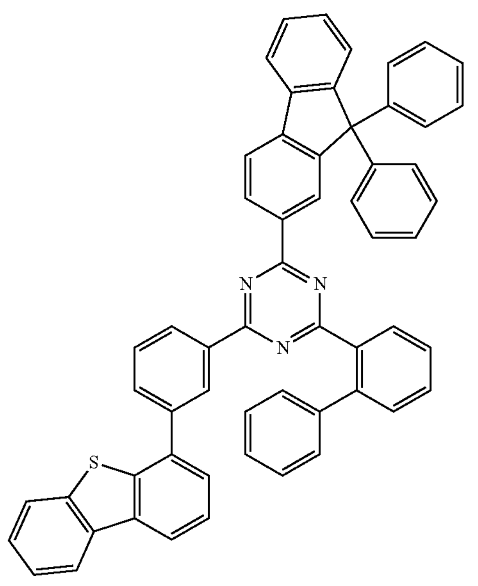
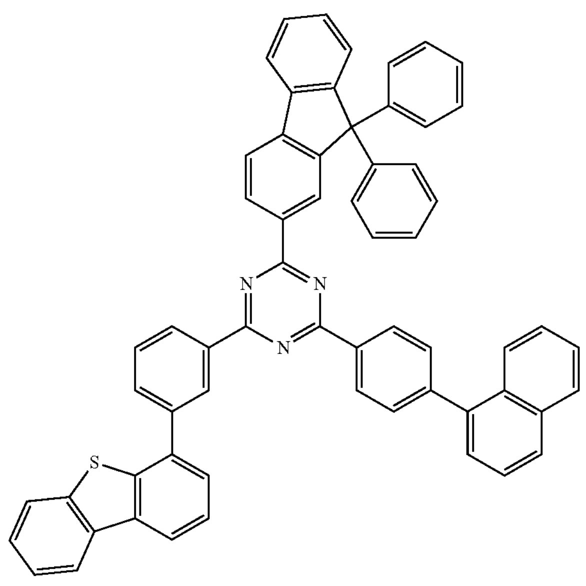

-continued
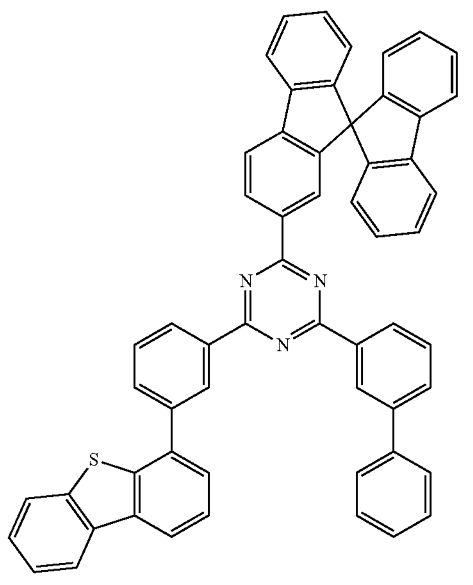
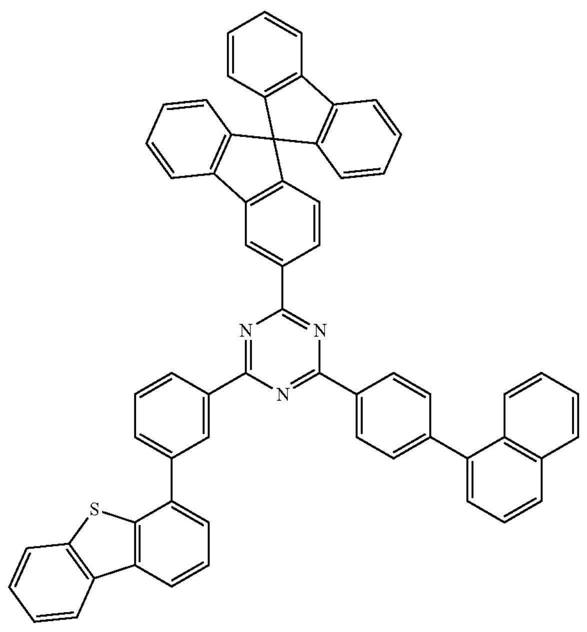
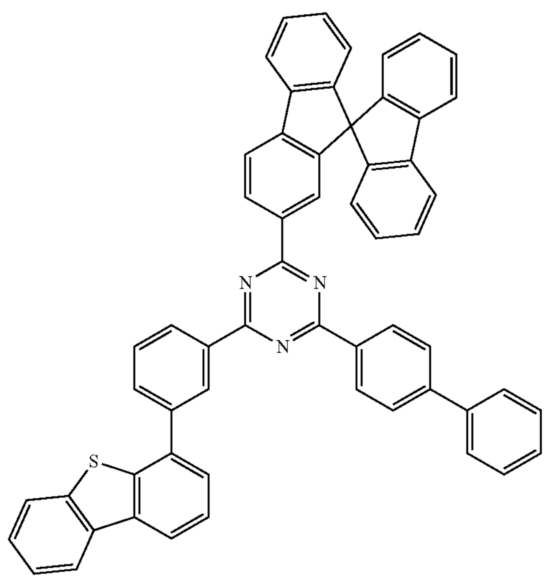
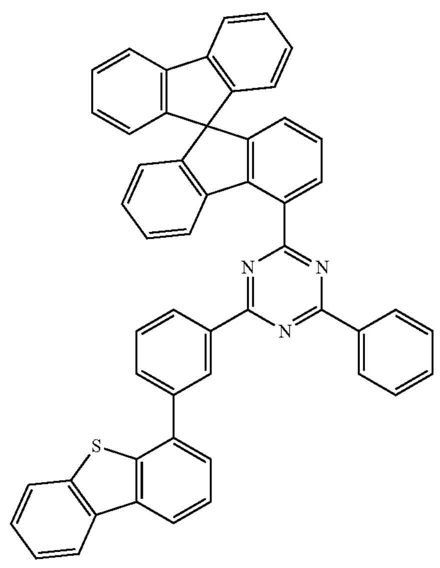

-continued
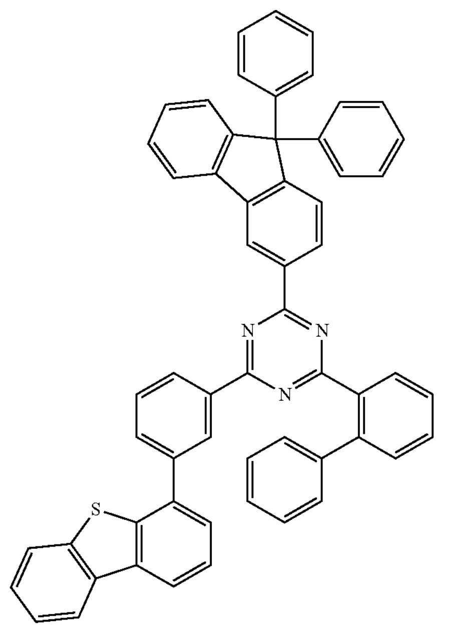
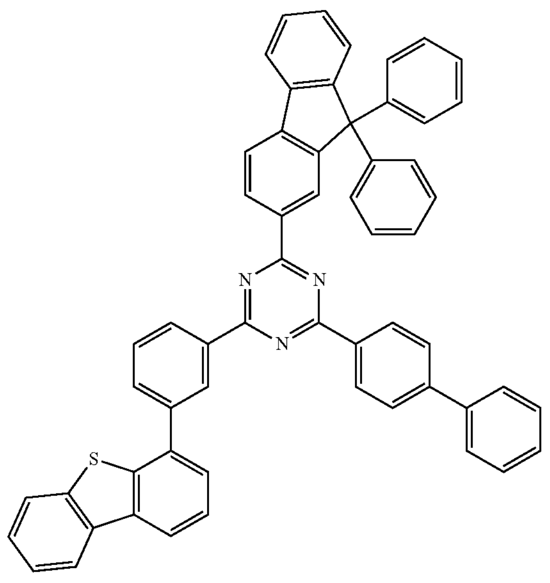
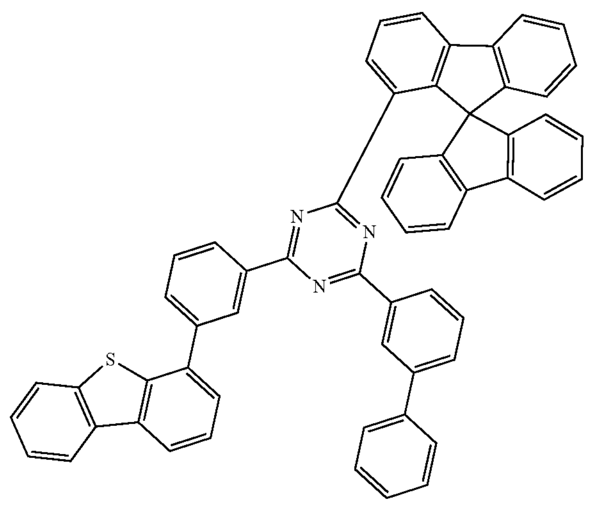
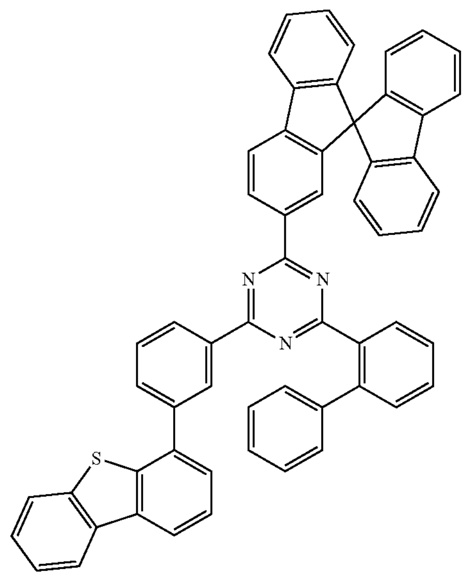

-continued
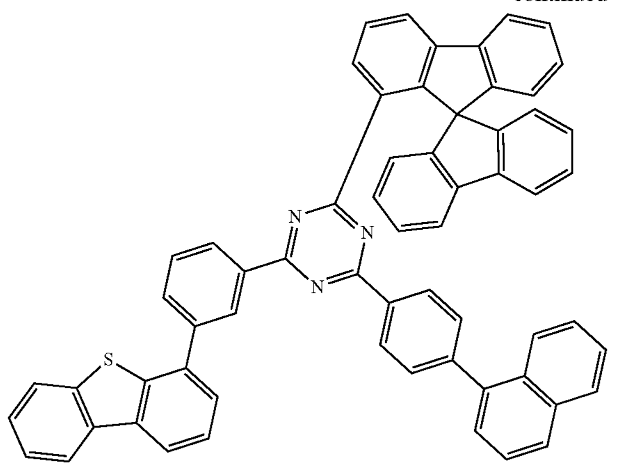
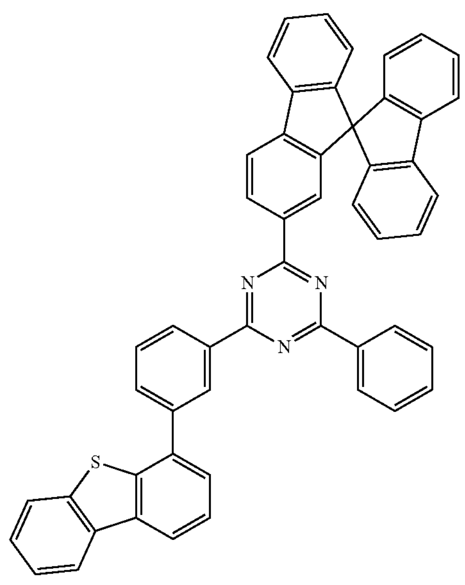
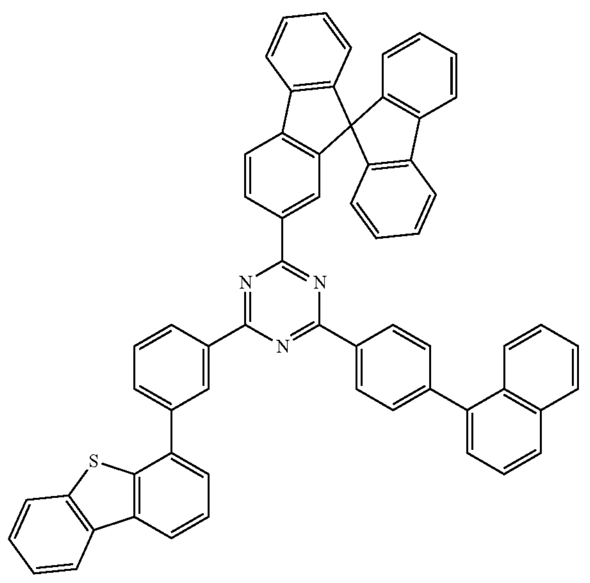
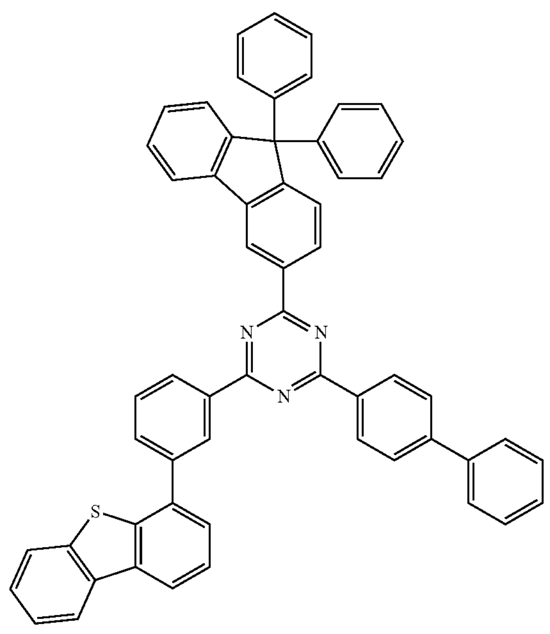

-continued
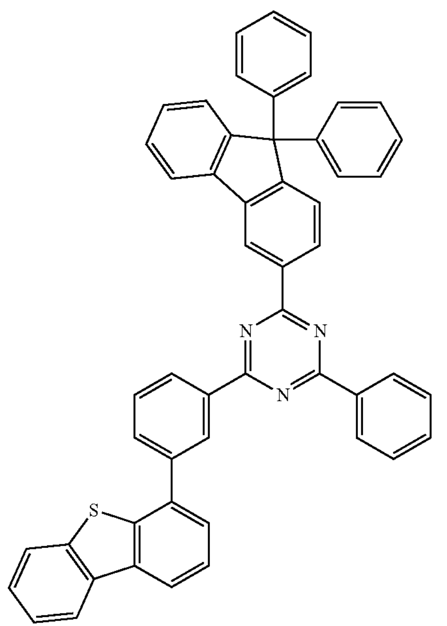
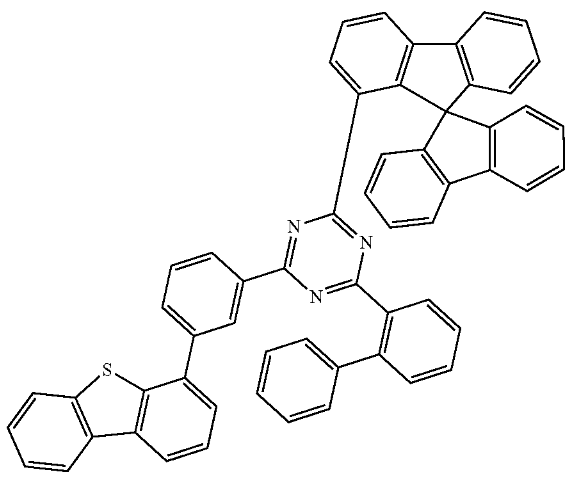
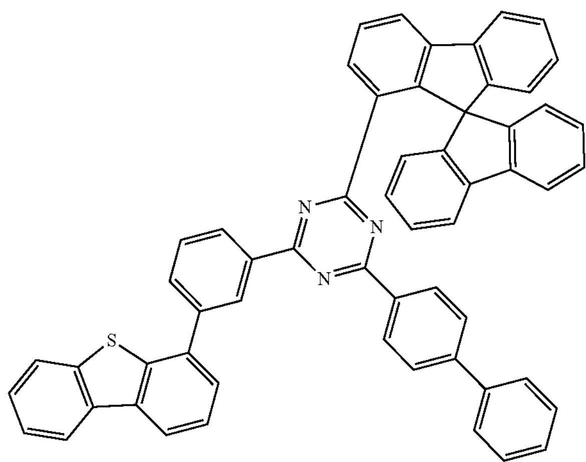
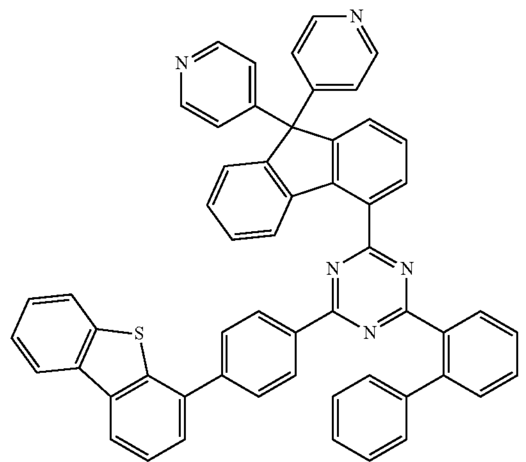
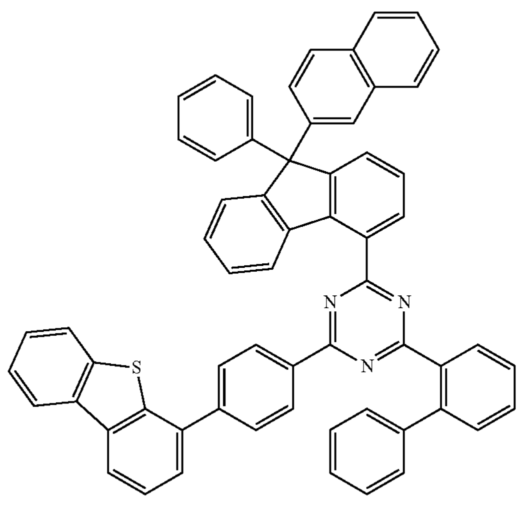
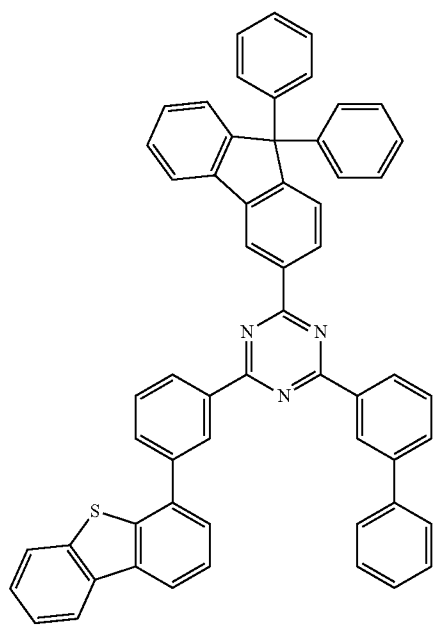

-continued
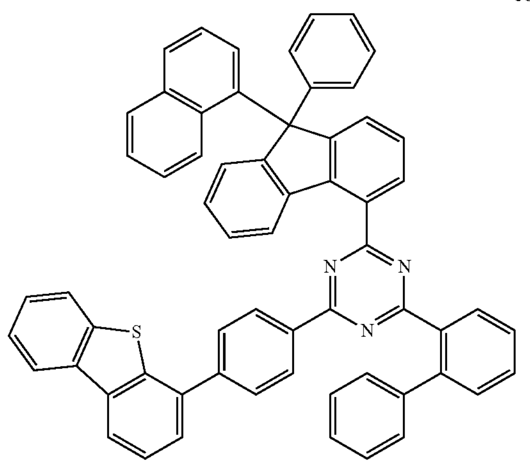
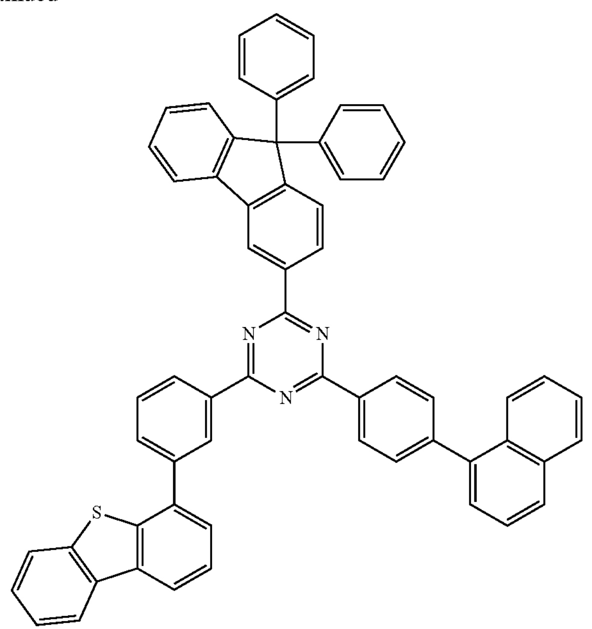
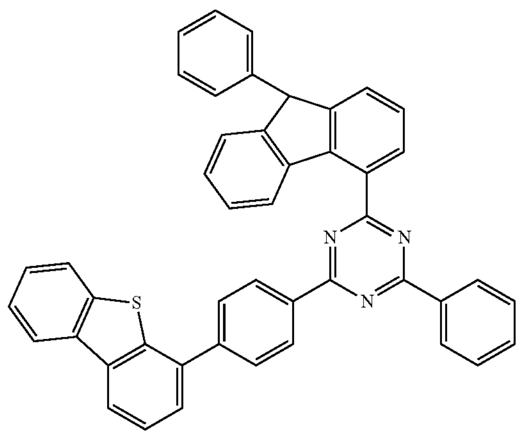
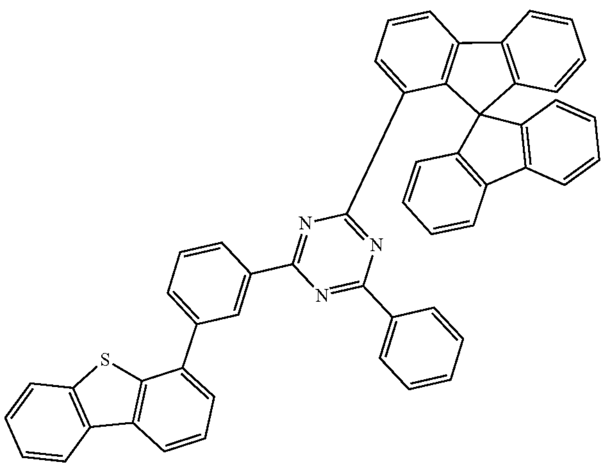
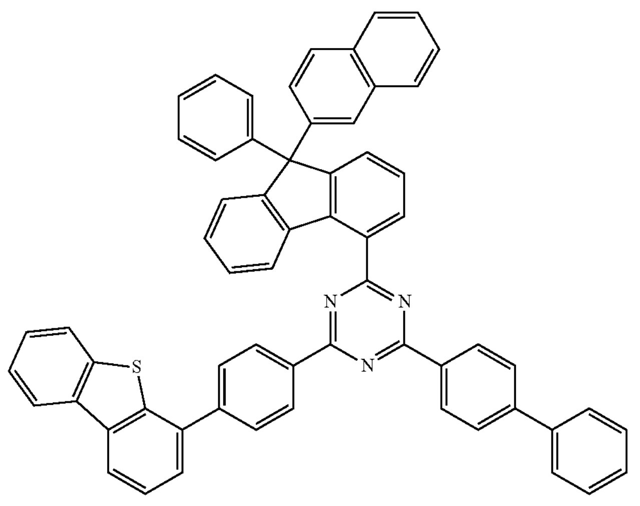

-continued
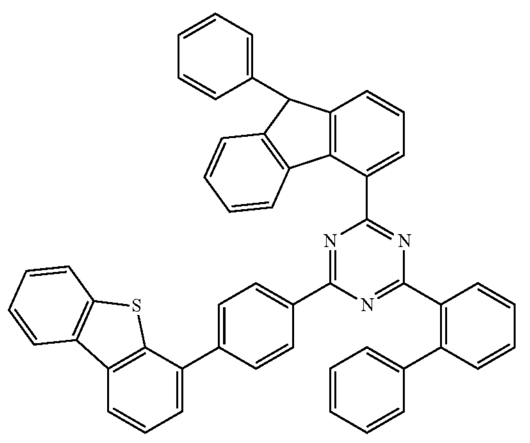
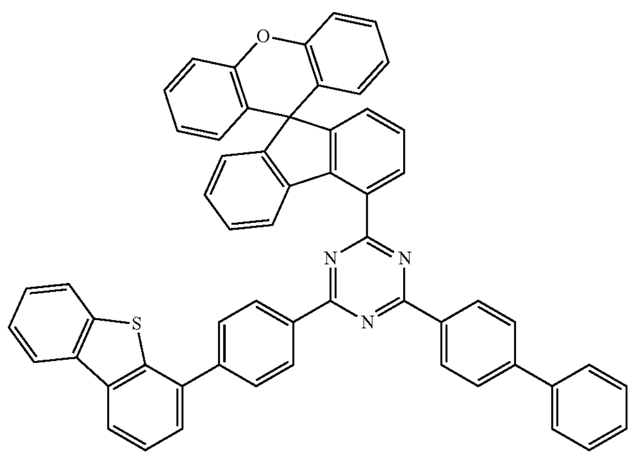
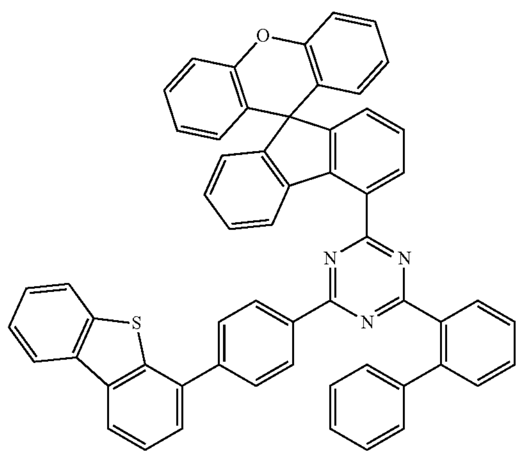
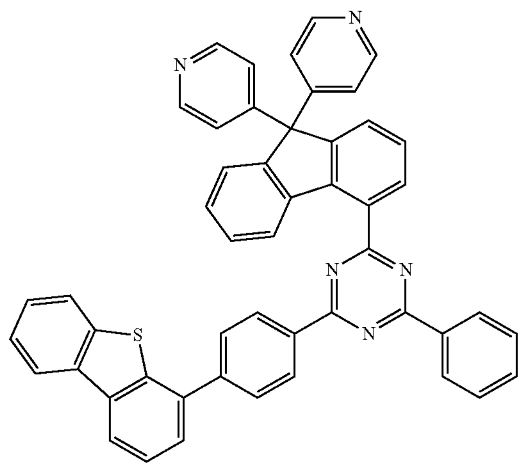

-continued
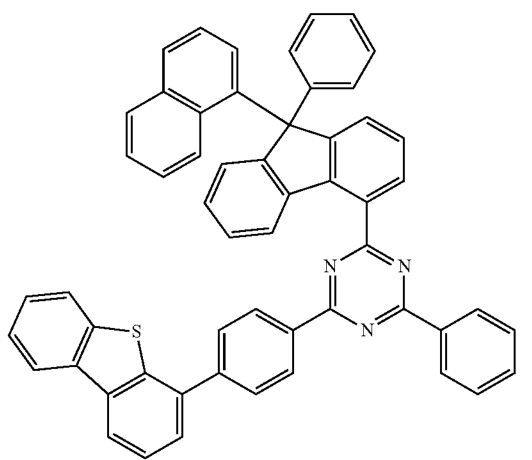
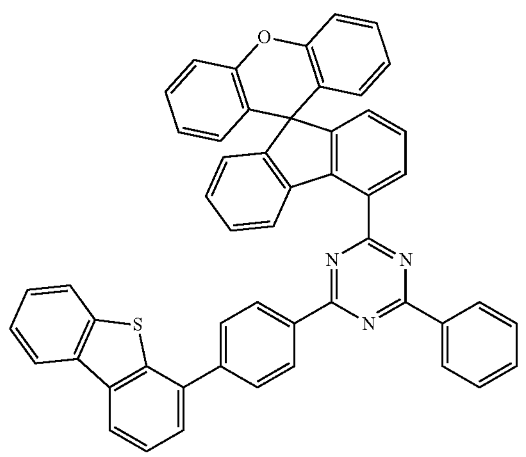
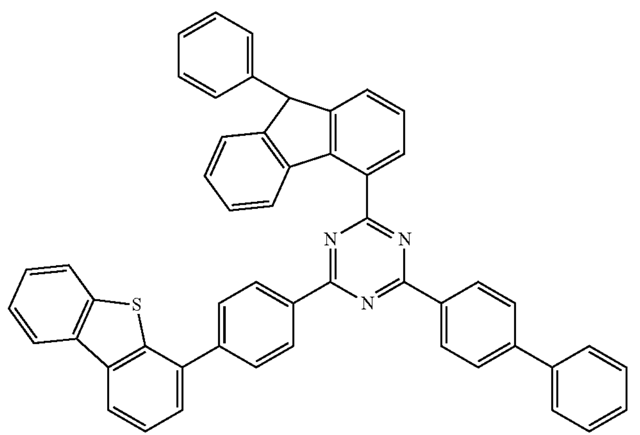
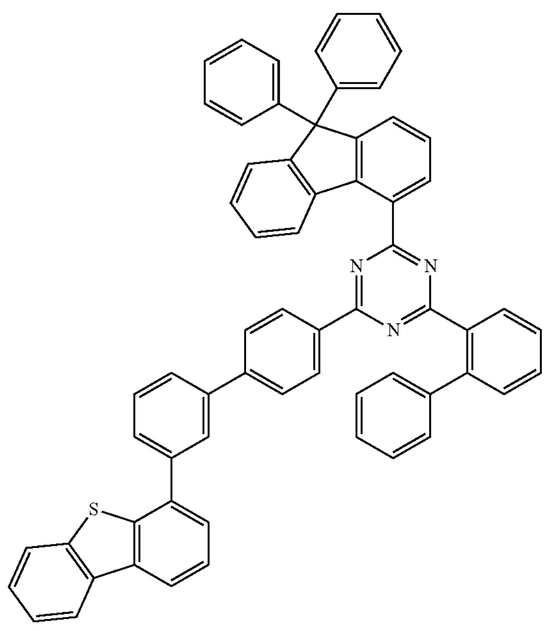

-continued
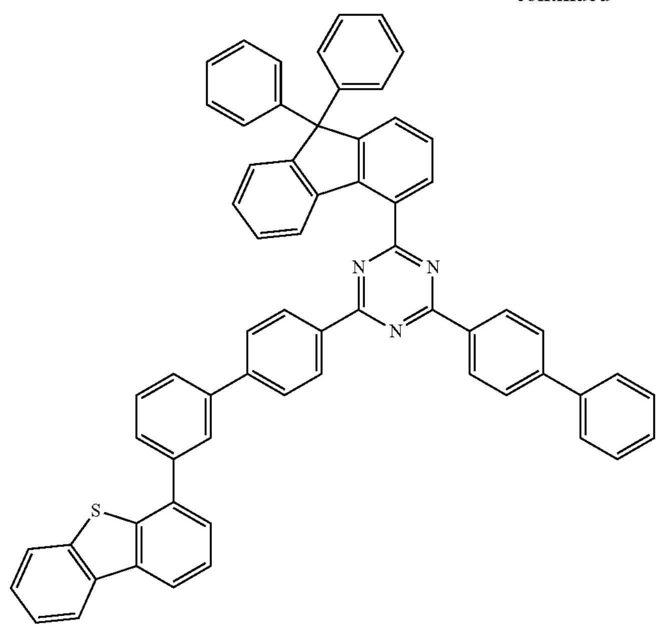
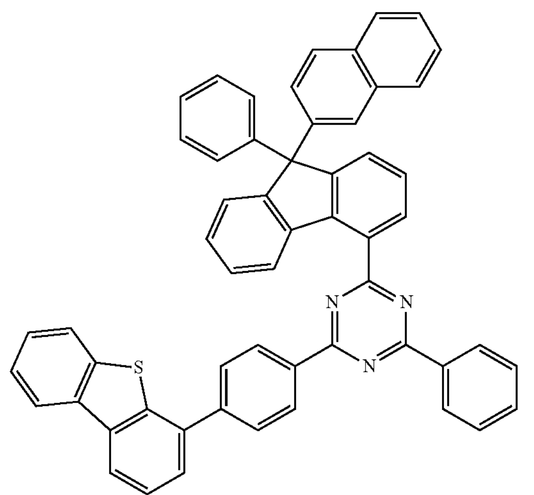
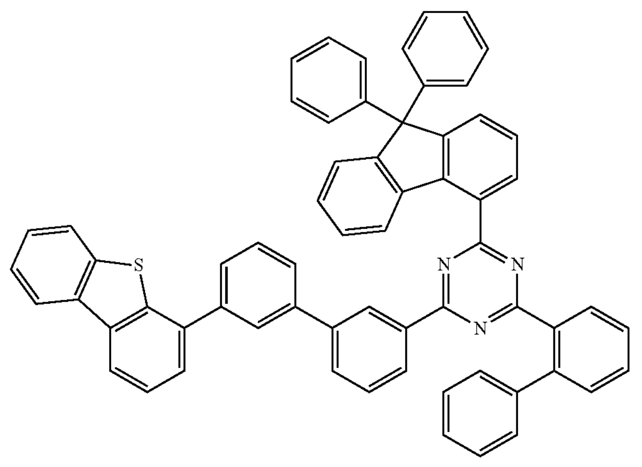

-continued
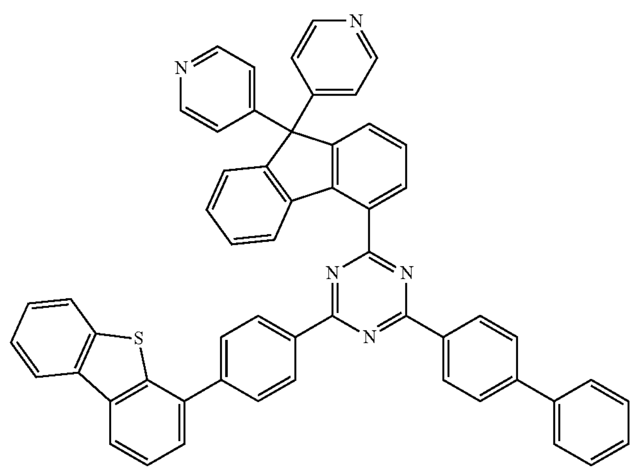
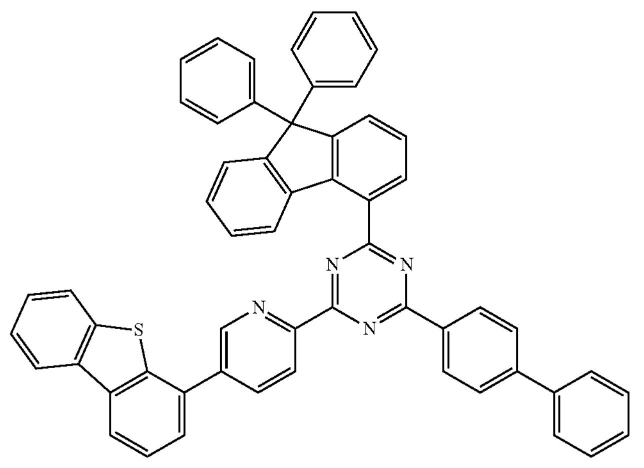
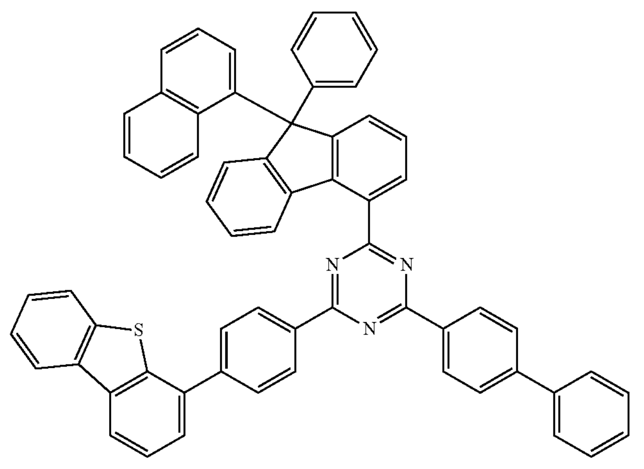

-continued
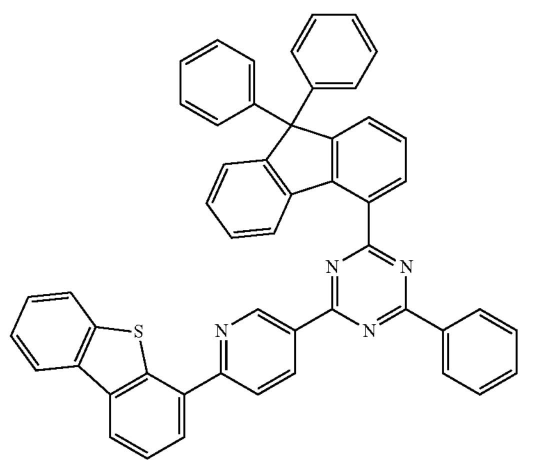
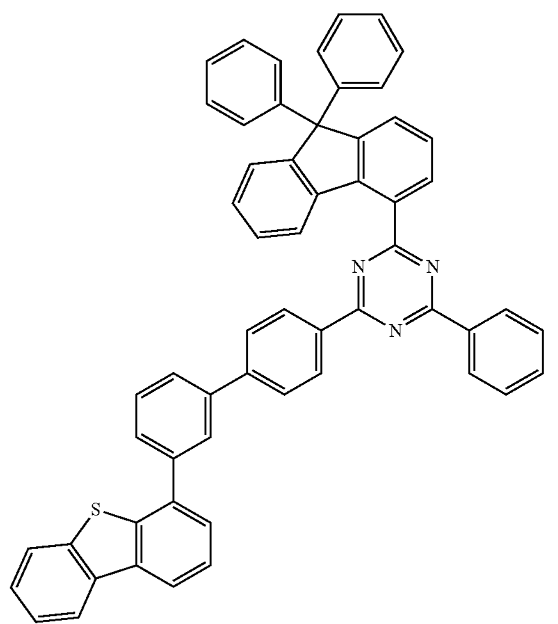
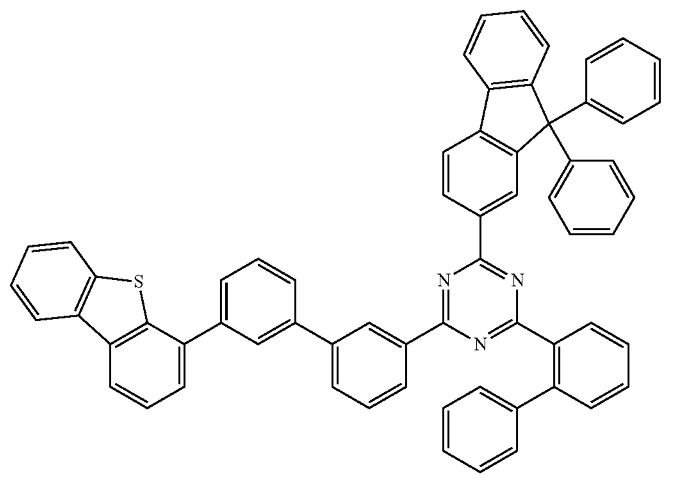

-continued
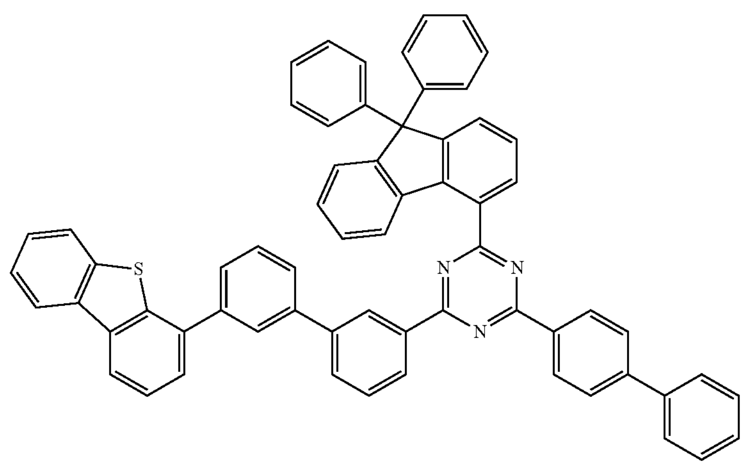
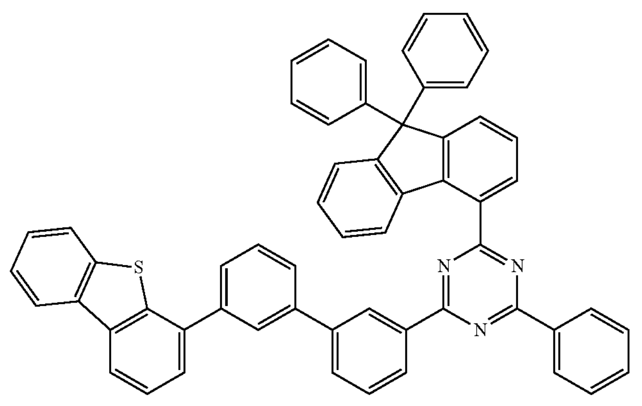
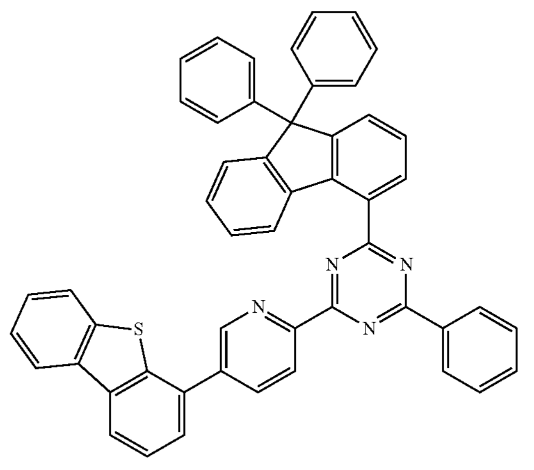

-continued
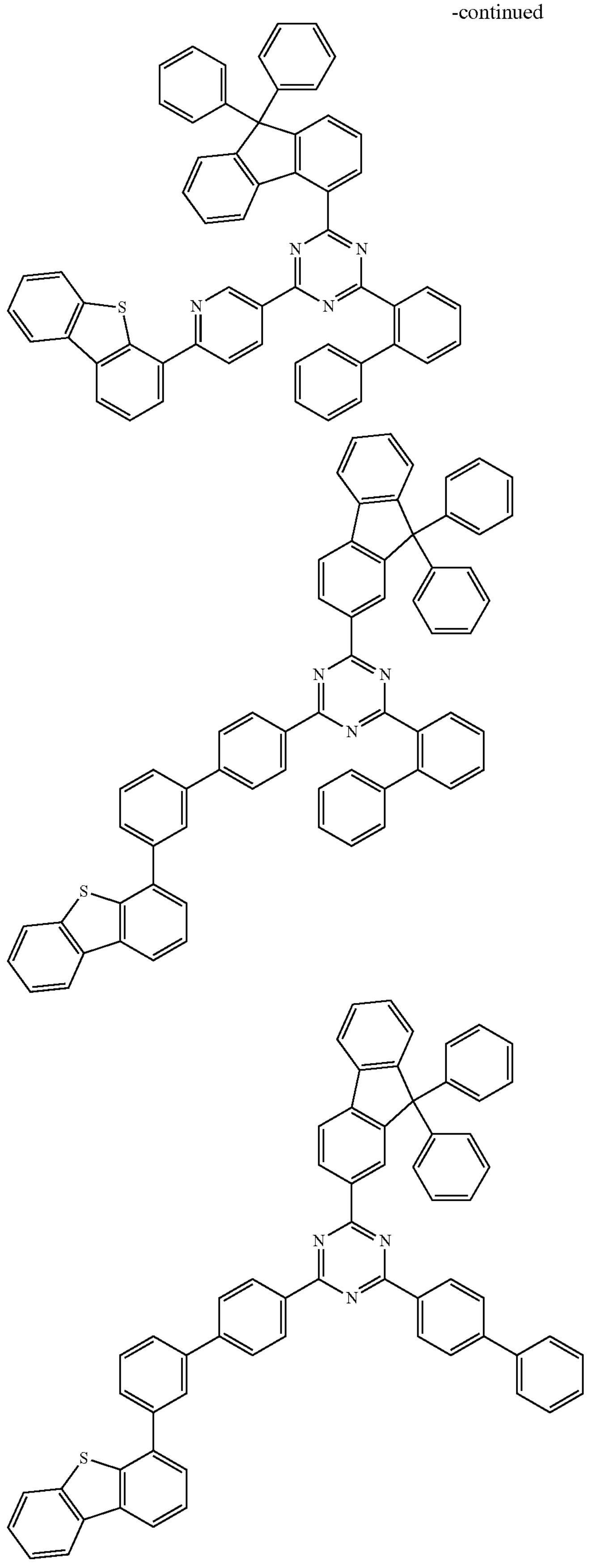

-continued
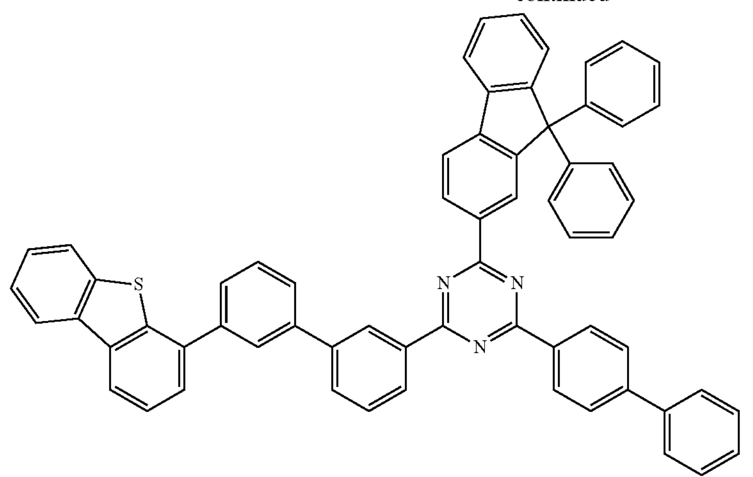
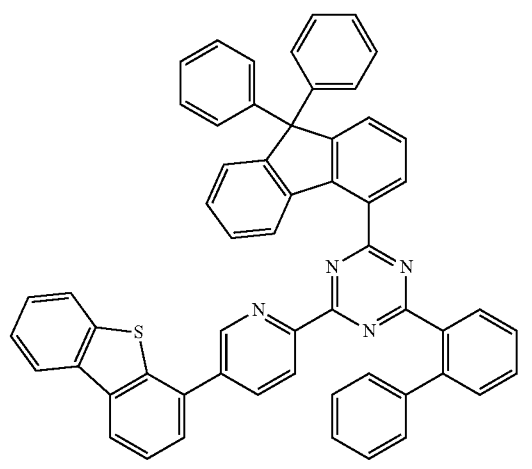
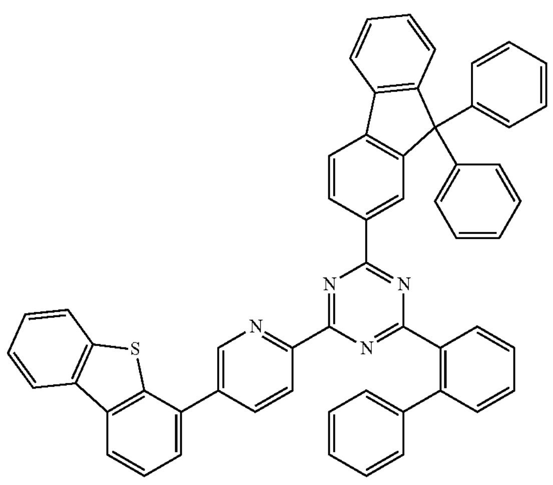
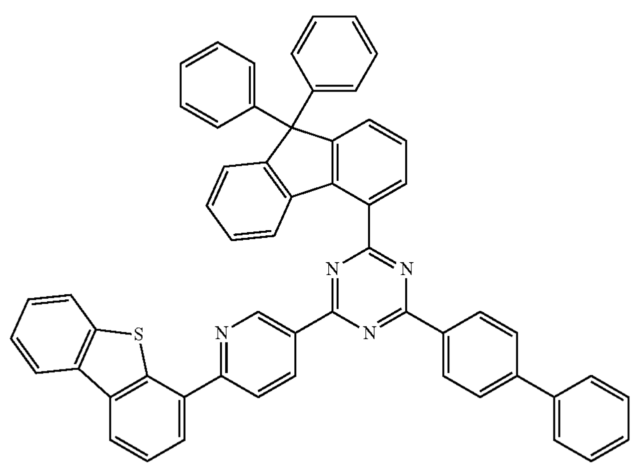

-continued
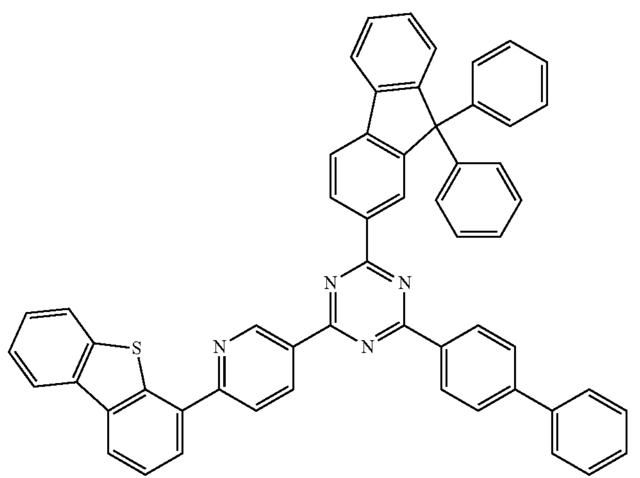
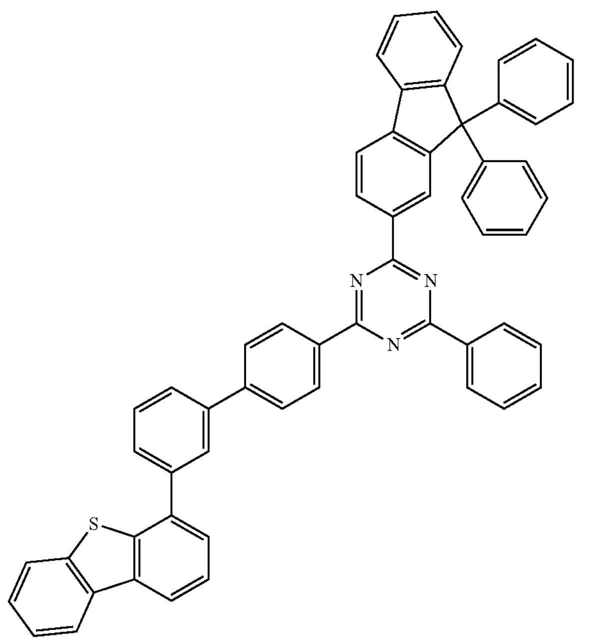
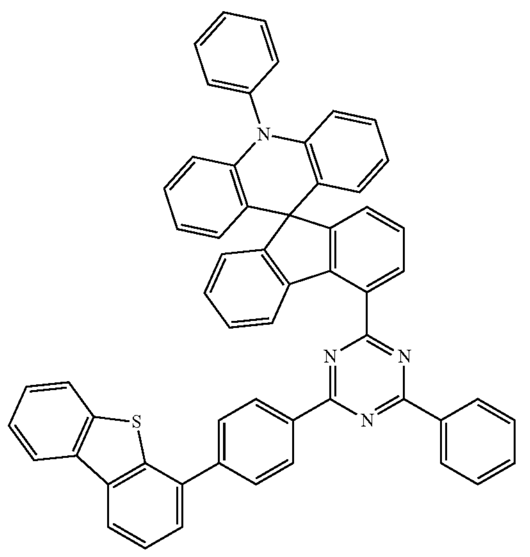

-continued
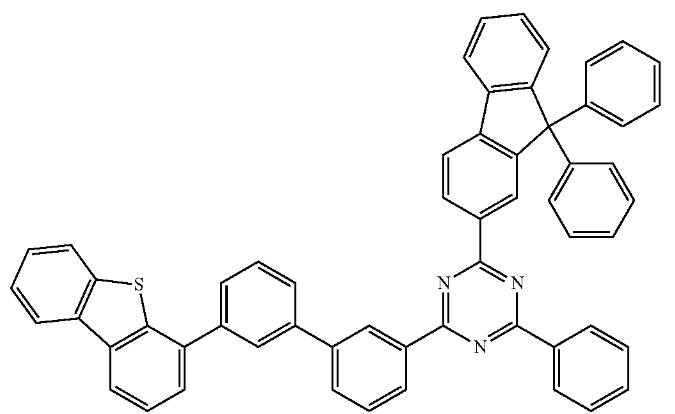
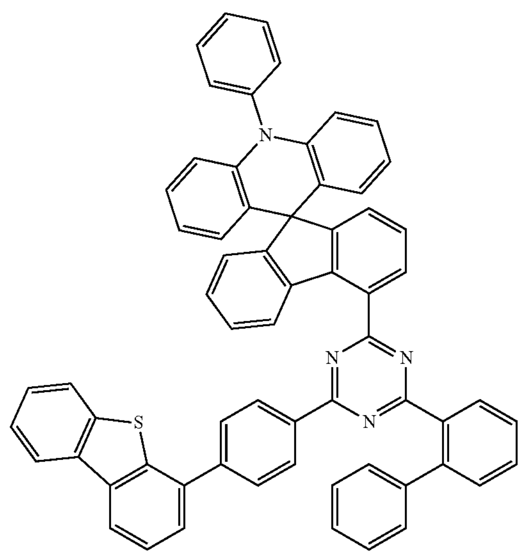 [SMILES: c1ccc(-c2ccccc2-c2nc(-c3ccc(-c4cccc5c4sc4ccccc45)cc3)nc(-c3cccc4c3-c3ccccc3C43c4ccccc4N(c4ccccc4)c4ccccc43)n2)cc1]
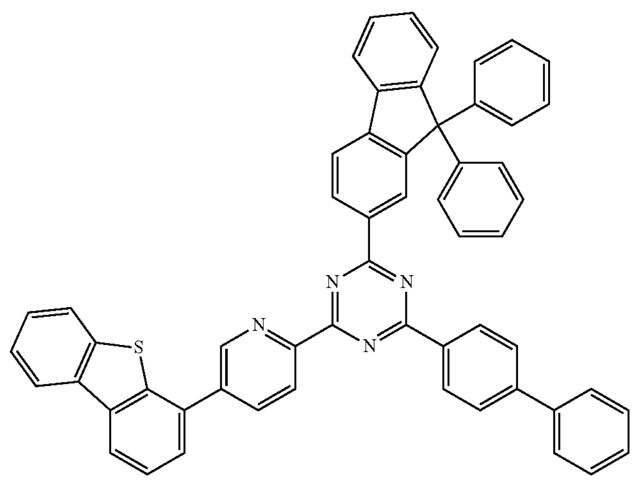

-continued
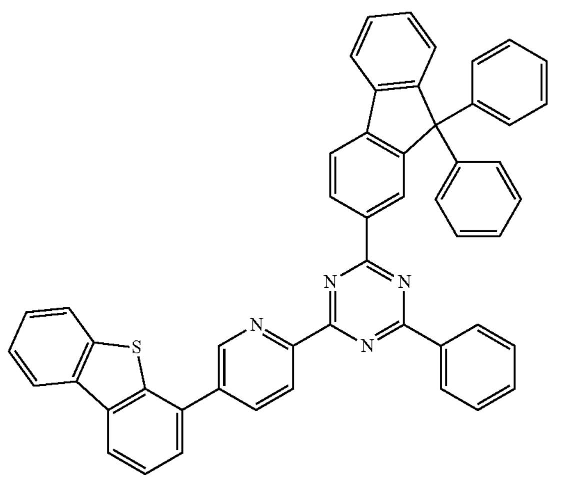
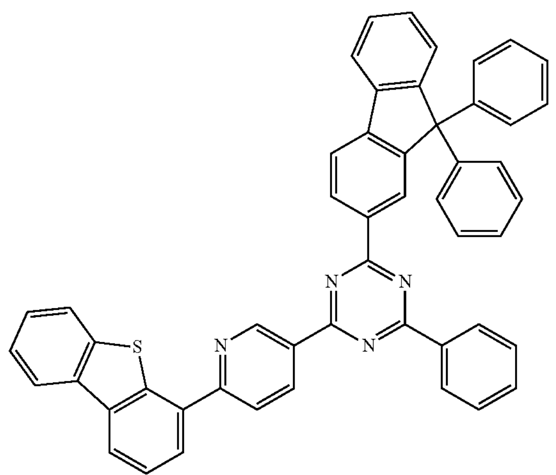
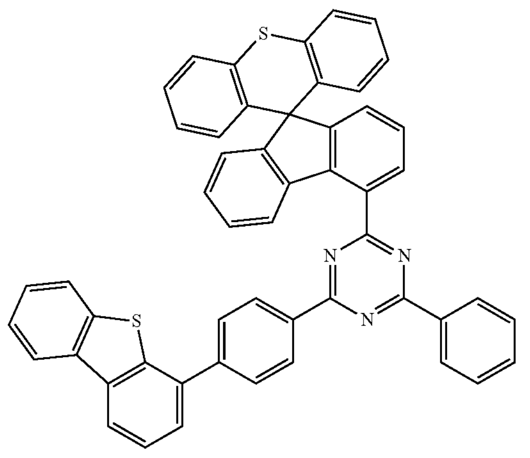
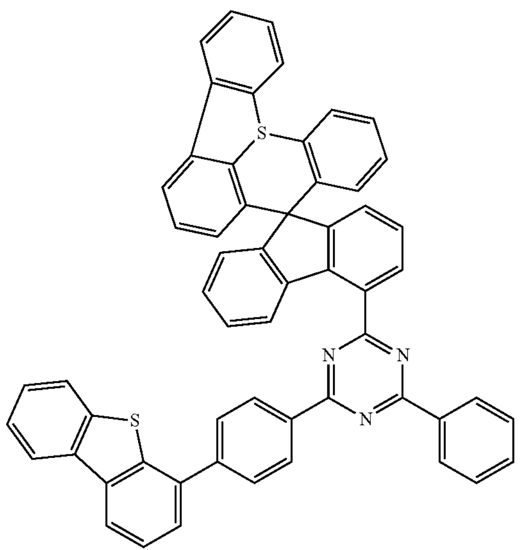
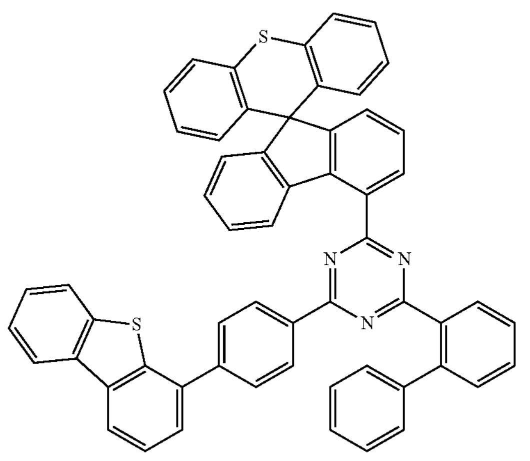
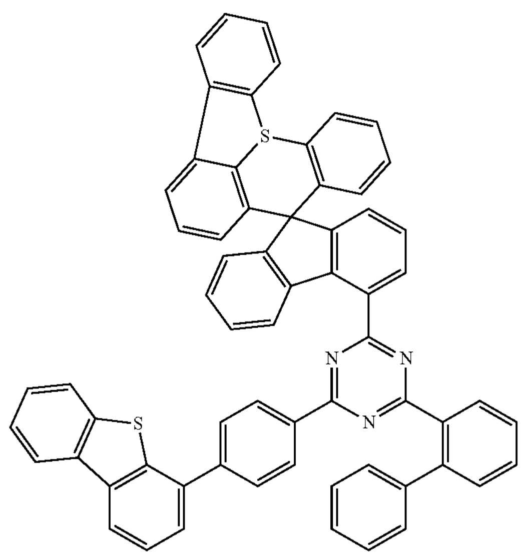

-continued
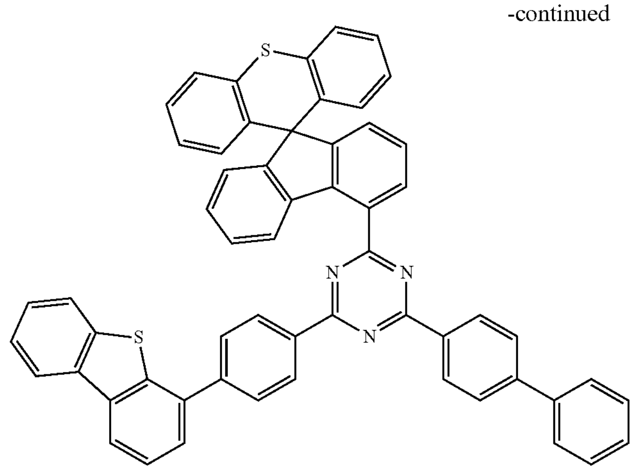
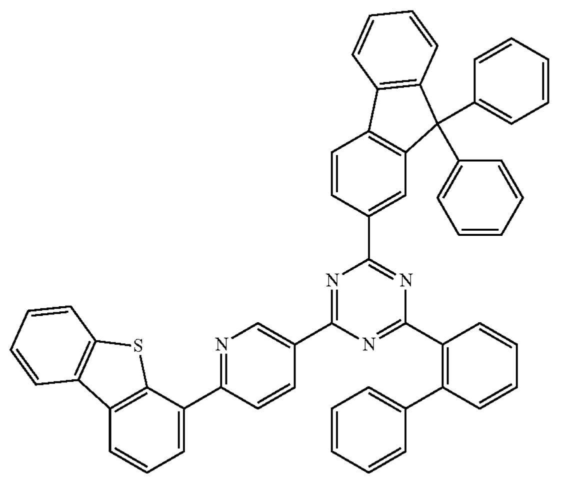
-continued
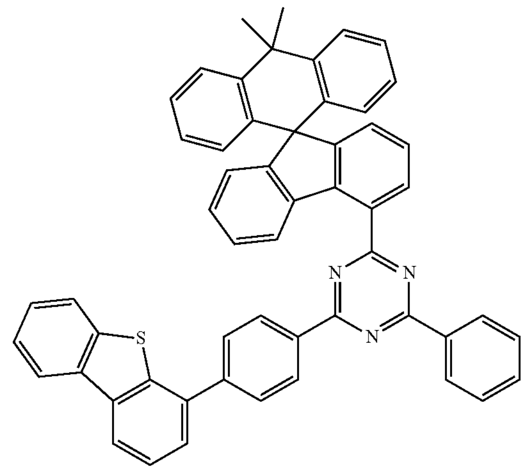
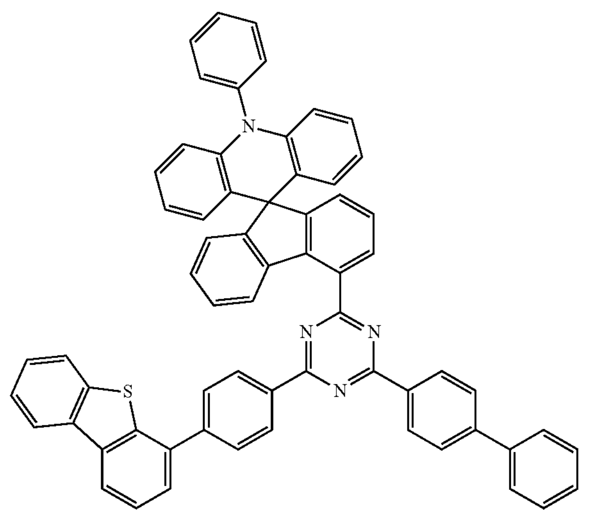

-continued
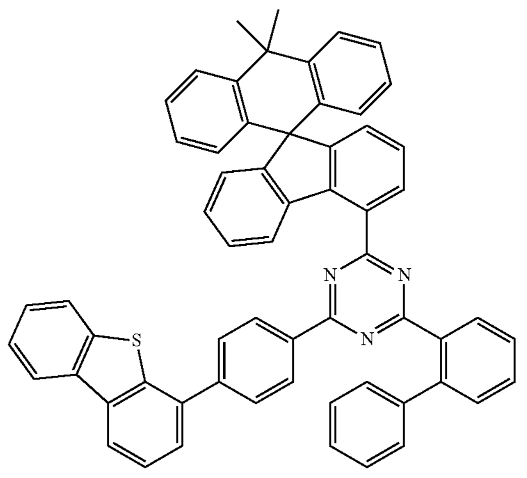
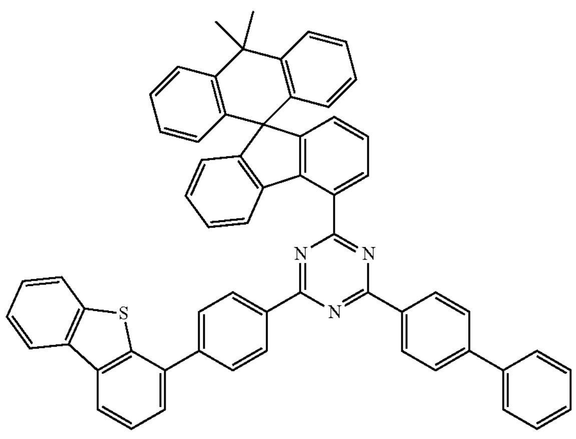
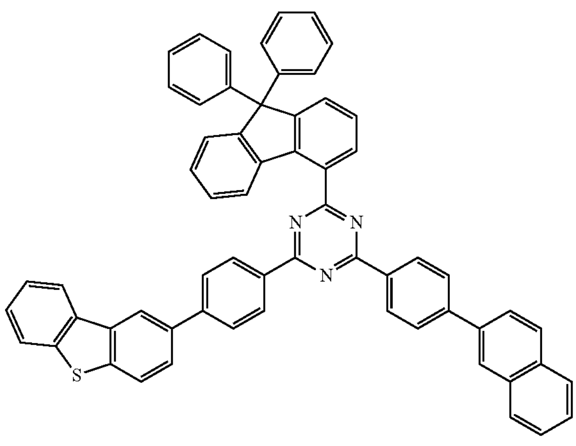
-continued
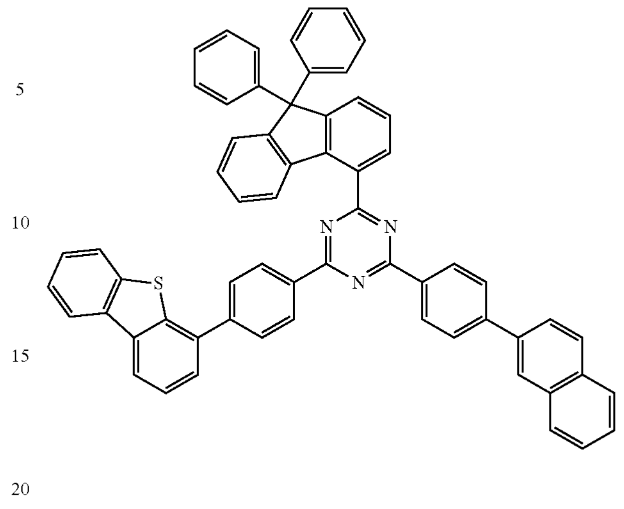
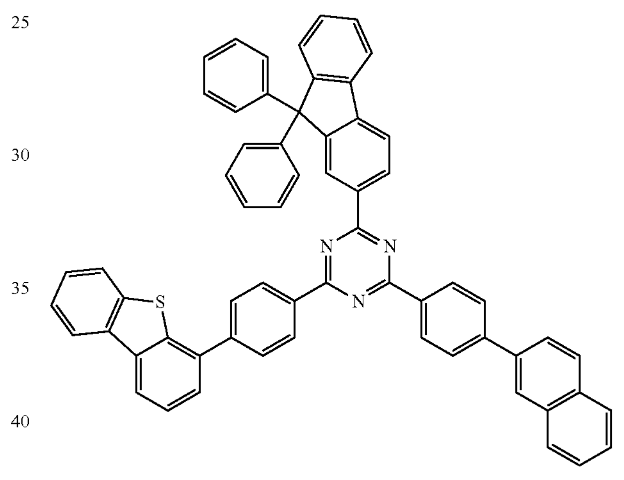
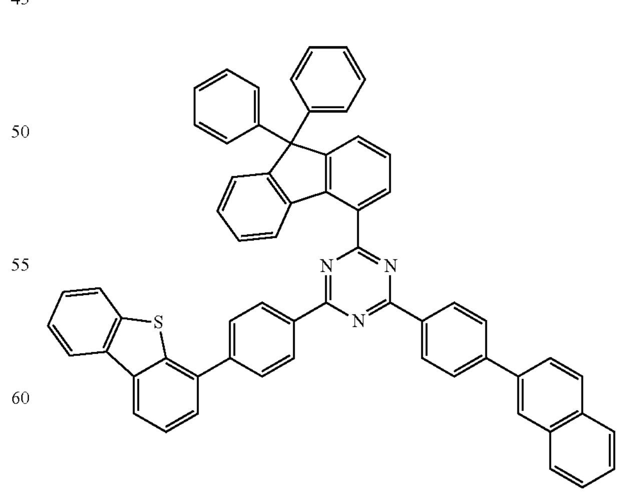

-continued
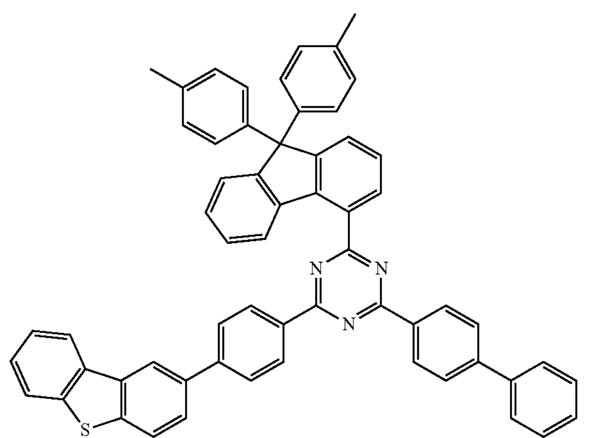
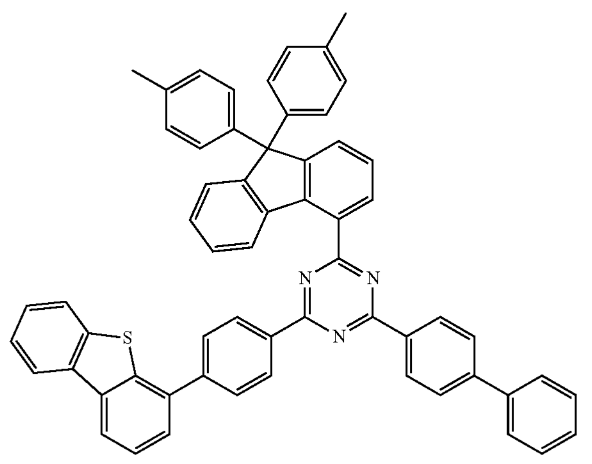
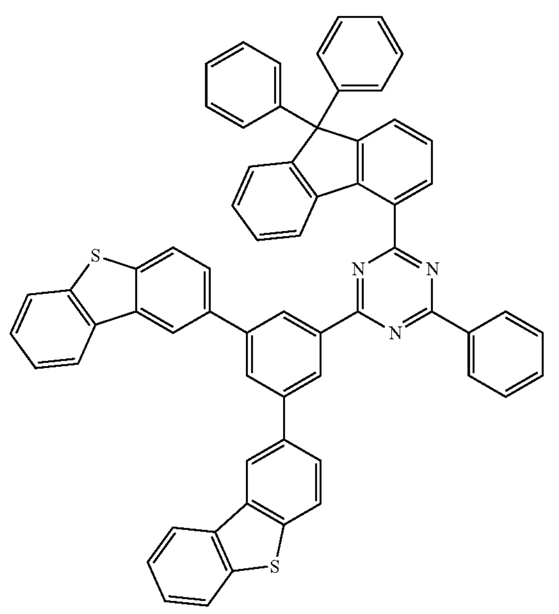
-continued
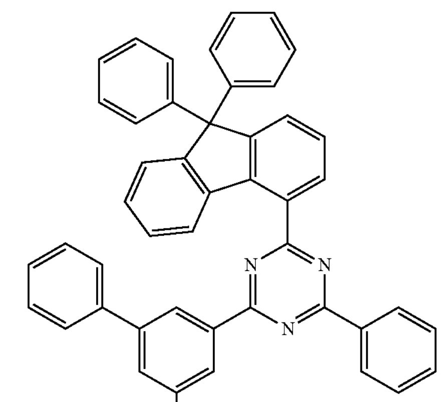
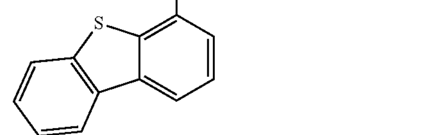
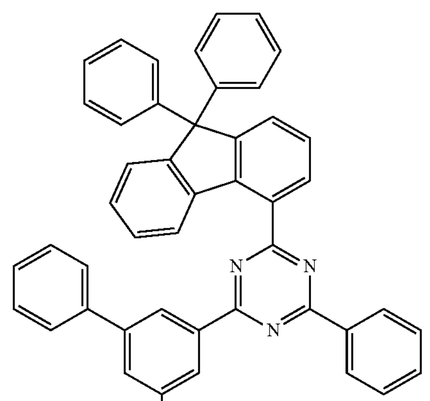

-continued
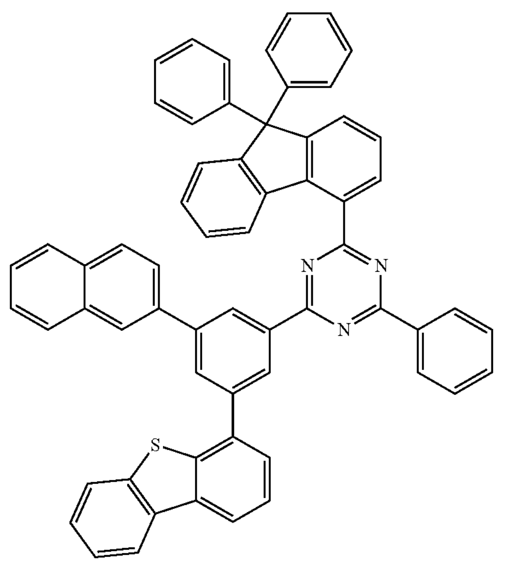
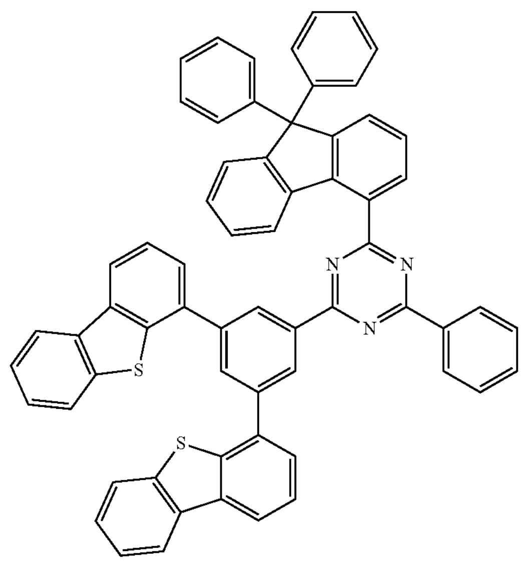
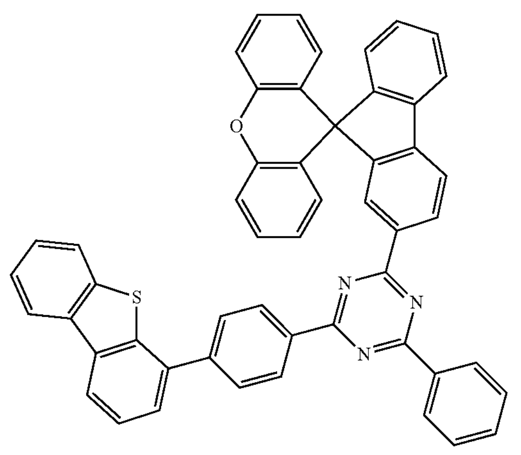
-continued
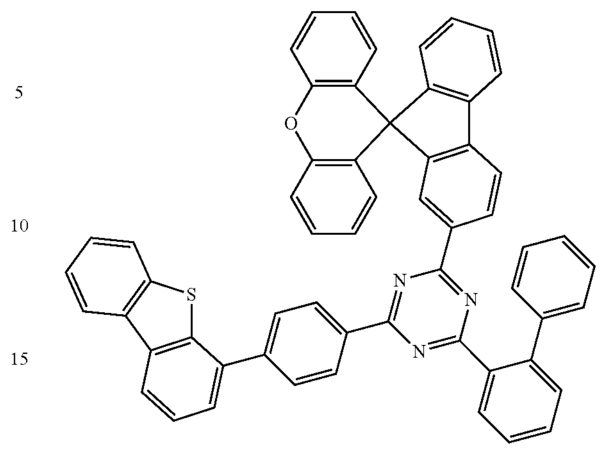
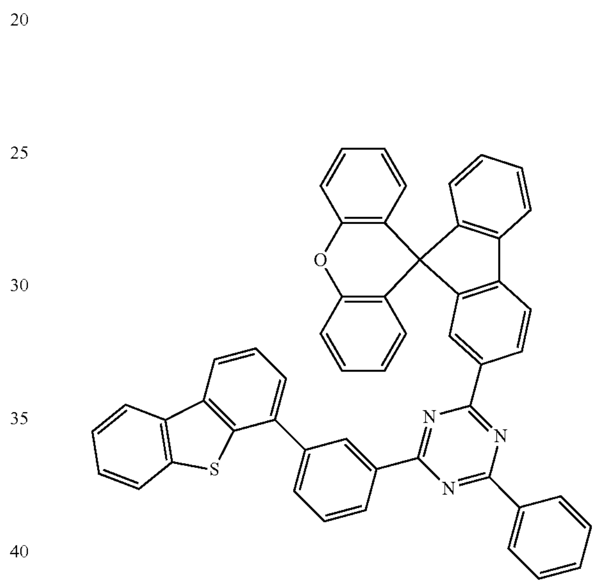
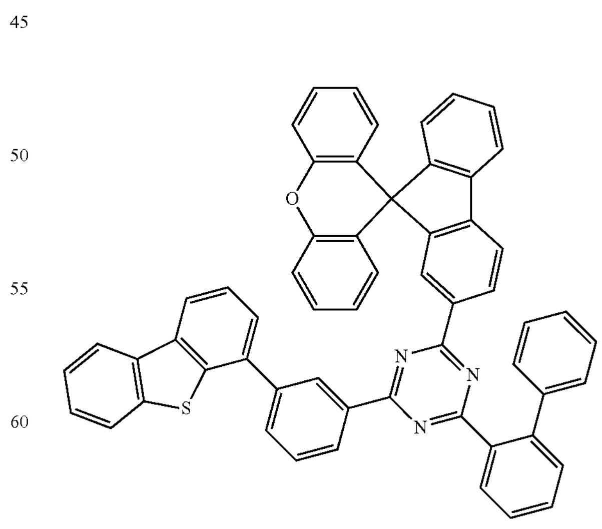

-continued
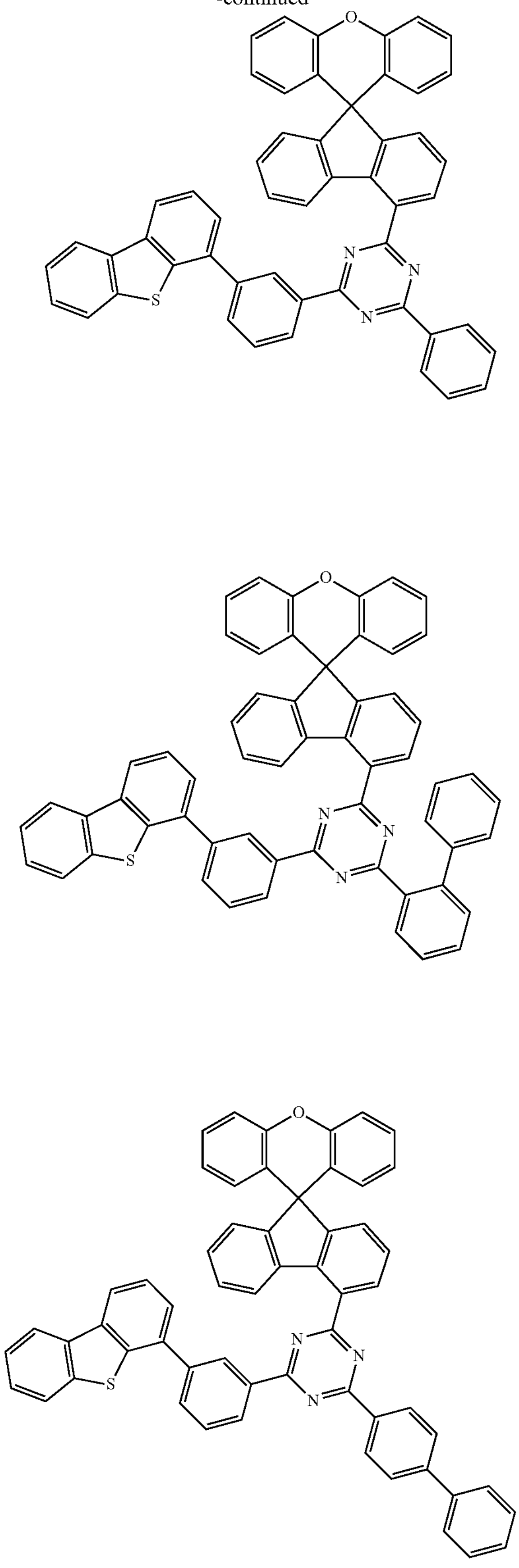
-continued
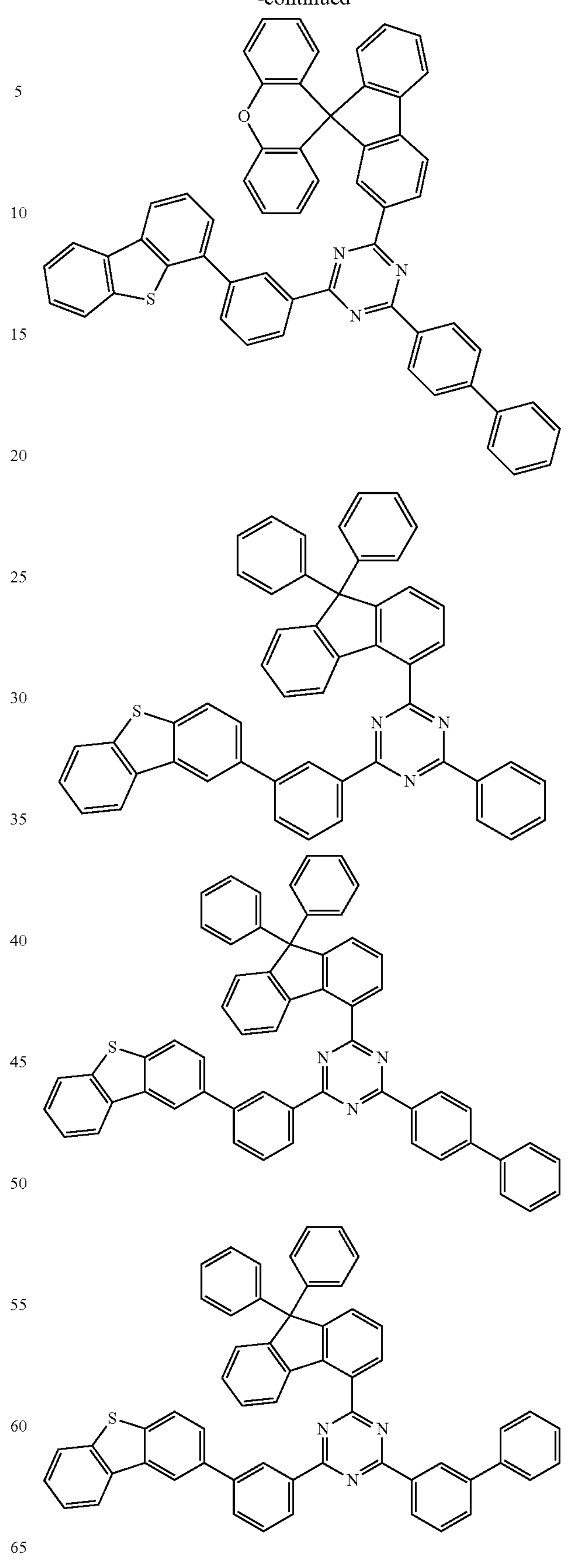

-continued
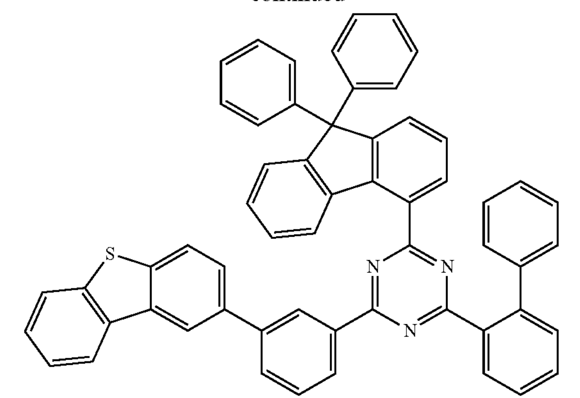
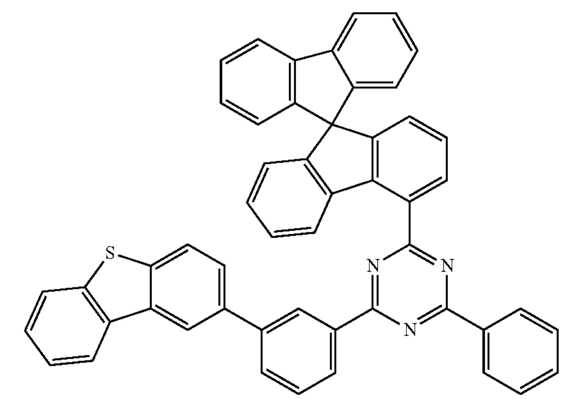
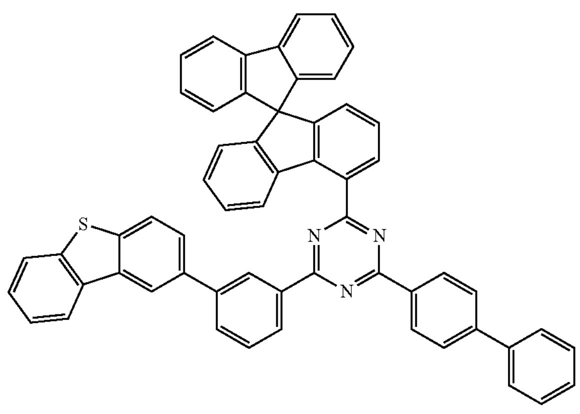
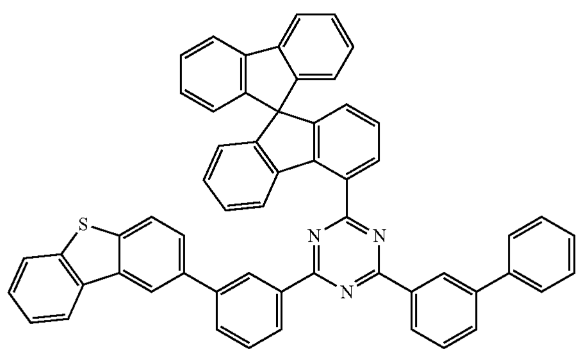
-continued
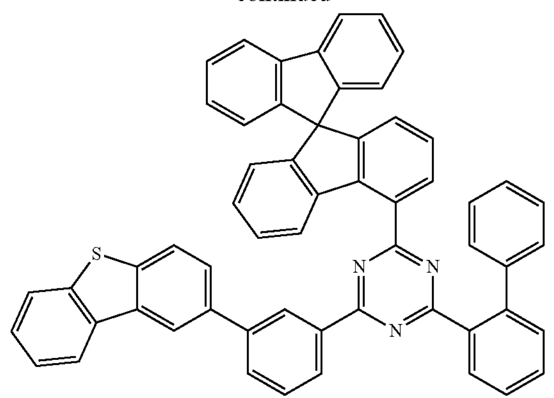
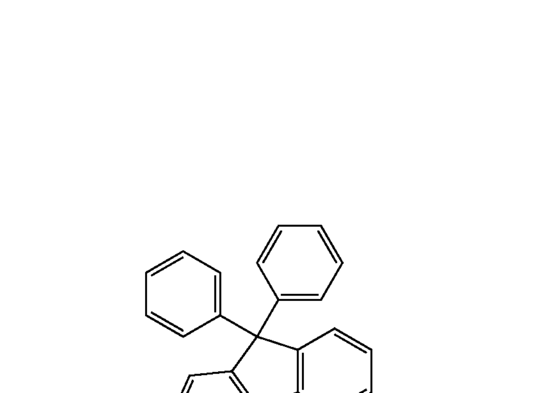
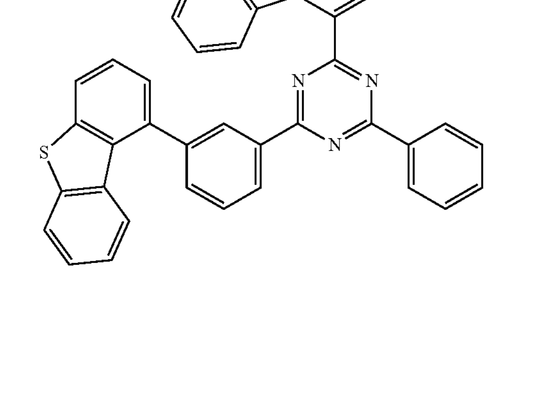
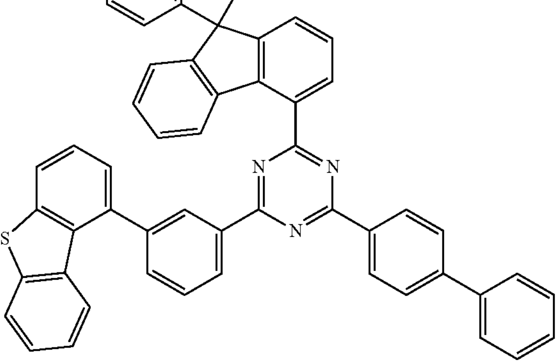

-continued
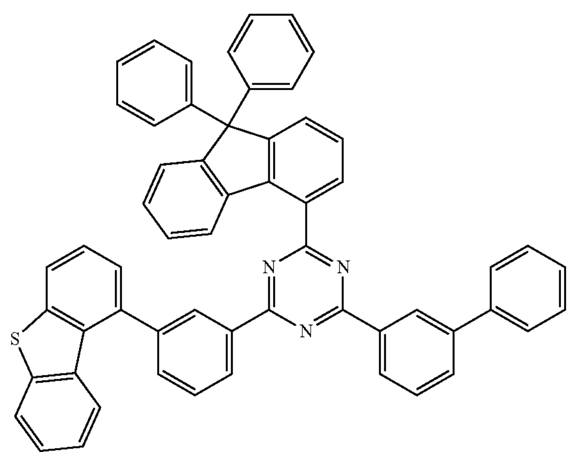
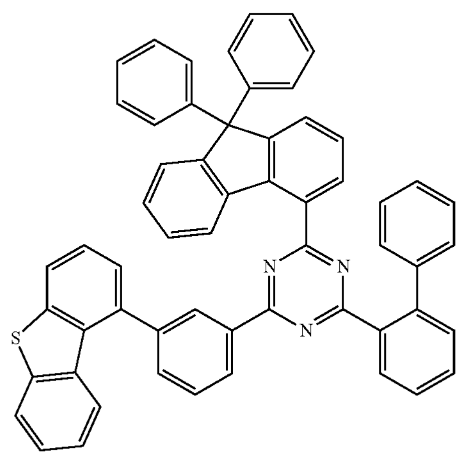
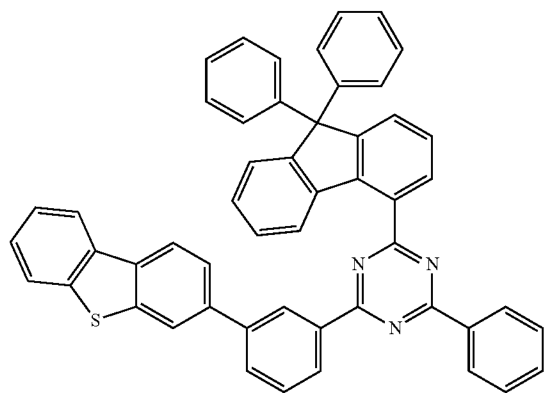
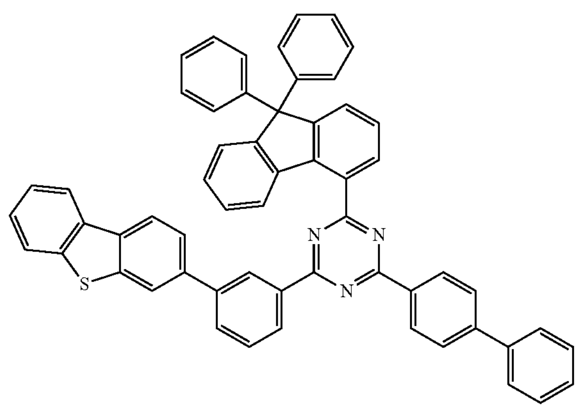
-continued
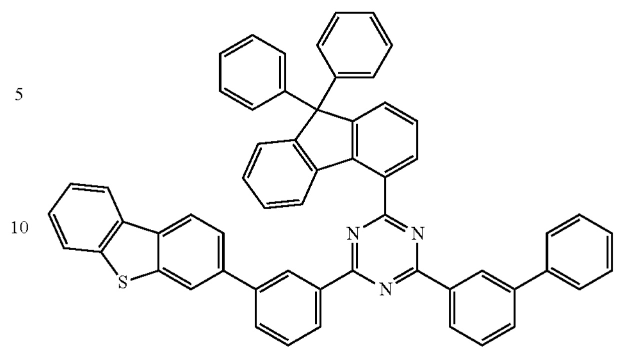
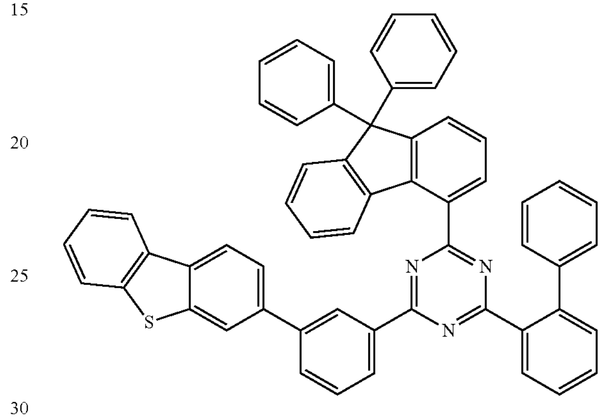
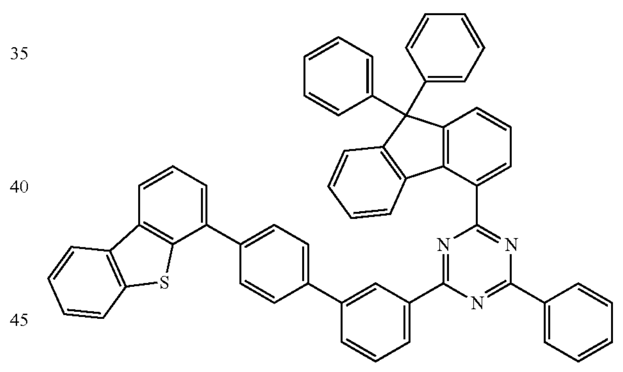
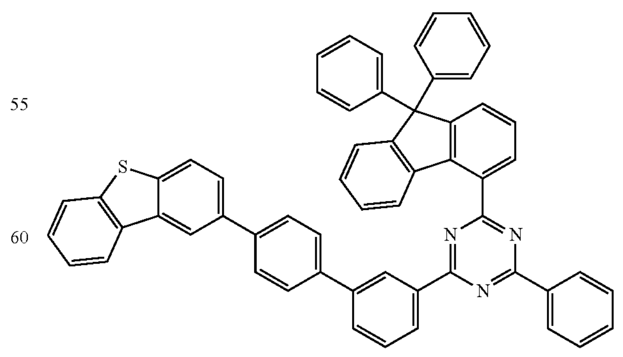

-continued
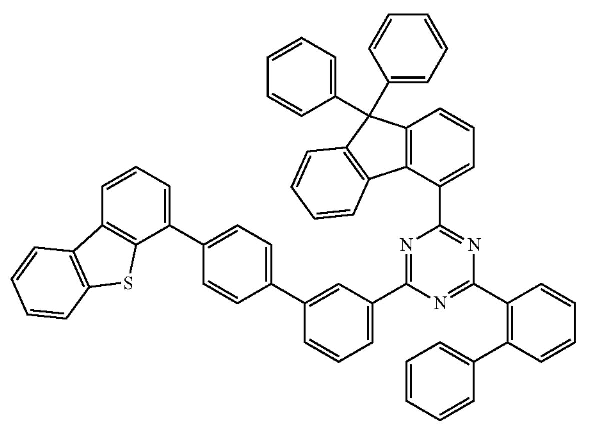
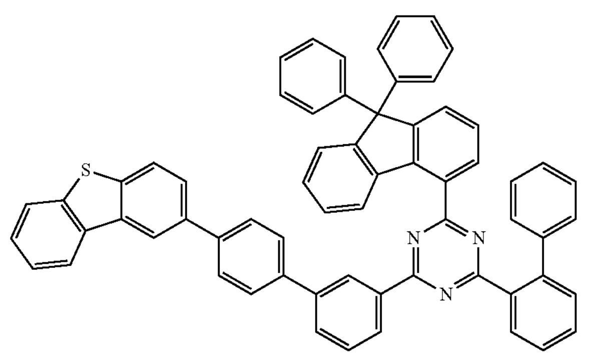
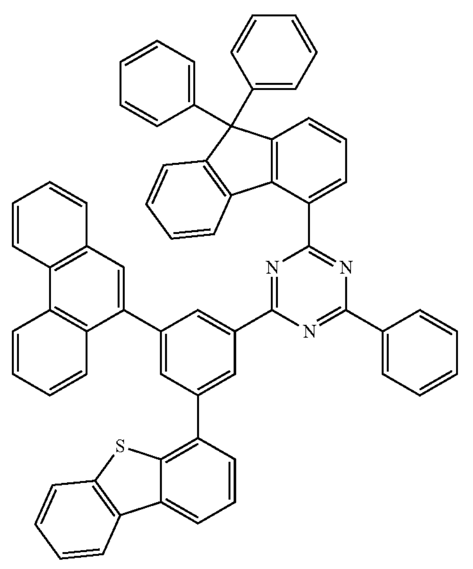
-continued
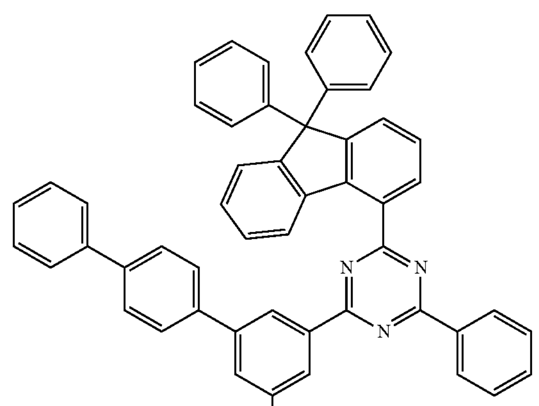
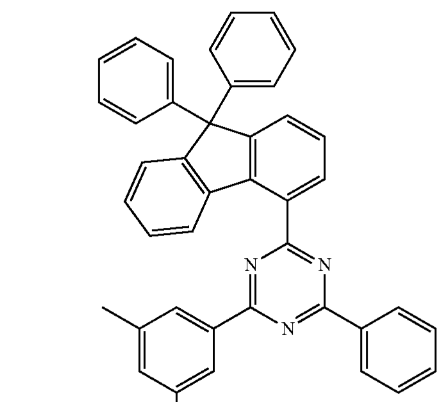
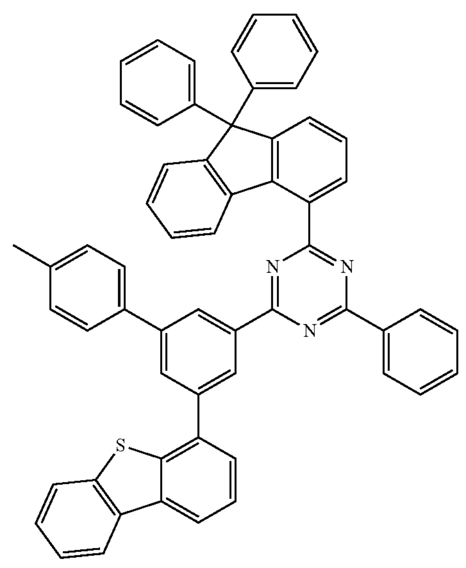

-continued

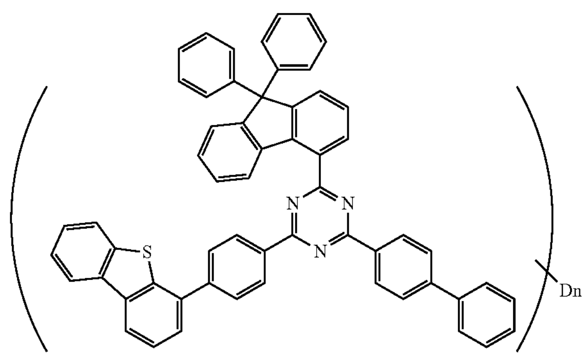

n is the number of deuterium atom included in compound and represents an integer of 1 to 37.

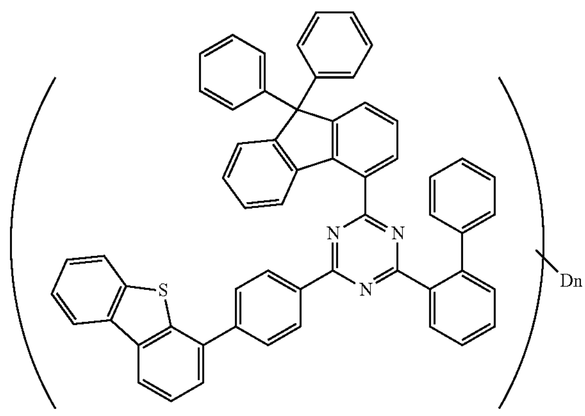

n is the number of deuterium atom included in compound and represents an integer of 1 to 37.

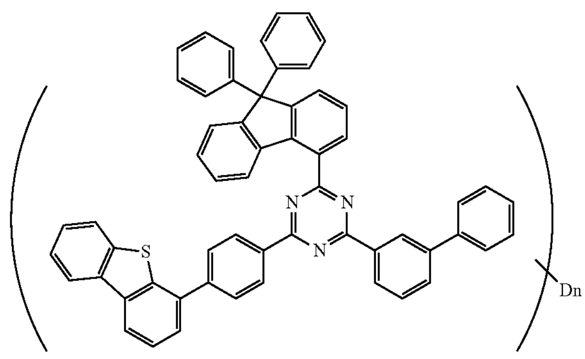

n is the number of deuterium atom included in compound and represents an integer of 1 to 37.

-continued

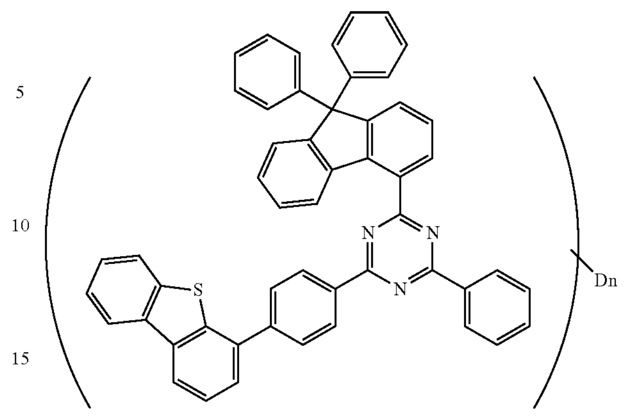

n is the number of deuterium atom included in compound and represents an integer of 1 to 33.

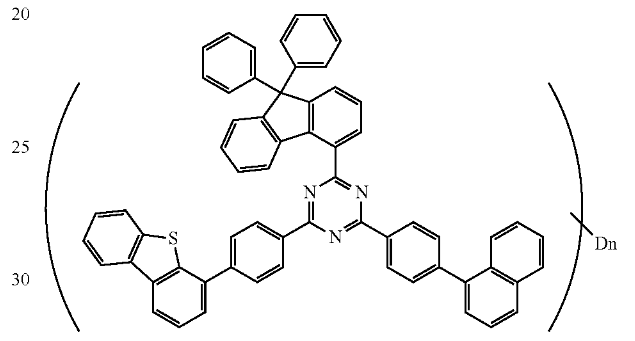

n is the number of deuterium atom included in compound and represents an integer of 1 to 39.

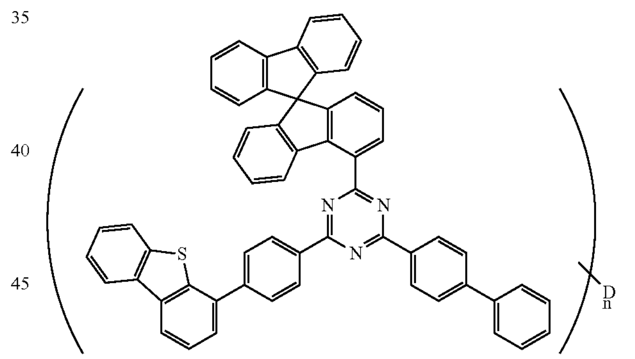

n is the number of deuterium atom included in compound and represents an integer of 1 to 35.

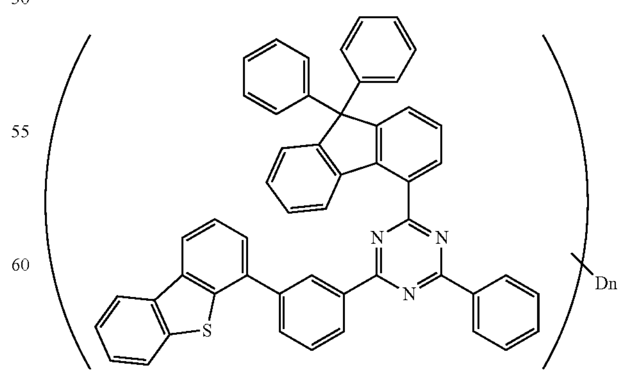

n is the number of deuterium atom included in compound and represents an integer of 1 to 33.

-continued

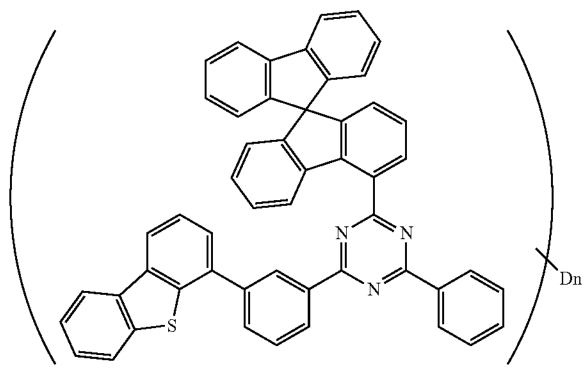

n is the number of deuterium atom included in compound and represents an integer of 1 to 31.

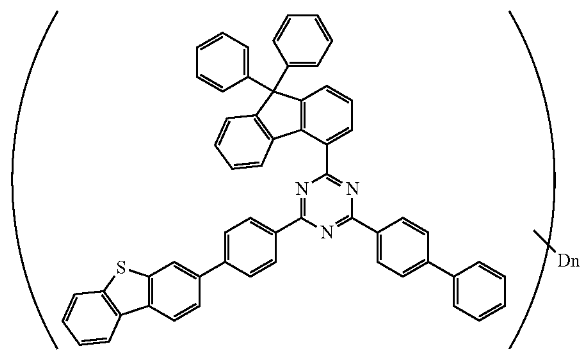

n is the number of deuterium atom included in compound and represents an integer of 1 to 37.

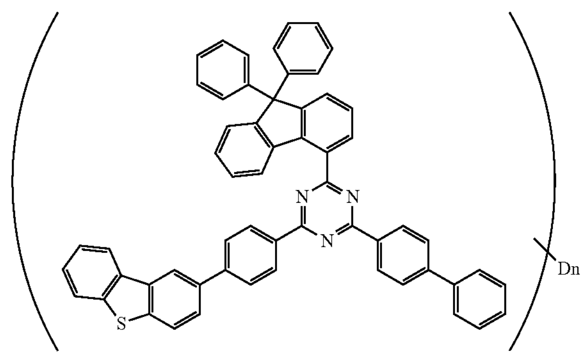

n is the number of deuterium atom included in compound and represents an integer of 1 to 37.

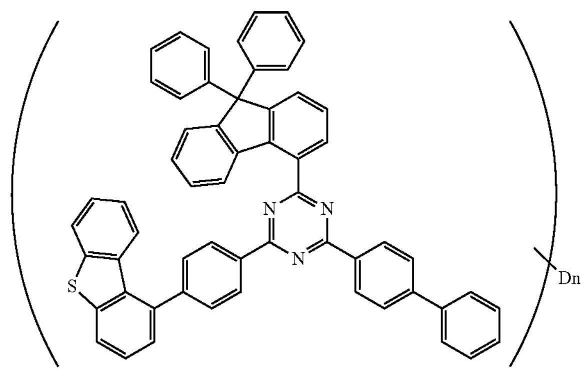

n is the number of deuterium atom included in compound and represents an integer of 1 to 37.

-continued

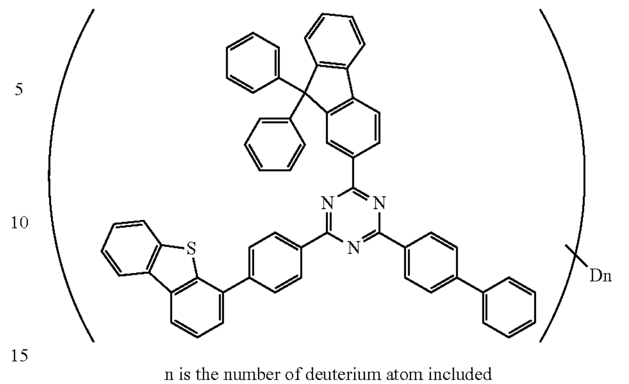

n is the number of deuterium atom included in compound and represents an integer of 1 to 37.

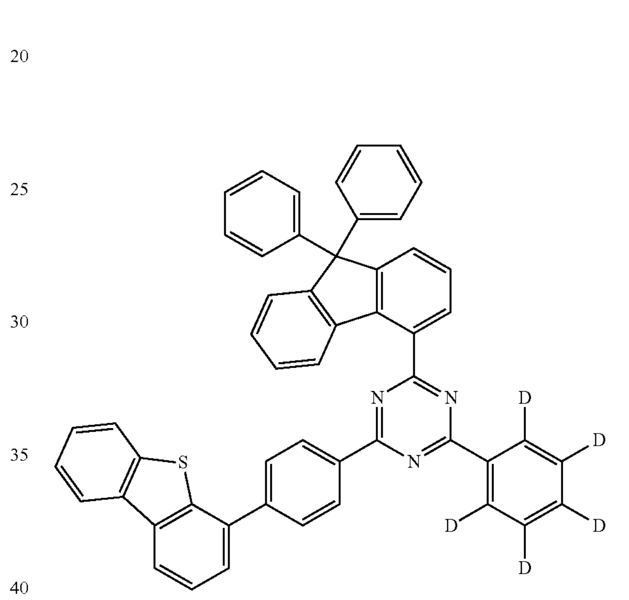

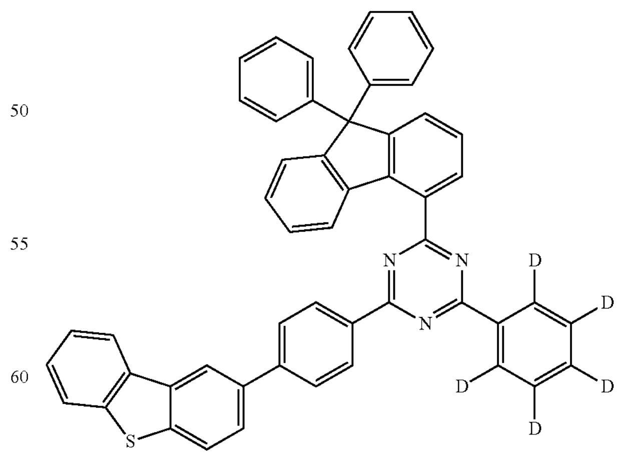

-continued
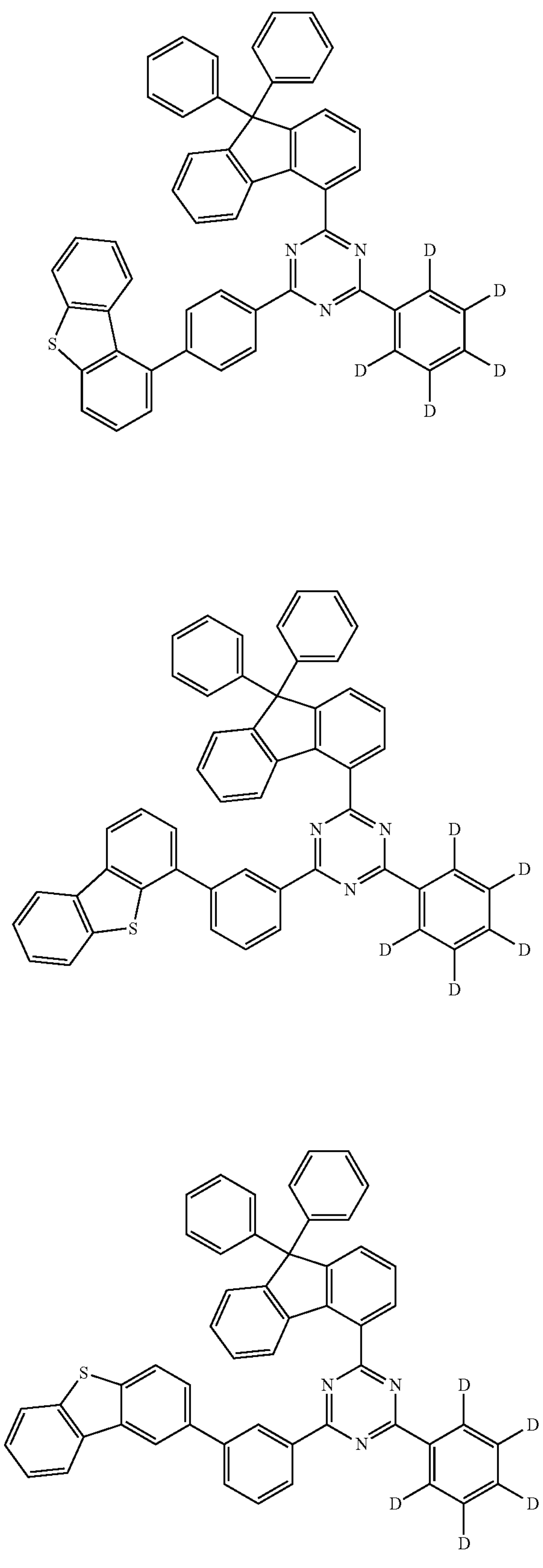
-continued
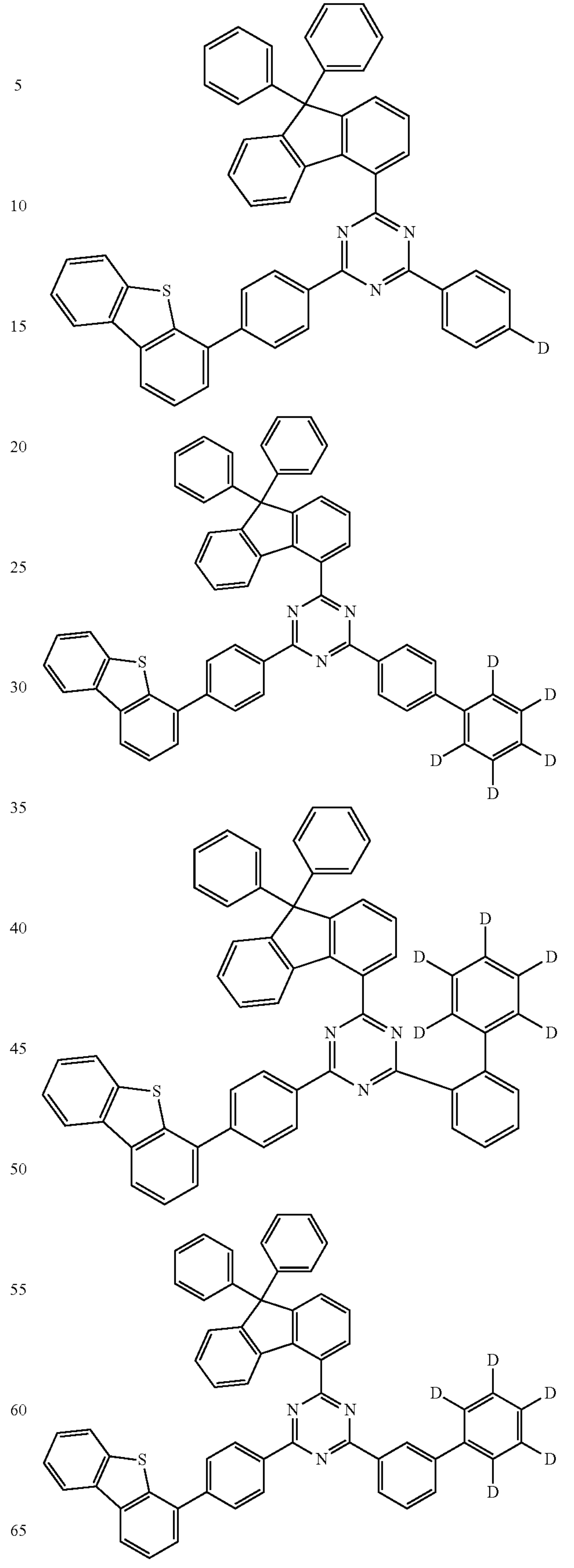

-continued
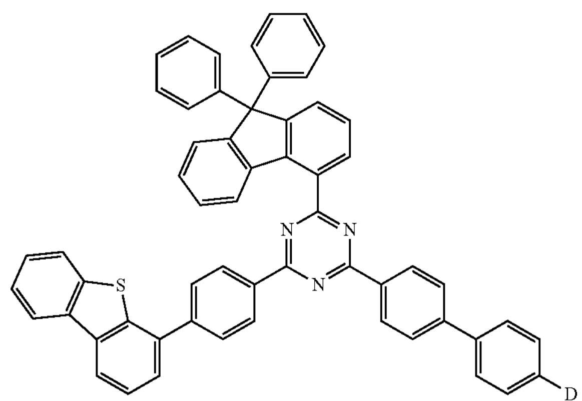
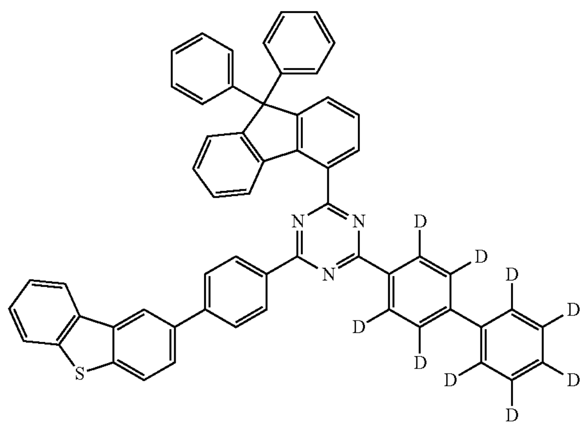
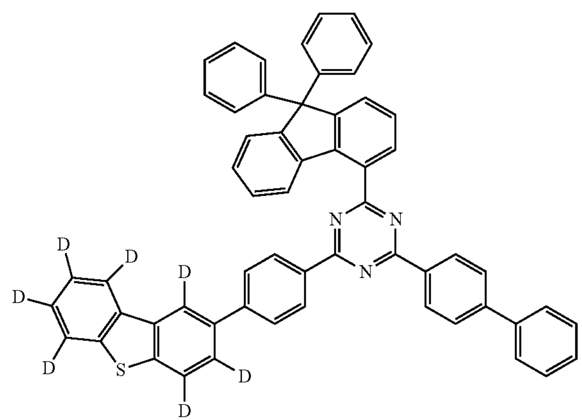
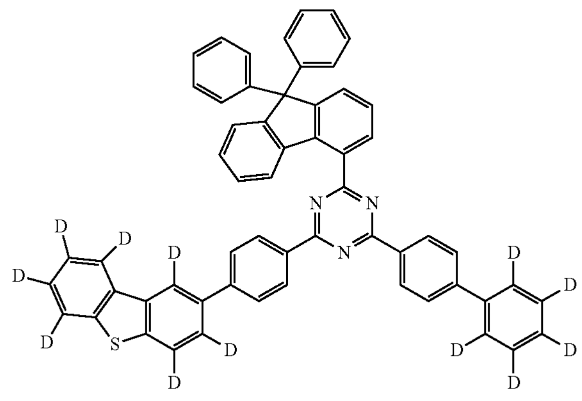
-continued
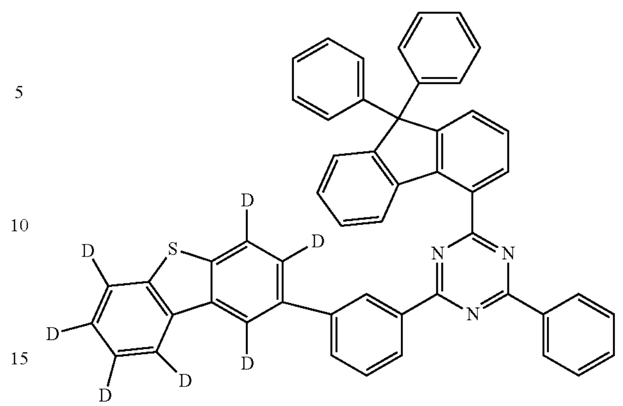
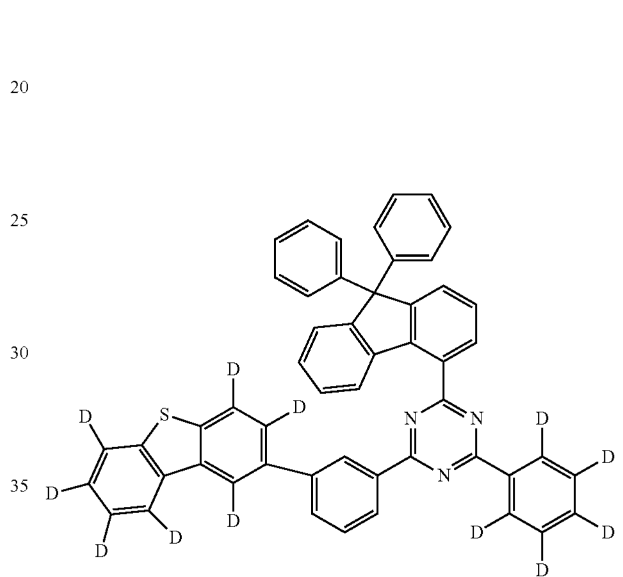
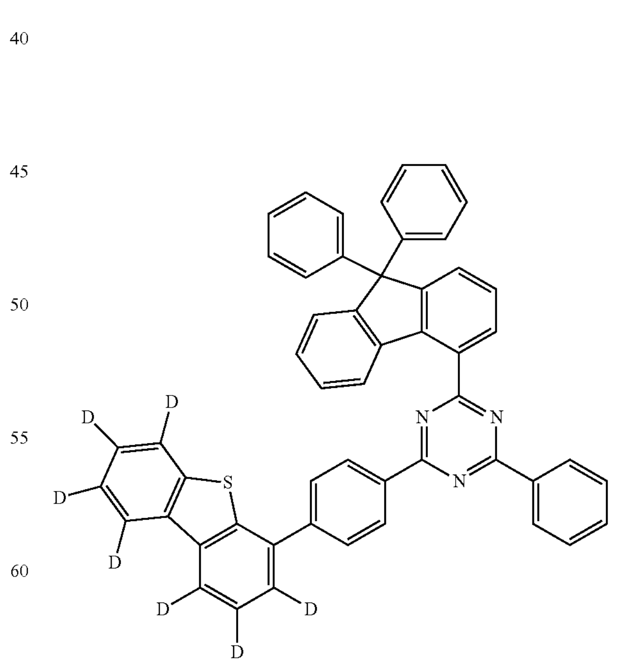

-continued
-continued
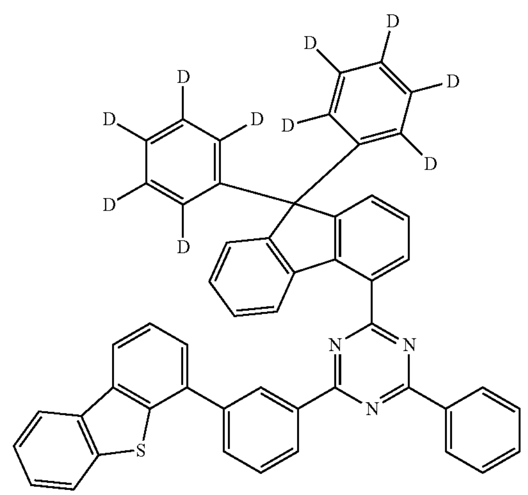
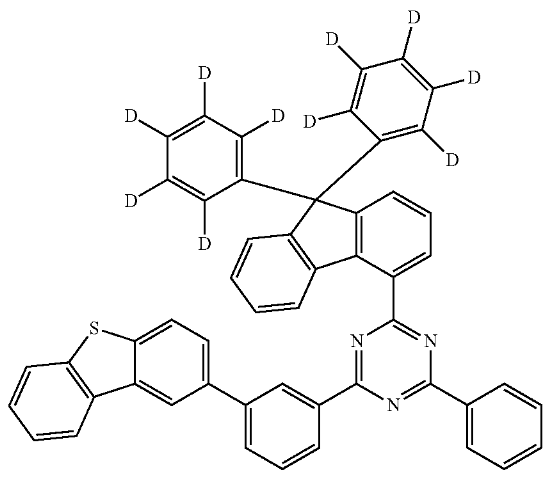
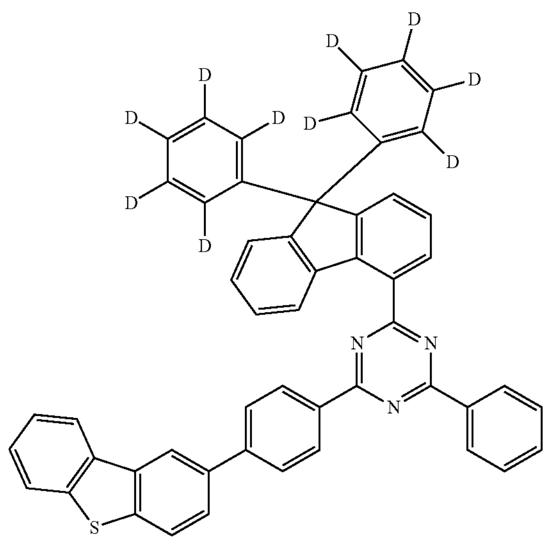

-continued

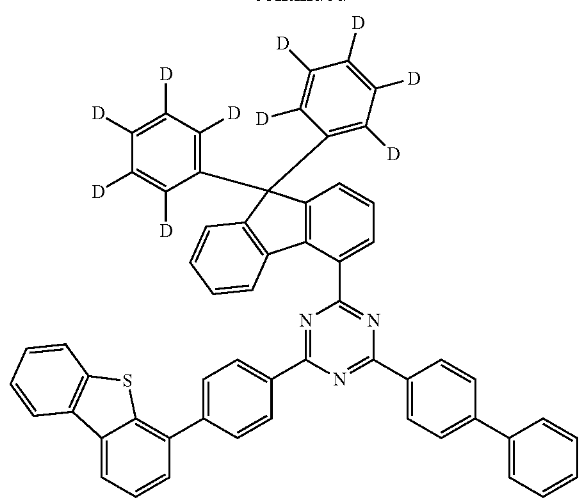

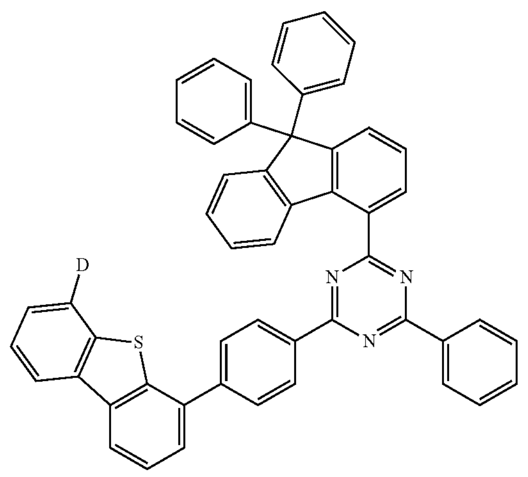

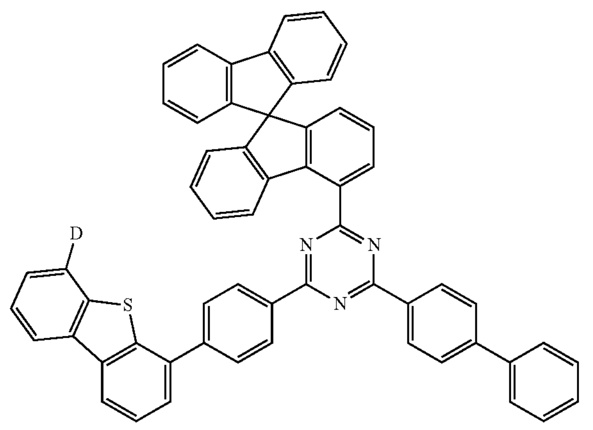

-continued

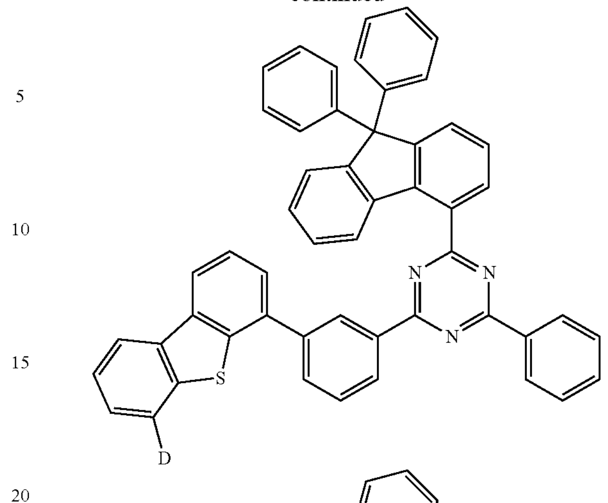

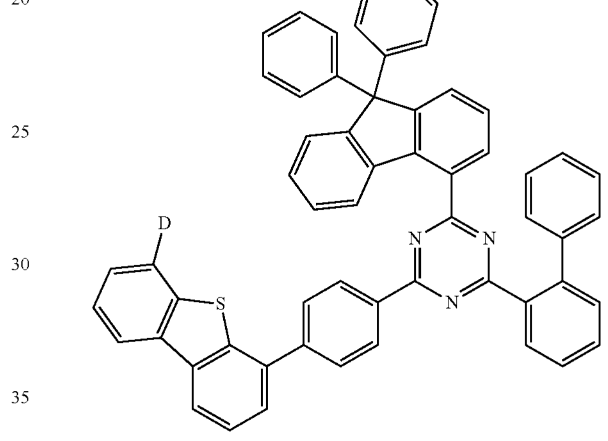

Material for Organic EL Devices

The material for organic EL devices of the present invention contains the inventive compound. The content of the inventive compound in the material for organic EL devices of the present invention may be 1% by mass or more (including 100%), and is preferably 10% by mass or more (including 100%), more preferably 50% by mass or more (including 100%), further preferably 80% by mass or more (including 100%), still further preferably 90% by mass or more (including 100%), still more further preferably 95% by mass or more (including 100%), yet more further preferably 99% by mass of more (including 100%), and most preferably 99.9% by mass of more (including 100%). The material for organic EL devices of the present invention is useful for the production of an organic EL device.

Organic EL Device

The organic EL device of the present invention includes an anode, a cathode, and organic layers intervening between the anode and the cathode. The organic layers include a light emitting layer, and at least one layer of the organic layers contains the inventive compound.

Examples of the organic layer containing the inventive compound include a hole transporting zone (such as a hole injecting layer, a hole transporting layer, an electron blocking layer, and an exciton blocking layer) intervening between the anode and the light emitting layer, the light emitting layer, a space layer, and an electron transporting zone (such as an electron injecting layer, an electron transporting layer, and a hole blocking layer) intervening between the cathode and the light emitting layer, but are not limited thereto. The inventive compound is preferably used as a material for the electron transporting zone or the light emitting layer in a fluorescent or phosphorescent EL device, more preferably as a material for the electron transporting zone, further preferably as a material for the electron injecting layer, the electron transporting layer, the hole blocking layer, or the exciton blocking layer, and particularly preferably as a material for the electron injecting layer or the electron transporting layer.

The organic EL device of the present invention may be a fluorescent or phosphorescent light emission-type monochromatic light emitting device or a fluorescent/phosphorescent hybrid-type white light emitting device, and may be a simple type having a single light emitting unit or a tandem type having a plurality of light emitting units. Above all, the fluorescent light emission-type device is preferred. The "light emitting unit" referred to herein refers to a minimum unit that emits light through recombination of injected holes and electrons, which includes organic layers among which at least one layer is a light emitting layer.

For example, as a representative device configuration of the simple type organic EL device, the following device configuration may be exemplified.

(1) Anode/Light Emitting Unit/Cathode

The light emitting unit may be a multilayer type having a plurality of phosphorescent light emitting layers or fluorescent light emitting layers. In this case, a space layer may intervene between the light emitting layers for the purpose of preventing excitons generated in the phosphorescent light emitting layer from diffusing into the fluorescent light emitting layer. Representative layer configurations of the simple type light emitting unit are described below. Layers in parentheses are optional.

(a) (hole injecting layer/) hole transporting layer/fluorescent light emitting layer/electron transporting layer (/electron injecting layer)

(b) (hole injecting layer/) hole transporting layer/phosphorescent light emitting layer/electron transporting layer (/electron injecting layer)

(c) (hole injecting layer/) hole transporting layer/first fluorescent light emitting layer/second fluorescent light emitting layer/electron transporting layer (/electron injecting layer)

(d) (hole injecting layer/) hole transporting layer/first phosphorescent light emitting layer/second phosphorescent light emitting layer/electron transporting layer (/electron injecting layer)

(e) (hole injecting layer/) hole transporting layer/phosphorescent light emitting layer/space layer/fluorescent light emitting layer/electron transporting layer (/electron injecting layer)

(f) (hole injecting layer/) hole transporting layer/first phosphorescent light emitting layer/second phosphorescent light emitting layer/space layer/fluorescent light emitting layer/electron transporting layer (/electron injecting layer)

(g) (hole injecting layer/) hole transporting layer/first phosphorescent light emitting layer/space layer/second phosphorescent light emitting layer/space layer/fluorescent light emitting layer/electron transporting layer (/electron injecting layer)

(h) (hole injecting layer/) hole transporting layer/phosphorescent light emitting layer/space layer/first fluorescent light emitting layer/second fluorescent light emitting layer/electron transporting layer (/electron injecting layer)

(i) (hole injecting layer;) hole transporting layer/electron blocking layer/fluorescent light emitting layer/electron transporting layer (/electron injecting layer)

(j) (hole injecting layer/) hole transporting layer/electron blocking layer/phosphorescent light emitting layer/electron transporting layer (/electron injecting layer)

(k) (hole injecting layer/) hole transporting layer/exciton blocking layer/fluorescent light emitting layer/electron transporting layer (/electron injecting layer)

(l) (hole injecting layer/) hole transporting layer/exciton blocking layer/phosphorescent light emitting layer/electron transporting layer (/electron injecting layer)

(m) (hole injecting layer/) first hole transporting layer/second hole transporting layer/fluorescent light emitting layer/electron transporting layer (/electron injecting layer)

(n) (hole injecting layer/) first hole transporting layer/second hole transporting layer/phosphorescent light emitting layer/electron transporting layer (/electron injecting layer)

(o) (hole injecting layer/) first hole transporting layer/second hole transporting layer/fluorescent light emitting layer/first electron transporting layer/second electron transporting layer (/electron injecting layer)

(p) (hole injecting layer/) first hole transporting layer/second hole transporting layer/phosphorescent light emitting layer/first electron transporting layer/second electron transporting layer (/electron injecting layer)

(q) (hole injecting layer/) hole transporting layer/fluorescent light emitting layer/hole blocking layer/electron transporting layer (/electron injecting layer)

(r) (hole injecting layer/) hole transporting layer/phosphorescent light emitting layer/hole blocking layer/electron transporting layer (/electron injecting layer)

(s) (hole injecting layer/) hole transporting layer/fluorescent light emitting layer/exciton blocking layer/electron transporting layer (/electron injecting layer)

(t) (hole injecting layer/) hole transporting layer/phosphorescent light emitting layer/exciton blocking layer/electron transporting layer (/electron injecting layer)

The phosphorescent and fluorescent light emitting layers may emit emission colors different from each other, respectively. Specifically, in the light emitting unit (f), a layer configuration, such as (hole injecting layer/) hole transporting layer/first phosphorescent light emitting layer (red light emission)/second phosphorescent light emitting layer (green light emission)/space layer/fluorescent light emitting layer (blue light emission)/electron transporting layer, may be exemplified.

An electron blocking layer may be properly provided between each light emitting layer and the hole transporting layer or the space layer. A hole blocking layer may be properly provided between each light emitting layer and the electron transporting layer. The employment of the electron blocking layer or the hole blocking layer allows to improve the emission efficiency by trapping electrons or holes within the light emitting layer and increasing the probability of charge recombination in the light emitting layer.

As a representative device configuration of the tandem type organic EL device, the following device configuration may be exemplified.

(2) Anode/First Light Emitting Unit/Intermediate Layer/Second Light Emitting Unit/Cathode For example, each of the first light emitting unit and the second light emitting unit may be independently selected from the above-described light emitting units.

The intermediate layer is also generally referred to as an intermediate electrode, an intermediate conductive layer, a charge generation layer, an electron withdrawing layer, a connecting layer, or an intermediate insulating layer, and a known material configuration can be used, in which electrons are supplied to the first light emitting unit, and holes are supplied to the second light emitting unit.

FIG. 1 is a schematic illustration showing an example of the configuration of the organic EL device of the present invention. The organic EL device 1 of this example includes a substrate 2, an anode 3, a cathode 4, and a light emitting unit 10 disposed between the anode 3 and the cathode 4. The light emitting unit 10 includes a light emitting layer 5. A hole transporting zone 6 (such as a hole injecting layer and a hole transporting layer) is provided between the light emitting layer 5 and the anode 3, and an electron transporting zone 7 (such as an electron injecting layer and an electron transporting layer) is provided between the light emitting layer 5 and the cathode 4. In addition, an electron blocking layer (which is not shown in the figure) may be provided on the side of the anode 3 of the light emitting layer 5, and a hole blocking layer (which is not shown in the figure) may be provided on the side of the cathode 4 of the light emitting layer 5. According to the configuration, electrons and holes are trapped in the light emitting layer 5, thereby enabling one to further increase the production efficiency of excitons in the light emitting layer 5.

Figure 2:
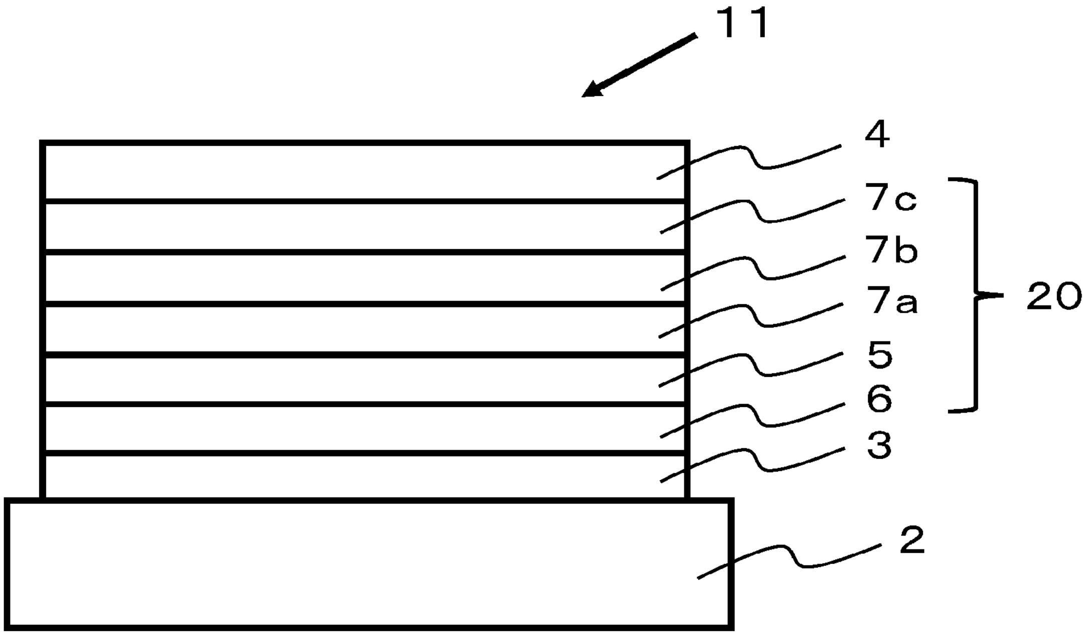
FIG. 2 is a schematic illustration showing another example of the layer configuration of the organic EL device according to one embodiment of the present invention.

FIG. 2 is a schematic illustration showing another configuration of the organic EL device of the present invention. An organic EL device 11 includes the substrate 2, the anode 3, the cathode 4, and a light emitting unit 20 disposed between the anode 3 and the cathode 4. The light emitting unit 20 includes the light emitting layer 5. A hole transporting zone 6 (such as a hole injecting layer and a hole transporting layer) is disposed between the anode 3 and the light emitting layer 5. An electron transporting zone is disposed between the light emitting layer 5 and the cathode 4, and the electron transporting zone includes a first electron transporting layer 7*a*, a second electron transporting layer 7*b*, and an electron injecting layer 7*c*.

In the present invention, a host combined with a fluorescent dopant (a fluorescent emitting material) is referred to as a fluorescent host, and a host combined with a phosphorescent dopant is referred to as a phosphorescent host. The fluorescent host and the phosphorescent host are not distinguished from each other merely by the molecular structures thereof. Specifically, the phosphorescent host means a material that forms a phosphorescent light emitting layer containing a phosphorescent dopant, but does not mean unavailability as a material that forms a fluorescent light emitting layer. The same also applies to the fluorescent host.

Substrate

The substrate is used as a support of the organic EL device. Examples of the substrate include a plate of glass, quartz, and plastic. In addition, a flexible substrate may be used. Examples of the flexible substrate include a plastic substrate made of polycarbonate, polyarylate, polyether sulfone, polypropylene, polyester, polyvinyl fluoride, or polyvinyl chloride. In addition, an inorganic vapor deposition film can be used.

Anode

It is preferred that a metal, an alloy, an electrically conductive compound, or a mixture thereof which has a high work function (specifically 4.0 eV or more) is used for the anode formed on the substrate. Specific examples thereof include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. Besides, examples there include gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the metals (for example, titanium nitride).

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide and 0.1 to 1 wt % of zinc oxide with respect to indium oxide. Besides, the manufacturing may be performed by a vacuum vapor deposition method, a coating method, an inkjet method, a spin coating method, or the like.

The hole injecting layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table of the elements).

It is also possible to use elements belonging to Group 1 or 2 of the periodic table of the elements, which are materials having low work functions, that is, alkali metals, such as lithium (Li) and cesium (Cs), alkaline earth metals, such as magnesium (Mg), calcium (Ca), and strontium (Sr), and alloys containing these (such as MgAg and AlLi), and rare earth metals, such as europium (Eu), and ytterbium (Yb) and alloys containing these. When the anode is formed by using the alkali metals, the alkaline earth metals, and alloys containing these, a vacuum vapor deposition method or a sputtering method can be used. Further, when a silver paste or the like is used, a coating method, an inkjet method, or the like can be used.

Hole Injecting Layer

The hole injecting layer is a layer containing a material having a high hole injection capability (a hole injecting material) and is provided between the anode and the light emitting layer, or between the hole transporting layer, if exists, and the anode.

As the hole injecting material, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, and the like can be used.

Examples of the hole injecting layer material also include aromatic amine compounds as low-molecular weight organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High-molecular weight compounds (such as oligomers, dendrimers, and polymers) may also be used. Examples thereof include high-molecular weight compounds, such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methac rylamide] (abbreviation: PTPDMA), and poly[N,N'-bis(4-butylphenyl)-N,N'-bis(phenyl)benzidine] (abbreviation: Poly-TPD). In addition, high-molecular weight compounds to which an acid is added, such as poly(3,4-ethylenedioxythiophene)/poly (styrene sulfonic acid) (PEDOT/PSS), and polyaniline/poly (styrenesulfonic acid) (PAni/PSS), can also be used.

Furthermore, it is also preferred to use an acceptor material, such as a hexaazatriphenylene (HAT) compound represented by formula (K).

(K)

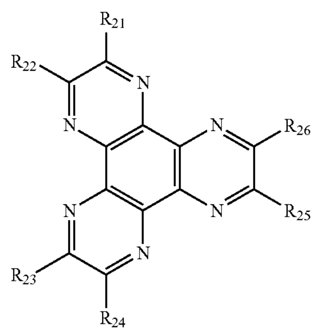

In the aforementioned formula, $R_{21}$ to $R_{26}$ each independently represent a cyano group, —$CONH_2$, a carboxy group, or —$COOR_{27}$ ($R_{27}$ represents an alkyl group having 1 to 20 carbon atoms or a cycloalkyl group having 3 to 20 carbon atoms). In addition, adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, an n-propyl group, an isopropyl group, an n-butyl group, an isobutyl group, a t-butyl group, a cyclopentyl group, and a cyclohexyl group.

Hole Transporting Layer

The hole transporting layer is a layer containing a material having a high hole transporting capability (a hole transporting material) and is provided between the anode and the light emitting layer, or between the hole injecting layer, if exists, and the light emitting layer.

The hole transporting layer may have a single layer structure or a multilayer structure including two or more layers. For example, the hole transporting layer may have a two-layer structure including a first hole transporting layer (anode side) and a second hole transporting layer (cathode side). In one embodiment of the present invention, the hole transporting layer having a single layer structure is preferably disposed adjacent to the light emitting layer, and the hole transporting layer that is closest to the cathode in the multilayer structure, such as the second hole transporting layer in the two-layer structure, is preferably disposed adjacent to the light emitting layer. In another embodiment of the present invention, an electron blocking layer described later and the like may be disposed between the hole transporting layer having a single layer structure and the light emitting layer, or between the hole transporting layer that is closest to the light emitting layer in the multilayer structure and the light emitting layer.

As the hole transporting material, for example, an aromatic amine compound, a carbazole derivative, an anthracene derivative, and the like can be used.

Examples of the aromatic amine compound include 4,4'-bis[N-(1-naphthyl)-N-phenylamino]biphenyl (abbreviation: NPB) or N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The aforementioned compounds have a hole mobility of $10^{-6}$ $cm^2/Vs$ or more.

Examples of the carbazole derivative include 4,4'-di(9-carbazolyl)biphenyl (abbreviation: CBP), 9-[4-(9-carbazolyl)phenyl]10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

High-molecular weight compounds, such as poly(N-vinylcarbazole) (abbreviation: PVK) and poly(4-vinyltriphenylamine) (abbreviation: PVTPA), can also be used.

However, compounds other than those as mentioned above can also be used so long as they are compounds high in the hole transporting capability rather than in the electron transporting capability.

Dopant Material of Light Emitting Layer

The light emitting layer is a layer containing a material having a high light emitting property (a dopant material), and various materials can be used. For example, a fluorescent emitting material or a phosphorescent emitting material can be used as the dopant material. The fluorescent emitting material is a compound that emits light from a singlet excited state, and the phosphorescent emitting material is a compound that emits from a light triplet excited state.

Examples of a blue-based fluorescent emitting material that can be used for the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

Examples of a green-based fluorescent emitting material that can be used for the light emitting layer include an aromatic amine derivative. Specific examples thereof include N-(9,10-diphenyl-2-anthryl)-N,9diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthrac ene-2-amine (abbreviation: 2YGABPhA), and N,N,9-triphenylanthracene-9-amine (abbreviation: DPhAPhA).

Examples of a red-based fluorescent emitting material that can be used for the light emitting layer include a tetracene derivative and a diamine derivative. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

Examples of a blue-based phosphorescent emitting material that can be used for the light emitting layer include a metal complex, such as an iridium complex, an osmium complex, and a platinum complex. Specific examples thereof include bis[2-(4',6'-difluorophenyl)pyridinato-N,C2']iridium(III)tetrakis(1-pyrazolyl)borat e (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III)acetylacetonate (abbreviation: FIracac).

Examples of a green-based phosphorescent emitting material that can be used for the light emitting layer include an iridium complex. Examples thereof include tris(2-phenylpyridinato-N,C2')iridium(III) (abbreviation: Ir(ppy)3), bis(2-phenylpyridinato-N,C2')iridium(III) acetylacetonate (abbreviation: Ir(ppy)2(acac)), bis(1,2-diphenyl-1H-benzimidazolato)iridium(III)acetylacetonate (abbreviation: Ir(pbi)2(acac)), and bis(benzo[h]quinolinato)iridium(III) acetylacetonate (abbreviation: Ir(bzq)2(acac)).

Examples of a red-based phosphorescent emitting material that can be used for the light emitting layer include a metal complex, such as an iridium complex, a platinum complex, a terbium complex, and a europium complex. Specific examples thereof include organic metal complexes, such as bis[2-(2'-benzo[4,5-α]thienyl)pyridinato-N,C3']iridium(III)acetylacetonate (abbreviation: Ir(btp)2(acac)), bis(1-phenylisoquinolinato-N, C2')iridium(III)acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrinplatinum(II) (abbreviation: PtOEP).

Rare earth metal complexes, such as tris(acetylacetonate)(monophenanthroline)terbium(III) (abbreviation: Tb(acac)3(Phen)), tris(1,3-diphenyl-1,3-propanedionate)(monophenanthroline)europium(III) (abbreviation: Eu(DBM)3(Phen)), and tris[1-(2-thenoyl)-3,3,3-trifluoroacetonate](monophenanthroline) europium(III) (abbreviation: Eu(TTA)3(Phen)), emit light from rare earth metal ions (electron transition between different multiplicities), and thus may be used as the phosphorescent emitting material.

Host Material of Light Emitting Layer

The light emitting layer may have a configuration in which the aforementioned dopant material is dispersed in another material (a host material). The host material is preferably a material that has a higher lowest unoccupied orbital level (LUMO level) and a lower highest occupied orbital level (HOMO level) than the dopant material.

Examples of the host material include:

(1) a metal complex, such as an aluminum complex, a beryllium complex, and a zinc complex, (2) a heterocyclic compound, such as an oxadiazole derivative, a benzimidazole derivative, and a phenanthroline derivative, (3) a fused aromatic compound, such as a carbazole derivative, an anthracene derivative, a phenanthrene derivative, a pyrene derivative, and a chrysene derivative, or (4) an aromatic amine compound, such as a triarylamine derivative and a fused polycyclic aromatic amine derivative.

For example, metal complexes, such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), and bathophenanthroline (abbreviation: BPhen), bathocuproine (abbreviation: BCP);

fused aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10diphenylanthracene (abbreviation: DPAnth), and 6,12-dimethoxy-5,11-diphenylchrysene; and aromatic amine compounds, such as N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluorene-2-yl)-N-phenylamino]biphenyl (abbreviation: DFLDPBi), and 4,4'-bis[N-(spiro-9,9'-bifluorene-2-yl)-N-phenylamino]biphenyl (abbreviation: BSPB) can be used. A plurality of host materials may be used.

In particular, in the case of a blue fluorescent device, it is preferred to use the following anthracene compounds as the host material.

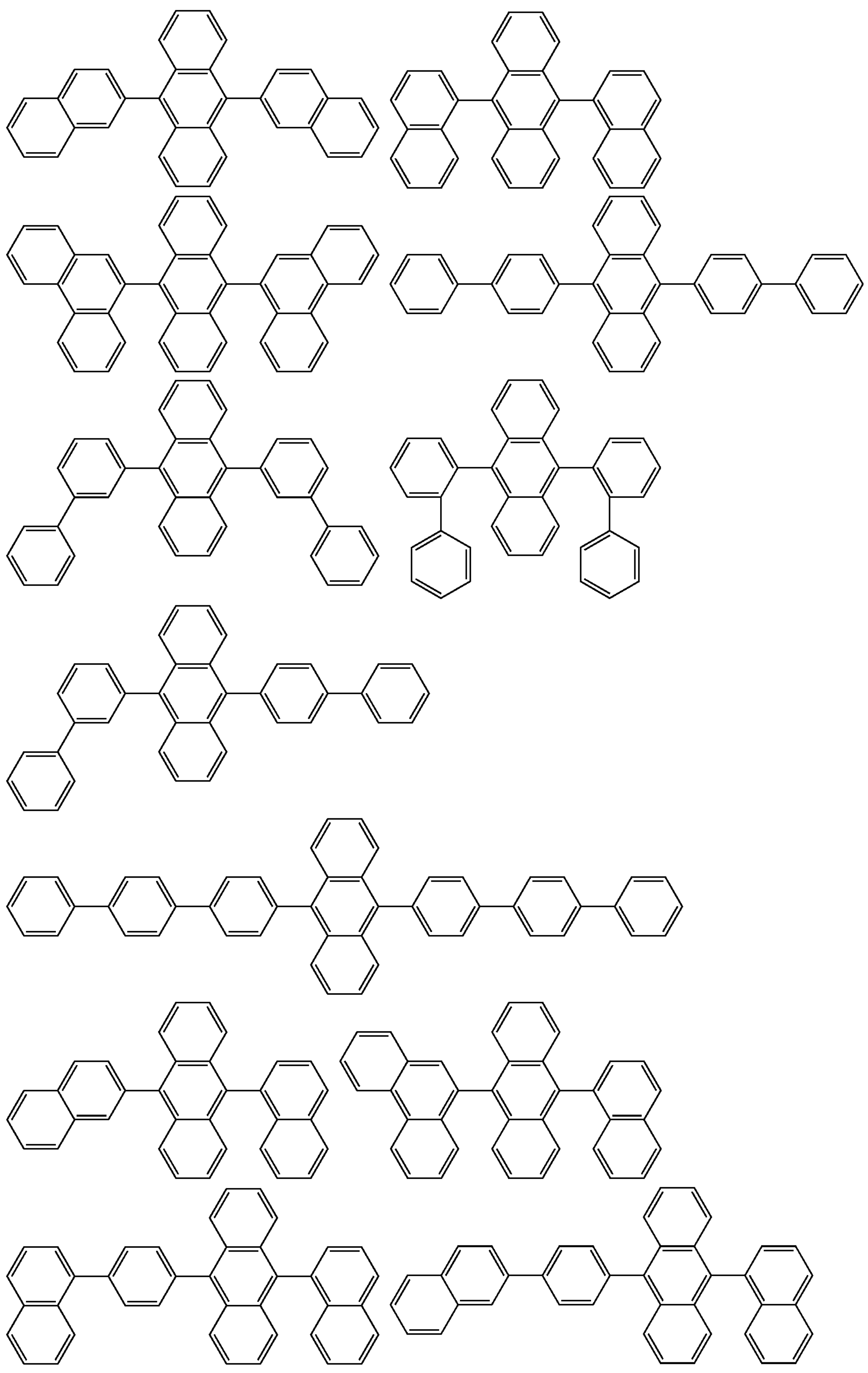

-continued
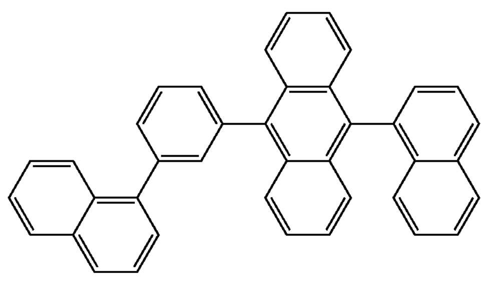
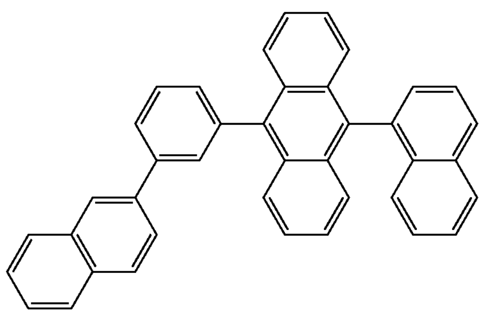
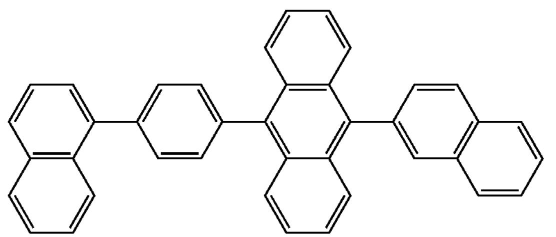
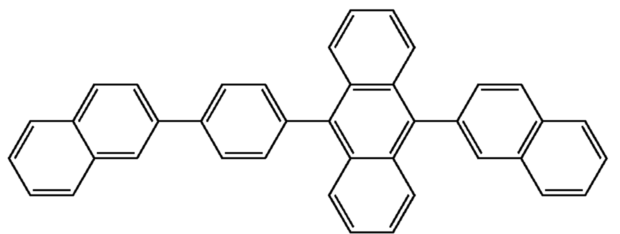
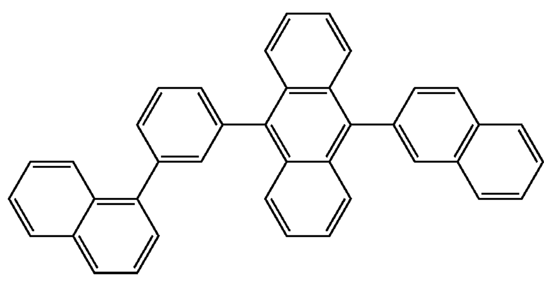
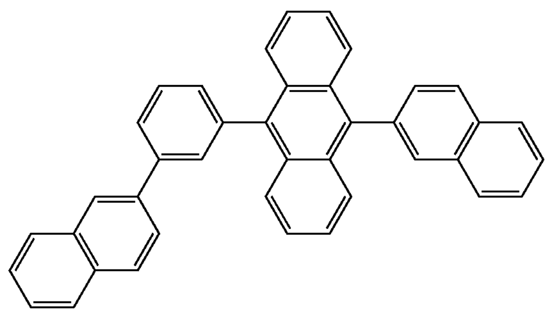
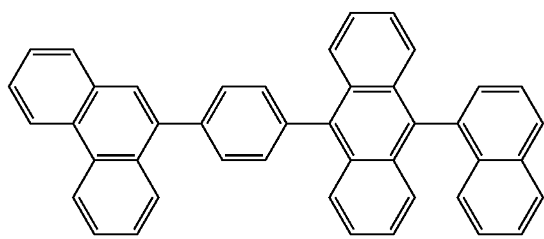
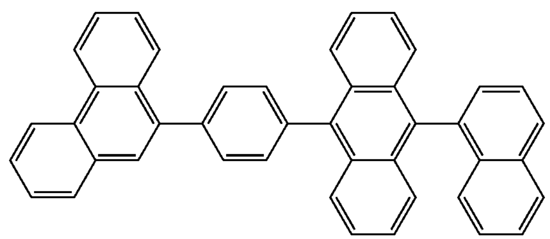
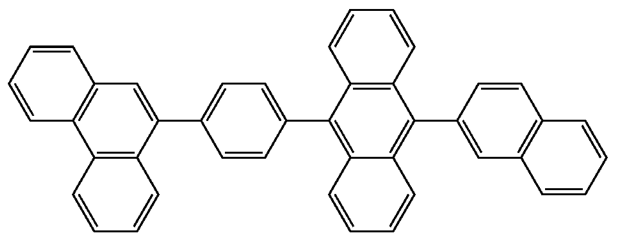

-continued
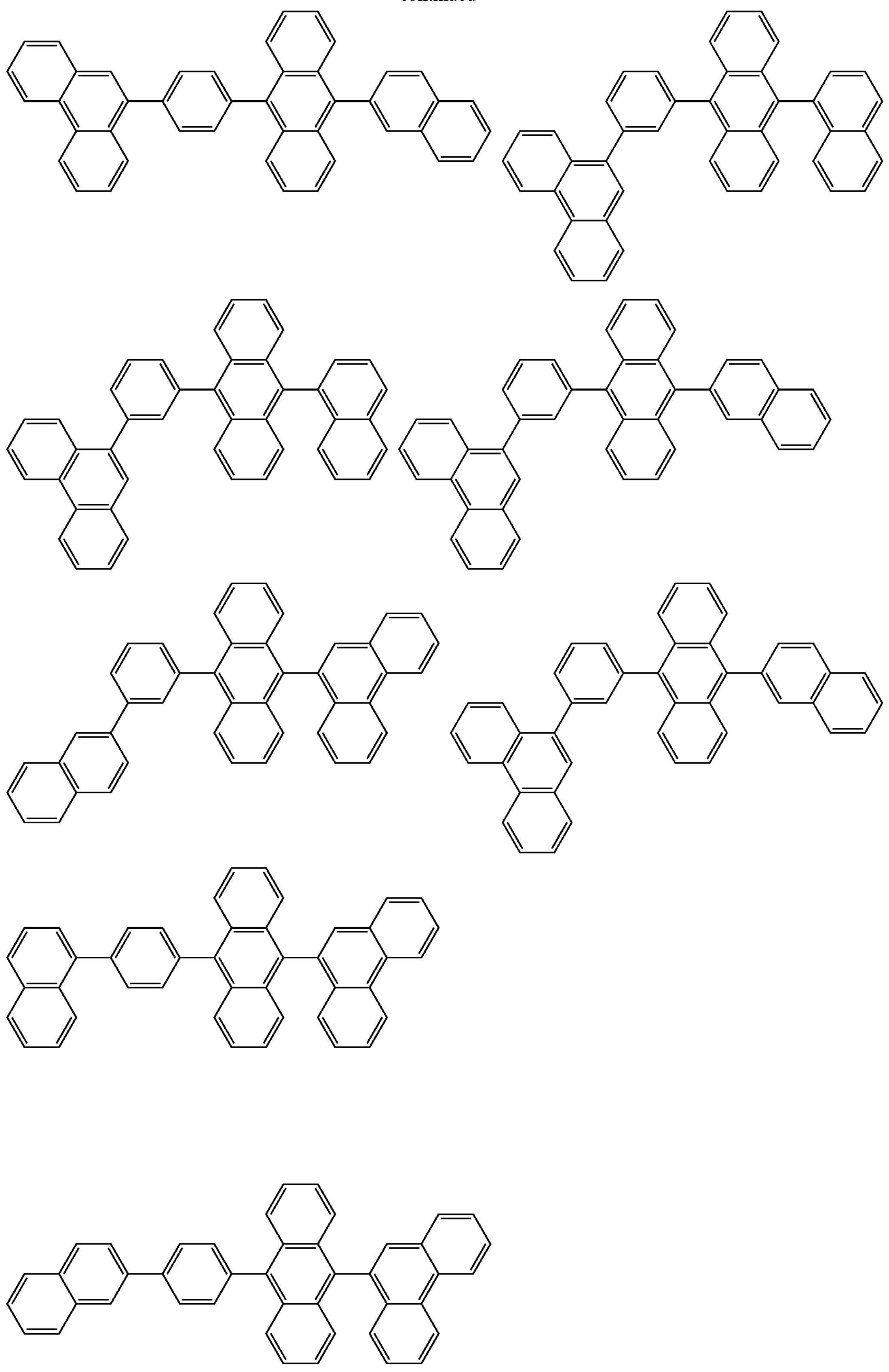

-continued
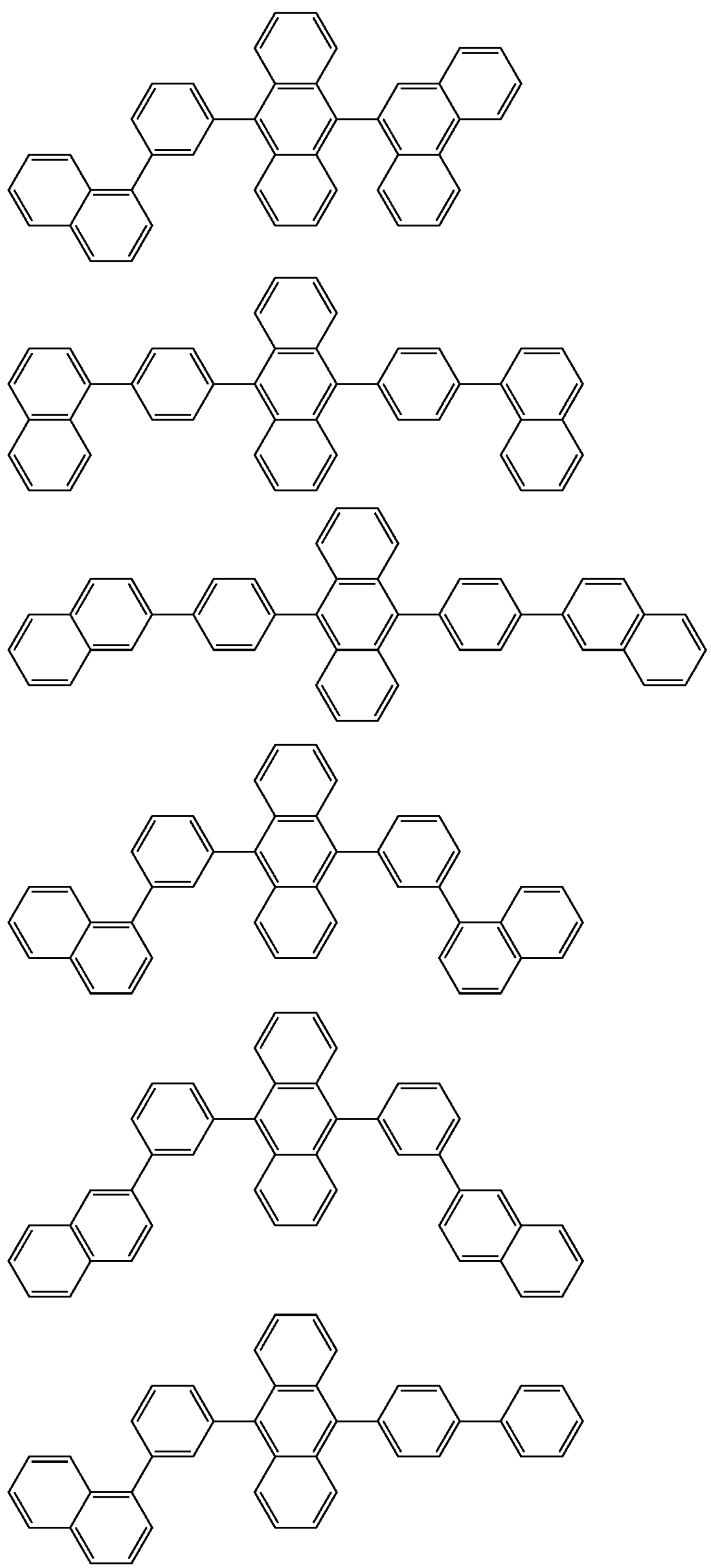

-continued
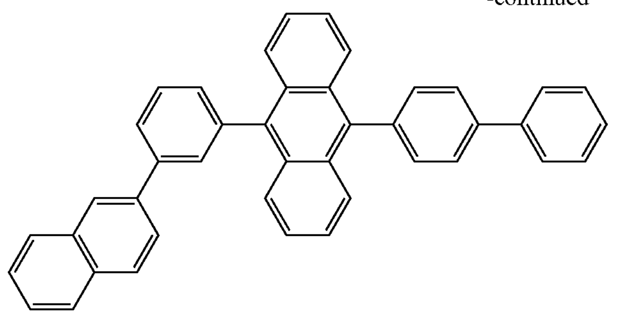
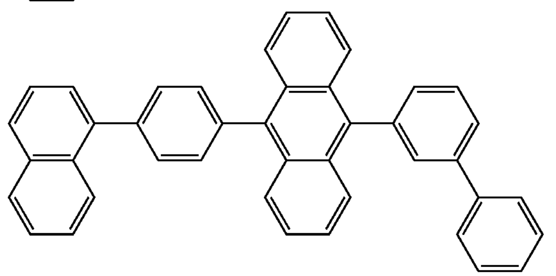
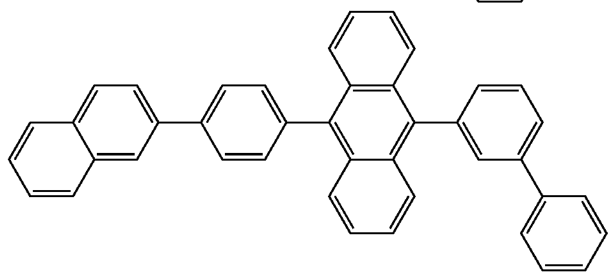
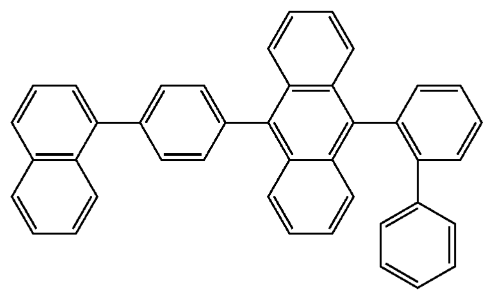
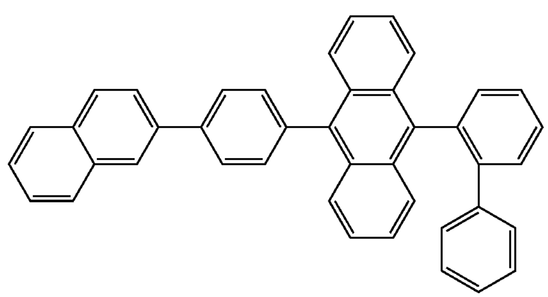
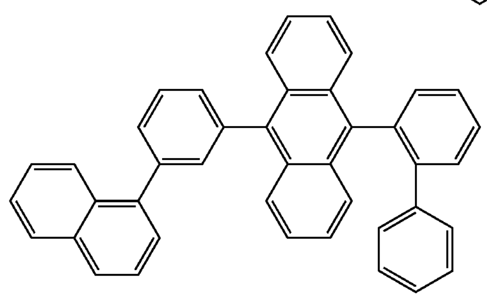
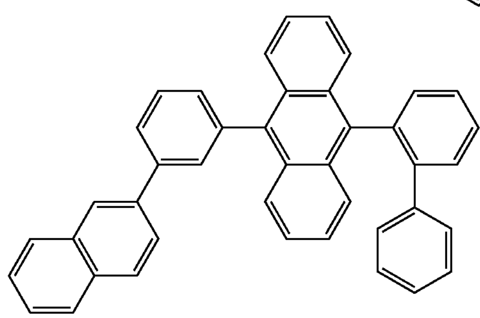
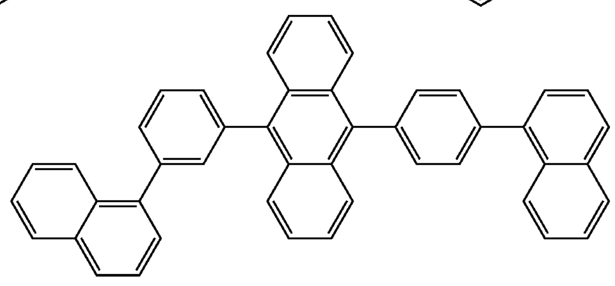
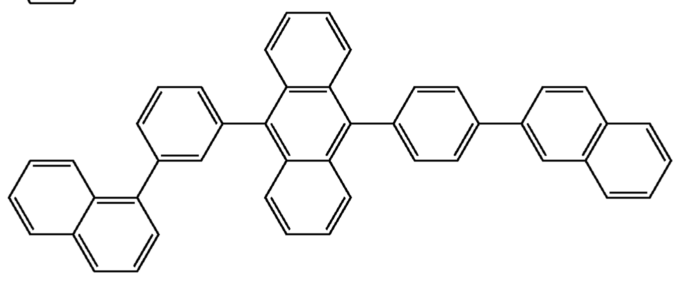

-continued
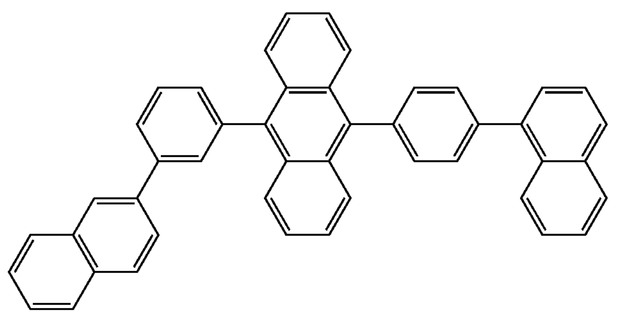
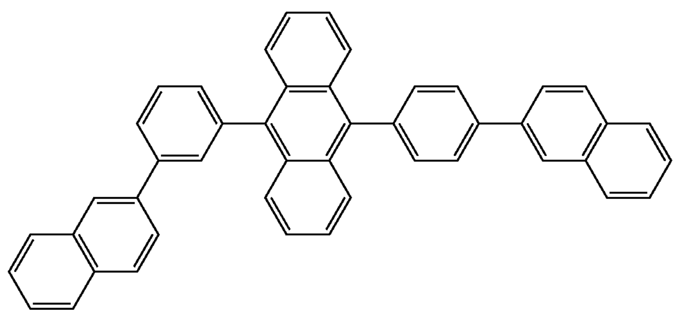
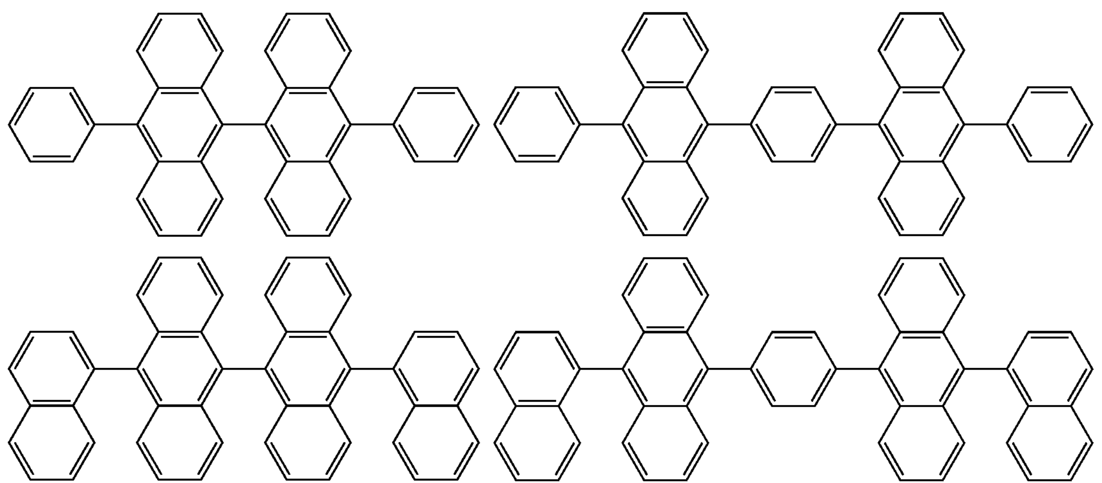
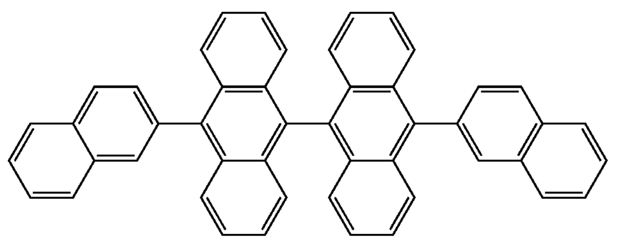
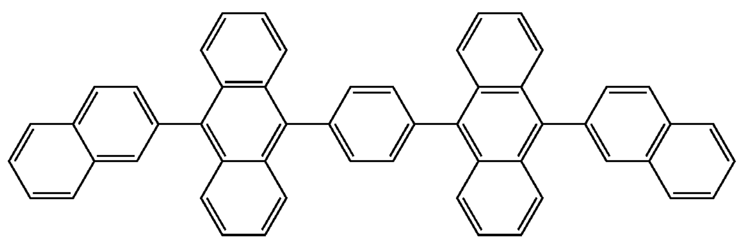

-continued
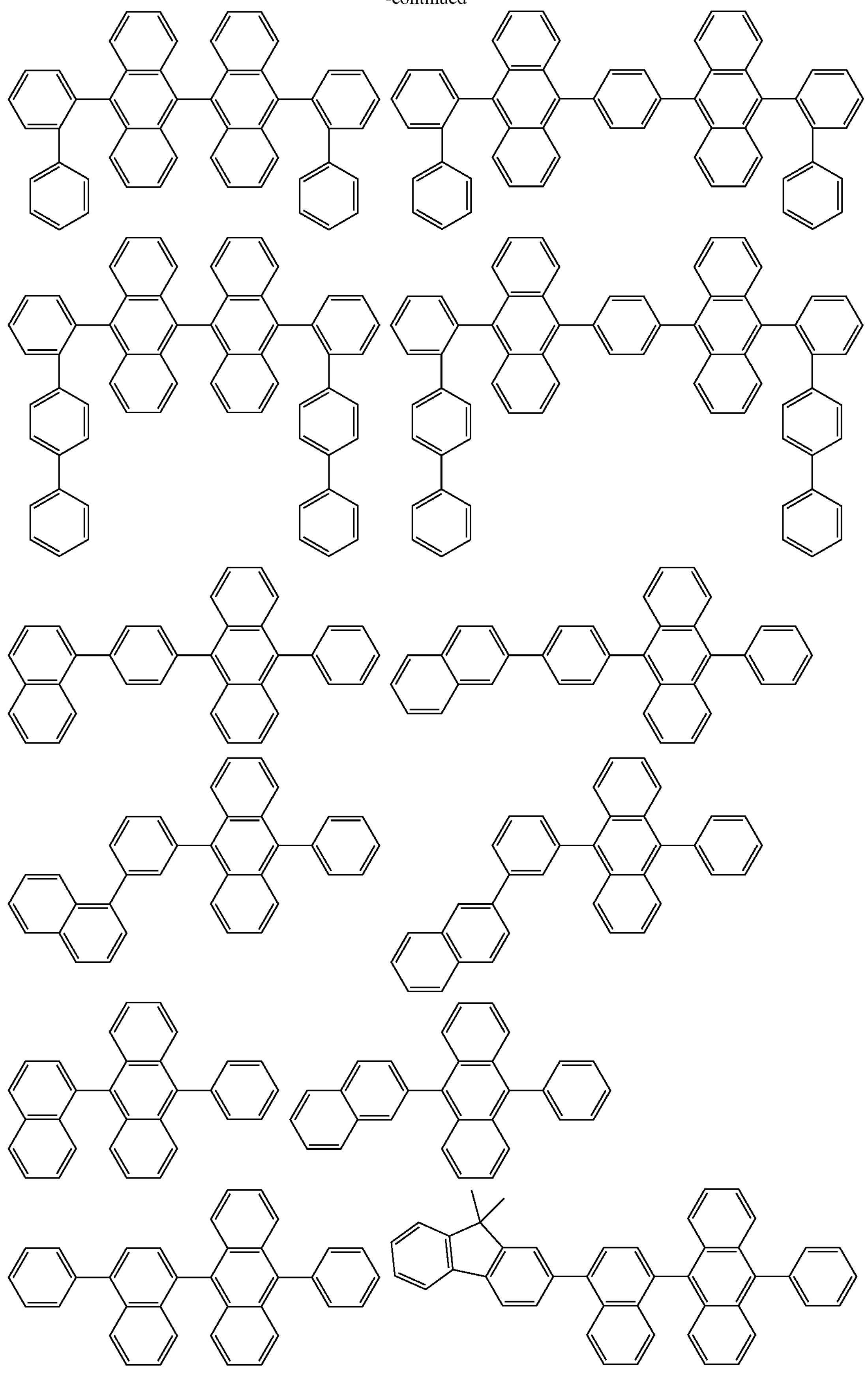

-continued
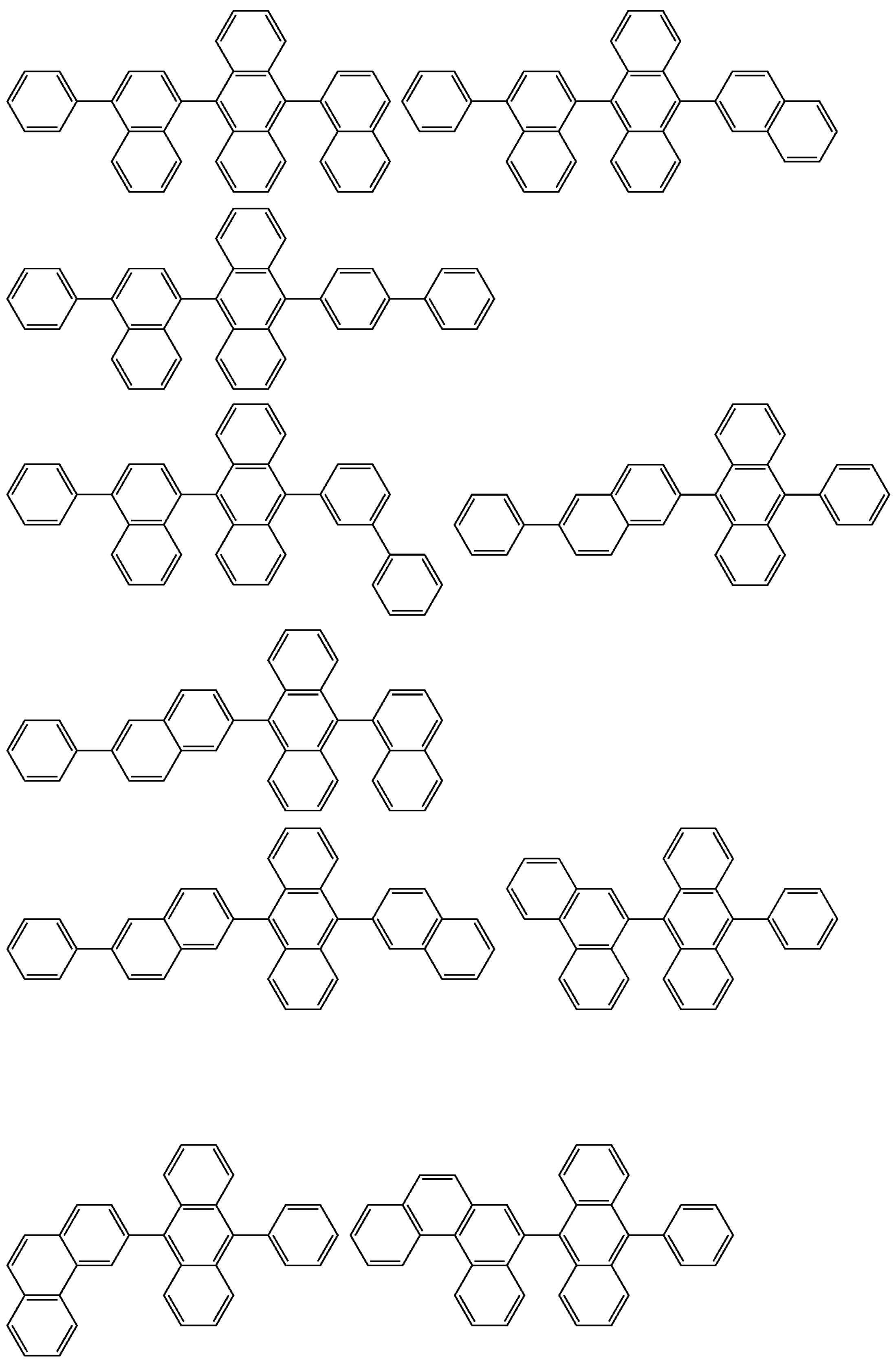

-continued
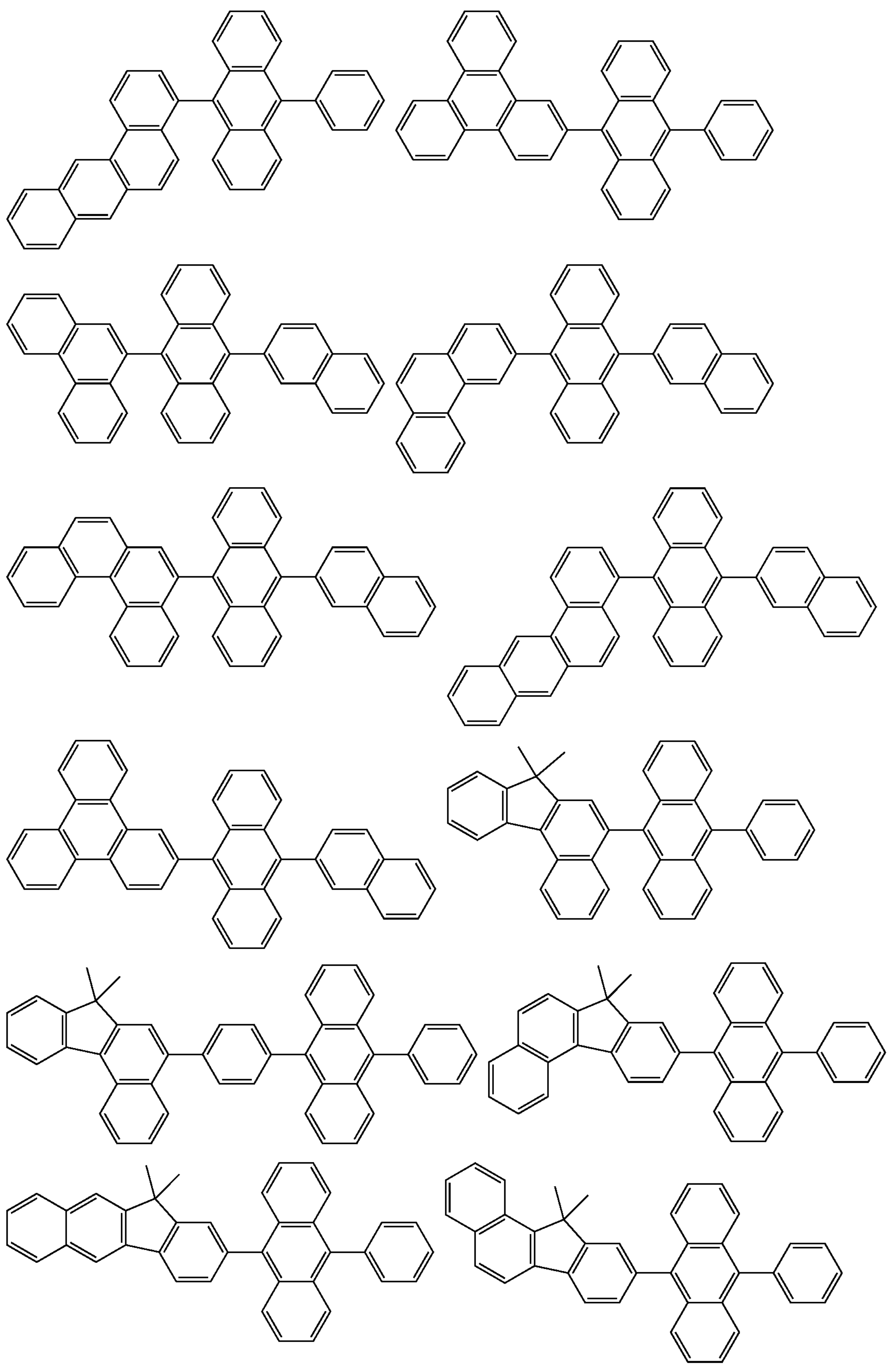

-continued
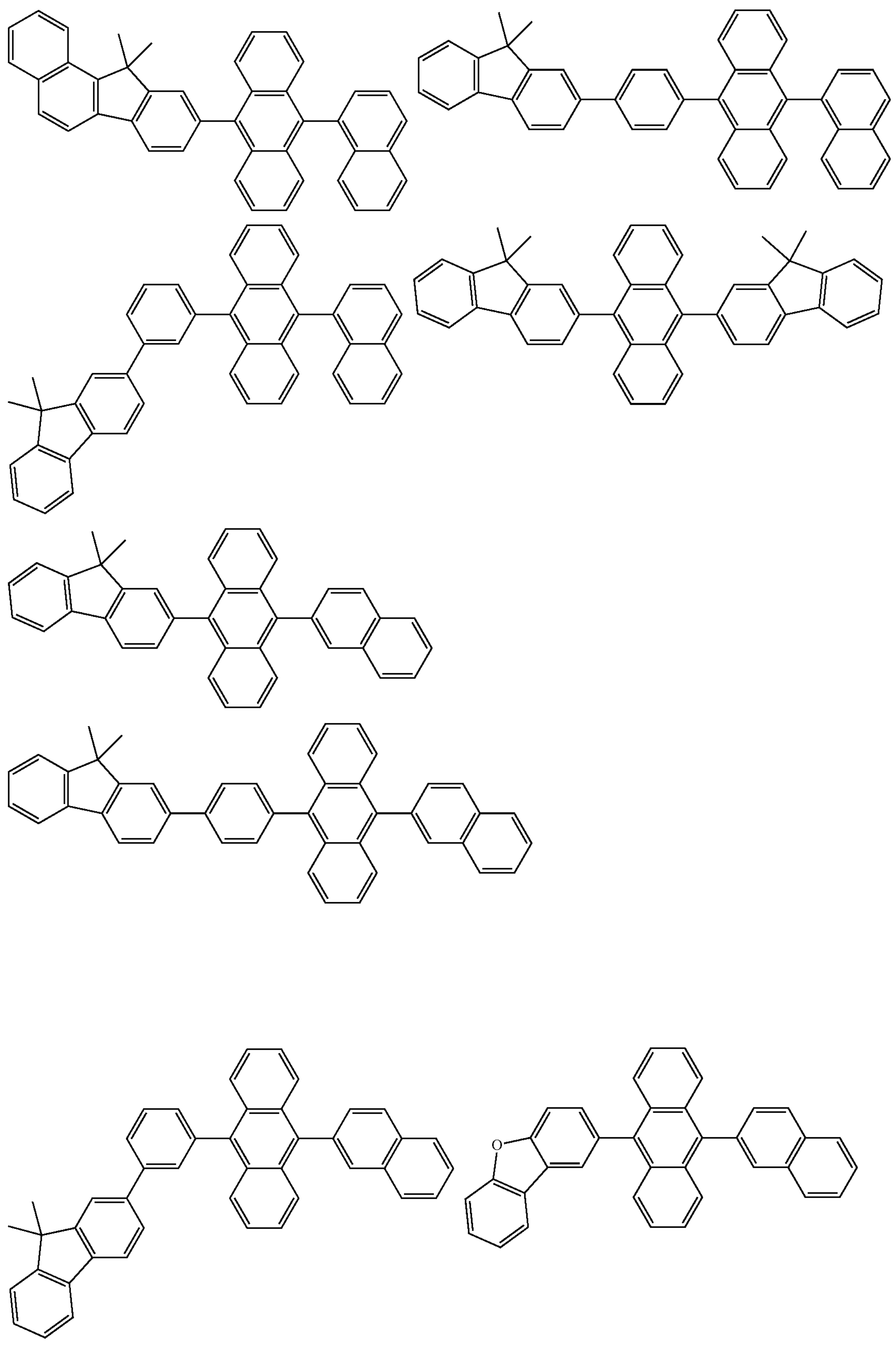

-continued
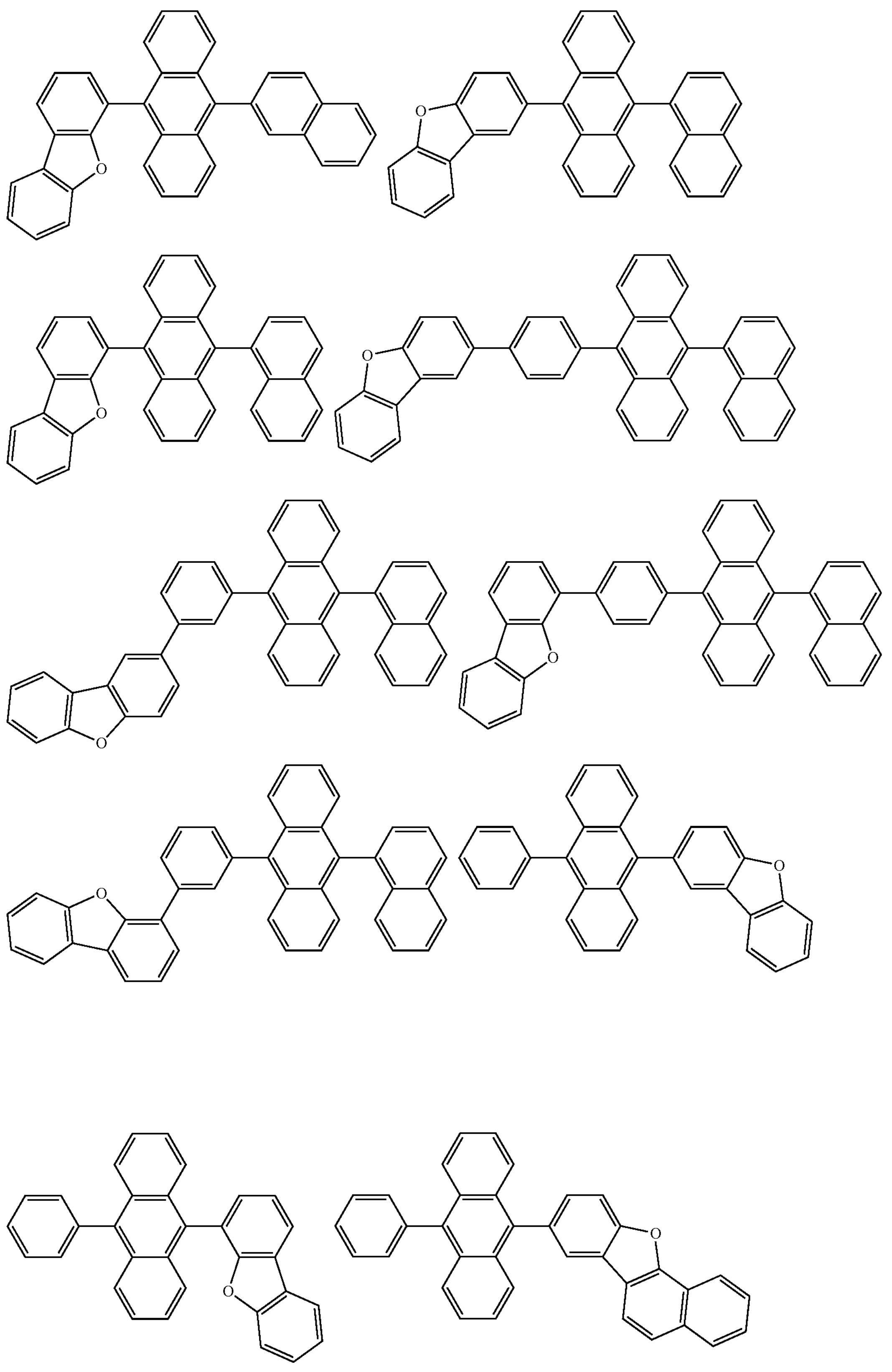

-continued
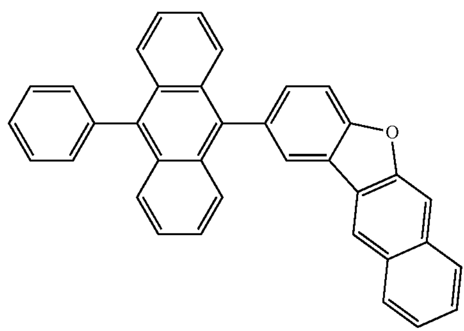
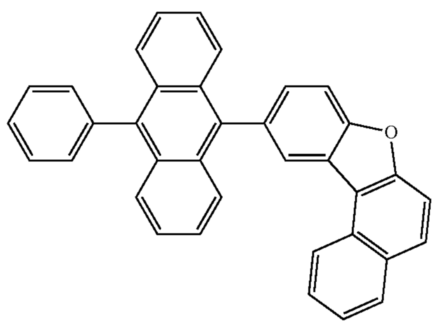
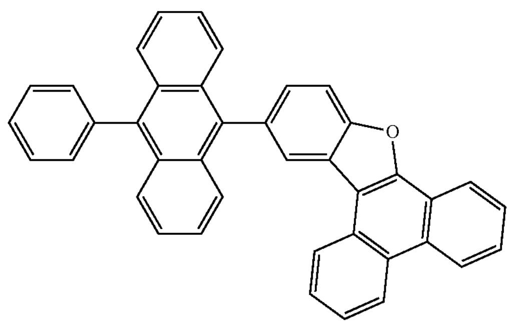
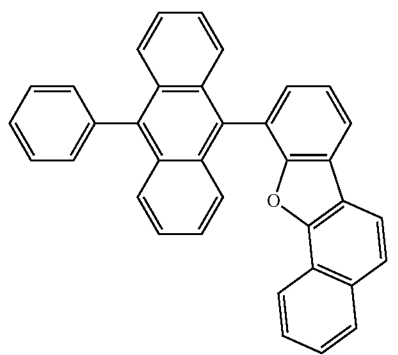
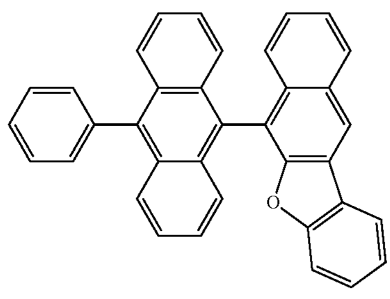
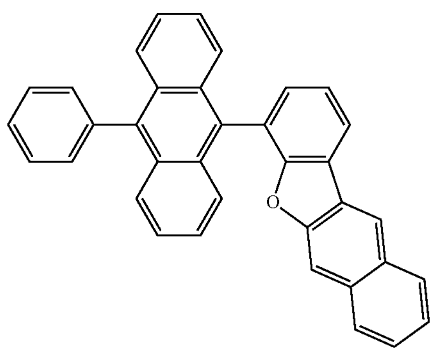
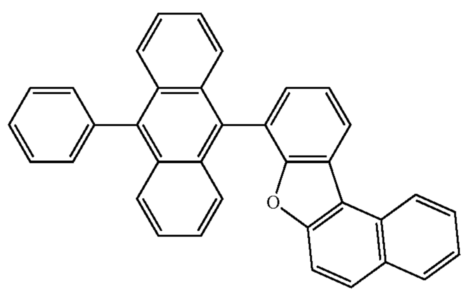
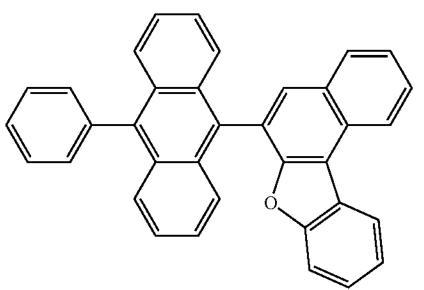
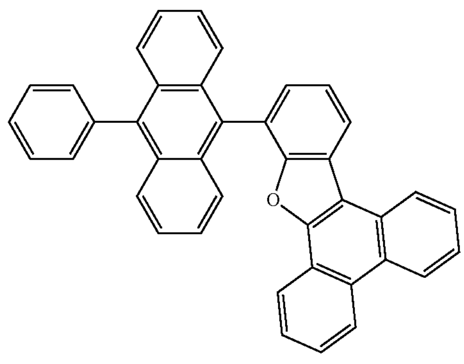
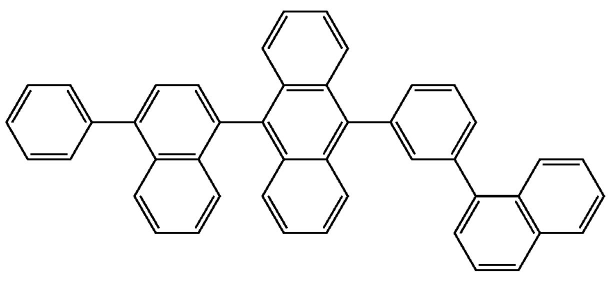

-continued
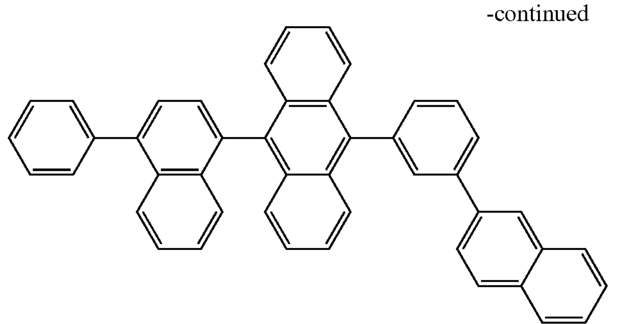
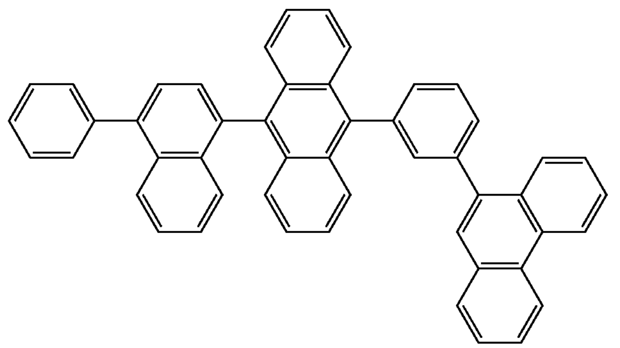
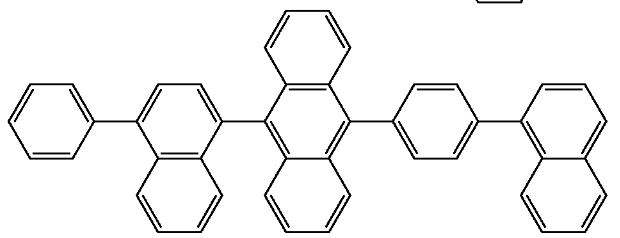
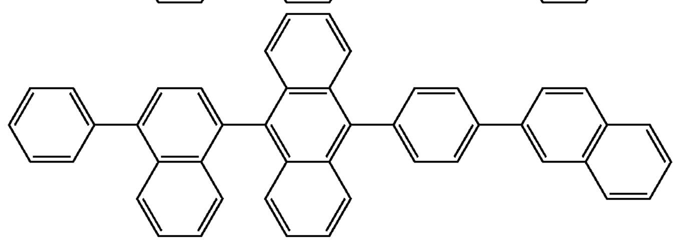
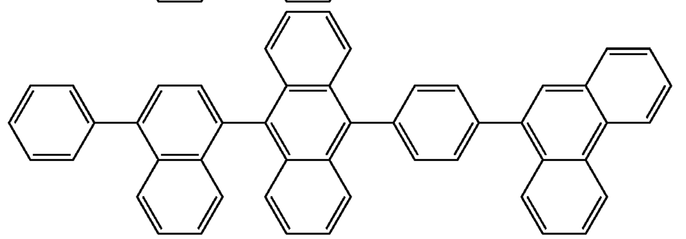
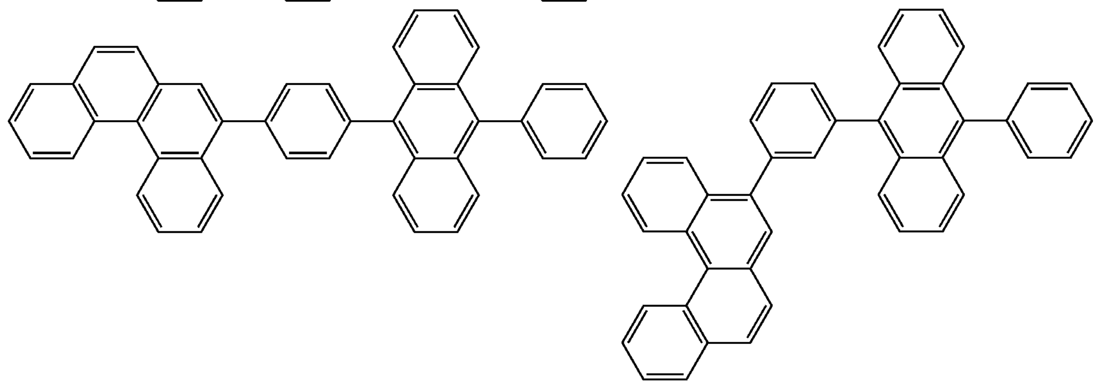

-continued

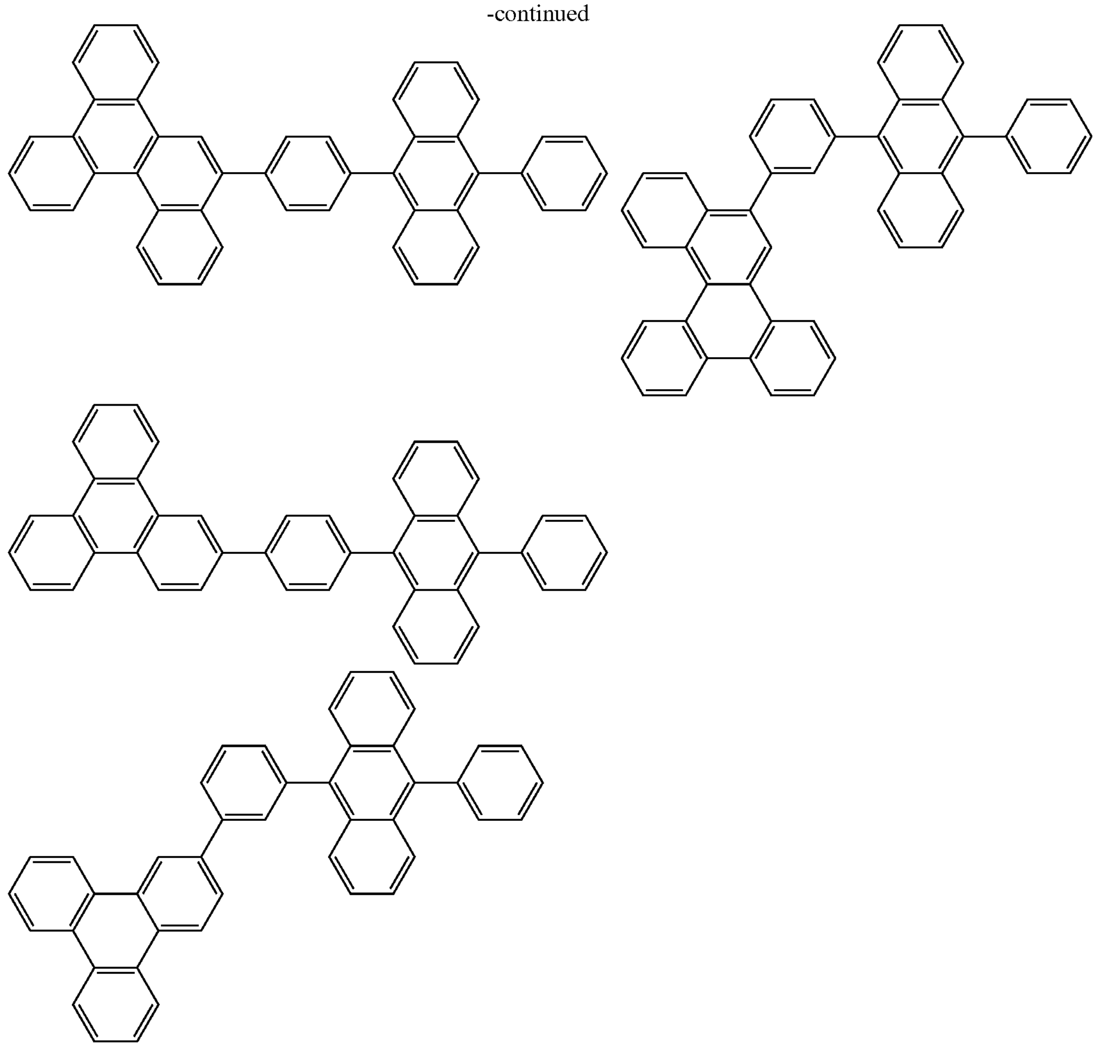

Electron Transporting Layer

The electron transporting layer is a layer containing a material having a high electron transporting capability (an electron transporting material) and is provided between the light emitting layer and the cathode, or between the electron injecting layer, if exists, and the light emitting layer. It is preferred that the inventive compound is used alone in the electron transporting layer or is used as a combination with the following compounds therein.

The electron transporting layer may have a single layer structure or a multilayer structure including two or more layers. For example, the electron transporting layer may have a two-layer structure including a first electron transporting layer (anode side) and a second electron transporting layer (cathode side). In one embodiment of the present invention, the electron transporting layer having a single layer structure is preferably disposed adjacent to the light emitting layer, and the electron transporting layer that is closest to the anode in the multilayer structure, such as the first electron transporting layer in the two-layer structure, is preferably disposed adjacent to the light emitting layer. In another embodiment of the present invention, a hole blocking layer described later and the like may be disposed between the electron transporting layer having a single layer structure and the light emitting layer, or between the electron transporting layer that is closest to the light emitting layer in the multilayer structure and the light emitting layer.

In the electron transporting layer having a two-layer structure, the inventive compound may be contained in one of the first electron transporting layer and the second electron transporting layer, and may be contained in both of them.

In one embodiment of the present invention, it is preferred that the inventive compound is contained only in the first electron transporting layer, and in another embodiment thereof, it is preferred that the inventive compound is contained only in the second electron transporting layer, and in still another embodiment thereof, it is preferred that the inventive compound is contained in the first electron transporting layer and the second electron transporting layer.

Examples of the material which can be used for the electron transporting layer other than the inventive compound include:

(1) a metal complex, such as an aluminum complex, a beryllium complex, and a zinc complex;

(2) a heteroaromatic compound, such as an imidazole derivative, a benzimidazole derivative, an azine derivative, a carbazole derivative, and a phenanthroline derivative; and (3) a high-molecular weight compound.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: $BeBq_2$), bis(2-methyl-8-quinolinolato)(4-phenylphenolato)aluminum (III) (abbreviation: BAlq), bis(8-quinolinolato)zinc(II) (abbreviation: Znq), bis[2-(2-benzoxazolyl)phenolato]zinc (II) (abbreviation: ZnPBO), and bis[2-(2-benzothiazolyl) phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzxazol-2-yl)stilbene (abbreviation: BzOs).

Examples of the high-molecular weight compound include poly[(9,9-dihexylfluorene-2,7-diyl)-co-(pyridine-3,5-diyl)] (abbreviation: PF-Py), and pol[(9,9-dioctylfluorene-2,7-diyl)-co-(2,2'-bipyridine-6,6'-diyl)] (abbreviation: PF-BPy).

The materials are materials having an electron mobility of $10^{-6}$ $cm^2/Vs$ or more. Materials other than those as mentioned above may also be used in the electron transporting layer so long as they are materials high in the electron transporting capability rather than in the hole transporting capability.

Electron Injecting Layer

The electron injecting layer is a layer containing a material having a high electron injection capability (an electron injecting material), and disposed between the cathode and the light emitting layer, or between the electron transporting layer, if exists, and the cathode. The inventive compound can be used in the electron injecting layer.

As the electron injecting material other than the inventive compound, alkali metals, such as lithium (Li) and cesium (Cs), alkaline earth metals, such as magnesium (Mg), calcium (Ca), and strontium (Sr), rare earth metals, such as europium (Eu) and ytterbium (Yb), and compounds containing these metals can be used. Examples of the compounds include an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. These compounds may be used as a mixture of a plurality thereof.

In addition, a material having an electron transporting capability, in which an alkali metal, an alkaline earth metal, or a compound thereof is contained, specifically Alq in which magnesium (Mg) is contained may be used. In this case, electron injection from the cathode can be more efficiently performed.

Otherwise, in the electron injecting layer, a composite material obtained by mixing an organic compound with an electron donor may be used. Such a composite material is excellent in the electron injection capability and the electron transporting capability because the organic compound receives electrons from the electron donor. In this case, the organic compound is preferably a material excellent in transporting received electrons, and specifically, examples thereof include a material constituting the aforementioned electron transporting layer (such as a metal complex and a heteroaromatic compound). As the electron donor, a material having an electron donation property for the organic compound may be used. Specifically, alkali metals, alkaline earth metals, and rare earth metals are preferred, and examples thereof include lithium, cesium, magnesium, calcium, erbium, and ytterbium. In addition, an alkali metal oxide or an alkaline earth metal oxide is preferred, and examples thereof include lithium oxide, calcium oxide, and barium oxide. In addition, a Lewis base, such as magnesium oxide, can also be used. In addition, an organic compound, such as tetrathiafulvalene (abbreviation: TTF), can also be used.

Cathode

It is preferred that a metal, an alloy, an electrically conductive compound, or a mixture thereof which has a low work function (specifically 3.8 eV or less) is used for the cathode. Specific examples of such a cathode material include elements belonging to group 1 or 2 of the periodic table of the elements, that is, alkali metals, such as lithium (Li) and cesium (Cs), alkaline earth metals, such as magnesium (Mg), calcium (Ca), and strontium (Sr), and alloys containing these (such as MgAg, and AlLi), and rare earth metals, such as europium (Eu), and ytterbium (Yb) and alloys containing these.

When the cathode is formed by using the alkali metals, the alkaline earth metals, and the alloys containing these, a vacuum vapor deposition method or a sputtering method can be adopted. In addition, when a silver paste or the like is used, a coating method, an inkjet method, of the like can be adopted.

By providing the electron injecting layer, the cathode can be formed using various conductive materials, such as Al, Ag, ITO, graphene, and indium oxide-tin oxide containing silicon or silicon oxide regardless of the magnitude of a work function. Such a conductive material can be deposited by using a sputtering method, an inkjet method, a spin coating method, or the like.

Insulating Layer

The organic EL device applies an electric field to an ultrathin film, and thus, pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of these may also be used.

Space Layer

The space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. The space layer can also be provided among the plurality of phosphorescent light emitting layers.

Since the space layer is provided between the light emitting layers, a material having both an electron transporting capability and a hole transporting capability is preferred. Also, one having a triplet energy of 2.6 eV or more is preferred in order to prevent triplet energy diffusion in the adjacent phosphorescent light emitting layer.

Examples of the material used for the space layer include the same as those used for the hole transporting layer as described above.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transporting layer, and the hole blocking layer is a layer that prevents holes from leaking from the light emitting layer to the electron transporting layer. The exciton blocking layer has a function of preventing excitons generated in the light emitting layer from diffusing into the surrounding layers, and trapping the excitons within the light emitting layer.

Each layer of the organic EL device may be formed by a conventionally known vapor deposition method, a coating method, or the like. For example, formation can be performed by a known method using a vapor deposition method such as a vacuum vapor deposition method, or a molecular beam vapor deposition method (MBE method), or a coating method using a solution of a compound for forming a layer, such as a dipping method, a spin-coating method, a casting method, a bar-coating method, and a roll-coating method.

The film thickness of each layer is not particularly limited, but is typically 5 nm to 10 μm, and more preferably 10 nm to 0.2 μm because in general, when the film thickness is too small, defects such as pinholes are likely to occur, and conversely, when the film thickness is too large, a high driving voltage is required and the efficiency decreases.

The organic EL device can be used for electronic devices, such as display components of an organic EL panel module and the like, display devices of a television, a mobile phone, a personal computer, and the like, and light emitting devices of lightings and vehicular lamps.

EXAMPLES

The present invention is hereunder described in more detail by reference to Examples, but it should be construed that the present invention is not limited to the following Examples.

Inventive Compounds Used for Production of Organic EL Devices of Examples 1-1 to 1-14 and Examples 2-1 and 2-2

Compound 1 (ET-1)

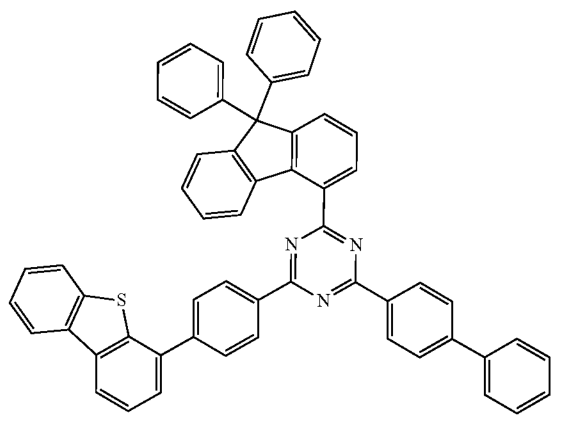

-continued

Compound 2 (ET-2)

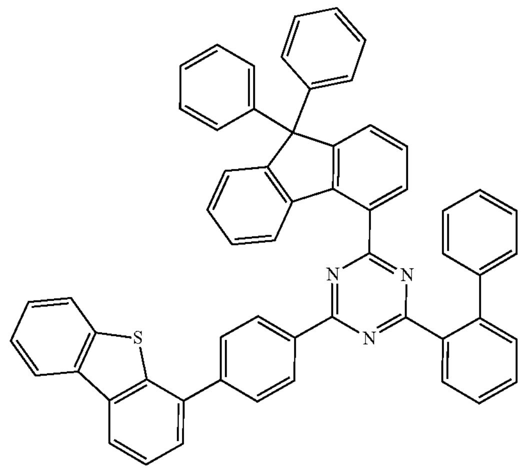

Compound 3 (ET-3)

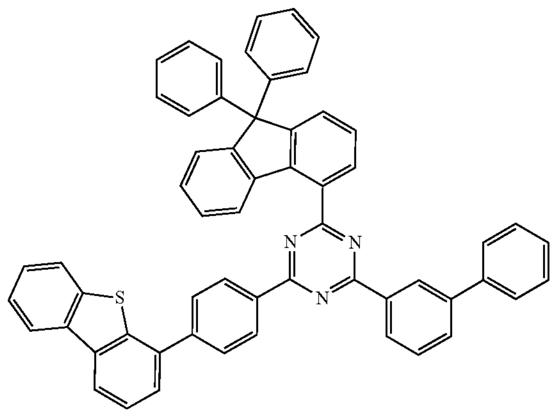

Compound 4 (ET-4)

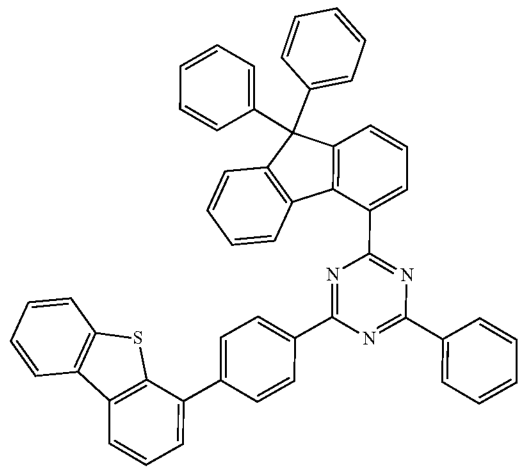

-continued
Compound 5 (ET-5)
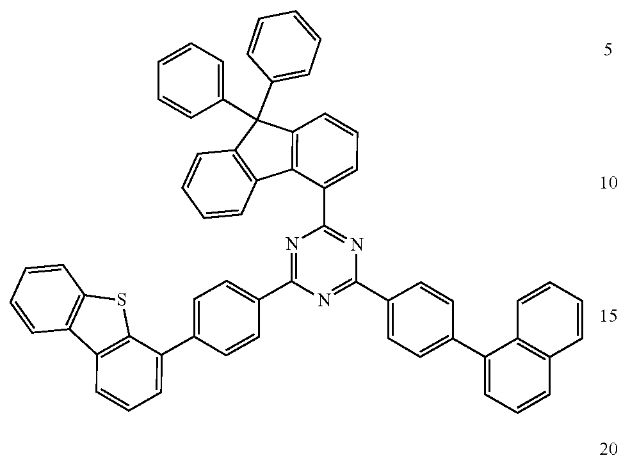
Compound 6 (ET-6)
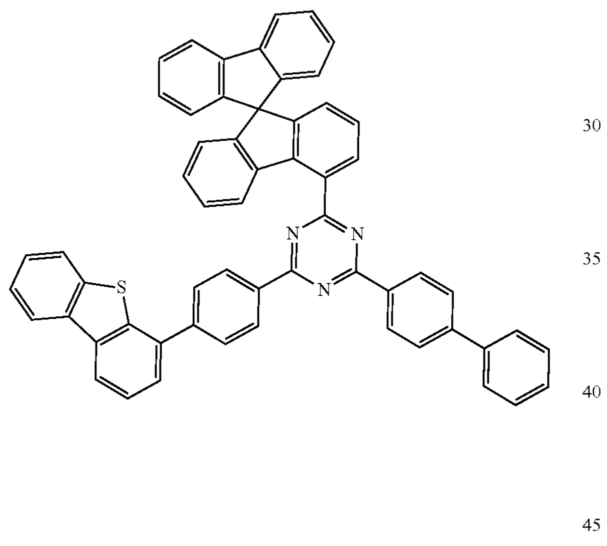
Compound 7 (ET-7)
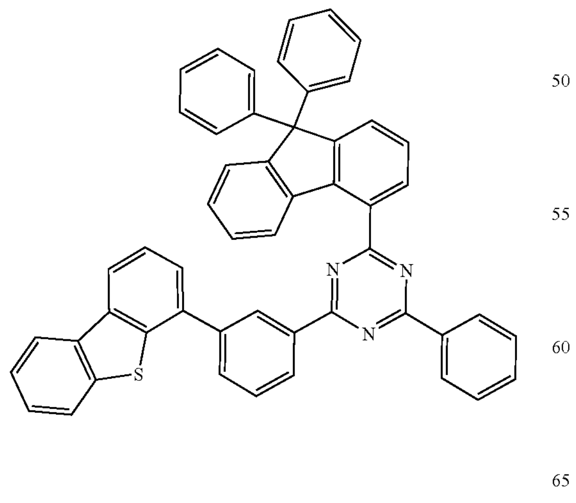
-continued
Compound 8 (ET-8)
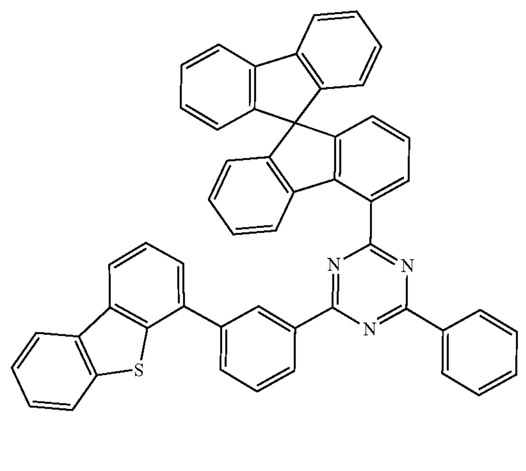
Compound 9 (ET-9)
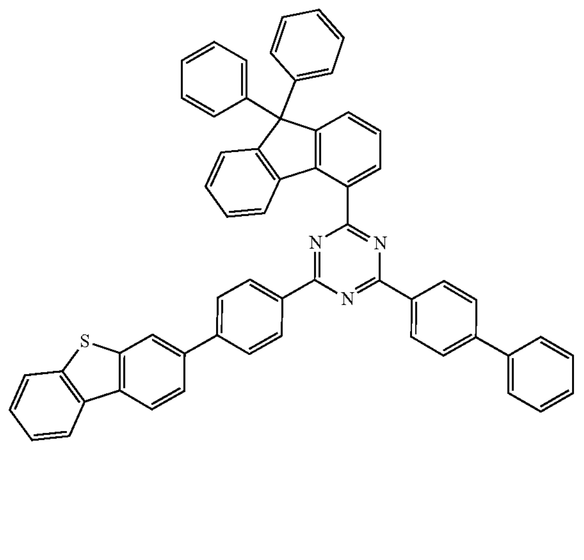
Compound 10 (ET-10)
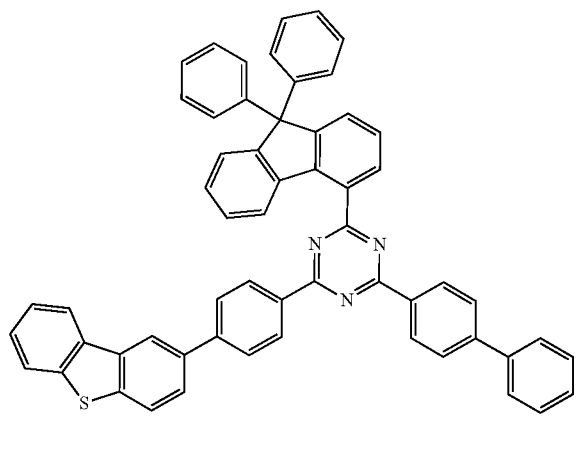

-continued
Compound 11 (ET-11)
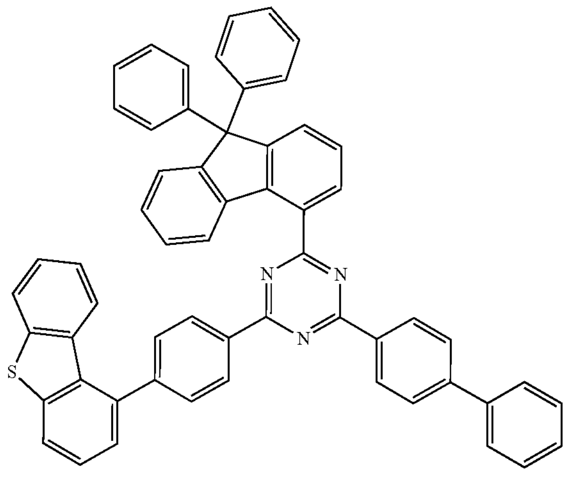
Compound 12 (ET-12)
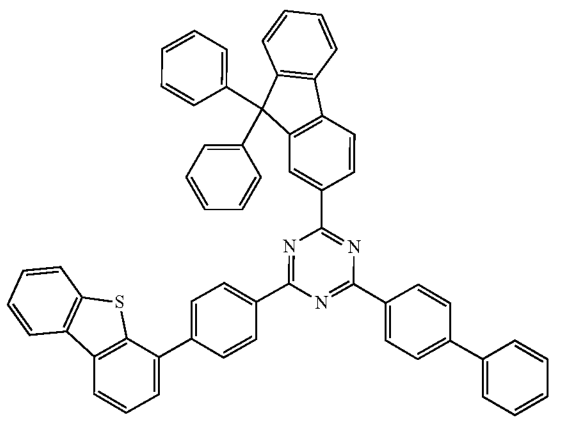
Compound 13 (ET-3)
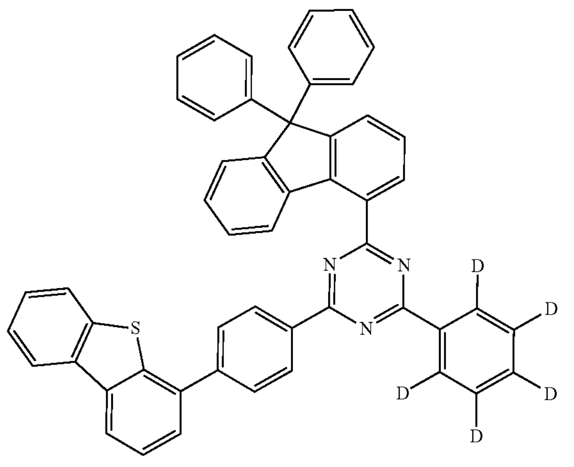
-continued
Compound 14 (ET-14)
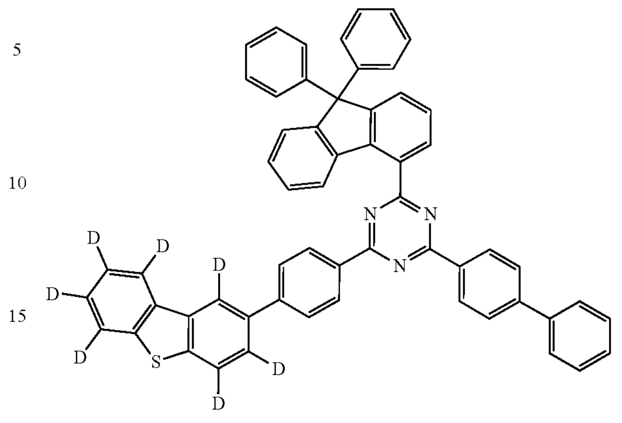
Comparative Compounds Used for Production of Organic EL Devices of Comparative Examples 1-1 and 1-2 and Comparative Examples 2-1 and 2-2
Comparative compound 1 (ET-A)
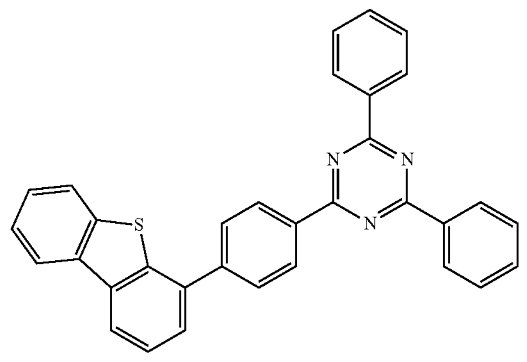
Comparative compound 2 (ET-B)
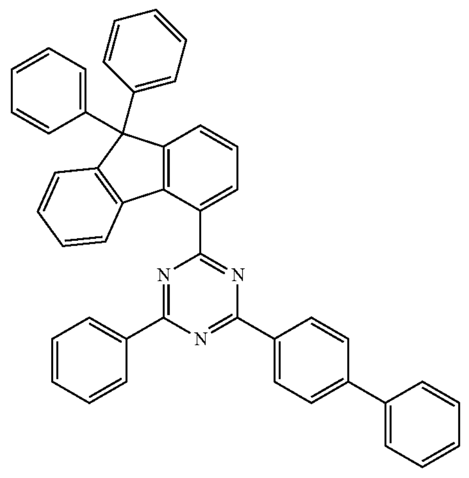

Other Compounds Used for Production of Organic EL Devices of Examples 1-1 to 1-14, Examples 2-1 and 2-2, Comparative Examples 1-1 and 1-2 and Comparative Examples 2-1 and 2-2
HT-a
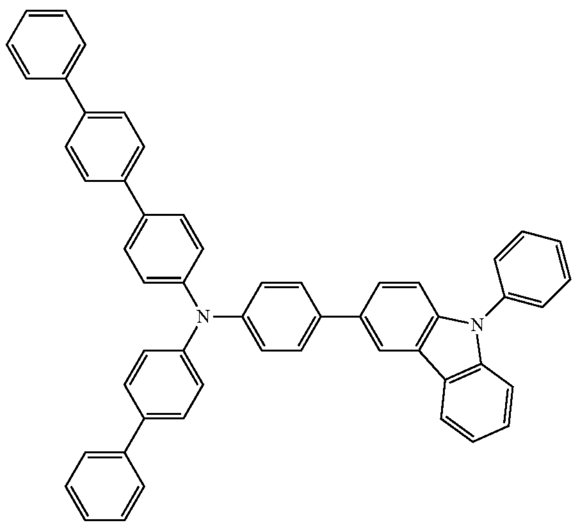
HI-a
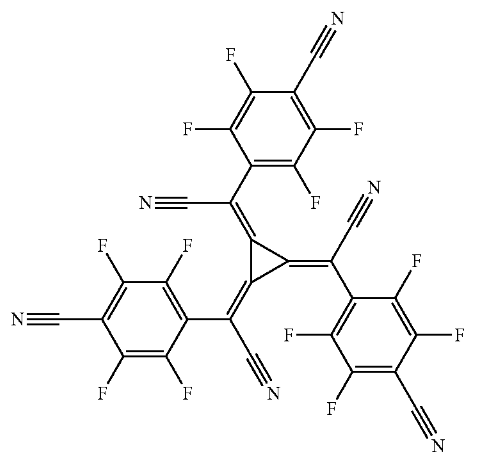
EBL-a
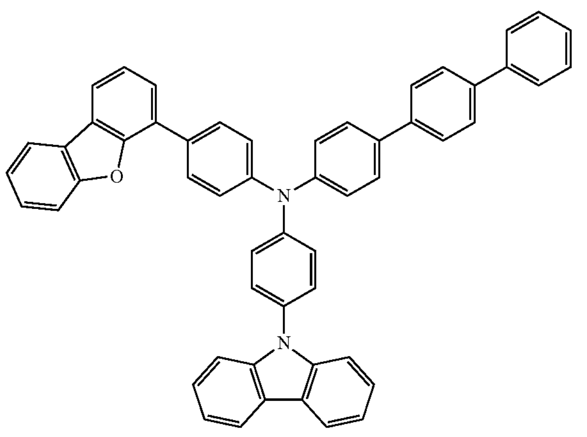
-continued
BH-a
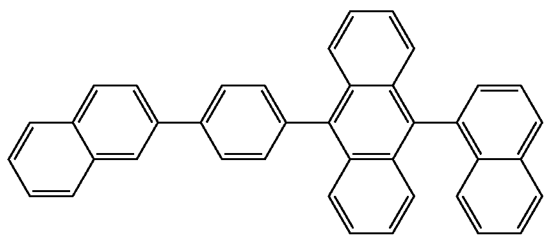
BD-a
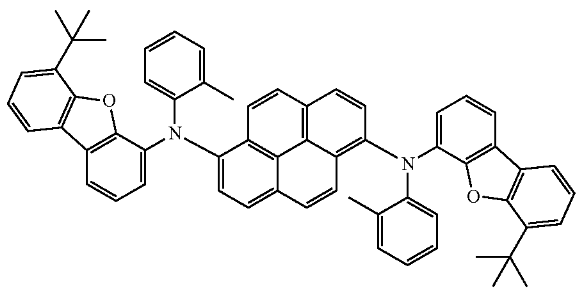
ET-c
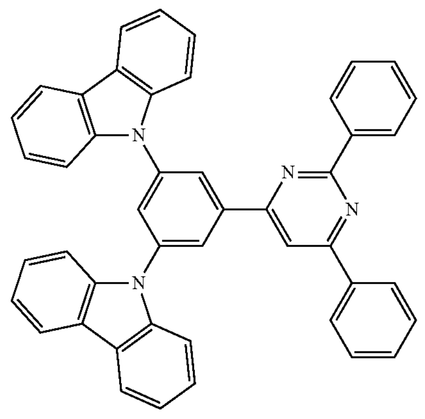
HT-b
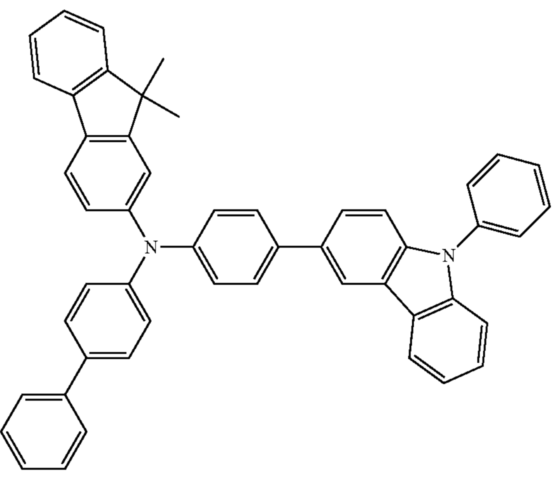

-continued

EBL-b

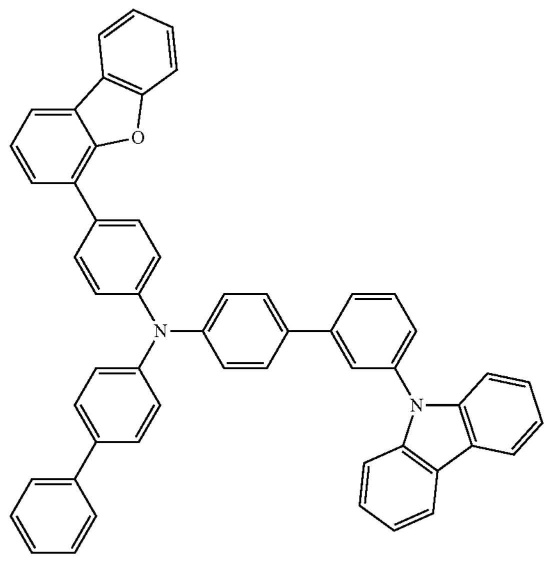

BH-b

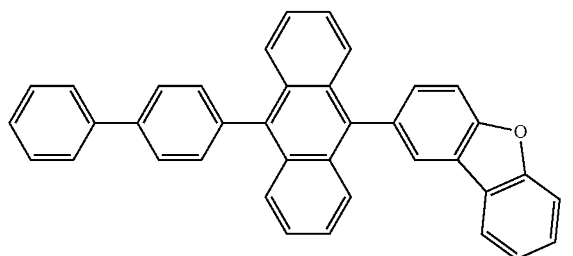

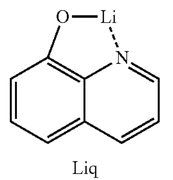

Liq

Organic EL devices were produced in the following manner, and the devices were evaluated for the EL device capability.

Production of Organic EL Device

Example 1-1

A glass substrate of 25 mm×75 mm×1.1 mm provided with an ITO transparent electrode (anode) (manufactured by GEOMATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with the ITO transparent electrode lines was mounted on a substrate holder of a vacuum vapor deposition apparatus, and firstly, Compound HT-a and Compound HI-a were vapor co-deposited on the surface having the transparent electrode lines formed thereon, so as to cover the transparent electrode, resulting in a hole injecting layer with a film thickness of 10 nm. The mass ratio of Compound HT-a and Compound HI-a was 97/3.

Subsequently, on this hole injecting layer, Compound HT-a was vapor deposited to form a first hole transporting layer with a film thickness of 80 nm.

Subsequently, on this first hole transporting layer, Compound EBL-a was vapor deposited to form a second hole transporting layer (electron blocking layer) with a film thickness of 5 nm.

Subsequently, on this second hole transporting layer (electron blocking layer), Compound BH-a (host material) and Compound BD-a (dopant material were vapor co-deposited to form a light emitting layer with a film thickness of 25 nm. The mass ratio of Compound BH-a and Compound BD-a was 96/4.

Subsequently, on this light emitting layer, Compound ET-c was vapor deposited to form a first electron transporting layer with a film thickness of 5 nm.

Subsequently, on this first electron transporting layer, Compound 1 (ET-1) and Compound Liq were vapor co-deposited to form a second electron transporting layer with a film thickness of 20 nm. The mass ratio of Compound 1 (ET-1) and Compound Liq was 50/50.

Subsequently, on this second electron transporting layer, LiF was vapor deposited to form an electron injecting electrode (cathode) with a film thickness of 1 nm.

Then, on this electron injecting electrode, metal Al was vapor deposited to form a metal cathode with a film thickness of 80 nm.

The layer configuration of the organic EL device of Example 1 thus obtained was as follows.

ITO(130)/(HT-a/HI-a=97/3)(10)/HT-a(80)/EBL-a(5)/(BH-a/BD-a=96/4) (25)/ET-c(5)/(ET-1/Liq=50/50)(20)/LiF(1)/Al(80)

In the layer configuration, the numeral in parentheses indicates the film thickness (nm), and the ratio of HT-a and HI-a, the ratio of BH-a and BD-a, and the ratio of ET-1 and Liq each are a mass ratio.

Examples 1-2 to 1-14

Organic EL devices of Examples 1-2 to 1-14 were produced in the same manner as in Example 1-1 except that Compound 2 (ET-2) to Compound 14 (ET-14) were used respectively in this order instead of Compound 1 (ET-1) of the second electron transporting layer in Example 1-1.

Example 2-1

An organic EL device of Example 2-1 was produced in the same manner as in Example 1-1 except that Compound BH-b (host material) was used instead of Compound BH-a (host material) of the light emitting layer in Example 1-1.

Example 2-2

An organic EL device of Example 2-2 was produced in the same manner as in Example 1-2 except that Compound BH-b (host material) was used instead of Compound BH-a (host material) of the light emitting layer in Example 1-2.

Comparative Example 1-1

An organic EL device of Comparative Example 1-1 was produced in the same manner as in Example 1-1 except that Comparative Compound 1 (ET-A) was used instead of Compound 1 (ET-1) of the second electron transporting layer in Example 1-1.

Comparative Example 1-2

An organic EL device of Comparative Example 1-2 was produced in the same manner as in Example 1-2 except that Comparative Compound 2 (ET-B) was used instead of Compound 2 (ET-2) of the second electron transporting layer in Example 1-2.

Comparative Example 2-1

An organic EL device of Comparative Example 2-1 was produced in the same manner as in Example 2-1 except that Comparative Compound 1 (ET-A) was used instead of Compound 1 (ET-1) of the second electron transporting layer in Example 2-1.

Comparative Example 2-2

An organic EL device of Comparative Example 2-2 was produced in the same manner as in Example 2-2 except that Comparative Compound 2 (ET-B) was used instead of Compound 2 (ET-2) of the second electron transporting layer in Example 2-2.

Evaluation of Organic EL Device

The organic EL devices thus produced each were evaluated for device lifetime. The evaluation results are shown in Tables 1 and 2.

Device Lifetime (LT95)

The resulting organic EL device was driven with direct current at a current density of 50 mA/cm$^2$, and the period of time until the luminance was reduced to 95% of the initial luminance was measured, and was defined as LT95 (95% lifetime).

TABLE 1

| | Compound ET | LT95 (hour) at 50 mA/cm$^2$ |
|---|---|---|
| Example 1-1 | Compound 1 (ET-1) | 153 |
| Example 1-2 | Compound 2 (ET-2) | 133 |
| Example 1-3 | Compound 3 (ET-3) | 148 |
| Example 1-4 | Compound 4 (ET-4) | 138 |
| Example 1-5 | Compound 5 (ET-5) | 152 |
| Example 1-6 | Compound 6 (ET-6) | 150 |
| Example 1-7 | Compound 7 (ET-7) | 136 |
| Example 1-8 | Compound 8 (ET 8) | 135 |
| Example 1-9 | Compound 9 (ET9) | 151 |
| Example 1-10 | Compound 10 (ET-10) | 149 |
| Example 1-11 | Compound 11 (ET-11) | 147 |
| Example 1-12 | Compound 12 (ET-12) | 155 |
| Example 1-13 | Compound 13 (ET-13) | 145 |
| Example 1-14 | Compound 14 (ET-14) | 152 |
| Comparative Example 1-1 | Comparative Compound 1 (ET-A) | 118 |
| Comparative Example 1-2 | Comparative Compound 2 (ET-B) | 120 |

TABLE 2

| | Compound ET | LT95 (hour) at 50 mA/cm$^2$ |
|---|---|---|
| Example 2-1 | Compound 1 (ET-1) | 106 |
| Example 2-2 | Compound 2 (ET-2) | 96 |
| Comparative Example 2-1 | Comparative Compound 1 (ET-A) | 84 |
| Comparative Example 2-2 | Comparative Compound 2 (ET-B) | 85 |

As apparent from the results in Tables 1 and 2, the compounds of the present invention having the structure having a fluorene skeleton, a phenyl group having a particular substituent or an unsubstituted phenyl group, and an unsubstituted dibenzothiophene through a particular linking group, which each are bonded to the center triazine skeleton, each exhibited an improved device lifetime as compared to Comparative Compound 1 or Comparative Compound 2, which did not satisfy the structural requirement of the present invention.

Synthesis of Intermediate I-B

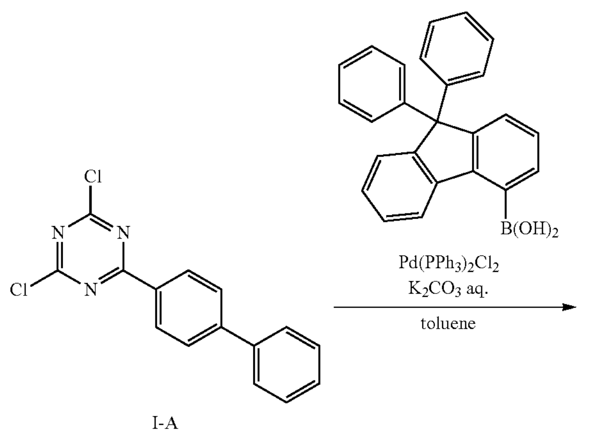

I-A

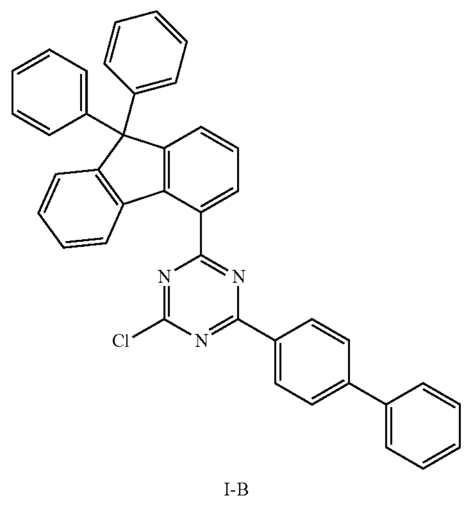

I-B

In an argon atmosphere, toluene (120 mL) and a potassium carbonate aqueous solution (2 M, 24 mL) were added to Intermediate I-A (7.25 g), 9,9-diphenylfluorene-4-boronic acid (9.56 g), and dichlorobis(triphenylphosphine) palladium(II) (0.08 g). The mixture was heated to 80° C. for 7 hours under agitation in an argon atmosphere. The reaction solution was extracted with toluene, then dried over anhydrous magnesium sulfate, and then filtered. The solvent was distilled off under reduced pressure, and the residue was purified by column chromatography, so as to provide Intermediate I-B (5.33 g, yield: 38%).

Synthesis of Intermediate I-D

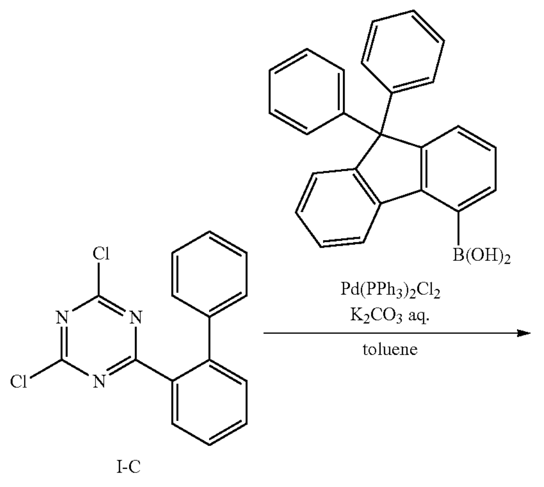

I-C

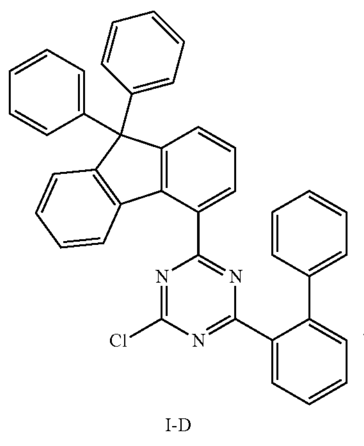

I-D

In an argon atmosphere, toluene (120 mL) and a potassium carbonate aqueous solution (2 M, 24 mL) were added to Intermediate I-C (7.16 g), 9,9-diphenylfluorene-4-boronic acid (9.44 g), and dichlorobis(triphenylphosphine) palladium(II) (0.08 g). The mixture was heated to 60° C. for 17 hours under agitation in an argon atmosphere. The reaction solution was extracted with toluene, then dried over anhydrous magnesium sulfate, and then filtered. The solvent was distilled off under reduced pressure, and the residue was purified by column chromatography, so as to provide Intermediate I-D (8.30 g, yield: 57%).

Synthesis of Intermediate I-F

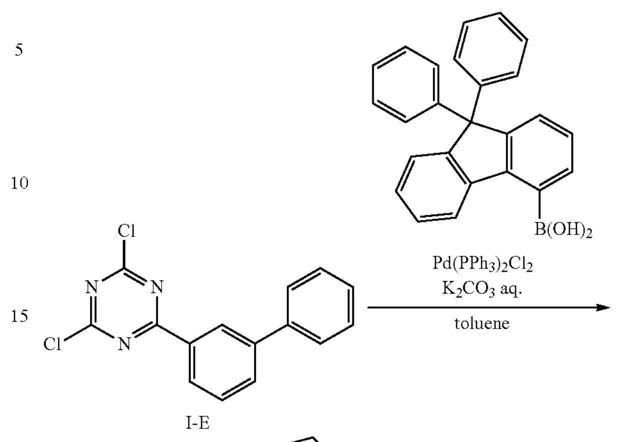

I-E

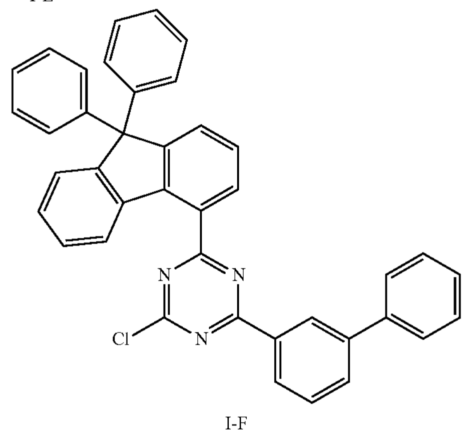

I-F

In an argon atmosphere, toluene (125 mL) and a potassium carbonate aqueous solution (2 M, 25 mL) were added to Intermediate I-E (7.55 g), 9,9-diphenylfluorene-4-boronic acid (9.96 g), and dichlorobis(triphenylphosphine) palladium(II) (0.09 g). The mixture was heated to 80° C. for 8 hours under agitation in an argon atmosphere. The reaction solution was extracted with toluene, then dried over anhydrous magnesium sulfate, and then filtered. The solvent was distilled off under reduced pressure, and the residue was purified by column chromatography, so as to provide Intermediate I-F (6.72 g, yield: 46%).

Synthesis of Intermediate I-I

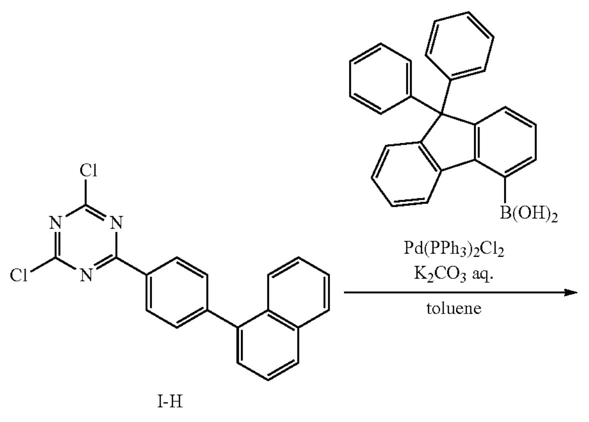

I-H

-continued

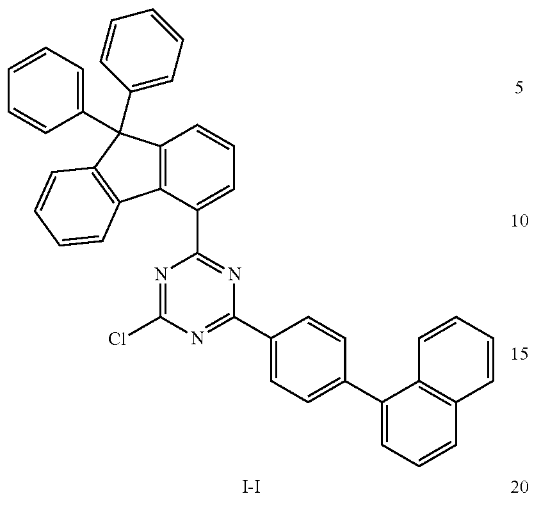

I-I

In an argon atmosphere, toluene (100 mL) and a potassium carbonate aqueous solution (2 M, 20 mL) were added to Intermediate I-H (7.04 g), 9,9-diphenylfluorene-4-boronic acid (7.97 g), and dichlorobis(triphenylphosphine) palladium(II) (0.07 g). The mixture was heated to 80° C. for 17 hours under agitation in an argon atmosphere. The reaction solution was extracted with toluene, then dried over anhydrous magnesium sulfate, and then filtered. The solvent was distilled off under reduced pressure, and the residue was purified by column chromatography, so as to provide Intermediate I-I (5.20 g, yield: 41%).

Synthesis of Intermediate I-J

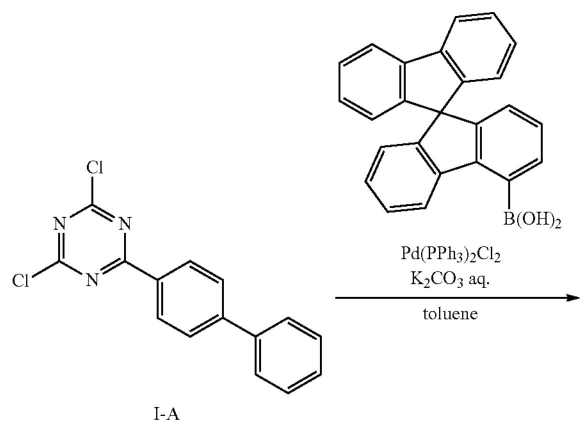

I-A

-continued

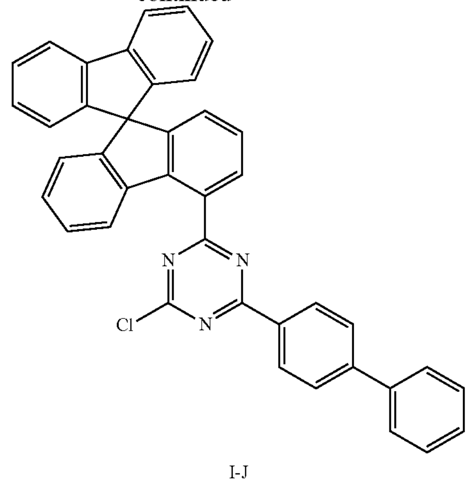

I-J

In an argon atmosphere, toluene (110 mL) and a potassium carbonate aqueous solution (2 M, 22 mL) were added to Intermediate I-A (6.65 g), 9,9-spirobifluorene-4-boronic acid (8.72 g), and dichlorobis(triphenylphosphine) palladium(II) (0.08 g). The mixture was heated to 80° C. for 8 hours under agitation in an argon atmosphere. The reaction solution was extracted with toluene, then dried over anhydrous magnesium sulfate, and then filtered. The solvent was distilled off under reduced pressure, and the residue was purified by column chromatography, so as to provide Intermediate I-J (5.51 g, yield: 43%).

Synthesis of Intermediate I-M

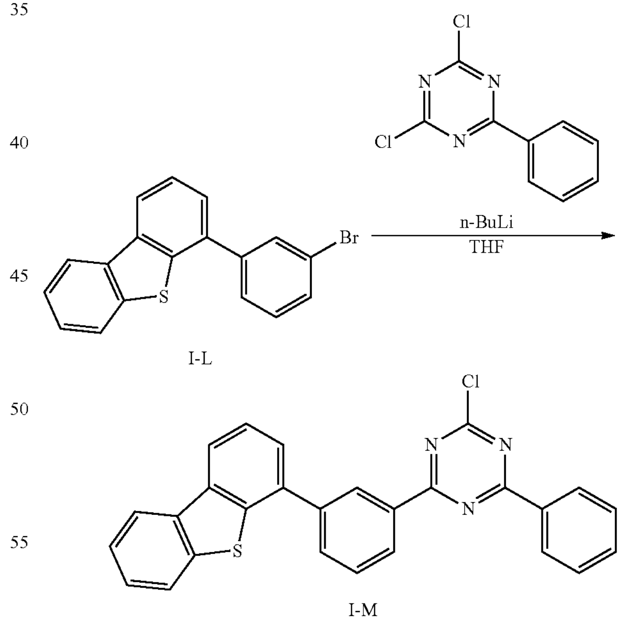

I-L

I-M

In an argon atmosphere, a tetrahydrofuran solution (450 mL) of Intermediate I-L (15.27 g) was cooled to −78° C., to which a n-hexane solution (1.6 M, 34 mL) of n-butyllithium was added dropwise over 30 minutes, and then agitated at −78° C. for 1 hour. The solution was added dropwise to a tetrahydrofuran solution (450 mL) of 2,4-dichloro-6-phenyl-1,3,5-triazine (10.17 g) cooled to −78° C. over 1 hour, and the mixture was agitated at room temperature overnight. The reaction liquid was returned to room temperature, and then the solvent was distilled off under reduced pressure to provide a solid matter. The solid matter was purified by column chromatography, so as to provide Intermediate I-M (11.14 g, yield: 55%).

Synthesis of Intermediate I-N

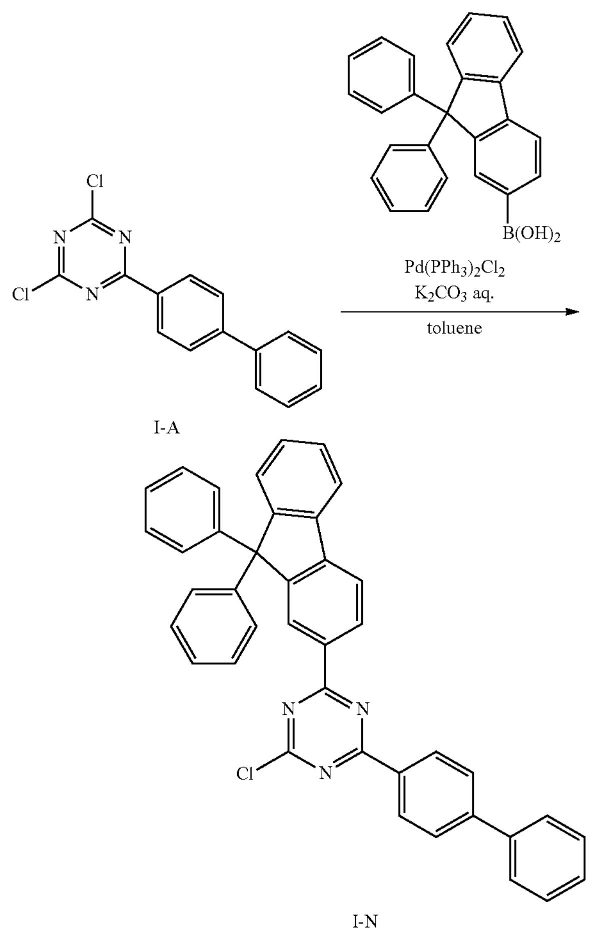

I-A

I-N

In an argon atmosphere, toluene (125 mL) and a potassium carbonate aqueous solution (2 M, 25 mL) were added to Intermediate I-A (7.55 g), 9,9-diphenylfluorene-2-boronic acid (9.96 g), and dichlorobis(triphenylphosphine) palladium(II) (0.09 g). The mixture was heated to 80° C. for 7 hours under agitation in an argon atmosphere. The reaction solution was extracted with toluene, then dried over anhydrous magnesium sulfate, and then filtered. The solvent was distilled off under reduced pressure, and the residue was purified by column chromatography, so as to provide Intermediate I-N (7.59 g, yield: 52%).

Synthesis of Intermediate I-O

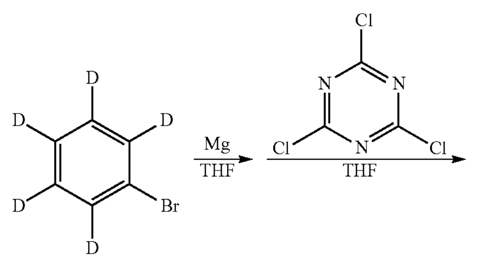

-continued

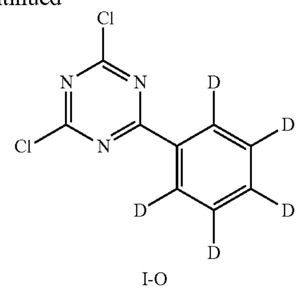

I-O

Magnesium (1.0 g) was added to tetrahydrofuran (THF, 10 mL), which were agitated in an argon gas atmosphere at room temperature. Subsequently, bromobenzene-d5 (5.5 g) dissolved in THF (50 mL) was added dropwise thereto, followed by heating to 50° C. After 1 hour, the solution was cooled to 0° C., to which a solution of cyanuric chloride (5.6 g) dissolved in THF (60 mL) was added. After the addition, the solution was agitated at room temperature for 24 hours. After adding 6N hydrochloric acid (10 mL) thereto to make the solution acidic, the solution was washed with a saturated sodium chloride aqueous solution, and the solvent of the reaction solution was distilled off to provide an oily matter, which was purified by column chromatography, so as to provide Intermediate I-O (3.5 g, yield: 45%).

Synthesis of Intermediate I-P

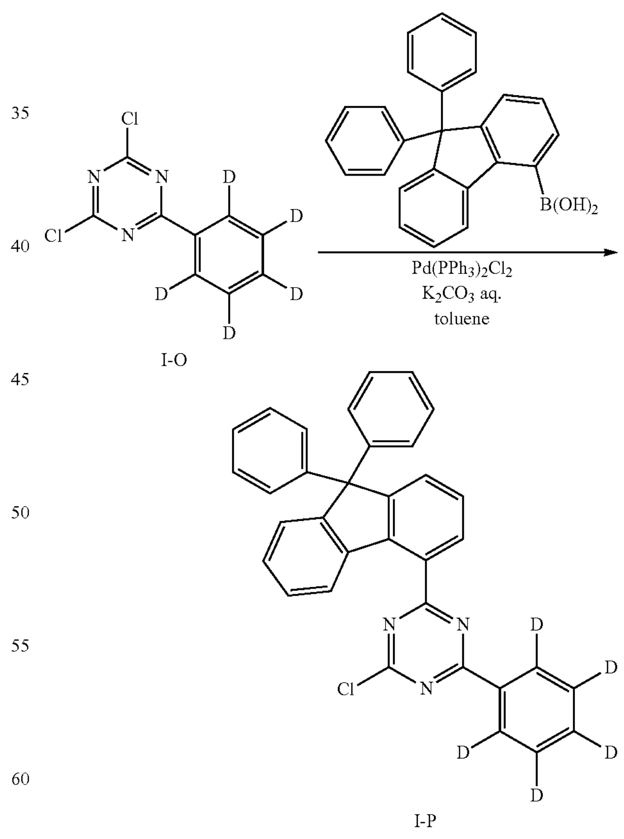

I-O

I-P

In an argon atmosphere, toluene (110 mL) and a potassium carbonate aqueous solution (2 M, 22 mL) were added to Intermediate I-0 (3.5 g), 9,9-diphenylfluorene-4-boronic acid (5.5 g), and dichlorobis(triphenylphosphine) palladium (II) (0.10 g). The mixture was heated to 80° C. for 8 hours under agitation in an argon atmosphere. The reaction solution was extracted with toluene, then dried over anhydrous magnesium sulfate, and then filtered. The solvent was distilled off under reduced pressure, and the residue was purified by column chromatography, so as to provide Intermediate I-P (3.1 g, yield: 40%).

Synthesis of Intermediate I-Q

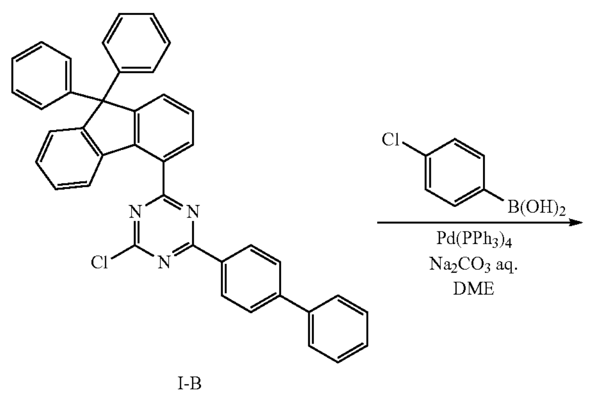

I-B

-continued

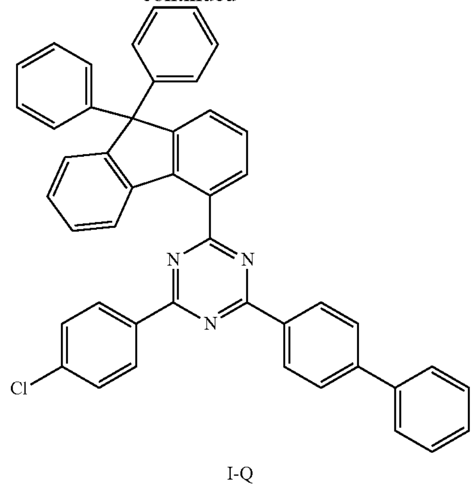

I-Q

In an argon atmosphere, 1,2-dimethoxyethane (DME) (100 mL) and a potassium carbonate aqueous solution (2 M, 10 mL) were added to Intermediate I-B (4.67 g), 4-chlorophenylboronic acid (1.25 g), and tetrakis(triphenylphosphine) palladium(0) (0.46 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide Intermediate I-Q (5.28 g, yield: 75%).

Synthesis of Intermediate I-R

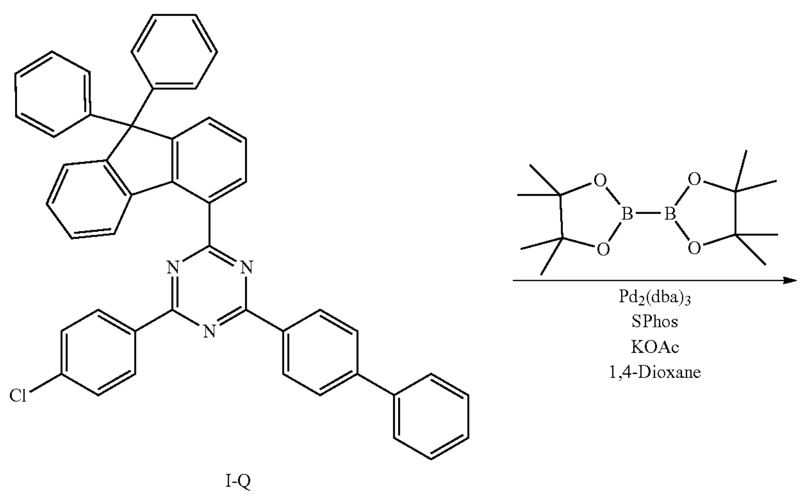

I-Q

-continued

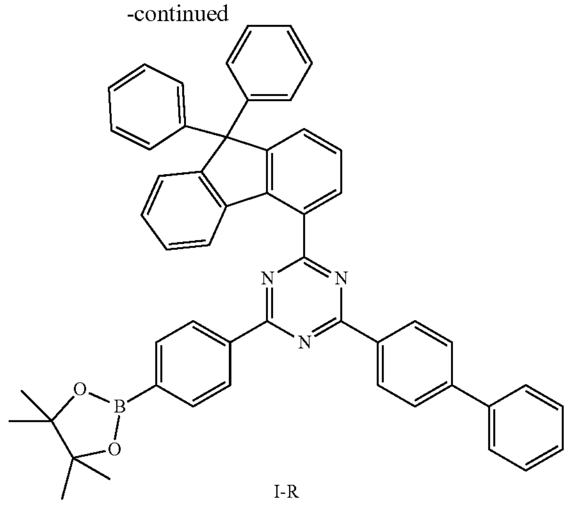

I-R

In an argon atmosphere, 1,4-dioxane (30 mL) and potassium acetate (1.34 g) were added to Intermediate I-Q (3.00 g), bis(pinacolato)diboron (2.31 g), $Pd_2(dba)_3$ (0.08 g), and SPhos (0.15 g). The mixture was heated to 75° C. for 8 hours under agitation in an argon atmosphere. The reaction mixture was filtered and then washed with distilled water and methanol. The resulting solid matter was purified by subjecting to column chromatography, so as to provide Intermediate I-R (1.95 g, yield: 57%).

Synthesis Example 1

Synthesis of Compound 1

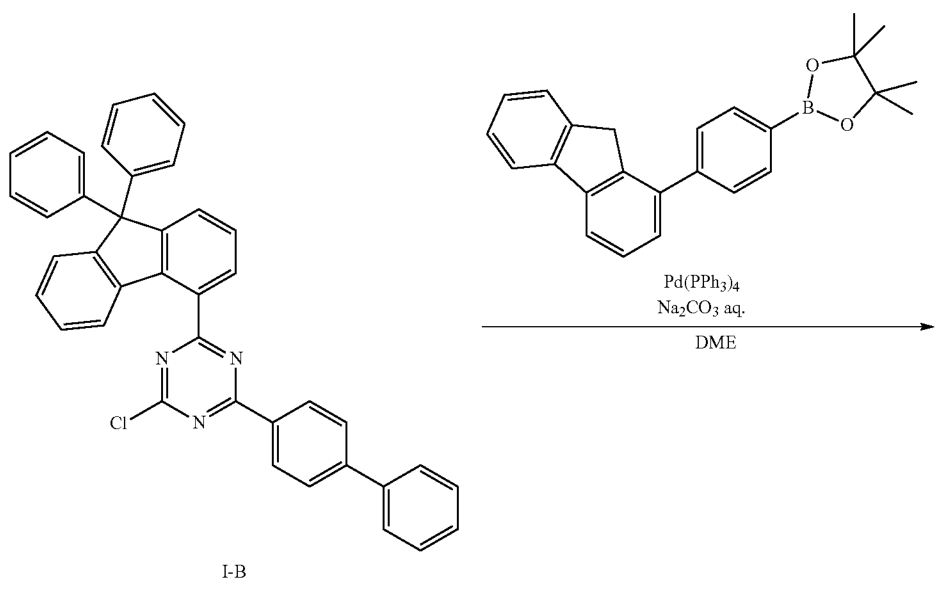

I-B

-continued

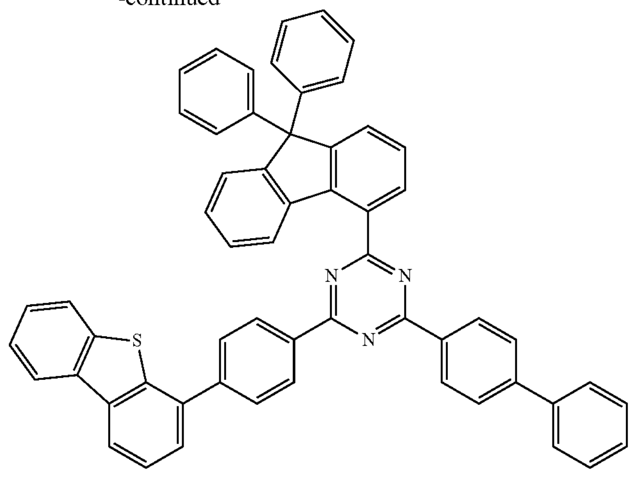

ET-1

In an argon atmosphere, 1,2-dimethoxyethane (DME) (80 mL) and a sodium carbonate aqueous solution (2 M, 10 mL) were added to Intermediate I-B (4.67 g), 4-[4-(4,4,5,5-tetramethyl-1,3,2-dioxaborolan-2-yl)phenyl]dibenzothiophene (4.64 g), and tetrakis(triphenylphosphine) palladium (0) (0.46 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-1 (2.91 g, yield: 45%). The result of mass spectrum analysis of the resulting compound revealed m/z (ratio of mass and charge)=807, from which the compound was identified as Compound 1 (ET-1).

Synthesis Example 2

Synthesis of Compound 2

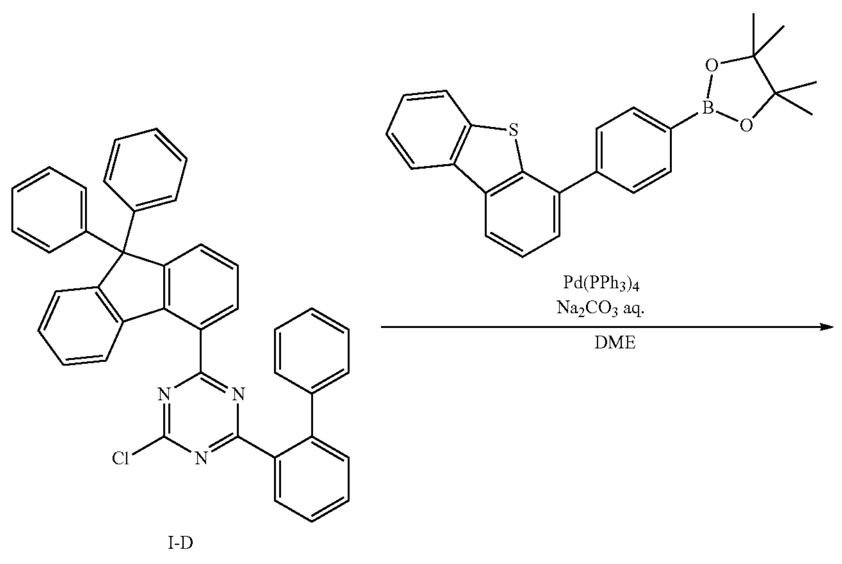

I-D

-continued

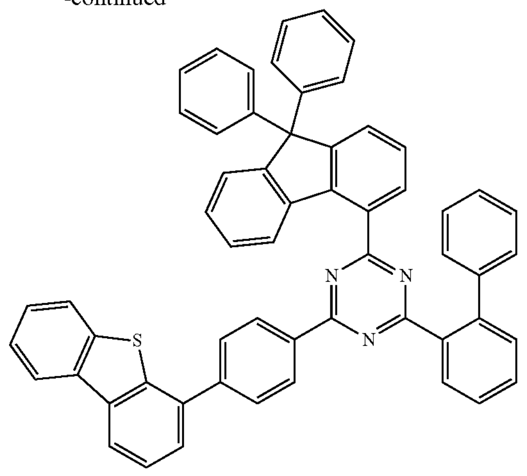

ET-2

In an argon atmosphere, 1,2-dimethoxyethane (DME) (70 mL) and a sodium carbonate aqueous solution (2 M, 9 mL) were added to Intermediate I-D (4.15 g), 4-[4-(4,4,5,5-tetramethyl-1,3,2-dioxaborolan-2-yl)phenyl]dibenzothiophene (4.12 g), and tetrakis(triphenylphosphine) palladium (0) (0.33 g). The mixture was heated to 75° C. for 17 hours under agitation in an argon atmosphere. The reaction mixture was filtered and then washed with distilled water and methanol. The resulting solid matter was subjected to column chromatography and then recrystallized from toluene, so as to provide ET-2 (3.56 g, yield: 62%). The result of mass spectrum analysis of the resulting compound revealed m/z (ratio of mass and charge)=807, from which the compound was identified as Compound 2 (ET-2).

Synthesis Example 3

Synthesis of Compound 3

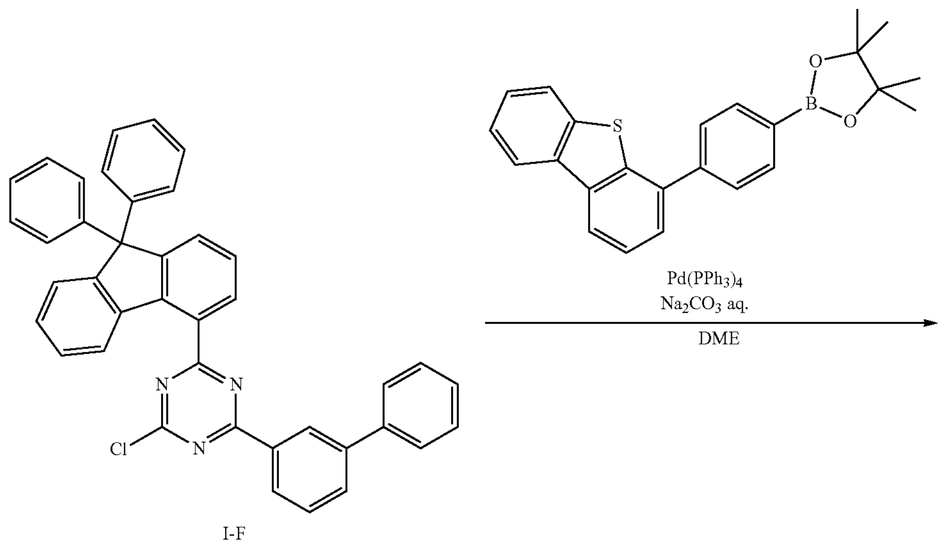

I-F

-continued

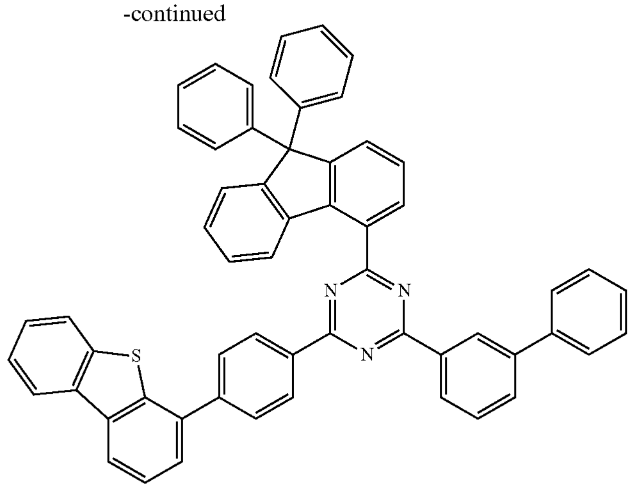

ET-3

In an argon atmosphere, 1,2-dimethoxyethane (DME) (75 mL) and a sodium carbonate aqueous solution (2 M, 9.4 mL) were added to Intermediate I-F (4.38 g), 4-[4-(4,4,5,5-tetramethyl-1,3,2-dioxaborolan-2-yl)phenyl]dibenzothiophene (4.35 g), and tetrakis(triphenylphosphine) palladium (0) (0.43 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-3 (3.51 g, yield: 58%). The result of mass spectrum analysis of the resulting compound revealed m/z (ratio of mass and charge)=807, from which the compound was identified as Compound 3 (ET-3).

Synthesis Example 4

Synthesis of Compound 4

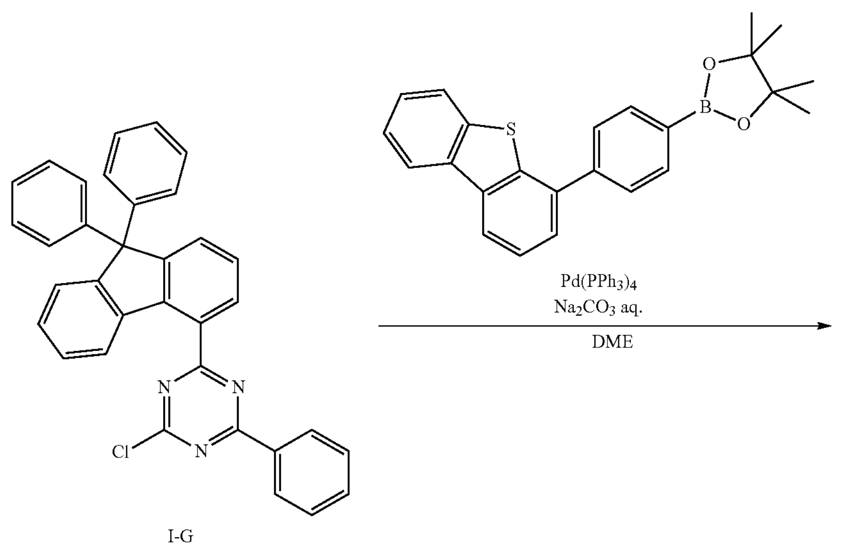

I-G

-continued

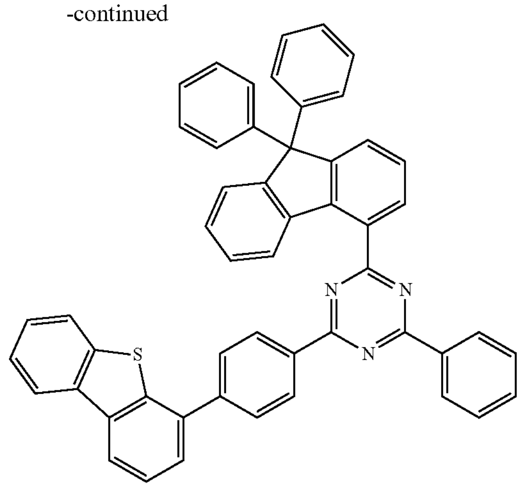

ET-4

In an argon atmosphere, 1,2-dimethoxyethane (DME) (80 mL) and a sodium carbonate aqueous solution (2 M, 12.5 mL) were added to Intermediate I-G (5.08 g), 4-[4-(4,4,5,5-tetramethyl-1,3,2-dioxaborolan-2-yl)phenyl]dibenzothiophene (5.79 g), and tetrakis(triphenylphosphine) palladium (0) (0.58 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-4 (4.76 g, yield: 65%). The result of mass spectrum analysis of the resulting compound revealed m/z (ratio of mass and charge)=731, from which the compound was identified as Compound 4 (ET-4).

Synthesis Example 5

Synthesis of Compound 5

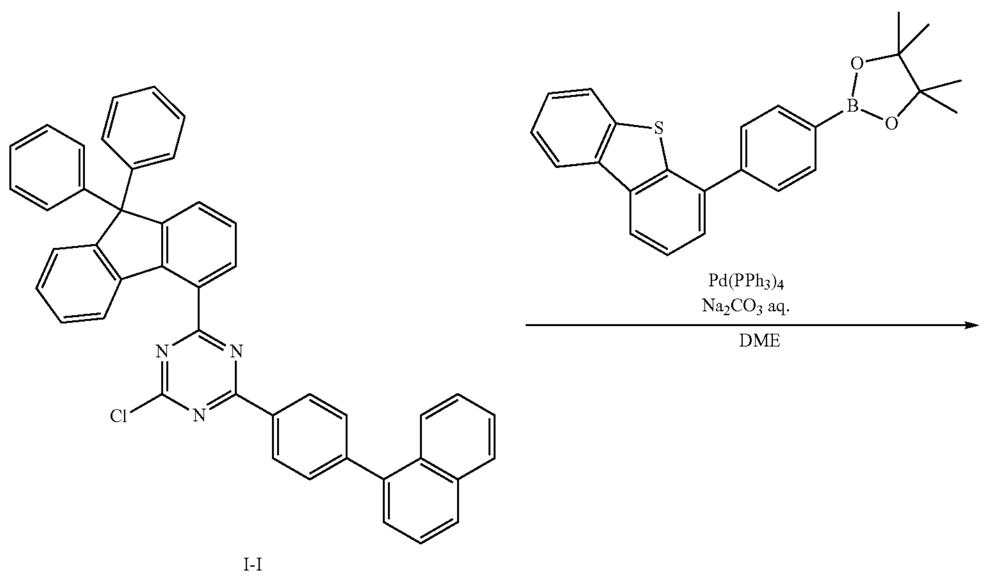

I-I

-continued

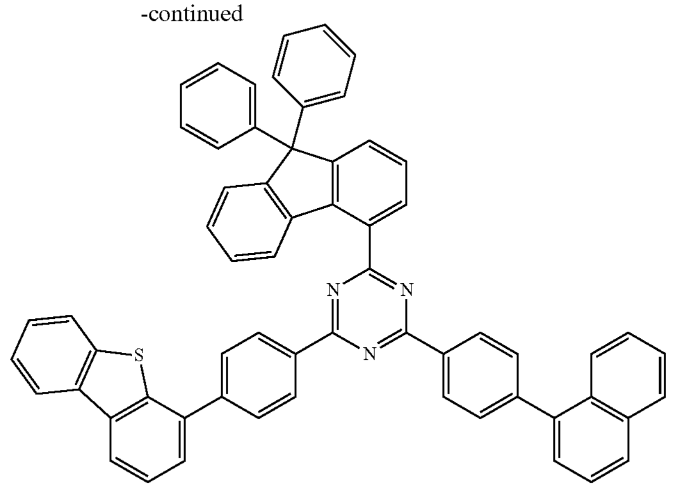

ET-5

In an argon atmosphere, 1,2-dimethoxyethane (DME) (80 mL) and a sodium carbonate aqueous solution (2 M, 10 mL) were added to Intermediate I-I (5.07 g), 4-[4-(4,4,5,5-tetramethyl-1,3,2-dioxaborolan-2-yl)phenyl]dibenzothiophene (4.64 g), and tetrakis(triphenylphosphine) palladium (0) (0.46 g). The mixture was heated to 75° C. for 17 hours under agitation in an argon atmosphere. The reaction mixture was filtered and then washed with distilled water and methanol. The resulting solid matter was subjected to column chromatography and then recrystallized from toluene, so as to provide ET-5 (3.50 g, yield: 51%). The result of mass spectrum analysis of the resulting compound revealed m/z (ratio of mass and charge)=857, from which the compound was identified as Compound 5 (ET-5).

Synthesis Example 6

Synthesis of Compound 6

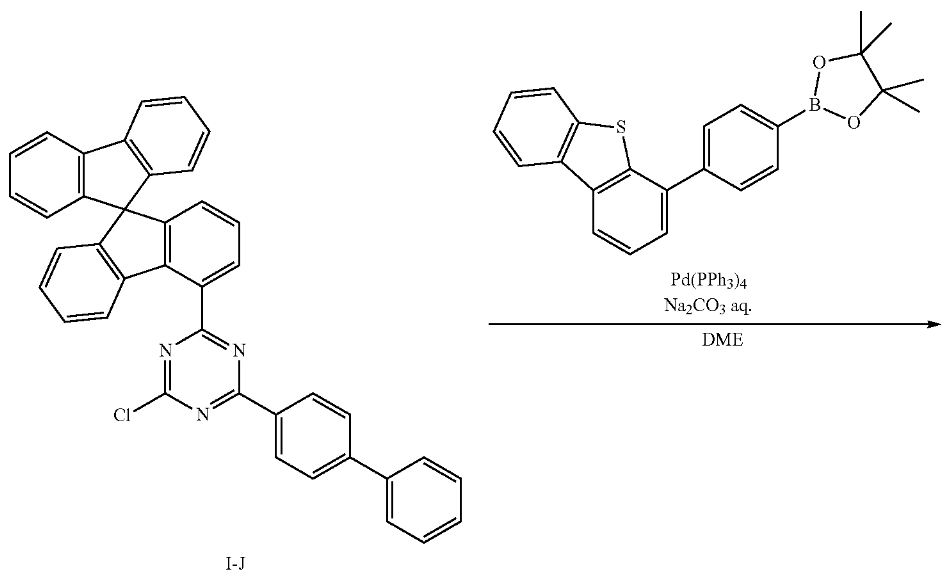

I-J

-continued

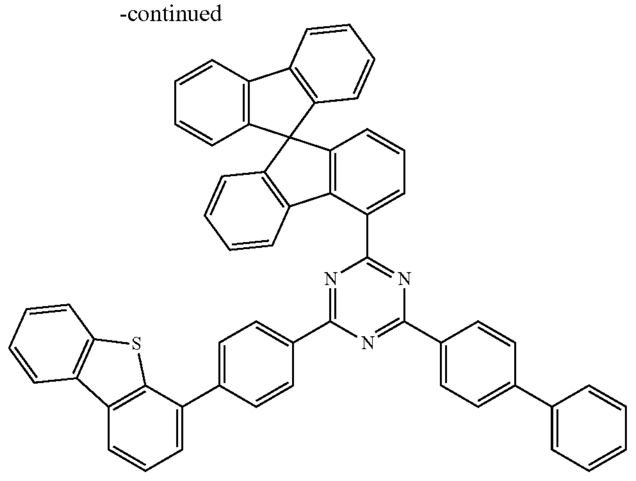

ET-6

In an argon atmosphere, 1,2-dimethoxyethane (DME) (87 mL) and a sodium carbonate aqueous solution (2 M, 8.8 mL) were added to Intermediate I-J (4.07 g), 4-[4-(4,4,5,5-tetramethyl-1,3,2-dioxaborolan-2-yl)phenyl]dibenzothiophene (4.06 g), and tetrakis(triphenylphosphine) palladium (0) (0.40 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-6 (2.60 g, yield: 46%). The result of mass spectrum analysis of the resulting compound revealed m/z (ratio of mass and charge)=805, from which the compound was identified as Compound 6 (ET-6).

Synthesis Example 7

Synthesis of Compound 7

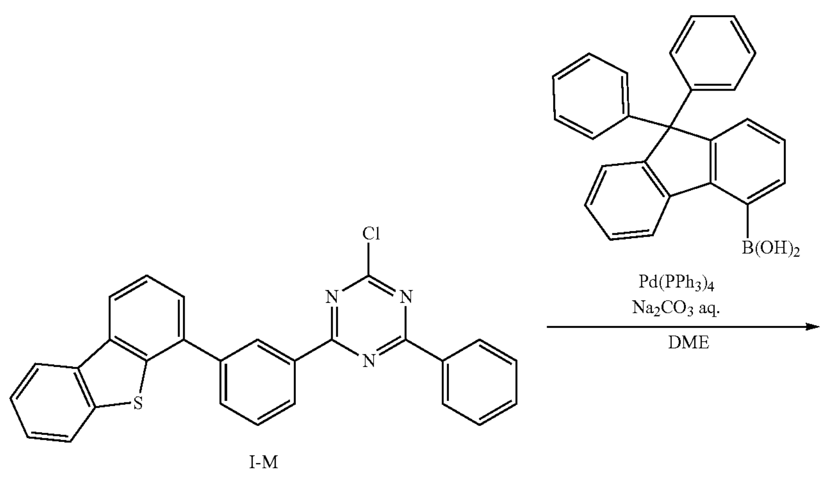

I-M

-continued

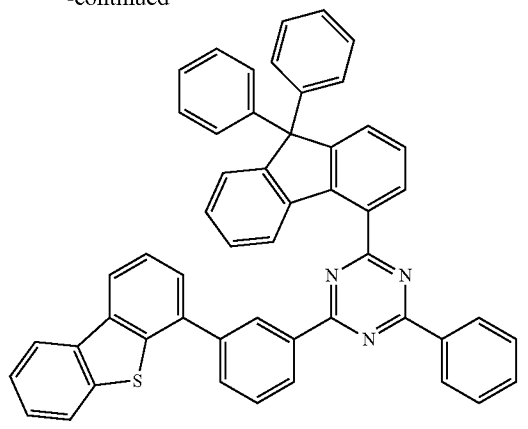

ET-7

In an argon atmosphere, 1,2-dimethoxyethane (DME) (80 mL) and a sodium carbonate aqueous solution (2 M, 10 mL) were added to Intermediate I-M (3.60 g), 9,9-diphenylfluorene-4-boronic acid (4.35 g), and tetrakis(triphenylphosphine) palladium(0) (0.46 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-8 (4.22 g, yield: 72%). The result of mass spectrum analysis of the resulting compound revealed m/z (ratio of mass and charge)=731, from which the compound was identified as Compound 7 (ET-7).

Synthesis Example 8

Synthesis of Compound 8

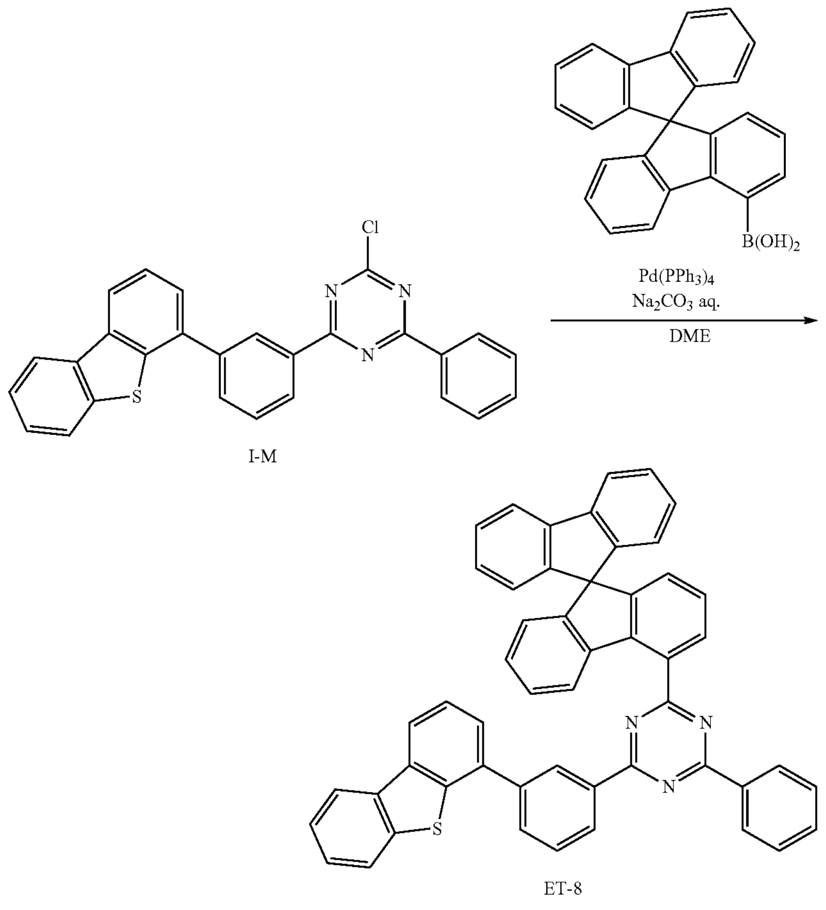

I-M

ET-8

In an argon atmosphere, 1,2-dimethoxyethane (DME) (80 mL) and a sodium carbonate aqueous solution (2 M, 10 mL) were added to Intermediate I-M (3.60 g), 9,9'-spirobifluorene-4-boronic acid (4.32 g), and tetrakis(triphenylphosphine) palladium(0) (0.46 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-9 (3.97 g, yield: 68%). The result of mass spectrum analysis of the resulting compound revealed m/z (ratio of mass and charge)=729, from which the compound was identified as Compound 8 (ET-8).

Synthesis Example 9

Synthesis of Compound 9

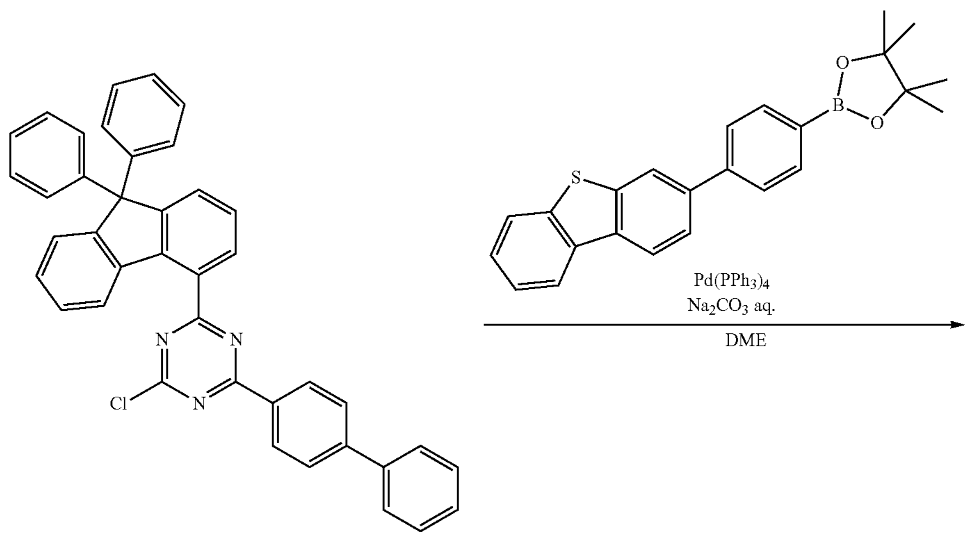

I-B

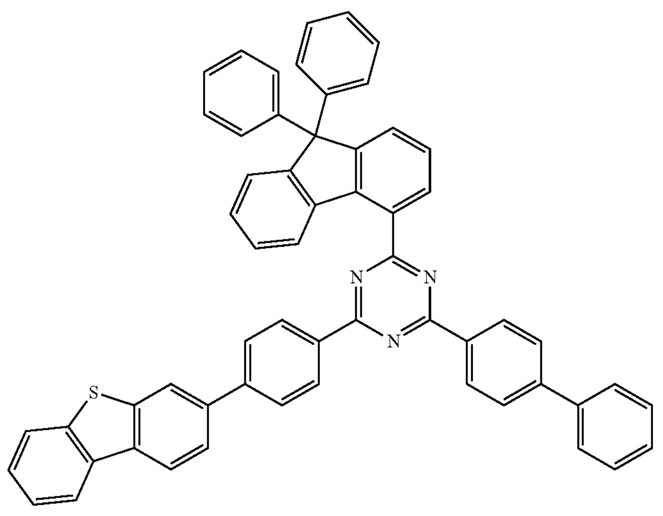

ET-9

In an argon atmosphere, 1,2-dimethoxyethane (DME) (80 mL) and a sodium carbonate aqueous solution (2 M, 10 mL) were added to Intermediate I-B (4.67 g), 3-[4-(4,4,5,5-tetramethyl-1,3,2-dioxaborolan-2-yl)phenyl]dibenzothiophene (4.64 g), and tetrakis(triphenylphosphine) palladium (0) (0.46 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-11 (3.62 g, yield: 56%). The result of mass spectrum analysis of the resulting compound revealed m/z (ratio of mass and charge)=807, from which the compound was identified as Compound 9 (ET-9).

Synthesis Example 10

Synthesis of Compound 10

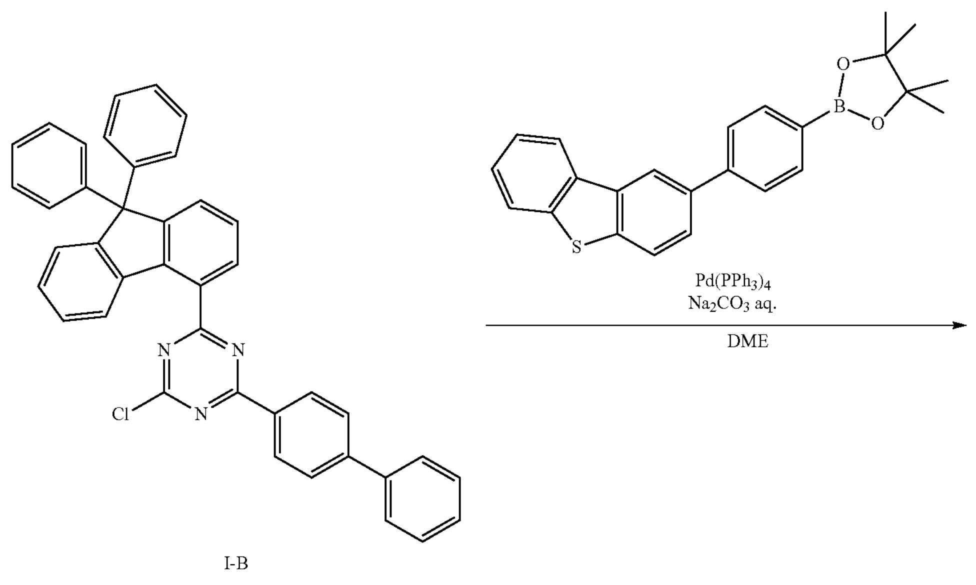

I-B

ET-10

In an argon atmosphere, 1,2-dimethoxyethane (DME) (80 mL) and a sodium carbonate aqueous solution (2 M, 10 mL) were added to Intermediate I-B (4.67 g), 2-[4-(4,4,5,5-tetramethyl-1,3,2-dioxaborolan-2-yl)phenyl]dibenzothiophene (4.64 g), and tetrakis(triphenylphosphine) palladium (0) (0.46 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-12 (4.01 g, yield: 62%). The result of mass spectrum analysis of the resulting compound revealed m/z (ratio of mass and charge)=807, from which the compound was identified as Compound 10 (ET-10).

Synthesis Example 11

Synthesis of Compound 11

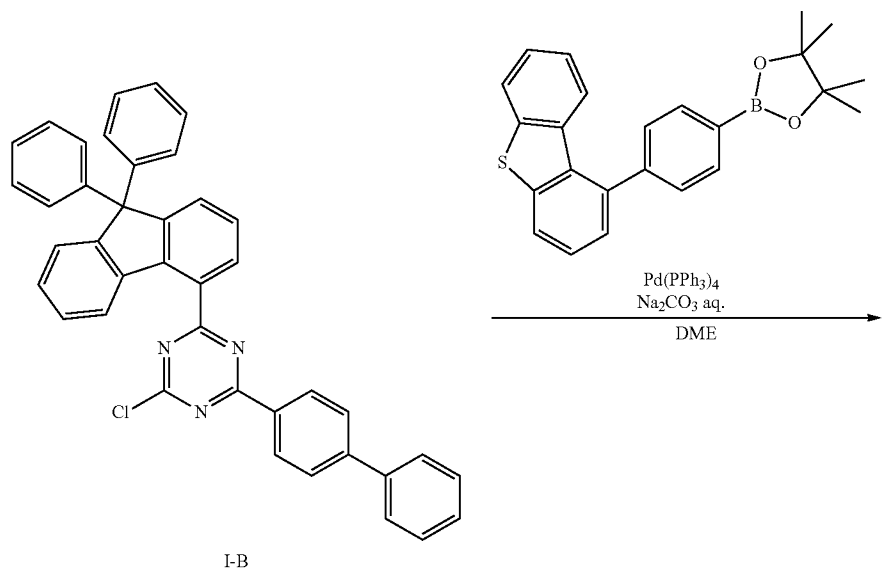

I-B

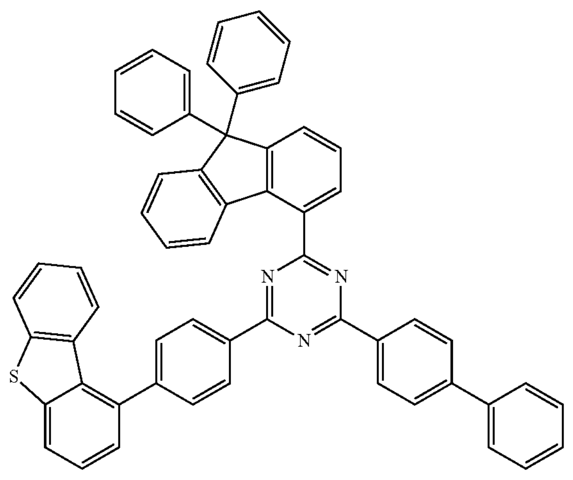

ET-11

In an argon atmosphere, 1,2-dimethoxyethane (DME) (80 mL) and a sodium carbonate aqueous solution (2 M, 10 mL) were added to Intermediate I-B (4.67 g), 1-[4-(4,4,5,5-tetramethyl-1,3,2-dioxaborolan-2-yl)phenyl]dibenzothiophene (4.64 g), and tetrakis(triphenylphosphine) palladium (0) (0.46 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-13 (2.84 g, yield: 44%). The result of mass spectrum analysis of the resulting compound revealed m/z (ratio of mass and charge)=807, from which the compound was identified as Compound 11 (ET-11).

Synthesis Example 12

Synthesis of Compound 12

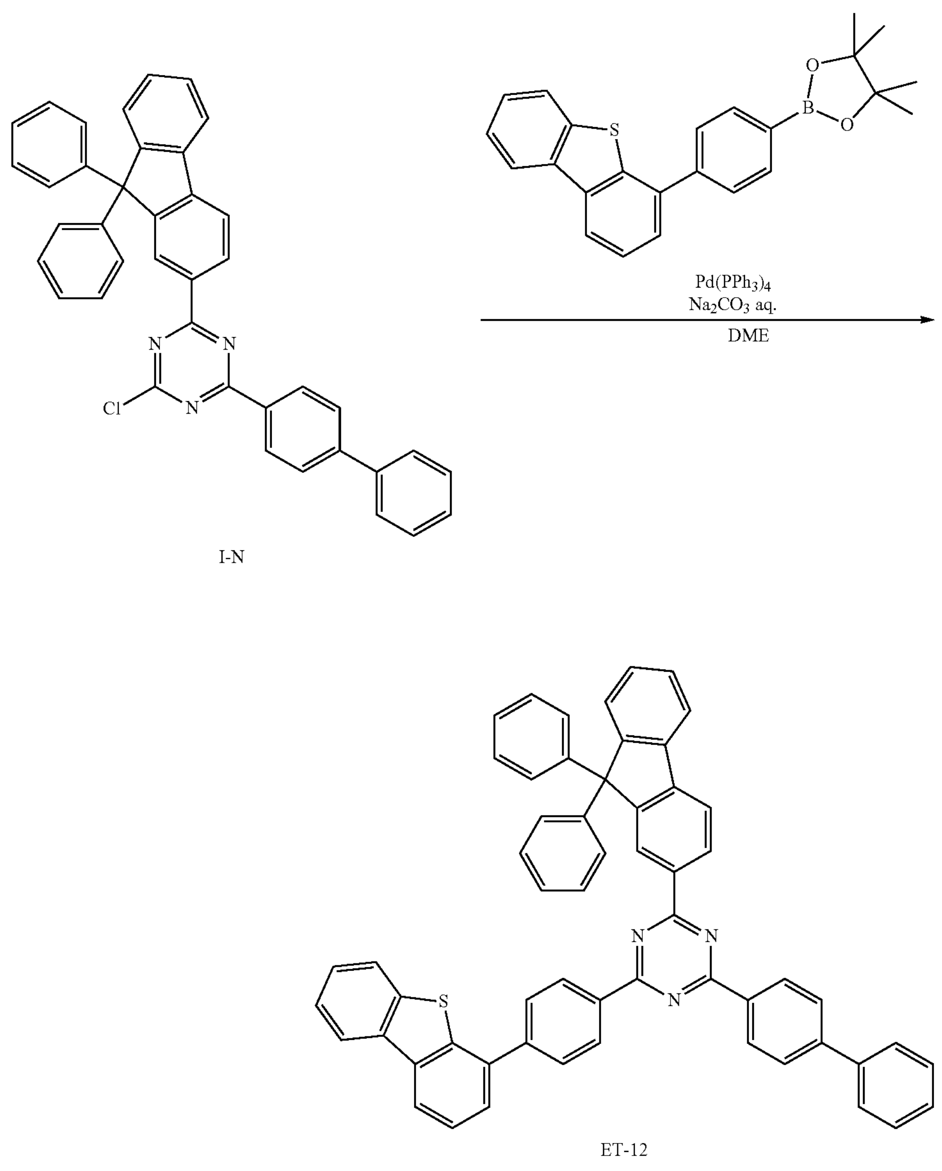

I-N

ET-12

In an argon atmosphere, 1,2-dimethoxyethane (DME) (85 mL) and a sodium carbonate aqueous solution (2 M, 11 mL) were added to Intermediate I-N (4.97 g), 4-[4-(4,4,5,5-tetramethyl-1,3,2-dioxaborolan-2-yl)phenyl]dibenzothiophene (4.93 g), and tetrakis(triphenylphosphine) palladium (0) (0.49 g). The mixture was heated to 75° C. for 8 hours under agitation in an argon atmosphere. The reaction mixture was filtered and then washed with distilled water and methanol. The resulting solid matter was subjected to column chromatography and then recrystallized from toluene, so as to provide ET-14 (4.05 g, yield: 59%). The result of mass spectrum analysis of the resulting compound revealed m/z (ratio of mass and charge)=807, from which the compound was identified as Compound 12 (ET-12).

Synthesis Example 13

Synthesis of Compound 13

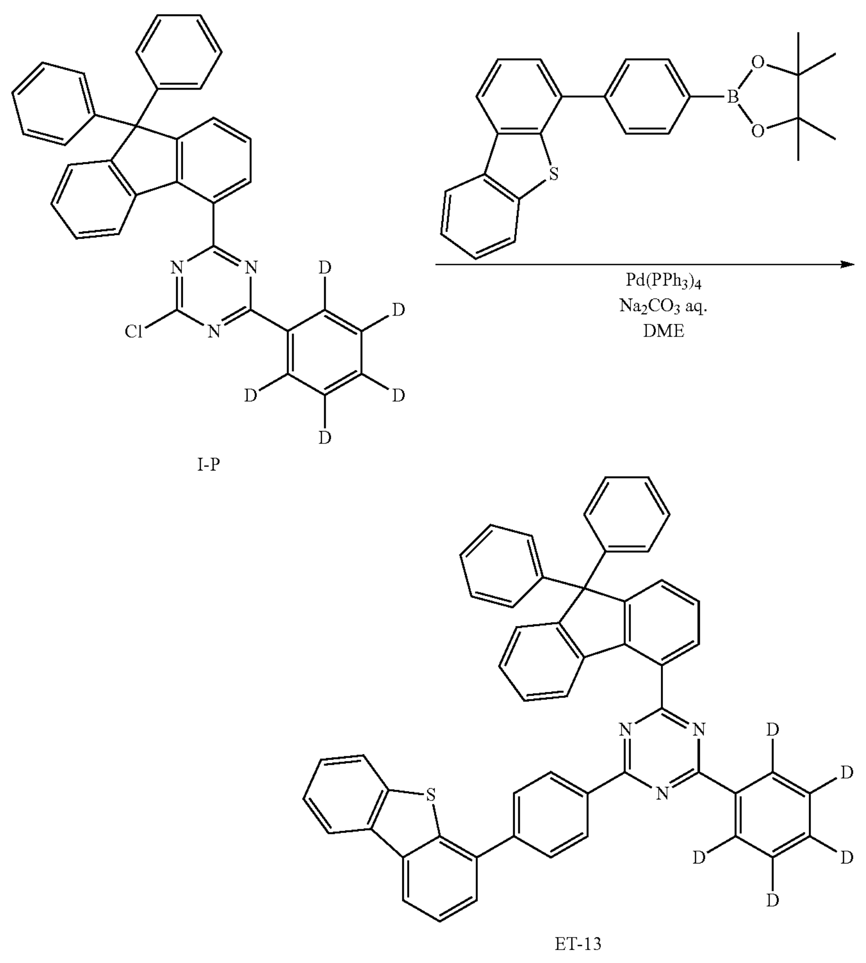

I-P

ET-13

ET-13 (2.1 g, yield: 48%) was obtained in the same manner as in Synthesis Example 1 by using Intermediate I-P (3.1 g) instead of Intermediate I-B. The result of mass spectrum analysis of the resulting compound revealed m/z (ratio of mass and charge)=736, from which the compound was identified as Compound 13 (ET-13).

Synthesis Example 14

Synthesis of Compound 14

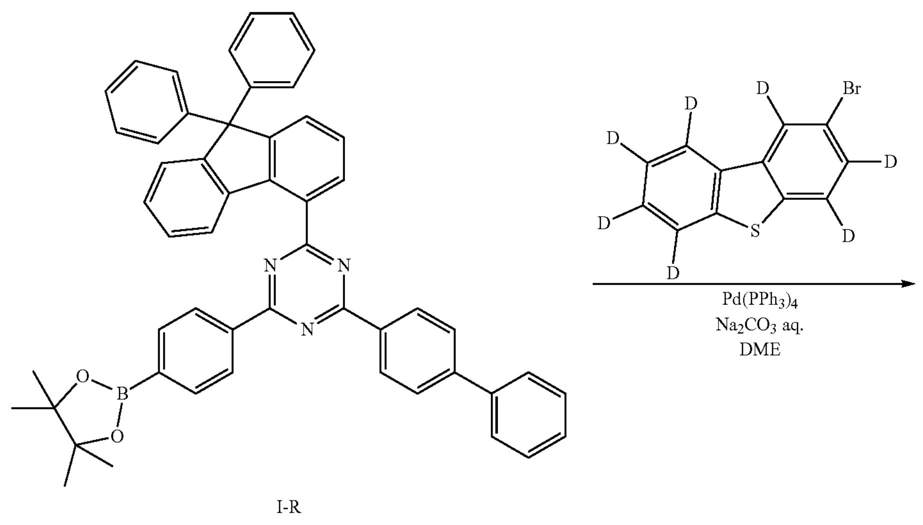

I-R

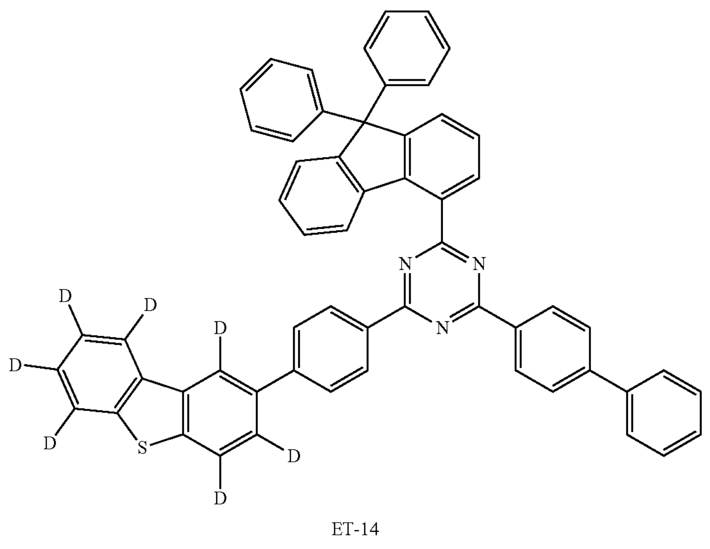

ET-14

In an argon atmosphere, 1,2-dimethoxyethane (DME) (30 mL) and a sodium carbonate aqueous solution (2 M, 4 mL) were added to Intermediate I-R (1.95 g), 2-bromodibenzothiophene-d7 (described in WO 2018-110887) (0.84 g), and tetrakis(triphenylphosphine) palladium(0) (0.15 g). The mixture was heated to 70° C. for 17 hours under agitation in an argon atmosphere. The reaction mixture was filtered and then washed with distilled water and methanol. The resulting solid matter was subjected to column chromatography and then recrystallized from toluene, so as to provide ET-14 (0.80 g, yield: 38%). The result of mass spectrum analysis of the resulting compound revealed m/z (ratio of mass and charge)=814, from which the compound was identified as Compound 14 (ET-14).

REFERENCE SIGNS LIST

1, 11: Organic EL device
2: Substrate
3: Anode
4: Cathode
5: Light emitting layer
6: Hole transporting zone (e.g., hole injecting layer and hole transporting layer)
7: Electron transporting zone (e.g., electron injecting layer and electron transporting layer)
7*a*: First electron transporting layer
7*b*: Second electron transporting layer
7*c*: Electron injecting layer
10, 20: Light emitting unit

The invention claimed is:

1. A compound of formula (1):

(1)

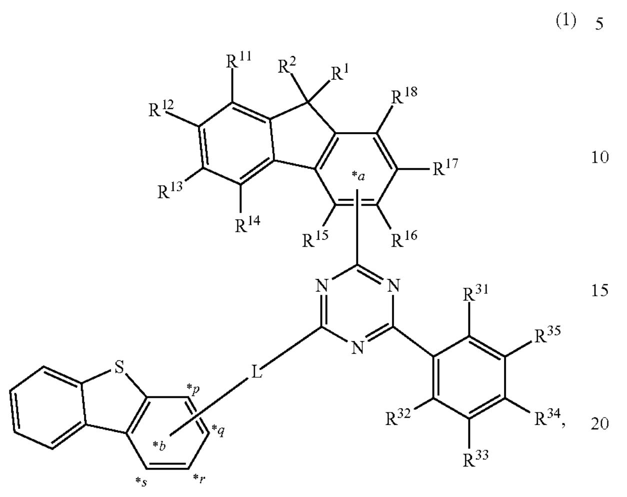

wherein $R^1$ and $R^2$ each are independently a hydrogen atom or a substituted or unsubstituted aryl group having 6 to 30 ring carbon atoms, in which $R^1$ and $R^2$ are not bonded to each other;

*p, *q, *r, and *s each represent a carbon atom;

*b is a bond bonded to one of the carbon atoms represented by *p, *q, *r, and *s;

$R^{15}$ or $R^{17}$ is a single bond bonded to *a, and remaining $R^{11}$ to $R^{18}$, that are not the single bond bonded to *a, are each are independently selected from a hydrogen atom, a substituted or unsubstituted aryl group having 6 to 30 ring carbon atoms, a substituted or unsubstituted alkyl group having 1 to 50 carbon atoms, a substituted or unsubstituted cycloalkyl group having 3 to 50 ring carbon atoms, and a cyano group;

L is a substituted or unsubstituted arylene group having 6 to 30 ring carbon atoms; and $R^{31}$ to $R^{35}$ each are independently a hydrogen atom or a substituted or unsubstituted aryl group having 6 to 30 ring carbon atoms, and no combination of two adjacent substituents selected from $R^{31}$ to $R^{35}$ is bonded to each other to form a ring.

2. The compound of claim 1, having formula (2) or (3):

(2)

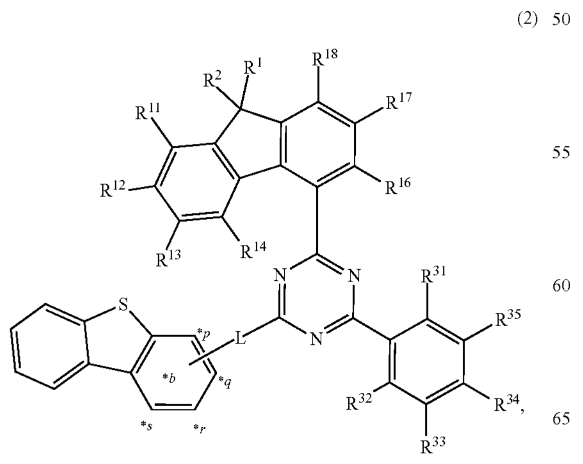

-continued (3)

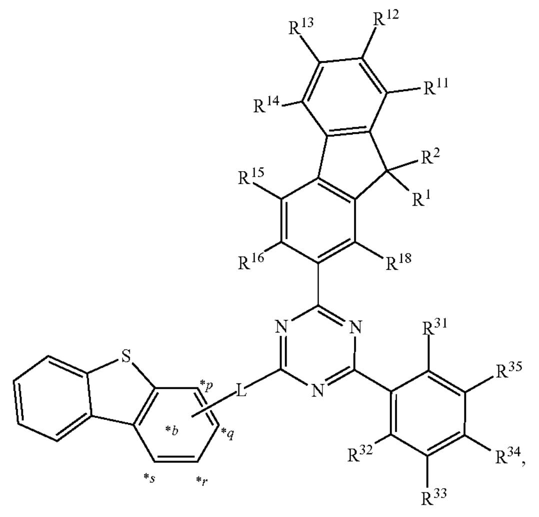

wherein *p, *q, *r, *s, *b, L, $R^1$, $R^2$, $R^{11}$ to $R^{18}$, and $R^{31}$ to $R^{35}$ have been defined in the formula (1).

3. The compound of claim 1, wherein $R^{31}$ to $R^{35}$ each are independently selected from a hydrogen atom, a substituted or unsubstituted phenyl group, and a substituted or unsubstituted naphthyl group.

4. The compound of claim 1, having formula (4) or (5):

(4)

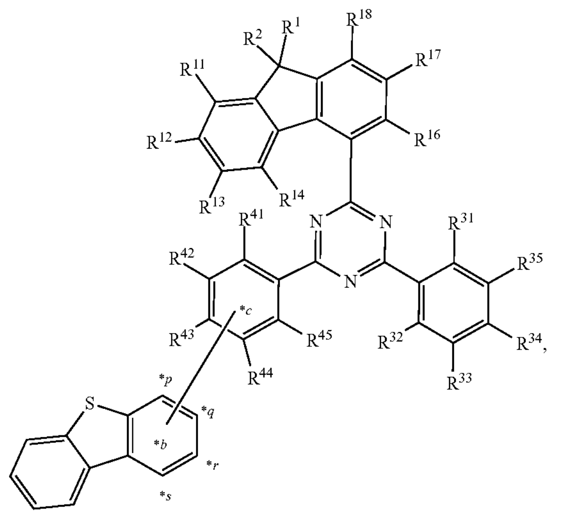

-continued (5)

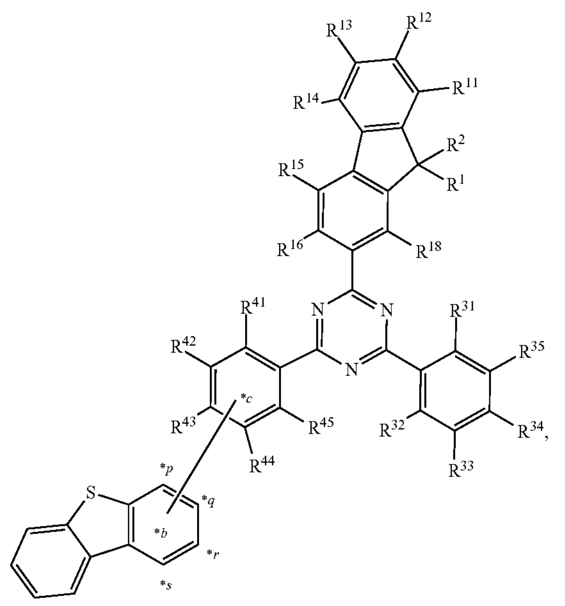

wherein *p, *q, *r, *s, *b, $R^1$, $R^2$, $R^{11}$ to $R^{18}$, and $R^{31}$ to $R^{35}$ have been defined in the formula (1), and $R^{41}$ to $R^{45}$ are the same as $R^{11}$ to $R^{18}$ defined in the formula (1), provided that one selected from $R^{41}$ to $R^{45}$ represents a single bond bonded to *c.

5. The compound of claim 4, wherein the $R^{41}$ to $R^{45}$ that is not a single bond bonded to *c are all hydrogen atoms.

6. The compound of claim 1, wherein a* is a bond to $R^{15}$.

7. The compound of claim 1, having formula (6) or (7):

(6)

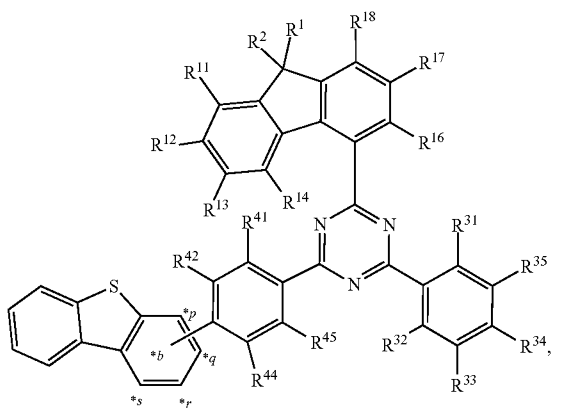

-continued (7)

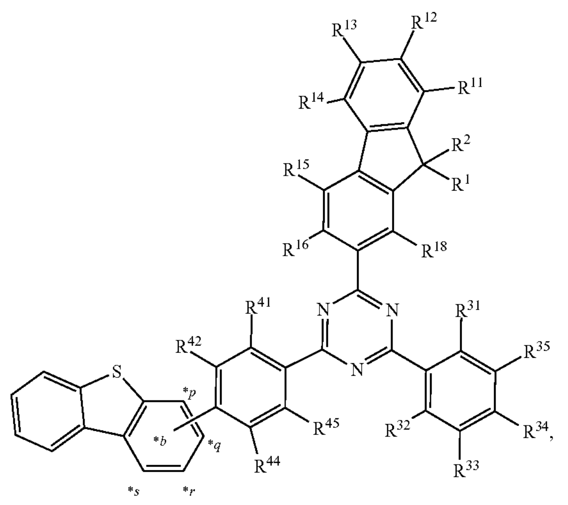

wherein *p, *q, *r, *s, *b, $R^1$, $R^2$, $R^{11}$ to $R^{18}$, and $R^{31}$ to $R^{35}$ have been defined in the formula (1), and $R^{41}$ to $R^{45}$ are the same as $R^{11}$ to $R^{18}$ defined in the formula (1).

8. The compound of claim 1, having formula (8) or (9):

(8)

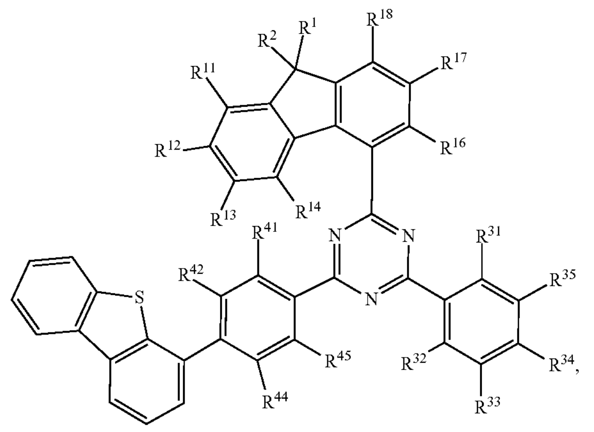

(9)

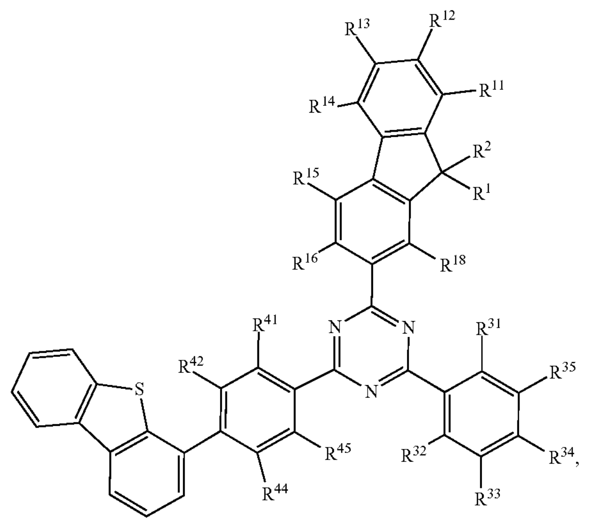

wherein $R^1$, $R^2$, $R^{11}$ to $R^{18}$, and $R^{31}$ to $R^{35}$ have been defined in the formula (1), and $R^{41}$ to $R^{45}$ are the same as $R^{11}$ to $R^{18}$ defined in the formula (1).

9. The compound of claim 1, wherein $R^1$ and $R^2$ each are independently selected from a phenyl group, a biphenylyl group, a terphenylyl group, and a naphthyl group.

10. The compound of claim 1, wherein $R^1$ and $R^2$ each are each a phenyl group.

11. The compound of claim 1, wherein L is selected from a phenylene group, a biphenyldiyl group, and a terphenyldiyl group.

12. The compound of claim 1, wherein L is a phenylene group.

13. The compound of claim 1, wherein the substituted or unsubstituted aryl group having 6 to 30 ring carbon atoms represented by $R^{11}$ to $R^{18}$ and $R^{41}$ to $R^{45}$ each are independently selected from a phenyl group, a biphenylyl group, a naphthyl group, and a phenanthryl group.

14. The compound of claim 1, wherein the substituted or unsubstituted alkyl group having 1 to 50 carbon atoms represented by $R^{11}$ to $R^{18}$ and $R^{41}$ to $R^{45}$ each are independently selected from a methyl group, an ethyl group, a n-propyl group, an isopropyl group, a n-butyl group, an isobutyl group, a s-butyl group, and a t-butyl group.

15. The compound of claim 1, wherein the substituted or unsubstituted cycloalkyl group having 3 to 50 ring carbon atoms represented by $R^{11}$ to $R^{18}$ and $R^{41}$ to $R^{45}$ each are independently selected from a cyclopropyl group, a cyclobutyl group, a cyclopentyl group, and a cyclohexyl group.

16. The compound of claim 1, wherein the $R^{11}$ to $R^{18}$ that is not the single bond bonded to *a are all hydrogen atoms.

17. The compound of claim 1, comprising a deuterium atom.

18. A material for organic electroluminescent devices, comprising:

the compound of claim 1.

19. An organic electroluminescent device, comprising:

a cathode;

an anode; and organic layers intervening between the cathode and the anode, wherein the organic layers comprising a light emitting layer, wherein at least one layer of the organic layers comprises the compound of claim 1.

20. The organic electroluminescent device of claim 19, wherein the organic layers comprise an electron transporting zone intervening between the cathode and the light emitting layer, and wherein the electron transporting zone comprises the compound.

21. The organic electroluminescent device of claim 20, wherein the electron transporting zone comprises a first electron transporting layer on a cathode side and a second electron transporting layer on a anode side, and wherein the first electron transporting layer, the second electron transporting layer, or both comprise the compound.

22. The organic electroluminescent device of claim 19, wherein the light emitting layer comprises a fluorescent dopant material.

23. The organic electroluminescent device of claim 19, wherein the light emitting layer comprises a phosphorescent dopant material.

24. An electronic device, comprising:

the organic electroluminescent device of claim 19.

* * * * *